US010183929B2

(12) United States Patent
K C et al.

(10) Patent No.: US 10,183,929 B2
(45) Date of Patent: Jan. 22, 2019

(54) 3-(BENZOIMIDAZOL-2-YL)-INDAZOLE INHIBITORS OF THE WNT SIGNALING PATHWAY AND THERAPEUTIC USES THEREOF

(71) Applicant: Samumed, LLC, San Diego, CA (US)

(72) Inventors: Sunil Kumar K C, San Diego, CA (US); John Hood, San Diego, CA (US)

(73) Assignee: Samumed, LLC, San Diego, CA (US)

( * ) Notice: Subject to any disclaimer, the term of this patent is extended or adjusted under 35 U.S.C. 154(b) by 0 days.

(21) Appl. No.: 15/889,403

(22) Filed: Feb. 6, 2018

(65) Prior Publication Data

US 2018/0162840 A1 Jun. 14, 2018

Related U.S. Application Data

(62) Division of application No. 14/149,948, filed on Jan. 8, 2014, now Pat. No. 9,908,867.

(60) Provisional application No. 61/750,221, filed on Jan. 8, 2013.

(51) Int. Cl.
  *C07D 401/14* (2006.01)
  *C07D 405/14* (2006.01)
  *C07D 409/14* (2006.01)

(52) U.S. Cl.
  CPC ......... *C07D 401/14* (2013.01); *C07D 405/14* (2013.01); *C07D 409/14* (2013.01)

(58) Field of Classification Search
  CPC .................................................... C07D 401/14
  USPC .......................................... 546/256; 514/333
  See application file for complete search history.

(56) References Cited

U.S. PATENT DOCUMENTS

| | | | |
|---|---|---|---|
| 4,164,559 A | 8/1979 | Miyata et al. |
| 4,474,752 A | 10/1984 | Haslam et al. |
| 4,603,139 A | 7/1986 | King |
| 5,037,844 A | 8/1991 | Hamminga et al. |
| 5,922,733 A | 7/1999 | Forbes et al. |
| 6,120,484 A | 9/2000 | Silverstein |
| 6,358,978 B1 | 3/2002 | Ritzeler et al. |
| 6,377,849 B1 | 4/2002 | Lenarz et al. |
| 6,440,102 B1 | 8/2002 | Arenberg et al. |
| 6,555,539 B2 | 4/2003 | Reich et al. |
| 6,648,873 B2 | 11/2003 | Arenberg et al. |
| 6,831,175 B2 | 12/2004 | Li et al. |
| 6,884,890 B2 | 4/2005 | Kania et al. |
| 6,897,208 B2 | 5/2005 | Edwards et al. |
| 6,911,211 B2 | 6/2005 | Eini et al. |
| 6,919,461 B2 | 7/2005 | Reich et al. |
| 7,008,953 B2 | 3/2006 | Kephart et al. |
| 7,064,215 B2 | 6/2006 | Renhowe et al. |
| 7,232,912 B2 | 6/2007 | Reich et al. |
| 7,285,565 B2 | 10/2007 | Zhu et al. |
| 7,390,815 B2 | 6/2008 | Davies et al. |
| 7,429,609 B2 | 9/2008 | Ohi et al. |
| 7,452,993 B2 | 11/2008 | Arnold et al. |
| 7,468,376 B2 | 12/2008 | Rosales et al. |
| 7,482,342 B2 | 1/2009 | D'Orchymont et al. |
| 7,488,737 B2 | 2/2009 | Xie et al. |
| 7,491,710 B2 | 2/2009 | Cherrier et al. |
| 7,541,367 B2 | 6/2009 | Chiu et al. |
| 7,626,021 B2 | 12/2009 | Arnold et al. |
| 7,642,278 B2 | 1/2010 | Jansen et al. |
| 7,666,867 B2 | 2/2010 | Makriyannis et al. |
| 7,812,043 B2 | 10/2010 | Lau et al. |
| 7,829,558 B2 | 11/2010 | Arnold et al. |
| 7,842,711 B2 | 11/2010 | D'Orchymont et al. |
| 7,902,217 B2 | 3/2011 | Xie et al. |
| 7,943,616 B2 | 5/2011 | Cox et al. |
| 8,008,481 B2 | 8/2011 | Ericsson et al. |
| 8,088,772 B2 | 1/2012 | Garcia et al. |
| 8,129,519 B2 | 3/2012 | Cholody et al. |
| 8,158,647 B2 | 4/2012 | Blaney et al. |
| 8,252,812 B2 | 8/2012 | Hood et al. |
| 8,288,425 B2 | 10/2012 | Edwards et al. |
| 8,304,408 B2 | 11/2012 | Wrasidlo et al. |
| 8,450,340 B2 | 5/2013 | Hood et al. |
| 8,604,052 B2 | 12/2013 | Hood et al. |
| 8,618,128 B1 | 12/2013 | Hood et al. |
| 8,637,508 B2 | 1/2014 | Badiger et al. |
| 8,664,241 B2 | 3/2014 | Hood et al. |
| 8,673,936 B2 | 3/2014 | Hood et al. |
| 8,697,887 B2 | 4/2014 | Hood et al. |
| 8,703,794 B2 | 4/2014 | Hood et al. |
| 8,815,897 B2 | 8/2014 | Hood et al. |
| 8,822,478 B2 | 9/2014 | Hood et al. |
| 8,846,714 B2 | 9/2014 | Hood et al. |
| 8,883,822 B2 | 11/2014 | Hood et al. |
| 8,901,150 B2 | 12/2014 | Hood et al. |

(Continued)

FOREIGN PATENT DOCUMENTS

| CN | 1394205 | 1/2003 |
|---|---|---|
| CN | 1671710 | 9/2005 |

(Continued)

OTHER PUBLICATIONS

"Application of Hamish Christopher Swan Wood, Norman Whittaker, Irene Stirling and Kyuji Ohta.," 582 F.2d 638 (Fed. Cir. 1978), 2 pages.

(Continued)

*Primary Examiner* — Patricia L Morris
(74) *Attorney, Agent, or Firm* — Fish & Richardson P.C.

(57) ABSTRACT

Indazole compounds for treating various diseases and pathologies are disclosed. More particularly, the present disclosure concerns the use of an indazole compound or analogs thereof, in the treatment of disorders characterized by the activation of Wnt pathway signaling (e.g., cancer, abnormal cellular proliferation, angiogenesis, Alzheimer's disease, lung disease and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

7 Claims, No Drawings

(56) References Cited

U.S. PATENT DOCUMENTS

| | | |
|---|---|---|
| 8,987,298 B2 | 3/2015 | Hood et al. |
| 9,012,472 B2 | 4/2015 | Hood et al. |
| 9,056,874 B2 | 6/2015 | Adams et al. |
| 9,067,939 B2 | 6/2015 | Hood et al. |
| 9,090,613 B2 | 7/2015 | Hood et al. |
| 9,174,967 B2 | 11/2015 | Körber et al. |
| 9,199,991 B2 | 12/2015 | Hood et al. |
| 9,221,793 B2 | 12/2015 | Hood et al. |
| 9,233,104 B2 | 1/2016 | Hood et al. |
| 9,381,192 B2 | 7/2016 | Hood et al. |
| 9,538,272 B2 | 1/2017 | Auclair et al. |
| 9,586,977 B2 | 3/2017 | Hood et al. |
| 9,745,271 B2 | 8/2017 | Hood et al. |
| 9,763,927 B2 | 9/2017 | Hood et al. |
| 9,763,951 B2 | 9/2017 | Kumar KC et al. |
| 9,802,916 B2 | 10/2017 | Hood et al. |
| 9,815,854 B2 | 11/2017 | Kumar KC et al. |
| 9,828,372 B2 | 11/2017 | Kumar KC et al. |
| 9,844,536 B2 | 12/2017 | Kumar KC et al. |
| 9,855,272 B2 | 1/2018 | Hood et al. |
| 2002/0103229 A1 | 8/2002 | Bhagwat et al. |
| 2002/0161022 A1 | 10/2002 | Reich et al. |
| 2003/0199516 A1 | 10/2003 | Moser et al. |
| 2004/0048868 A1 | 3/2004 | Edwards et al. |
| 2004/0077681 A1 | 4/2004 | Rawlings et al. |
| 2004/0176325 A1 | 9/2004 | Munson et al. |
| 2004/0236101 A1 | 11/2004 | Makriyannis et al. |
| 2005/0009894 A1 | 1/2005 | Babin et al. |
| 2005/0026960 A1 | 2/2005 | Kephart et al. |
| 2005/0090529 A1 | 4/2005 | McAlpine et al. |
| 2005/0192262 A1 | 9/2005 | Hagstrom et al. |
| 2005/0208582 A1 | 9/2005 | Ohi et al. |
| 2005/0261339 A1 | 11/2005 | Ohi et al. |
| 2006/0004000 A1 | 1/2006 | D'Orchymont et al. |
| 2006/0014756 A1 | 1/2006 | Edwards et al. |
| 2006/0079564 A1 | 4/2006 | Jansen et al. |
| 2006/0094706 A1 | 5/2006 | Paruch et al. |
| 2006/0111322 A1 | 5/2006 | Reich et al. |
| 2006/0116519 A1 | 6/2006 | Ma et al. |
| 2006/0135589 A1 | 6/2006 | Berdino et al. |
| 2006/0142345 A1 | 6/2006 | Kephart et al. |
| 2006/0167056 A1 | 7/2006 | Rynberg et al. |
| 2006/0264897 A1 | 11/2006 | Lobl |
| 2007/0027140 A1 | 2/2007 | Lau et al. |
| 2007/0049598 A1 | 3/2007 | Billedeau et al. |
| 2007/0060616 A1 | 3/2007 | Bennett et al. |
| 2007/0078147 A1 | 4/2007 | Schumacher et al. |
| 2007/0185187 A1 | 8/2007 | D'Orchymont et al. |
| 2007/0219257 A1 | 9/2007 | Beachy et al. |
| 2007/0282101 A1 | 12/2007 | Ericsson et al. |
| 2008/0004270 A1 | 1/2008 | Gill et al. |
| 2008/0255085 A1 | 10/2008 | Arvidsson et al. |
| 2008/0262205 A1 | 10/2008 | Haar et al. |
| 2008/0287452 A1 | 11/2008 | Bursavich et al. |
| 2009/0005356 A1 | 1/2009 | Blaney et al. |
| 2009/0005377 A1 | 1/2009 | Almansa Rosales et al. |
| 2009/0048249 A1 | 2/2009 | Chiu et al. |
| 2009/0054397 A1 | 2/2009 | Ohi et al. |
| 2009/0099062 A1 | 4/2009 | Lee et al. |
| 2009/0203690 A1 | 8/2009 | Akritopoulou-Zanze et al. |
| 2009/0247504 A1 | 10/2009 | Churcher et al. |
| 2009/0264446 A9 | 10/2009 | Rosales et al. |
| 2009/0286983 A1 | 11/2009 | Almansa Rosales et al. |
| 2010/0298377 A1 | 11/2010 | Aletru et al. |
| 2011/0009353 A1 | 1/2011 | Chen-Kiang et al. |
| 2011/0021467 A1 | 1/2011 | D'Orchymont et al. |
| 2011/0034441 A1 | 2/2011 | Hood et al. |
| 2011/0034497 A1 | 2/2011 | Hood et al. |
| 2011/0082144 A1 | 4/2011 | Lau et al. |
| 2011/0178075 A1 | 7/2011 | Xie et al. |
| 2012/0053345 A1 | 3/2012 | Ericson et al. |
| 2012/0059047 A1 | 3/2012 | Prins et al. |
| 2012/0129837 A1 | 5/2012 | Cholody et al. |
| 2012/0277229 A1 | 11/2012 | Bearss et al. |
| 2013/0039906 A1 | 2/2013 | Do et al. |
| 2013/0040976 A1 | 2/2013 | Hood et al. |
| 2013/0079329 A1 | 3/2013 | Hood et al. |
| 2013/0225576 A1 | 8/2013 | Hood et al. |
| 2013/0267548 A1 | 10/2013 | Follmann et al. |
| 2013/0296302 A1 | 11/2013 | Hood et al. |
| 2013/0296307 A1 | 11/2013 | Hood et al. |
| 2014/0179696 A1 | 6/2014 | Hood et al. |
| 2014/0194441 A1 | 7/2014 | K.C. et al. |
| 2014/0323479 A1 | 10/2014 | Hood et al. |
| 2015/0045360 A1 | 2/2015 | Hood et al. |
| 2015/0045379 A1 | 2/2015 | Hood et al. |
| 2015/0072981 A1 | 3/2015 | Hood et al. |
| 2015/0087687 A1 | 3/2015 | Brown et al. |
| 2015/0150862 A1 | 6/2015 | Hood et al. |
| 2015/0152105 A1 | 6/2015 | Hood et al. |
| 2016/0068529 A1 | 3/2016 | K.C. et al. |
| 2016/0068547 A1 | 3/2016 | K.C. et al. |
| 2016/0068548 A1 | 3/2016 | K.C. et al. |
| 2016/0068549 A1 | 3/2016 | K.C. et al. |
| 2016/0068550 A1 | 3/2016 | K.C. et al. |
| 2016/0068551 A1 | 3/2016 | K.C. et al. |
| 2016/0075701 A1 | 3/2016 | Kumar KC |
| 2016/0090380 A1 | 3/2016 | Kumar KC |
| 2016/0101092 A1 | 4/2016 | Hood et al. |
| 2016/0297812 A1 | 10/2016 | Hood et al. |
| 2017/0224697 A1 | 8/2017 | Kumar KC et al. |
| 2017/0333409 A1 | 11/2017 | Hood et al. |
| 2017/0349584 A1 | 12/2017 | Kumar KC et al. |
| 2018/0086754 A1 | 3/2018 | Kumar KC et al. |
| 2018/0133199 A1 | 5/2018 | Dellamary |
| 2018/0141963 A1 | 5/2018 | Kumar KC et al. |
| 2018/0148444 A1 | 5/2018 | Kumar KC et al. |
| 2018/0153873 A1 | 6/2018 | Hood et al. |
| 2018/0177787 A1 | 6/2018 | Kumar KC et al. |
| 2018/0185343 A1 | 7/2018 | Deshmukh et al. |
| 2018/0201624 A1 | 7/2018 | Kumar KC et al. |
| 2018/0207141 A1 | 7/2018 | Kumar KC et al. |

FOREIGN PATENT DOCUMENTS

| | | |
|---|---|---|
| CN | 1829713 | 9/2006 |
| CN | 101440092 | 5/2009 |
| KZ | 20122 | 1/2010 |
| RU | 2331640 | 8/2008 |
| WO | WO1987005297 | 9/1987 |
| WO | WO1996002537 | 2/1996 |
| WO | WO2001002369 | 1/2001 |
| WO | WO2001053268 | 7/2001 |
| WO | WO2003004488 | 1/2003 |
| WO | WO2003035005 | 5/2003 |
| WO | WO2003035065 | 5/2003 |
| WO | WO2003035644 | 5/2003 |
| WO | WO2003051366 | 6/2003 |
| WO | WO2003070236 | 8/2003 |
| WO | WO2003070706 | 8/2003 |
| WO | WO2003097610 | 11/2003 |
| WO | WO2003101968 | 12/2003 |
| WO | WO2003101993 | 12/2003 |
| WO | WO2004014864 | 2/2004 |
| WO | WO2004031158 | 4/2004 |
| WO | WO2004076450 | 9/2004 |
| WO | WO2005009997 | 2/2005 |
| WO | WO2005012301 | 2/2005 |
| WO | WO2005014554 | 2/2005 |
| WO | WO2005047266 | 5/2005 |
| WO | WO2005049019 | 6/2005 |
| WO | WO2005092890 | 10/2005 |
| WO | WO2005099703 | 10/2005 |
| WO | WO2005110410 | 11/2005 |
| WO | WO2006001894 | 1/2006 |
| WO | WO2006015124 | 2/2006 |
| WO | WO2006024945 | 3/2006 |
| WO | WO2006054143 | 5/2006 |
| WO | WO2006054151 | 5/2006 |
| WO | WO2006063302 | 6/2006 |
| WO | WO2006063841 | 6/2006 |
| WO | WO2006130673 | 12/2006 |
| WO | WO2007061360 | 5/2007 |

(56) References Cited

FOREIGN PATENT DOCUMENTS

| WO | WO2007107346 | 9/2007 |
|---|---|---|
| WO | WO2007117465 | 10/2007 |
| WO | WO2007147874 | 12/2007 |
| WO | WO2008061109 | 5/2008 |
| WO | WO2008071397 | 6/2008 |
| WO | WO2008071398 | 6/2008 |
| WO | WO2008071451 | 6/2008 |
| WO | WO2008124848 | 10/2008 |
| WO | WO2008137408 | 11/2008 |
| WO | WO2008140792 | 11/2008 |
| WO | WO2008147713 | 12/2008 |
| WO | WO2008150914 | 12/2008 |
| WO | WO2008154241 | 12/2008 |
| WO | WO2008156757 | 12/2008 |
| WO | WO2009011850 | 1/2009 |
| WO | WO2009016072 | 2/2009 |
| WO | WO2009029609 | 3/2009 |
| WO | WO2009061345 | 5/2009 |
| WO | WO2010064875 | 6/2010 |
| WO | WO2010107765 | 9/2010 |
| WO | WO2010111060 | 9/2010 |
| WO | WO2011011722 | 1/2011 |
| WO | WO2011019648 | 2/2011 |
| WO | WO2011019651 | 2/2011 |
| WO | WO2011050245 | 4/2011 |
| WO | WO2011079076 | 6/2011 |
| WO | WO2011084486 | 7/2011 |
| WO | WO2011123890 | 10/2011 |
| WO | WO2012068589 | 5/2012 |
| WO | WO2012104388 | 8/2012 |
| WO | WO2012129562 | 9/2012 |
| WO | WO2013024011 | 2/2013 |
| WO | WO2013030138 | 3/2013 |
| WO | WO2013113722 | 8/2013 |
| WO | WO2017079765 | 5/2017 |

OTHER PUBLICATIONS

Adaimy et al., "Mutation in WNT10A is Associated with an Autosomal Recessive Ectodermal Dysplasia: The Odonto-onychodermal Dysplasia," *Am. J. Hum. Genet.*, (Oct. 2007), 81(4), 821-828.
Anastas and Moon, "WNT signalling pathways as therapeutic targets in cancer," *Nat Rev Cancer*, 13(1):11-26, Jan. 2013.
Andres, "Molecular genetics and animal models in autistic disorder," *Brain Research Bulletin*, (2002), 57(1), 109-119.
Barker and Clevers, "Mining the Wnt pathway for cancer therapeutics," *Nat Rev Drug Discov.*, 5(12):997-1014, Dec 2006.
Beyer et al., "Extended report: β-catenin is a central mediator of pro-fibrotic Wnt signaling in systemic sclerosis," *Ann Rheum Dis*, 71:761-767, online Feb. 2012.
Biason-Lauber et al., "A WNT4 Mutation Associated with Müllerian-Duct Regression and Virilization in a 46,XX Woman," *N. Engl. J. Med.*, (Aug. 2004), 351(8), 792-798.
Blaydon et al., "The gene encoding R-spondin 4 (RSPO4), a secreted protein implicated in Wnt signaling, is mutated in inherited anonychia," *Nat. Genet.*, (Nov. 2006), 38(11), 1245-1247.
Blom et al., "Involvement of the Wnt signaling pathway in experimental and human osteoarthritis: prominent role of Wnt-induced signaling protein 1," *Arthritis Rheum.*, 60(2):501-512, Feb. 2009.
Boyden et al., "High Bone Density Due to a Mutation in LDL-Receptor-Related Protein 5," *N. Engl. J. Med.*, (May 2002), 346(20):1513-1521.
Brack et al., "Increased Wnt signaling during aging alters muscle stem cell fate and increases fibrosis," *Science.*, 317(5839):807-810, Aug. 2007.
Brown et al., "Toxicity and toxicokinetics of the cyclin-dependent kinase inhibitor AG-024322 in cynomolgus monkeys following intravenous infusion," *Cancer Chemother Pharmacol.*, 62(6):1091-1101, Epub May 2008.
Chilosi et al., "The pathogenesis of COPD and IPF: Distinct horns of the same devil?," *Respiratory Research*, 13:3, 2012.
Chou and Talalay, "Quantitative analysis of dose-effect relationships: the combined effects of multiple drugs or enzyme inhibitors," *Advances in Enzyme Regulation* (1984), 22, 27-55.
Chou, "Drug combination studies and their synergy quantification using the Chou-Talalay method," *Cancer Res.*, 70(2):440-446, Jan. 2010.
Chou, "Graphic rule for drug metabolism systems," *Current Drug Metabolism*, (May 2010) 11(4):369-378.
Christodoulides et al., "WNT10B mutations in human obesity," *Diabetologia*, (2006) 49(4):678-684.
Clevers and Nusse, "Wnt/β-catenin signaling and disease," *Cell*, (Jun. 2012), 149(6):1192-1205.
Clevers, "Wnt/beta-catenin signaling in development and disease," *Cell*, (Nov. 2006), 127(3), 469-480.
Corr, "Wnt-beta-catenin signaling in the pathogenesis of osteoarthritis," *Nat Clin Pract Rheumatol.*, 4(10):550-556, Oct. 2008.
D'Alessio et al., "Benzodipyrazoles: a new class of potent CDK2 inhibitors," *Bioorganic & Medicinal Chemistry Letters* (2005), 15(5), 1315-1319.
Dann et al., "Insights into Wnt binding and signaling from the structures of two Frizzled cysteine-rich domains," Nature, (Jul. 2001), 412, pp. 86-90.
Datta et al., "Novel therapeutic approaches for pulmonary fibrosis," *Br J Pharmacol.*, 163(1):141-172, May 2011.
Davidson et al., "Emerging links between CDK cell cycle regulators and Wnt signaling," Trends Cell Biol., Aug. 2010, 20(8):453-460.
De Ferrari and Inestrosa, "Wnt signaling function in Alzheimer's disease," *Brain Research Reviews*, (2000), 33(1): 1-12.
De Ferrari and Moon, "The ups and downs of Wnt signaling in prevalent neurological disorders," Oncogene, (2006) 25(57): 7545-7553.
De Ferrari et al., "Common genetic variation within the Low-Density Lipoprotein Receptor-Related Protein 6 and late-onset Alzheimer's disease," Proc. Natl. Acad. Sci. USA, (May 2007), 104(22):9434-9439.
Dermer, "Another Anniversary for the War on Cancer," *Nature Biotechnology*, 12:320 (1994).
Dessalew et al., "3D-QSAR CoMFA and CoMSIA study on benzodipyrazoles as cyclin dependent kinase 2 inhibitors," *Medicinal Chemistry*, (2008), 4(4), 313-321.
Dong et al., "QSAR study of Akt/protein kinase B (PKB) inhibitors using support vector machine," *European Journal of Medicinal Chemistry*, (Oct. 2009), pp. 44(10): 4090-4097.
du Bois, "Strategies for treating idiopathic pulmonary fibrosis," *Nature Reviews Drug Discovery*, 9(2): 129-140 (Feb. 2010).
Edamoto et al., "Alterations of RB1, p53 and Wnt pathways in hepatocellular carcinomas associated with hepatitis C, hepatitis B and alcoholic liver cirrhosis," *Int J Cancer.*, 106(3):334-341, Sep. 1, 2003.
Egloff et al., "Gastrin-releasing peptide receptor expression in non-cancerous bronchial epithelia is associated with lung cancer: a case-control study," *Respiratory Research*, 13:9, Feb. 2012.
Espada et al., "Wnt signalling and cancer stem cells," *Clin. Transl. Oncol.*, (2009), 11(7), 411-27.
Ewan et al., "A useful approach to identify novel small-molecule inhibitors of Wnt-dependent transcription," *Cancer Res.* (2010), 70(14), 5963-5973.
Florez et al., "TCF7L2 Polymorphisms and Progression to Diabetes in the Diabetes Prevention Program," *N. Engl. J. Med.*, (Jul. 2006), 355(3):241-250.
Freese et al., "Wnt signaling in development and disease," *Neurobiology of Disease*, (2010) 38(2):148-153.
Fujii et al., "An antagonist of dishevelled protein-protein interaction suppresses beta-catenin-dependent tumor cell growth," *Cancer Res.*, 67(2):573-579, Jan. 2007.
Fukuzawa et al., "Beckwith-Wiedemann Syndrome-associated Hepatoblastoma: Wnt Signal Activation Occurs Later in Tumorigenesis in Patients with 11p15.5 Uniparental Disomy," *Pediatric and Developmental Pathology* (2003), 6(4): 299-306.
Giles et al., "Caught up in a Wnt storm: Wnt signaling in cancer," Biochim Biophys Acta., 1653(1):1-24, Jun. 2003.

(56) References Cited

OTHER PUBLICATIONS

Handeli and Simon, "A small-molecule inhibitor of Tcf/beta-catenin signaling down-regulates PPARgamma and PPARdelta activities," *Mol Cancer Ther.*, 7(3):521-529, Mar. 2008.

Henderson Jr. et al., "Inhibition of Wnt/beta-catenin/CREB binding protein (CBP) signaling reverses pulmonary fibrosis," *Proc Natl Acad Sci U S A.*, 107(32):14309-14314, Epub Jul. 2010.

Hu et al., "Discovery of indazoles as inhibitors of Tpl2 kinase," *Bioorganic & Medicinal Chemistry Letters*, (Aug. 2011) 21(16): 4758-4761.

Huang et al., "Tankyrase inhibition stabilizes axin and antagonizes Wnt signaling," *Nature*, (Oct. 2009), 461(7264): 614-620.

Huang et al., "Synthesis of 3-(1H-benzimidazol-2-yl)-5-isoquinolin-4-ylpyrazolo[1,2-b]pyridine, a potent cyclin dependent kinase 1 (CDK1) inhibitor," *Bioorganic & Medicinal Chemistry Letters*, (2007) 17(5): 1243-1245.

Hübner et al., "Standardized quantification of pulmonary fibrosis in histological samples," *Biotechniques*, 44(4):507-511, 514-517, Apr. 2008.

Im et al., "Wnt inhibitors enhance chondrogenesis of human mesenchymal stem cells in a long-term pellet culture," *Biotechnol Lett.*, 33(5):1061-1068, Epub Jan. 2011.

Inestrosa and Toledo, "The role of Wnt signaling in neuronal dysfunction in Alzheimer's Disease," *Mol Neurodegener*, 3:9, doi:10. 1186/1750-1326-3-9, 13 pages, Jul. 2008.

Janssens et al., "The Wnt-dependent signaling pathways as target in oncology drug discovery," *Invest New Drugs.*, 24(4):263-280, Jul. 2006.

Jenkins et al., "Germline mutations in WTX cause a sclerosing skeletal dysplasia but do not predispose to tumorigenesis," *Nat. Genet.* (Jan. 2009), 41(1), 95-100.

Jessen et al., "Peripheral white blood cell toxicity induced by broad spectrum cyclin-dependent kinase inhibitors," *Journal of Applied Toxicology* (Jan. 2007), 27(2), 133-142.

Johnson et al., "A stem cell-based approach to cartilage repair," *Science.*, 336(6082):717-721, Epub Apr. 5, 2012.

Kanazawa et al., "Association of the Gene Encoding Wingless-Type Mammary Tumor Virus Integration-Site Family Member 5B (WNT5B) with Type 2 Diabetes," *Am. J. Hum. Genet.* (2004), 75(5), 832-843.

Karlberg et al., "Structural basis for the interaction between tankyrase-2 and a potent Wnt-signaling inhibitor," *J. Med. Chem.* (2010), 53(14), 5352-5.

Kibar et al., "Mutations in VANGL1 Associated with Neural-Tube Defects," *N. Engl. J. Med.*, (Apr. 2007), 356(14):1432-1437.

King et al., "BUILD-3: a randomized, controlled trial of bosentan in idiopathic pulmonary fibrosis," *Am J Respir Crit Care Med.*, 184(1):92-99, Epub Apr. 2011.

Kishimoto et al: "Wnt/Beta-CATENIN Signaling Suppresses Expressions of Ses, Mkx and Tnmd in Tendon-Derived Cells," Plos One, Jul. 27, 2017, 12(7), E0182051, pp. 1-17.

Kuwajima et al., "Necdin Promotes GABAergic Neuron Differentiation in Cooperation with Dlx Homeodomain Proteins," *Journal of Neuroscience* (May 2006), 26(20), 5383-5392.

Lammi et al., "Mutations in AXIN2 Cause Familial Tooth Agenesis and Predispose to Colorectal Cancer," *Am. J. Hum. Genet.* (2004), 74(5), 1043-1050.

Leyns et al., "Frzb-1 is a Secreted Antagonist of Wnt Signaling Expressed in the Spemann Organizer," *Cell* (Mar. 1997), 88(6), 747-756.

Li et al., "Artesunate attenuates the growth of human colorectal carcinoma and inhibits hyperactive Wnt/beta-catenin pathway," *Int J Cancer.*, 121(6):1360-1365, Sep. 2007.

Lin et al., "Synthesis and evaluation of pyrazolo[3,4-b]pyridine CDK1 inhibitors as anti-tumor agents," *Bioorganic & Medicinal Chemistry Letters*, (Aug. 2007), 17(15): 4297-4302.

Liu, et.al., "Fibrotic lung fibroblasts show blunted inhibition by cAMP due to deficient cAMP response element-binding protein phosphorylation," *J Pharmacol Exp Ther.*, 315(2):678-687, Epub Aug. 3, 2005.

Lories et al., "To Wnt or not to Wnt: the bone and joint health dilemma," *Nat Rev Rheumatol.*, 9(6):328-339, Epub Mar. 2013.

Low et al., "Phenotypic fingerprinting of small molecule cell cycle kinase inhibitors for drug discovery," *Curr Chem Genomics.*, 3:13-21, Mar. 2009.

Lu et al., "Structure-activity relationship studies of small-molecule inhibitors of Wnt response," *Bioorganic & Medicinal Chemistry Letters*, (Jul. 2009), 19(14):3825-3827.

Lui: "Histopathological Changes in Tendinopathypotential Roles of BMPs?" Rheumatology, May 2013, 52:2116-2126.

Luo et al., "Fragile X Mental Retardation Protein Regulates Proliferation and Differentiation of Adult Neural Stem/Progenitor Cells," *PLoS Genetics*, (Apr. 2010), 6(4):e1000898, 15 pages.

Luu et al., "Wnt/beta-catenin signaling pathway as a novel cancer drug target," *Curr Cancer Drug Targets.*, 4(8):653-671, Dec. 2004.

Luyten et al., "Wnt signaling and osteoarthritis," *Bone*, 44(4):522-527, Epub Dec. 14, 2008.

MacDonald et al., "Wnt/beta-catenin signaling: components, mechanisms, and diseases," *Dev. Cell* (Jul. 2009), 17(1), 9-26.

Mandel et al., "SERKAL Syndrome: An Autosomal-Recessive Disorder Caused by a Loss-of-Function Mutation in WNT4," *Am. J. Hum. Genet.*, (Jan. 2008), 82(1), 39-47.

Mani, et al., "LRP6 Mutation in a Family with Early Coronary Disease and Metabolic Risk Factors," *Science*, (Mar. 2007), 315(5816), 1278-1282.

McBride, et al. "Design and structure-activity relationship of 3-benzimidazol-2-yl-1H-indazoles as inhibitors of receptor tyrosine kinases," *Bioorganic & Medicinal Chemistry Letters* (2006), 16(13), 3595-3599.

Misra et al., "1H-Pyrazolo[3,4-b]pyridine inhibitors of cyclin-dependent kinases: highly potent 2,6-Difluorophenacyl analogues," *Bioorganic & Medicinal Chemistry Letters*, (2003), 13:2405-2408.

Morrisey, "Wnt signaling and pulmonary fibrosis," *Am J Pathol.*, 162(5):1393-1397, May 2003.

Muddassar et al., "Elucidation of binding mode and three dimensional quantitative structure-activity relationship studies of a novel series of protein kinase B/Akt inhibitors ," *Journal of Molecular Modeling*, (2009), 15(2): 183-192.

Niemann et al., "Homozygous WNT3 Mutation Causes Tetra-Amelia in a Large Consanguineous Family," *Am. J. Hum. Genet.* (2004), 74(3), 558-563.

Nishisho et al., "Mutations of chromosome 5q21 genes in FAP and colorectal cancer patients," *Science*, (Aug. 1991), 253(5020):665-669.

Nusse, "Wnt signaling in disease and in development," *Cell Res.*, 15(1):28-32, Jan. 2005.

Oates et al., "Increased DNA Methylation at the AXIN1 Gene in a Monozygotic Twin from a Pair Discordant for a Caudal Duplication Anomaly," *Am. J. Hum. Genet.* (2006 ), 79(1), 155-162.

Oduor et al., "Trypanosoma brucei glycogen synthase kinase-3, a target for anti-trypanosomal drug development: a public-private partnership to identify novel leads," *PLoS Negl Trop Dis.*, 5(4):e1017, Apr. 2011.

Okerlund and Cheyette, "Synaptic Wnt signaling—a contributor to major psychiatric disorders?" *J Neurodev Disord.*, (2011) 3(2):162-174.

Polakis, "Wnt signaling and cancer," *Genes Dev.*, 14: 1837-1851, 2000.

PUBCHEM. Substance Record for SID 164345938. Deposit Date: Nov. 4, 2013. [retrieved on Nov. 16, 2015]. Retrieved from the Internet. <URL: https://pubchem.ncbi.nlm.nih.gov/substance/ 164345938#section=Top>, 5 pages.

Qin et al. "Complexity of the genotype-phenotype correlation in familial exudative vitreoretinopathy with mutations in the LRP5 and/or FZD4 genes," *Hum. Mutat.* (2005), 26(2), 104-112.

Reya and Clevers, "Wnt signalling in stem cells and cancer," *Nature* 434: 843-850, Apr. 2005.

Richards et al., "Peripheral blood proteins predict mortality in idiopathic pulmonary fibrosis," *Am J Respir Crit Care Med.*, 185(1):67-76, Jan. 2012.

Rivera et al., "An X Chromosome Gene, WTX, is Commonly Inactivated in Wilms Tumor," *Science*, (Feb. 2007), 315(5812):642-645, published online Jan. 4, 2007.

(56) References Cited

OTHER PUBLICATIONS

Robitaille et al., "Mutant frizzled-4 disrupts retinal angiogenesis in familial exudative vitreoretinopathy," *Nat. Genet.*, (Sep. 2002), 32(2):326-330.
Ryu et al., "Natural derivatives of curcumin attenuate the Wnt/beta-catenin pathway through down-regulation of the transcriptional coactivator p300," *Biochem Biophys Res Commun.*, 377(4):1304-1308, print Dec. 2008, Epub Nov. 2008.
Salinas, "Wnt signaling in the vertebrate central nervous system: from axon guidance to synaptic function," *Cold Spring Harb Perspect Biol.*, (2012) 4(2). pii: a008003, 15 pages.
Sato, "Upregulation of the Wnt/beta-catenin pathway induced by transforming growth factor-beta in hypertrophic scars and keloids," *Acta Derm Venereol.*, 86(4):300-307, 2006.
Seah et al., "Neuronal Death Resulting from Targeted Disruption of the Snf2 Protein ATRX is Mediated by p53," *Journal of Neuroscience* (Nov. 2008), 28(47), 12570-12580.
Shih et al., "Pharmacophore modeling and virtual screening to identify potential RET kinase inhibitors," *Bioorg Med Chem Lett.*, 21(15):4490-4497, Epub Jun. 2011.
Shruster et al., "Wnt signaling enhances neurogenesis and improves neurological function after focal ischemic injury," *PLoS One*, (Jul. 2012), 7(7):e40843, 11 pages.
Silva et al, "Advances in Prodrug Design," *Mini-Revs. In Med. Chem.* (2005), 5: 893-914.
Solowiej et al., "Characterizing the Effects of the Juxtamembrane Domain on Vascular Endothelial Growth Factor Receptor-2 Enzymatic Activity, Autophosphorylation, and Inhibition by Axitinib," *Biochemistry*, (2009), 48(29), 7019-7031.
Staines et al., "Cartilage development and degeneration: a Wnt situation," *Cell Biochem Funct.*, 30(8):633-642, Epub Jun. 2012.
Sutherland et al., "A robust high-content imaging approach for probing the mechanism of action and phenotypic outcomes of cell-cycle modulators," *Molecular Cancer Therapeutics*, (Feb. 2011), 10(2):242-254.
Swaney et al., "A novel, orally active LPA(1) receptor antagonist inhibits lung fibrosis in the mouse bleomycin model," *Br J Pharmacol.*, 160(7):1699-1713, Aug. 2010.
Takahashi-Yanaga et al., "Celecoxib-induced degradation of T-cell factors-1 and -4 in human colon cancer cells," *Biochem Biophys Res Commun.*, 377(4):1185-1190, print Dec. 2008, Epub Nov. 2008.
Tamamura et al., "Developmental regulation of Wnt/beta-catenin signals is required for growth plate assembly, cartilage integrity, and endochondral ossification," *J Biol Chem.*, 280(19):19185-95. Epub Mar. 2005.
Thompson et al., "WNT/beta-catenin signaling in liver health and disease," *Hepatology.*, 45(5):1298-1305, May 2007.
Trujillo et al., "2-(6-Phenyl-1H-indazol-3-yl)-1H-benzo[d]imidazoles: design and synthesis of a potent and isoform selective PKC-zeta inhibitor," *Bioorg Med Chem Lett.*, 19(3):908-911, Epub Dec. 6, 2008.
Ugur et al., "Homozygous WNT10b mutation and complex inheritance in Split-Hand/Foot Malformation," *Hum. Mol. Genet.* (2008), 17(17), 2644-2653.
Vulpetti et al., "Structure-Based Approaches to Improve Selectivity: CDK2-GSK3β Binding Site Analysis," *Journal of Chemical Information and Modeling* (2005), 45(5), 1282-1290.
Wagner et al., "The therapeutic potential of the Wnt signaling pathway in bone disorders," *Curr Mol Pharmacol.*, 4(1):14-25, Jan. 2011.
Walters and Kleeberger, "Mouse models of bleomycin-induced pulmonary fibrosis," *Current Protocols in Pharmacology*, (2008) Chapter 5: Unit 5.46, 1-17.
Wang, et al., "Mutations in X-linked PORCN, a putative regulator of Wnt signaling, cause focal dermal hypoplasia," *Nat. Genet.* (Jul. 2007), 39(7), 836-838.
Wantanabe and Dai, "Winning WNT: race to Wnt signaling inhibitors," *Proc Natl Acad Sci U S A.* 108(15):5929-5930, Epub Mar. 2011.

Watts et.al., "RhoA signaling modulates cyclin D1 expression in human lung fibroblasts; implications for idiopathic pulmonary fibrosis," *Respir Res.*, 7:88, Jun. 15, 2006.
Weng et al., "Control of Dkk-1 ameliorates chondrocyte apoptosis, cartilage destruction, and subchondral bone deterioration in osteoarthritic knees," *Arthritis Rheum.*, 62(5):1393-1402, May 2010.
Witherington et al., "5-Aryl-pyrazolo[3,4-b]pyridazines: potent inhibitors of glycogen synthase kinase-3 (GSK-3)," *Bioorganic & Medicinal Chemistry Letters*, (May 2003), 13(9):1581-1584.
Woods, S. et al., "Mutations in WNT7A Cause a Range of Limb Malformations, Including Fuhrmann Syndrome and Al-Awadi/Raas-Rothschild/Schinzel Phocomelia Syndrome," *Am. J. Hum. Genet.* (Aug. 2006), 79(2), 402-408.
Yardy and Brewster, "Wnt signalling and prostate cancer," *Prostate Cancer Prostatic Dis*, 8(2):119-126, 2005.
Zhang et al., "Small-molecule synergist of the Wnt/beta-catenin signaling pathway," *Proc Natl Acad Sci U S A.*, 104(18):7444-7448, Epub Apr. 2007 and correction 104(30):12581, Jul. 2007.
Zhong et al., "Characterization of in vitro and in vivo metabolism of AG-024322, a novel cyclin-dependent kinase (CDK) inhibitor," *Health* (2009), 1(4): 249-262.
Chinese Search Report for application No. 201080044979.2, dated Mar. 14, 2013, 4 pages.
Chinese Search Report for application No. 201080061866.3, dated Aug. 28, 2013, 4 pages.
European Search Report and Written Opinion for App. No. EP12830938.2 dated Mar. 3, 2015, 6 pages.
European Search Report for Application No. 13772420.9 dated Mar. 19, 2015, 4 pages.
European Search Report for Application No. 15177852.9 dated Jan. 8. 2016, 10 pages.
European Search Report in Application No. 10808586.1, dated Jan. 8, 2013, 8 pages.
European Search Report in Application No. 10808589.5, dated Jan. 8, 2013, 4 pages.
European Search Report in Application No. 10842538, dated Apr. 25, 2013, 5 pages.
International Preliminary Report on Patentability for PCT/US2010/060514 dated Jun. 26, 2012, 9 pages.
International Preliminary Report on Patentability for PCT/US2012/055172 dated Mar. 27, 2014, 8 pages.
International Preliminary Report on Patentability for PCT/US2013/031055, dated Oct. 16, 2014, 9 pages.
International Preliminary Report on Patentability for PCT/US2013/039484, dated Nov. 4, 2014, 7 pages.
International Preliminary Report on Patentability for PCT/US2014/010607, dated Jul. 23, 2015, 7 pages.
International Preliminary Report on Patentability PCT/US2010/044865 dated Feb. 14, 2012, 6 pages.
International Preliminary Report on Patentability PCT/US2010/044872 dated Feb. 14, 2012, 11 pages.
International Search Report and Written Opinion for PCT/US2010/060514, dated Mar. 2, 2011, 11 pages.
International Search Report and Written Opinion for PCT/US2012/055172, dated Nov. 13, 2012, 10 pages.
International Search Report and Written Opinion for PCT/US2013/031055, dated May 21, 2013, 14 pages.
International Search Report and Written Opinion for PCT/US2014/10607, dated Aug. 15, 2014, 12 pages.
International Search Report and Written Opinion for PCT/US2015/048660, dated Jan. 11, 2016, 14 pages.
International Search Report and Written Opinion for PCT/US2015/048663, dated Jan. 11, 2016, 14 pages.
International Search Report and Written Opinion for PCT/US2015/048668, dated Jan. 11, 2016, 14 pages.
International Search Report and Written Opinion for PCT/US2015/048680, dated Jan. 11, 2016, 14 pages.
International Search Report and Written Opinion for PCT/US2015/048683, dated Jan. 12, 2016.
International Search Report and Written Opinion for PCT/US2015/048689, dated Jan. 11, 2016, 14 pages.
International Search Report and Written Opinion for PCT/US2015/048705, dated Dec. 15, 2015, 14 pages.

(56) References Cited

OTHER PUBLICATIONS

International Search Report and Written Opinion for PCT/US2015/048709, dated Dec. 4, 2015, 14 pages.
International Search Report and Written Opinion PCT/US2010/044865 dated Sep. 29, 2010, 2 pages.
International Search Report and Written Opinion PCT/US2010/044872 dated Oct. 5, 2010, 13 pages.
International Search Report for PCT/US2013/039484 dated Dec. 5, 2013, 14 pages.
Invitation to Pay for International App. No. PCT/US2015/048668, dated Nov. 2, 2015, 2 pages.
Invitation to Pay for International App. No. PCT/US2015/048683, dated Nov. 5, 2015, 2 pages.
Extended European Search Report for Application No. 14737972.1, dated Jul. 6, 2016, 7 pages.
Cecil Textbook of Medicine, edited by Bennet, J.C., and Plum F., 20th edition, vol. 1, 1004-1010, 1996.
Chockalingam et al., "Elevated aggrecanase activity in a rat model of joint injury is attenuated by an aggrecanase specific inhibitor," Osteoarthritis Cartilage, Mar. 2011, 19(3): 315-323.
Dermer et al., "Another Anniversary for the War on Cancer," Bio/Technology, Mar. 1994, 12:320.
Freshney et al., Culture of Animal Cells, A Manual of Basic Technique, Alan R. Liss, Inc., 1983, New York, p. 1-6.
Golub et al., "Molecular Classification of Cancer: Class Discovery and Class Prediction by Gene Expression Monitoring," Science, Oct. 1999, 286(5439):531-537.
Lacy et al., "Generation and characterization of ABT-981, a dual variable domain immunoglobulin (DVD-Ig(TM)) molecule that specifically and potently neutralizes both IL-1$\alpha$ and IL-1$\beta$," Mabs, May 2015, 7(3): 605-619.
Parsons et al., "Benzo[d]imidazole Transient Receptor Potential Vanilloid 1 Antagonists for the Treatment of Pain: Discovery of trans-2-(2-{2-[2-(4-Trifluoromethyl-phenyl)-vinyl]-1H-benzimidazol-5-yl}-phenyl)-propan-2-ol (Mavatrep)," J Med Chem, May 2015, 58(9): 3859-3874.
Piersanti et al., "Synthesis of benzo[1,2-d;3,4-d']diimidazole and 1 H-pyrazolo[4,3-b]pyridine as putative A2A receptor antagonists," Organic and Biomolecular Chemistry, Aug. 2007, 5(16):2567-2571.
Rother et al., "Efficacy and safety of epicutaneous ketoprofen in Transfersome (IDEA-033) versus oral celecoxib and placebo in osteoarthritis of the knee: multicentre randomised controlled trial," Annals of the Rheumatic Diseases, Sep. 2007, 66(9): 1178-1183.
Yamada et al., "Emergence of TNIK inhibitors in cancer therapeutics," Cancer Sci, May 2017, 108(5):818-823.
Zhu et al. "Design and synthesis of pyridine-pyrazolopyridine-based inhibitors of protein kinase B/Akt," Bioorganic & Medicinal Chemistry, Mar. 2007, 15(6):2441-2452.

3-(BENZOIMIDAZOL-2-YL)-INDAZOLE INHIBITORS OF THE WNT SIGNALING PATHWAY AND THERAPEUTIC USES THEREOF

RELATED APPLICATIONS

This application is a divisional application of U.S. application Ser. No. 14/149,948, filed Jan. 8, 2014, and claims the benefit of U.S. Provisional Application No. 61/750,221, filed Jan. 8, 2013, each of which is incorporated herein by reference in its entirety.

BACKGROUND

Technical Field

This disclosure relates to inhibitors of one or more proteins in the Wnt pathway, including inhibitors of one or more Wnt proteins, and compositions comprising the same. More particularly, it concerns the use of an indazole compound or salts or analogs thereof, in the treatment of disorders characterized by the activation of Wnt pathway signaling (e.g., cancer, abnormal cellular proliferation, angiogenesis, Alzheimer's disease, lung disease, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

Background

The Wnt growth factor family includes more than 10 genes identified in the mouse and at least 19 genes identified in the human. Members of the Wnt family of signaling molecules mediate many short- and long-range patterning processes during invertebrate and vertebrate development. The Wnt signaling pathway is known for its role in the inductive interactions that regulate growth and differentiation, and it also plays roles in the homeostatic maintenance of post-embryonic tissue integrity. Wnt stabilizes cytoplasmic β-catenin, which stimulates the expression of genes including c-myc, c jun, fra-1, and cyclin Dl. In addition, misregulation of Wnt signaling can cause developmental defects and is implicated in the genesis of several human cancers. More recently, the Wnt pathway has been implicated in the maintenance of stem or progenitor cells in a growing list of adult tissues that now includes skin, blood, gut, prostate, muscle and the nervous system.

SUMMARY

The present disclosure provides methods and reagents, involving contacting a cell with an agent, such as an indazole compound, in a sufficient amount to antagonize a Wnt activity, e.g., to reverse or control an aberrant growth state or correct a genetic disorder due to mutations in Wnt signaling components.

Some embodiments disclosed herein include Wnt inhibitors containing an indazole core. Other embodiments disclosed herein include pharmaceutical compositions and methods of treatment using these compounds.

One embodiment disclosed herein includes compounds of Formula I:

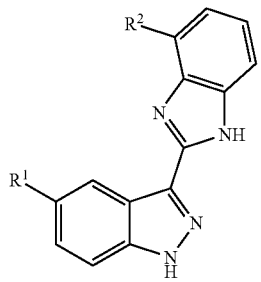

In some embodiments of Formula (I):

$R^1$ is -heteroaryl$R^3R^4$;

$R^2$ is selected from the group consisting of H, halide, $C_{1-3}$ alkyl, —CN, —OR$^8$, —OH, —($C_{1-3}$ alkyl)OR$^8$, —NR$^9R^{10}$, —($C_{1-3}$ alkyl)NR$^9R^{10}$, -heteroaryl$R^5$, -heterocyclyl$R^6$ and -aryl$R^7$;

$R^3$ is 1 substituent attached to the heteroaryl ring and is selected from the group consisting of H, $C_{1-3}$ alkyl, —CF$_3$, —NR$^9R^{10}$, —NHC(=O)R$^8$, —($C_{1-3}$ alkyl)heterocyclyl$R^6$ and —($C_{1-3}$ alkyl)NR$^9R^{10}$;

$R^4$ is 1 substituent attached to the heteroaryl ring and is selected from the group consisting of H, $C_{1-3}$ alkyl, —CF$_3$, halide, —CN, —OR$^8$, —OH, —($C_{1-3}$ alkyl)OR$^8$, —NR$^9R^{10}$, —($C_{1-3}$ alkyl)NR$^9R^{10}$ and —OCF$_3$;

$R^5$ is 1-3 substituents attached to the heteroaryl ring and each is independently selected from the group consisting of H, $C_{1-3}$ alkyl, —CF$_3$, halide, —CN, —OR$^8$, —OH, —($C_{1-3}$ alkyl)OR$^8$, —NR$^9R^{10}$, —($C_{1-3}$ alkyl)NR$^9R^{10}$ and —OCF$_3$;

$R^6$ is 1-3 substituents attached to the heterocyclyl ring and each is independently selected from the group consisting of H, $C_{1-3}$ alkyl, —CF$_3$, halide, —CN, —OR$^8$, —OH, —($C_{1-3}$ alkyl)OR$^8$, —NR$^9R^{10}$, —($C_{1-3}$ alkyl)NR$^9R^{10}$ and —OCF$_3$;

$R^7$ is 1-3 substituents attached to the aryl ring and each is independently selected from the group consisting of H, $C_{1-3}$ alkyl, —CF$_3$, halide, —CN, —OR$^8$, —OH, —($C_{1-3}$ alkyl)OR$^8$, —NR$^9R^{10}$, —($C_{1-3}$ alkyl)NR$^9R^{10}$ and —OCF$_3$;

each $R^8$ is independently selected from the group consisting of $C_{1-9}$ alkyl, -heteroaryl$R^{12}$, -heterocyclyl$R^{13}$, -aryl$R^{14}$, carbocyclyl$R^{11}$, —($C_{1-3}$ alkyl)heteroaryl$R^{12}$, —($C_{1-3}$ alkyl)heterocyclyl$R^{13}$, —($C_{1-3}$ alkyl)aryl$R^{14}$ and —($C_{1-3}$ alkyl)carbocyclyl$R^{11}$; each $R^9$ is independently selected from the group consisting of H, $C_{1-6}$ alkyl, -heteroaryl$R^{12}$, -heterocyclyl$R^{13}$, -aryl$R^{14}$, carbocyclyl$R^{11}$, —($C_{1-3}$ alkyl)heteroaryl$R^{12}$, —($C_{1-3}$ alkyl)heterocyclyl$R^{13}$, —($C_{1-3}$ alkyl)aryl$R^{14}$ and —($C_{1-3}$ alkyl)carbocyclyl$R^{11}$;

each $R^{10}$ is independently selected from the group consisting of H and $C_{1-6}$ alkyl; or $R^9$ and $R^{10}$ are optionally linked to form a five or six membered heterocyclyl ring;

$R^{11}$ is 1-3 substituents attached to the carbocyclyl ring and each independently selected from the group consisting of H, $C_{1-3}$ alkyl, —CF$_3$, halide, —CN, —O(R$^{10}$), —($C_{1-3}$ alkyl)OR$^{10}$, —N(R$^{10}$)$_2$, —($C_{1-3}$ alkyl)N(R$^{10}$)$_2$ and —OCF$_3$;

$R^{12}$ is 1-3 substituents attached to the heteroaryl ring and each independently selected from the group consisting of H, $C_{1-3}$ alkyl, —CF$_3$, halide, —CN, —O(R$^{10}$), —($C_{1-3}$ alkyl)OR$^{10}$, —N(R$^{10}$)$_2$, —($C_{1-3}$ alkyl)N(R$^{10}$)$_2$ and —OCF$_3$;

$R^{13}$ is 1-3 substituents attached to the heterocyclyl ring and each independently selected from the group consisting of H, $C_{1-3}$ alkyl, —CF$_3$, halide, —CN, —O(R$^{10}$), —($C_{1-3}$ alkyl)OR$^{10}$, —N(R$^{10}$)$_2$, —($C_{1-3}$ alkyl)N(R$^{10}$)$_2$ and —OCF$_3$;

$R^{14}$ is 1-3 substituents attached to the aryl ring and each independently selected from the group consisting of H, $C_{1-3}$ alkyl, —CF$_3$, halide, —CN, —O(R$^{10}$), —(C$_{1-3}$ alkyl)OR$^{10}$, —N(R$^{10}$)$_2$, —(C$_{1-3}$ alkyl)N(R$^{10}$)$_2$ and —OCF$_3$;
with the proviso that a compound of Formula I is not a compound selected from the group consisting of:
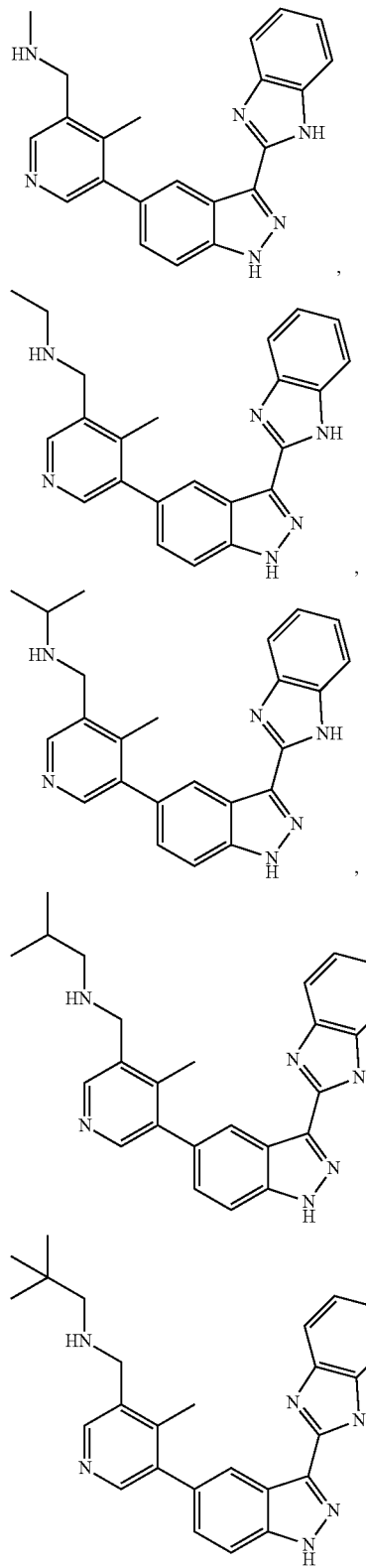
-continued
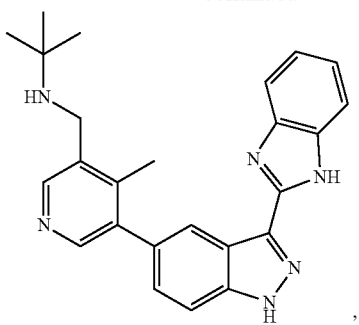
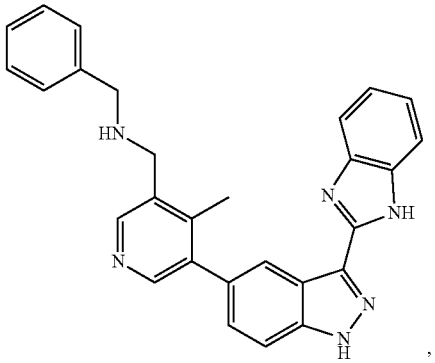
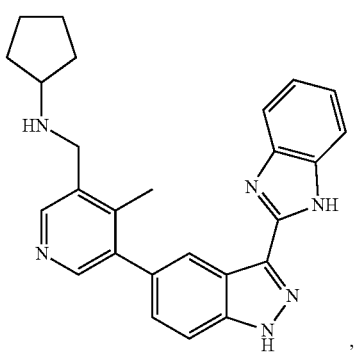
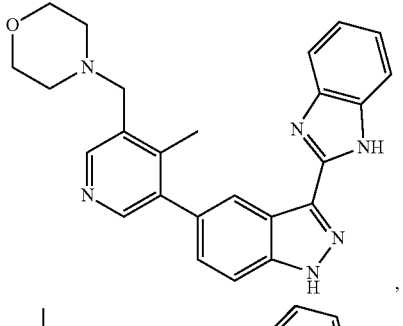
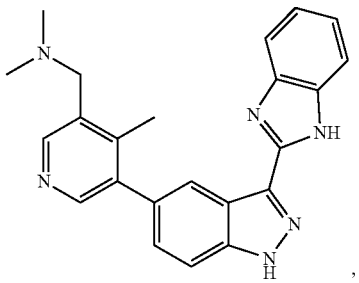

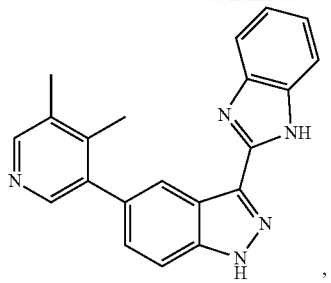,
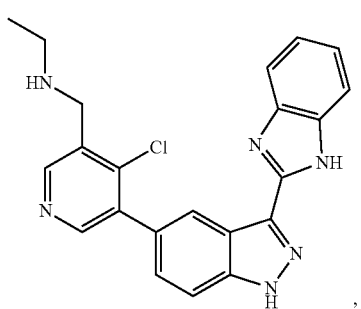,
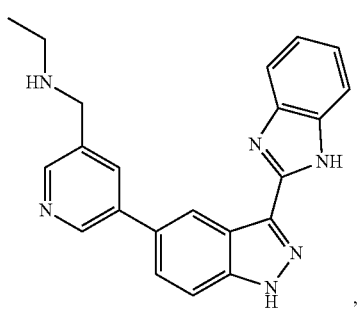,
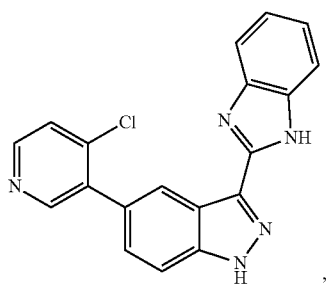,
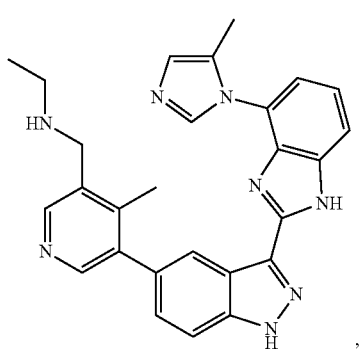,
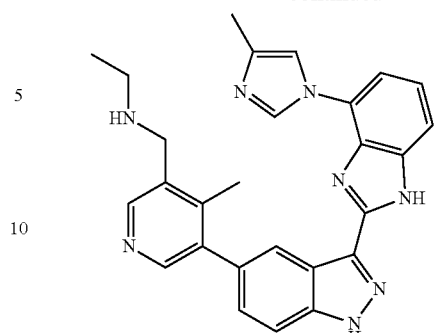,
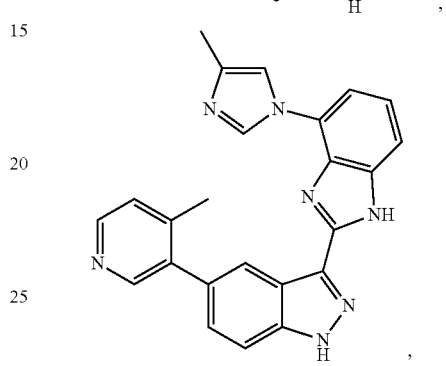,
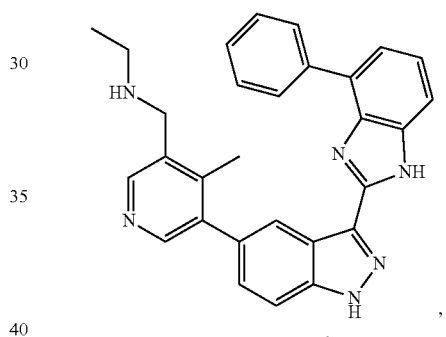,
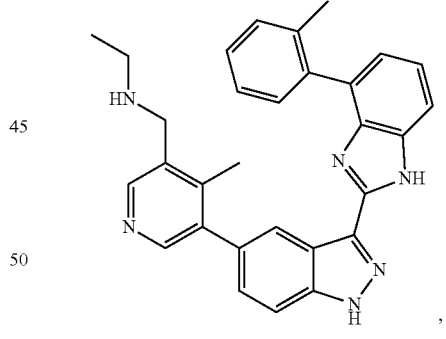,
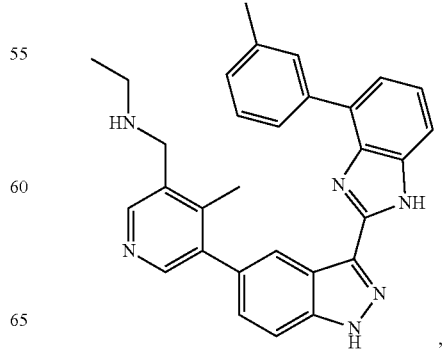, 7
-continued
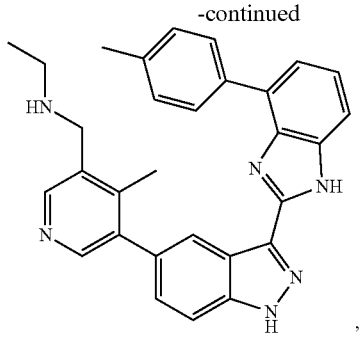
,
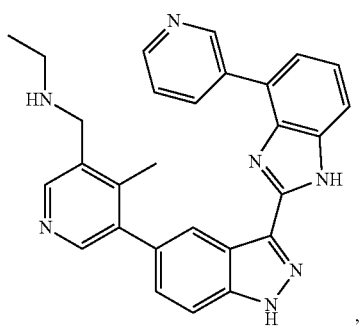
,
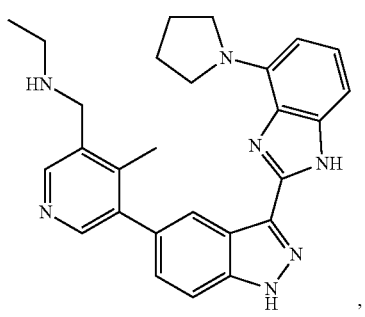
,
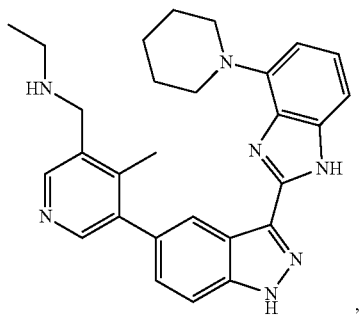
,
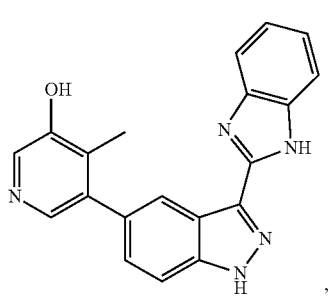
,
8
-continued
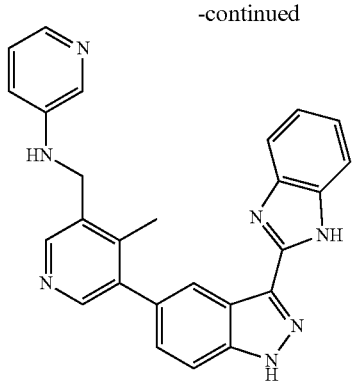
,
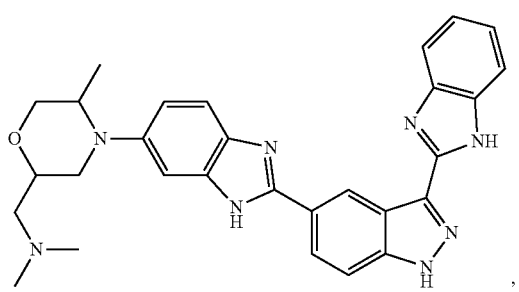
,
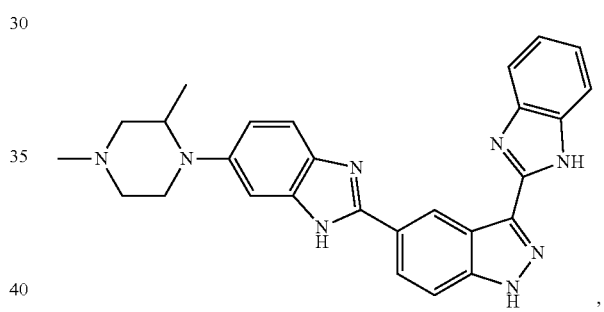
,
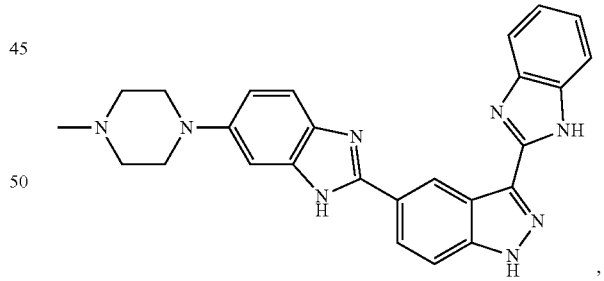
,
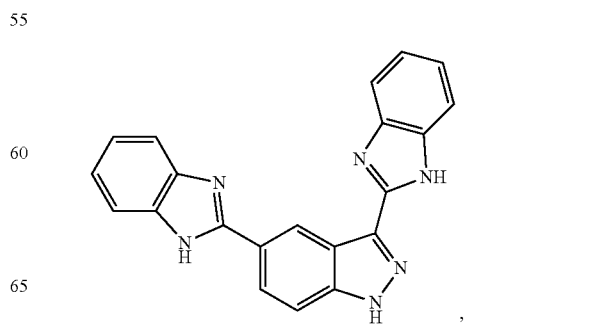
,

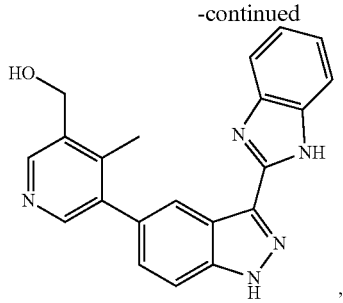
,
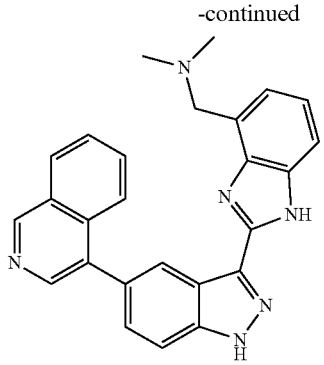
,
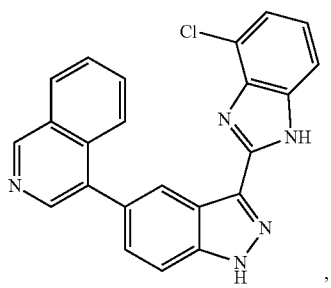
,
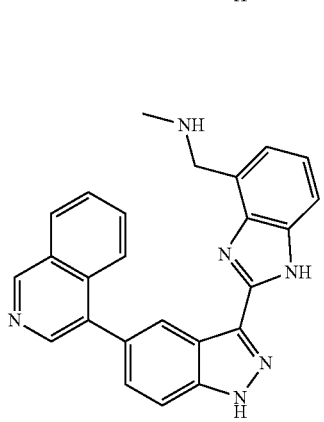
,
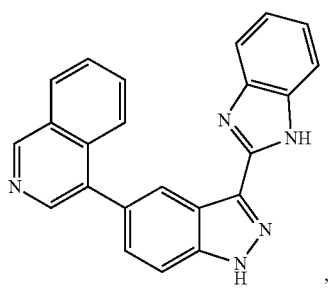
,
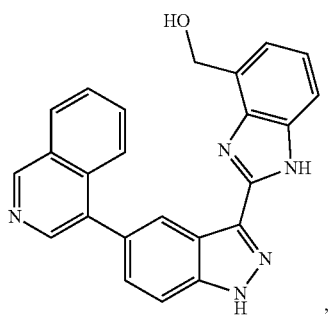
,
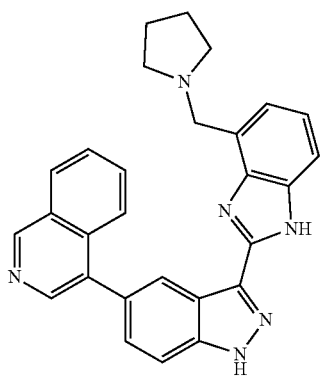
,
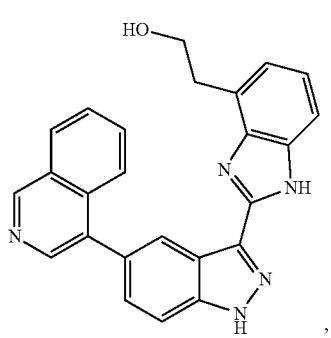
,
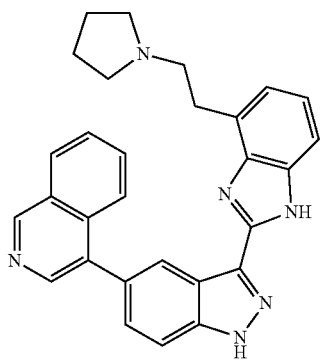
, 11
-continued
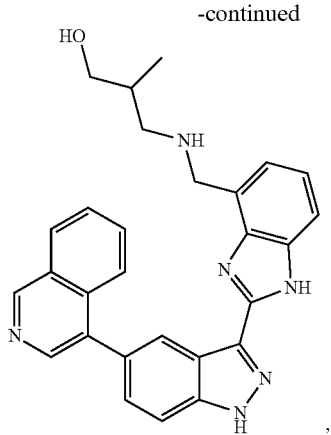
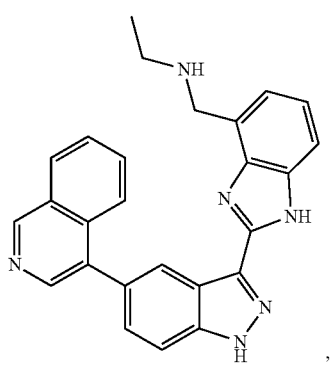
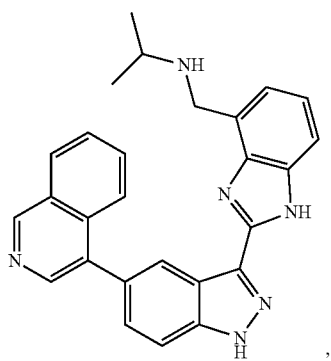
12
-continued
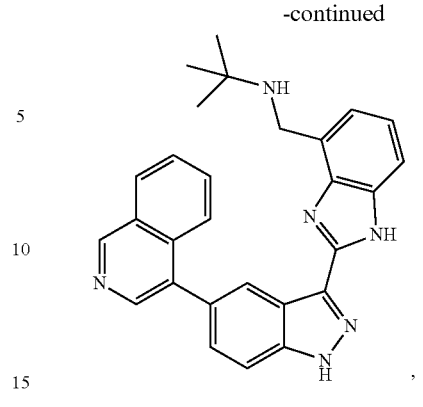
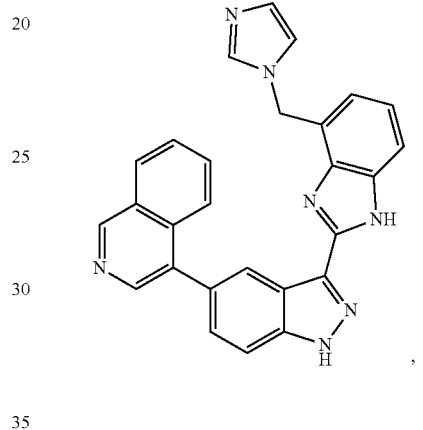
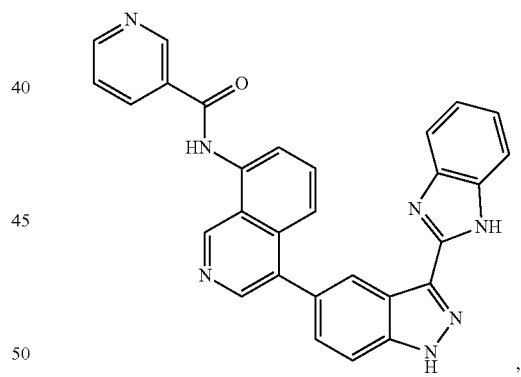
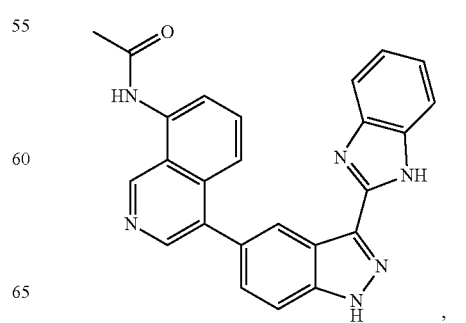

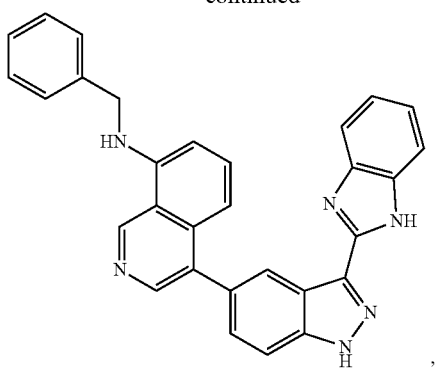

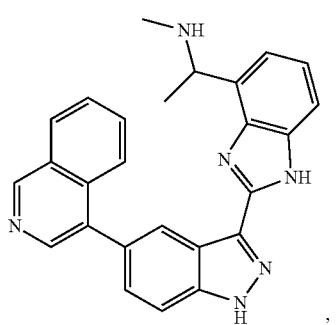

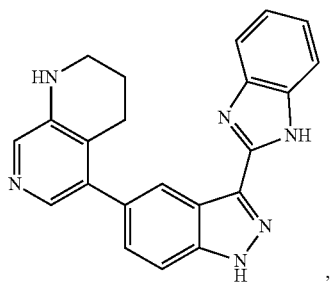

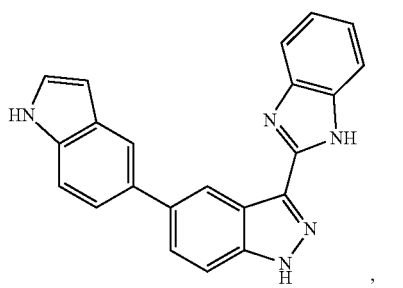

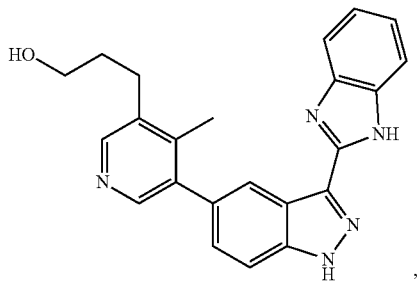

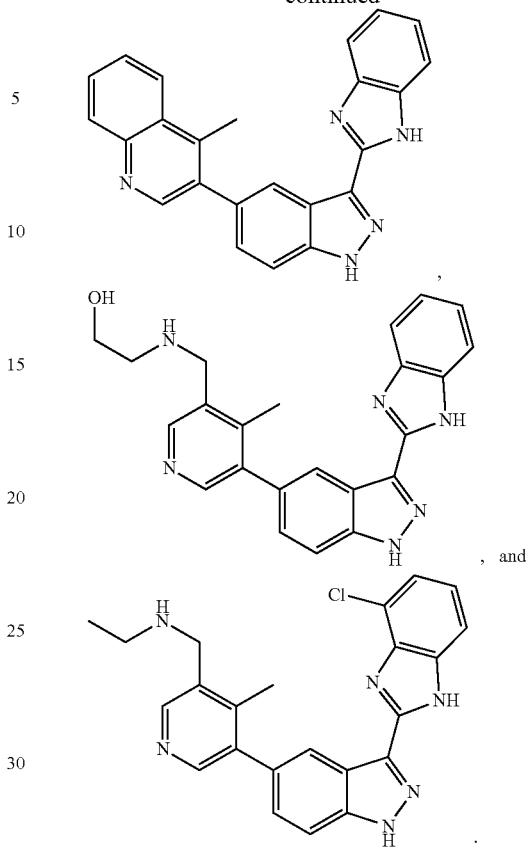

Some embodiments include stereoisomers and pharmaceutically acceptable salts of a compound of Formula (I).

Some embodiments include pro-drugs of a compound of Formula (I).

Some embodiments of the present disclosure include pharmaceutical compositions comprising a compound of Formula (I) and a pharmaceutically acceptable carrier, diluent, or excipient.

Other embodiments disclosed herein include methods of inhibiting one or more members of the Wnt pathway, including one or more Wnt proteins by administering to a patient affected by a disorder or disease in which aberrant Wnt signaling is implicated, such as cancer and other diseases associated with abnormal angiogenesis, cellular proliferation, cell cycling and mutations in Wnt signaling components, a compound according to Formula (I). Accordingly, the compounds and compositions provided herein can be used to treat cancer, to reduce or inhibit angiogenesis, to reduce or inhibit cellular proliferation and correct a genetic disorder due to mutations in Wnt signaling components.

Non-limiting examples of diseases which can be treated with the compounds and compositions provided herein include a variety of cancers, diabetic retinopathy, pulmonary fibrosis, rheumatoid arthritis, sepsis, anklyosing spondylitism, psoriasis, scleroderma, mycotic and viral infections, osteochondrodysplasia, Alzheimer's disease, lung disease, osteoarthritis, articular cartilage (chondral) defects, degenerative disc disease (or intervertebral disc degeneration), polyposis coli, osteoporosis-pseudoglioma syndrome, familial exudative vitreoretinopathy, retinal angiogenesis, early coronary disease, tetra-ameliasyndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Some embodiments of the present disclosure include methods to prepare compounds of Formula (I).

It is to be understood that both the foregoing general description and the following detailed description are exemplary and explanatory only and are not restrictive of the invention, as claimed.

DETAILED DESCRIPTION

Compositions and methods for inhibiting one or more members of the Wnt pathway, including one or more Wnt proteins are useful.

Some embodiments relate to a method for treating a disease including, but not limited to, cancers, diabetic retinopathy, pulmonary fibrosis, rheumatoid arthritis, sepsis, anklyosing spondylitism, psoriasis, scleroderma, mycotic and viral infections, bone and cartilage diseases, Alzheimer's disease, lung disease, osteoarthritis, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease, and Rett syndrome.

In some embodiments, non-limiting examples of bone and cartilage diseases which can be treated with the compounds and compositions provided herein include bone spur (osteophytes), craniosynostosis, fibrodysplasia ossificans progressive, fibrous dysplasia, giant cell tumor of bone, hip labral tear, meniscal tears, osteoarthritis, articular cartilage (chondral) defects, degenerative disc disease (or intervertebral disc degeneration), osteochondritis dissecans, osteochondroma (bone tumor), osteopetrosis, relapsing polychondritis, and Salter-Harris fractures.

In some embodiments, pharmaceutical compositions are provided that are effective for treatment of a disease of an animal, e.g., a mammal, caused by the pathological activation or mutations of the Wnt pathway. The composition includes a pharmaceutically acceptable carrier and a compound as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl, and neo-pentyl. Alkyl groups can either be unsubstituted or substituted with one or more substituents, e.g., halide, alkoxy, acyloxy, amino, amido, cyano, nitro, hydroxyl, thio, carboxy, carbonyl, benzyloxy, aryl, heteroaryl, or other functionality that may be suitably blocked, if necessary for purposes of the disclosure, with a protecting group. Alkyl groups can be saturated or unsaturated (e.g., containing —C=C— or —C≡C— subunits), at one or several positions. Typically, alkyl groups will comprise 1 to 9 carbon atoms (e.g., 1 to 6, 1 to 4, or 1 to 2 carbon atoms).

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents, e.g., alkyl, halide, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the disclosure, with a protecting group. Typically, carbocyclyl groups will comprise 3 to 10 carbon atoms (e.g., 3 to 6 carbon atoms).

As used herein, "lower alkyl" means a subset of alkyl having 1 to 3 carbon atoms, and can be linear or branched. Examples of lower alkyl groups include methyl, ethyl, n-propyl, and isopropyl. Likewise, radicals using the terminology "lower" refer to radicals having 1 to about 3 carbons in the alkyl portion of the radical.

As used herein, "amido" means a H—CON—, alkyl-CON—, carbocyclyl-CON—, aryl-CON—, heteroaryl-CON—, or heterocyclyl-CON group wherein the alkyl, carbocyclyl, aryl or heterocyclyl group is as herein described.

As used herein, "aryl" means an aromatic radical having a single-ring (e.g., phenyl) or multiple condensed rings (e.g., naphthyl or anthryl) with only carbon atoms present in the ring backbone. Aryl groups can either be unsubstituted or substituted with one or more substituents, e.g., amino, cyano, hydroxyl, lower alkyl, haloalkyl, alkoxy, nitro, halo, mercapto, and other substituents. An exemplary carbocyclic aryl is phenyl.

As used herein, the term "heteroaryl" means a mono-, bi-, tri- or polycyclic group having 5 to 14 ring atoms, alternatively 5, 6, 9, or 10 ring atoms; having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents, e.g., amino, cyano, hydroxyl, lower alkyl, haloalkyl, alkoxy, nitro, halo, mercapto, and other substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, 2,3-dihydrobenzo[b][1,4]oxathiine, and others.

As used herein, "amide" includes both RNR'CO— (in the case of R=alkyl, alkaminocarbonyl-) and RCONR'— (in the case of R=alkyl, alkylcarbonylamino-). In both cases, R'=H or alkyl. In some embodiments, R' is H.

As used herein, the term "ester" includes both ROCO— (in the case of R=alkyl, alkoxycarbonyl-) and RCOO— (in the case of R=alkyl, alkylcarbonyloxy-).

As used herein, "acyl" means an H—CO— or alkyl-CO—, carbocyclyl-CO-aryl-CO—, heteroaryl-CO— or heterocyclyl-CO— group wherein the alkyl, carbocyclyl, aryl or heterocyclyl group is as herein described. In some embodiments, acyls contain a lower alkyl. Exemplary alkyl acyl groups include formyl, acetyl, propanoyl, 2-methylpropanoyl, t-butylacetyl, butanoyl, and palmitoyl.

As used herein, "halo", "halide" or "halogen" is a chloro, bromo, fluoro, or iodo atom radical. In some embodiments, the halide is fluorine.

As used herein, "haloalkyl" means a hydrocarbon substituent, which is a linear or branched or cyclic alkyl, substituted with chloro, bromo, fluoro, or iodo atom(s). In some emdobiments, a haloalkyls are fluoroalkyls, wherein one or more of the hydrogen atoms have been substituted by fluoro. Haloalkyls can be of 1 to about 3 carbons in length, (e.g., 1 to about 2 carbons). In some embodiments, the haloalkyls are 1 carbon in length.

As used herein, "heterocyclyl" means a nonaromatic cyclic ring system comprising at least one heteroatom in the ring system backbone. Heterocyclyls may include multiple fused rings. Heterocyclyls may be substituted or unsubstituted with one or more substituents, e.g., alkyl, halide, alkoxy, acyloxy, amino, amido, cyano, nitro, hydroxyl, mercapto, carboxy, carbonyl, benzyloxy, aryl, heteroaryl, and other substituents, and are attached to other groups via any available valence (e.g., any available carbon or nitrogen). In some embodiments, heterocycles have 5-7 members. In six membered monocyclic heterocycles, the heteroatom(s) are selected from one up to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

As used herein, "substituted amino" means an amino radical which is substituted by one or two alkyl, cycloalkyl, aryl, heteroaryl, or heterocyclyl groups, wherein the alkyl, cycloalkyl, aryl, heteroaryl or heterocyclyl are defined as above.

As used herein, "substituted thiol" refers to an RS— group wherein R is an alkyl, a cycloalkyl, an aryl, heteroaryl, or a heterocyclyl group, wherein the alkyl, cycloalkyl, aryl, heteroaryl, or heterocyclyl are defined as above.

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions, and it is within the purview of the skilled artisan to both envision such rings and the methods of their formations. In some embodiments, rings have from 3-7 members (e.g., 5 or 6 members). As used herein the term "ring" or "rings" when formed by the combination of two radicals refers to heterocyclic, carbocyclic, aryl, or heteroaryl rings.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this disclosure, though such resonance forms or tautomers are not represented herein.

The compounds provided herein may encompass various stereochemical forms. The compounds also encompass diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The term "administration" or "administering" refers to a method of giving a dosage of a compound or pharmaceutical composition provided herein to a vertebrate or invertebrate, including a mammal, a bird, a fish, or an amphibian, where the method is, e.g., orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification and characterization of a health or disease state. The diagnostic can be used in standard assays as is known in the art.

The term "mammal" is used in its usual biological sense. Thus, it specifically includes humans, cattle, horses, dogs, cats, mice, rats, sheeps, pigs, goats, and non-human primates, but also includes many other species.

The term "pharmaceutically acceptable carrier" or "pharmaceutically acceptable excipient" includes any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics*, 12th Ed., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. In some embodiments, the bases can be derived from the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297.

"Solvate" refers to the compound formed by the interaction of a solvent and a compound provided herein, a metabolite, or salt thereof. Suitable solvates are pharmaceutically acceptable solvates including hydrates.

"Patient" or "subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

By "therapeutically effective amount" or "pharmaceutically effective amount" of a compound as provided herein is one which is sufficient to achieve the desired effect and may vary according to the nature and severity of the disease condition, and the potency of the compound. "Therapeutically effective amount" is also intended to include one or more of the compounds of Formulas (I) and/or (Ia) in combination with one or more other agents that are effective to inhibit Wnt related diseases and/or conditions. In some embodiments, the combination of compounds is a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease, and can include curing a disease. "Curing" means that the symptoms of an active disease are eliminated. However, certain long-term or permanent effects of the disease may exist even after a cure is obtained (such as extensive tissue damage).

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

Compounds

The compounds and compositions described herein can be used as anti-proliferative agents, e.g., anti-cancer and anti-angiogenesis agents, and/or as inhibitors of the Wnt signaling pathway, e.g., for treating diseases or disorders associated with aberrant Wnt signaling. In addition, the compounds can be used as inhibitors of one or more kinases, kinase receptors, or kinase complexes. Such compounds and compositions are also useful for controlling cellular proliferation, differentiation, and/or apoptosis.

Some embodiments of the present disclosure include compounds, salts, pharmaceutically acceptable salts or prodrug thereof of Formula (I):

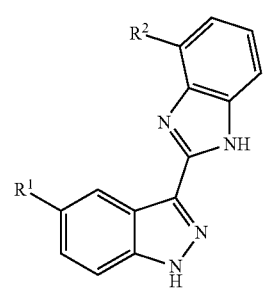

I

In some embodiments of Formula I, $R^1$ is -heteroaryl$R^3R^4$.

In some embodiments of Formula I, $R^2$ is selected from the group consisting of H, halide, $C_{1-3}$ alkyl, —CN, —OR$^8$, —OH, —($C_{1-3}$ alkyl)OR$^8$, —NR$^9$R$^{10}$, —($C_{1-3}$ alkyl)NR$^9$R$^{10}$, -heteroaryl$R^5$, -heterocyclyl$R^6$ and -aryl$R^7$.

In some embodiments of Formula I, $R^3$ is 1 substituent attached to the heteroaryl ring and is selected from the group consisting of H, $C_{1-3}$ alkyl, —CF$_3$, —NR$^9$R$^{10}$, —NHC(=O)R$^8$, —($C_{1-3}$ alkyl)heterocyclyl$R^6$ and —($C_{1-3}$ alkyl)NR$^9$R$^{10}$.

In some embodiments of Formula I, $R^4$ is 1 substituent attached to the heteroaryl ring and is selected from the group consisting of H, $C_{1-3}$ alkyl, —$CF_3$, halide, —CN, —$OR^8$, —OH, —($C_{1-3}$ alkyl)$OR^8$, —$NR^9R^{10}$, —($C_{1-3}$ alkyl)$NR^9R^{10}$ and —$OCF_3$.

In some embodiments of Formula I, $R^5$ is 1-3 substituents attached to the heteroaryl ring and each is independently selected from the group consisting of H, $C_1$-3 alkyl, —$CF_3$, halide, —CN, —$OR^8$, —OH, —($C_{1-3}$ alkyl)$OR^8$, —$NR^9R^{10}$, —($C_{1-3}$ alkyl)$NR^9R^{10}$ and —$OCF_3$.

In some embodiments of Formula I, $R^6$ is 1-3 substituents attached to the heterocyclyl ring and each is independently selected from the group consisting of H, $C_{1-3}$ alkyl, —$CF_3$, halide, —CN, —$OR^8$, —OH, —($C_{1-3}$ alkyl)$OR^8$, —$NR^9R^{10}$, —($C_{1-3}$ alkyl)$NR^9R^{10}$ and —$OCF_3$.

In some embodiments of Formula I, $R^7$ is 1-3 substituents attached to the aryl ring and each is independently selected from the group consisting of H, $C_{1-3}$ alkyl, —$CF_3$, halide, —CN, —$OR^8$, —OH, —($C_{1-3}$ alkyl)$OR^8$, —$NR^9R^{10}$, —($C_{1-3}$ alkyl)$NR^9R^{10}$ and —$OCF_3$.

In some embodiments of Formula I, each $R^8$ is selected from the group consisting of $C_{1-9}$ alkyl, -heteroaryl$R^{12}$, -heterocyclyl$R^{13}$, -aryl$R^{14}$, carbocyclyl$R^{11}$, —($C_{1-3}$ alkyl)heteroaryl$R^{12}$, —($C_{1-3}$ alkyl)heterocyclyl$R^{13}$, —($C_{1-3}$ alkyl)aryl$R^{14}$ and —($C_{1-3}$ alkyl)carbocyclyl$R^{11}$.

In some embodiments of Formula I, each $R^9$ is selected from the group consisting of H, $C_{1-6}$ alkyl, -heteroaryl$R^{12}$, -heterocyclyl$R^{13}$, -aryl$R^{14}$, carbocyclyl$R^{11}$, —($C_{1-3}$ alkyl)heteroaryl$R^{12}$, —($C_{1-3}$ alkyl)heterocyclyl$R^{13}$, —($C_{1-3}$ alkyl)aryl$R^{14}$ and —($C_{1-3}$ alkyl)carbocyclyl$R^{11}$.

In some embodiments of Formula I, each $R^{10}$ is selected from the group consisting of H and $C_{1-6}$ alkyl.

In some embodiments of Formula I, $R^9$ and $R^{10}$ are linked to form a five or six membered heterocyclyl ring.

In some embodiments of Formula I, $R^{11}$ is 1-3 substituents attached to the carbocyclyl ring and each independently selected from the group consisting of H, $C_{1-3}$ alkyl, —$CF_3$, halide, —CN, —O($R^{10}$), —($C_{1-3}$ alkyl)$OR^{10}$, —$N(R^{10})_2$, —($C_{1-3}$ alkyl)$N(R^{10})_2$ and —$OCF_3$;

In some embodiments of Formula I, $R^{12}$ is 1-3 substituents attached to the heteroaryl ring and each is independently selected from the group consisting of H, $C_{1-3}$ alkyl, —$CF_3$, halide, —CN, —O($R^{10}$), —($C_{1-3}$ alkyl)$OR^{10}$, —$N(R^{10})_2$, —($C_{1-3}$ alkyl)$N(R^{10})_2$ and —$OCF_3$;

In some embodiments of Formula I, $R^{13}$ is 1-3 substituents attached to the heterocyclyl ring and each is independently selected from the group consisting of H, $C_{1-3}$ alkyl, —$CF_3$, halide, —CN, —O($R^{10}$), —($C_{1-3}$ alkyl)$OR^{10}$, —$N(R^{10})_2$, —($C_{1-3}$ alkyl)$N(R^{10})_2$ and —$OCF_3$;

In some embodiments of Formula I, $R^{14}$ is 1-3 substituents attached to the aryl ring and each is independently selected from the group consisting of H, $C_{1-3}$ alkyl, —$CF_3$, halide, —CN, —O($R^{10}$), —($C_{1-3}$ alkyl)$OR^{10}$, —$N(R^{10})_2$, —($C_{1-3}$ alkyl)$N(R^{10})_2$ and —$OCF_3$;

In some embodiments of Formula I, there is the proviso that a compound of Formula I is not a compound selected from the group consisting of:

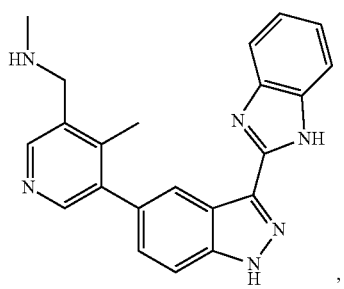

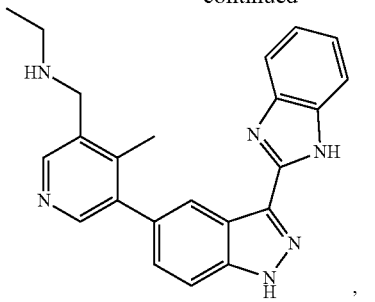

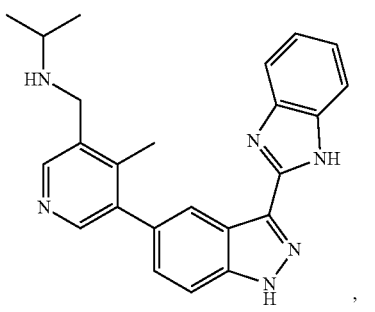

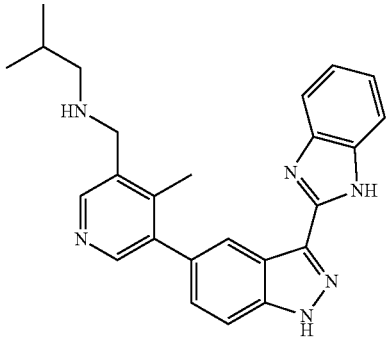

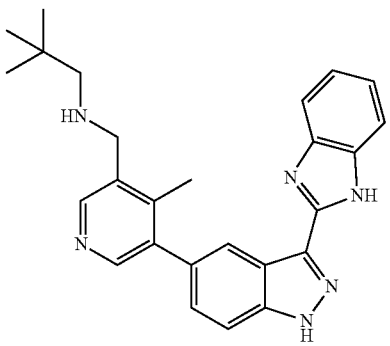

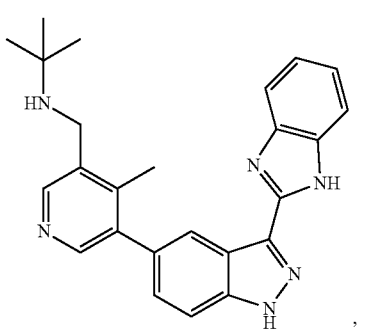

-continued
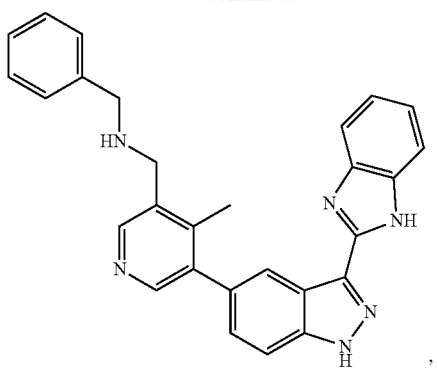
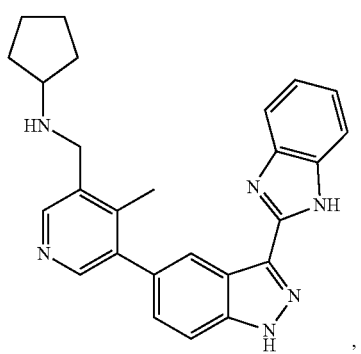
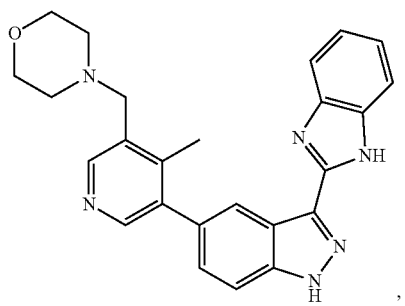
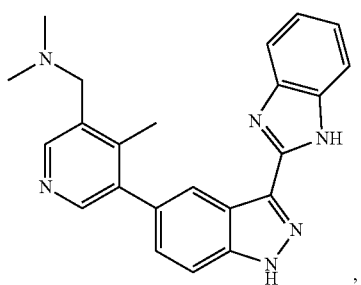
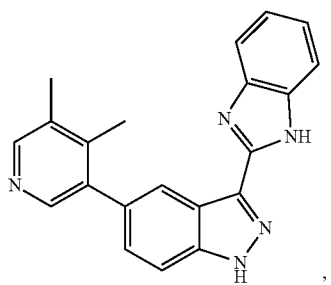
-continued
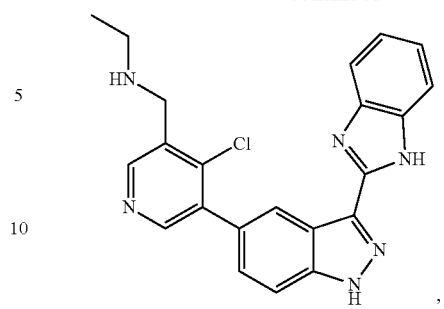
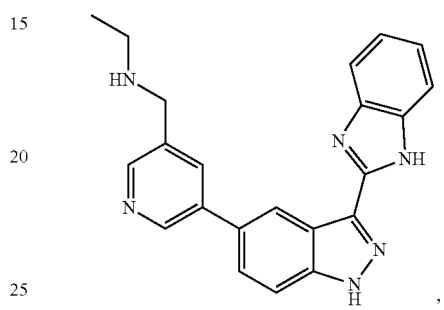
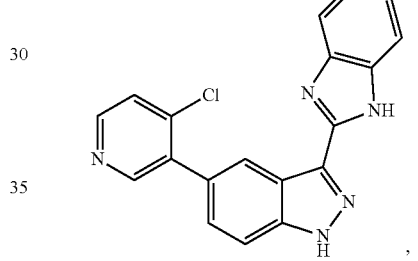
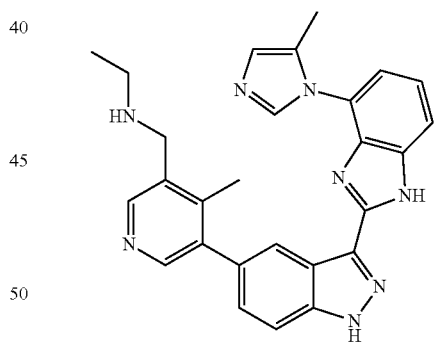
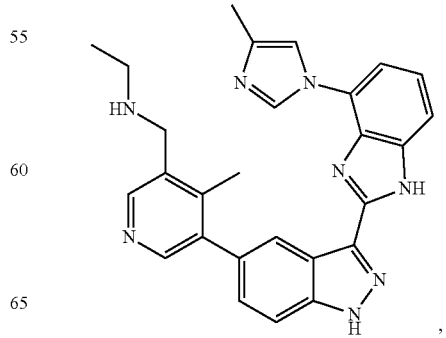

-continued
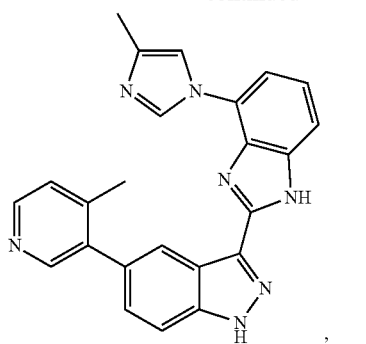
,
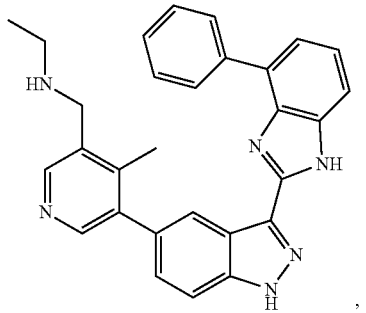
,
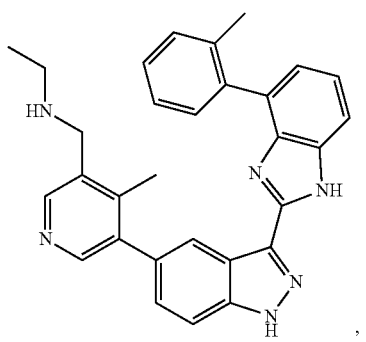
,
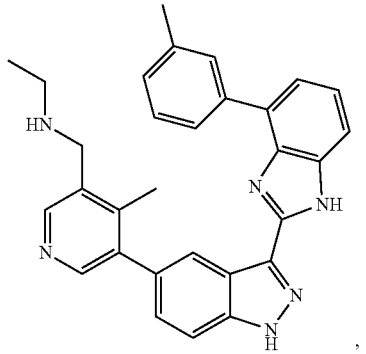
,
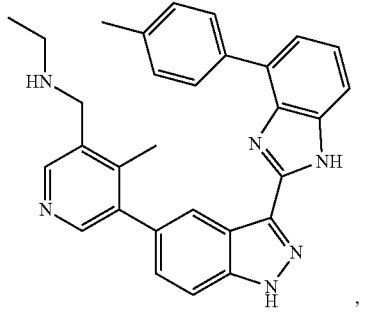
,
-continued
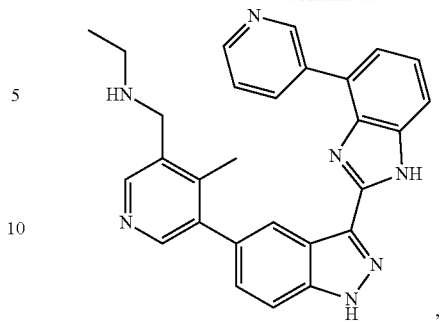
,
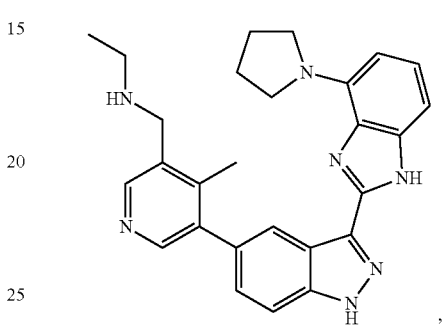
,
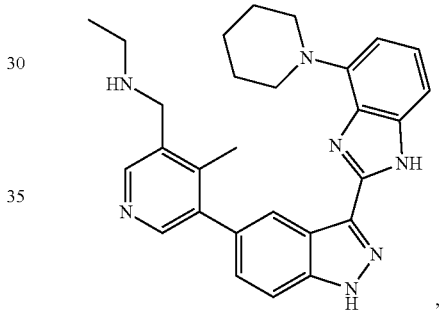
,
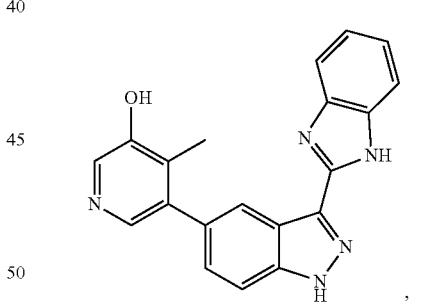
,
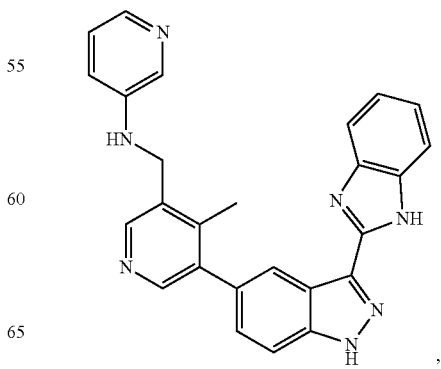
, 27
-continued
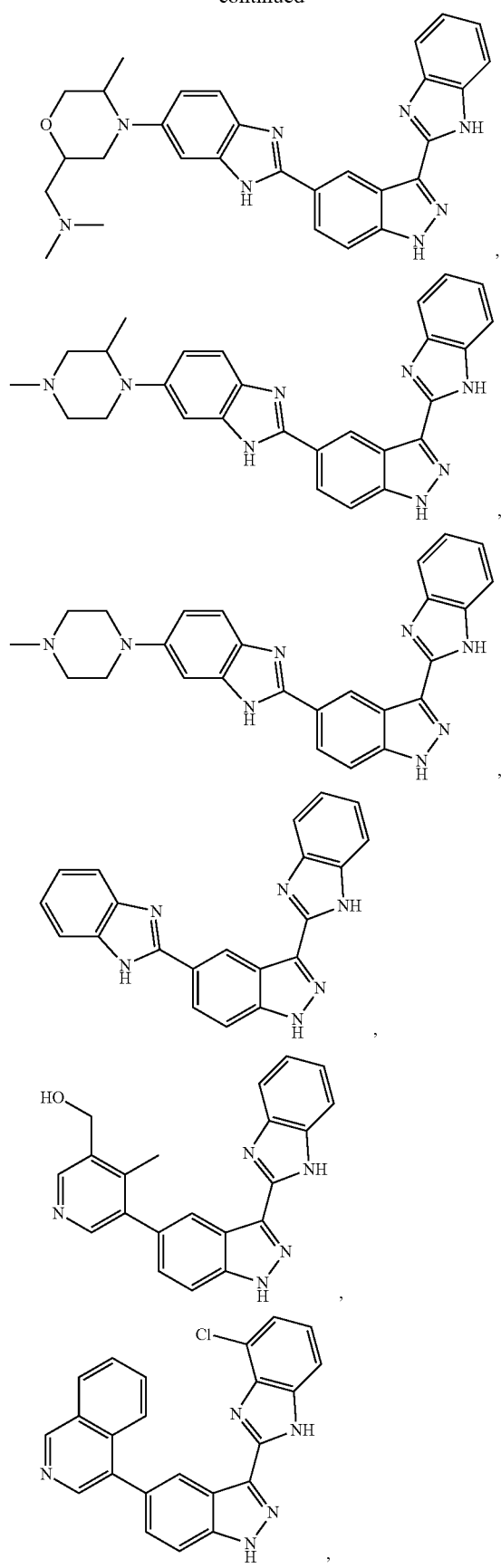
28
-continued
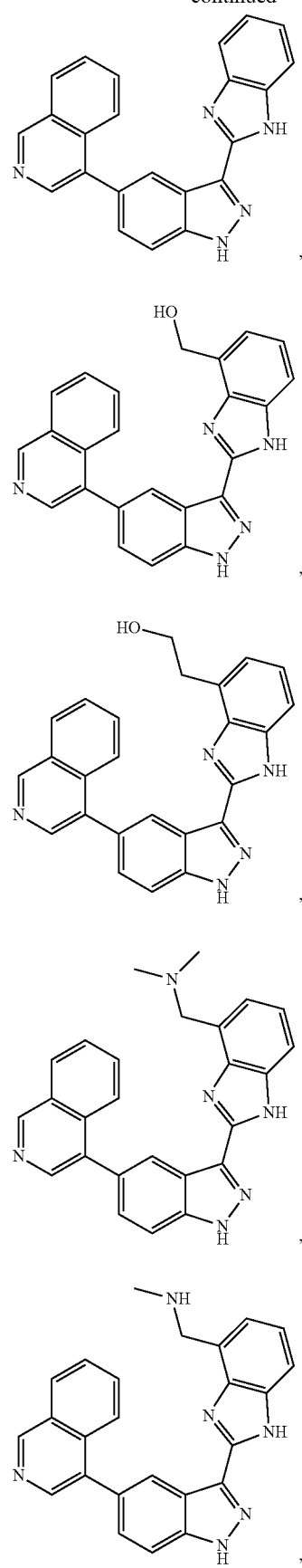

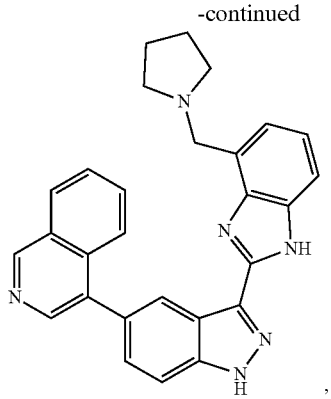
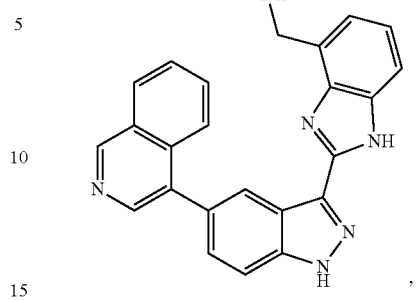
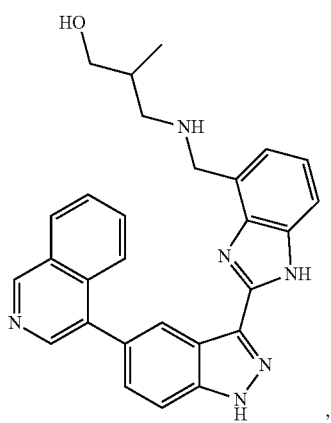
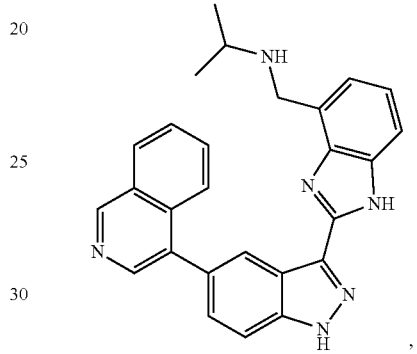
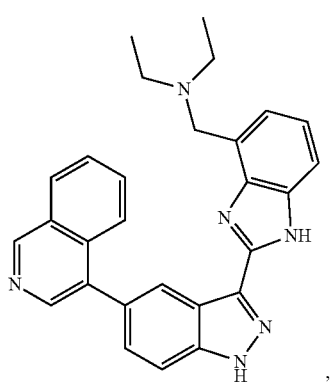
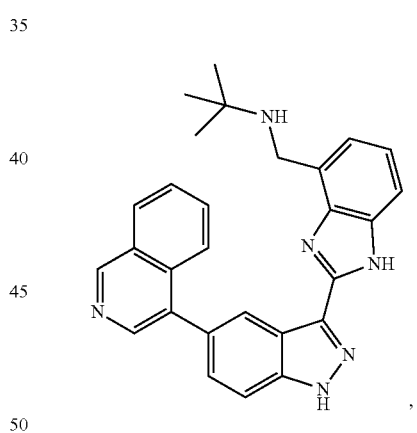
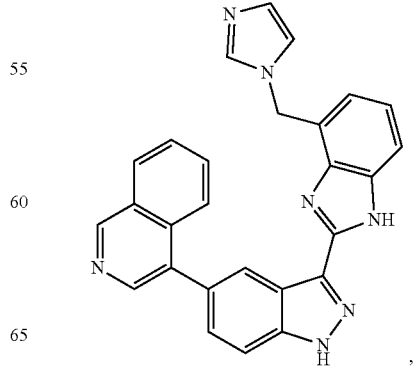

-continued

-continued

Some embodiments of the present disclosure include compounds, salts, pharmaceutically acceptable salts or pro-drug thereof of Formula (Ia):

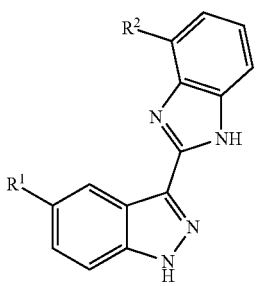

In some embodiments of Formula Ia, $R^1$ is -pyridine$R^3R^4$.

In some embodiments of Formula Ia, $R^2$ is selected from the group consisting of H, halide, $C_{1-3}$ alkyl, —CN, —$OR^8$, —OH, —($C_{1-3}$ alkyl)$OR^8$, —$NR^9R^{10}$, —($C_{1-3}$ alkyl)$NR^9R^{10}$, -heteroaryl$R^5$, -heterocyclyl$R^6$ and -aryl$R^7$.

In some embodiments of Formula Ia, $R^3$ is 1 substituent attached to the heteroaryl ring and is selected from the group consisting of H, $C_{1-3}$ alkyl, —$CF_3$, —$NR^9R^{10}$, —NHC(=O)$R^8$, —($C_{1-3}$ alkyl)heterocyclyl$R^6$ and —($C_{1-3}$ alkyl)$NR^9R^{10}$.

In some embodiments of Formula Ia, $R^4$ is H.

In some embodiments of Formula Ia, $R^5$ is 1-3 substituents attached to the heteroaryl ring and each is independently selected from the group consisting of H, $C_{1-3}$ alkyl, —$CF_3$, halide, —CN, —$OR^8$, —OH, —($C_{1-3}$ alkyl)$OR^8$, —$NR^9R^{10}$, —($C_{1-3}$ alkyl)$NR^9R^{10}$ and —$OCF_3$.

In some embodiments of Formula Ia, $R^6$ is 1-3 substituents attached to the heterocyclyl ring and each is independently selected from the group consisting of H, $C_{1-3}$ alkyl, —$CF_3$, halide, —CN, —$OR^8$, —OH, —($C_{1-3}$ alkyl)$OR^8$, —$NR^9R^{10}$, —($C_{1-3}$ alkyl)$NR^9R^{10}$ and —$OCF_3$.

In some embodiments of Formula Ia, $R^7$ is 1-3 substituents attached to the aryl ring and each is independently selected from the group consisting of H, $C_{1-3}$ alkyl, —$CF_3$, halide, —CN, —$OR^8$, —OH, —($C_{1-3}$ alkyl)$OR^8$, —$NR^9R^{10}$, —($C_{1-3}$ alkyl)$NR^9R^{10}$ and —$OCF_3$.

In some embodiments of Formula Ia, each $R^8$ is selected from the group consisting of $C_{1-9}$ alkyl, -heteroaryl$R^{12}$, -heterocyclyl$R^{13}$, -aryl$R^{14}$, carbocyclyl$R^{11}$, —($C_{1-3}$ alkyl)heteroaryl$R^{12}$, —($C_{1-3}$ alkyl)heterocyclyl$R^{13}$, —($C_{1-3}$ alkyl)aryl$R^{14}$ and —($C_{1-3}$ alkyl)carbocyclyl$R^{11}$.

In some embodiments of Formula Ia, each $R^9$ is selected from the group consisting of H, $C_{1-6}$ alkyl, -heteroaryl$R^{12}$, -heterocyclyl$R^{13}$, -aryl$R^{14}$, carbocyclyl$R^{11}$, —($C_{1-3}$ alkyl)heteroaryl$R^{12}$, —($C_{1-3}$ alkyl)heterocyclyl$R^{13}$, —($C_{1-3}$ alkyl)aryl$R^{14}$ and —($C_{1-3}$ alkyl)carbocyclyl$R^{11}$.

In some embodiments of Formula Ia, each $R^{10}$ is selected from the group consisting of H and $C_{1-6}$ alkyl.

In some embodiments of Formula Ia, $R^9$ and $R^{10}$ are linked to form a five or six membered heterocyclyl ring.

In some embodiments of Formula Ia, $R^{11}$ is 1-3 substituents attached to the carbocyclyl ring and each independently selected from the group consisting of H, $C_{1-3}$ alkyl, —$CF_3$, halide, —CN, —O($R^{10}$), —($C_{1-3}$ alkyl)$OR^{10}$, —N($R^{10}$)$_2$, —($C_{1-3}$ alkyl)N($R^{10}$)$_2$ and —$OCF_3$;

In some embodiments of Formula Ia, $R^{12}$ is 1-3 substituents attached to the heteroaryl ring and each is independently selected from the group consisting of H, $C_{1-3}$ alkyl, —$CF_3$, halide, —CN, —O($R^{10}$), —($C_{1-3}$ alkyl)$OR^{10}$, —N($R^{10}$)$_2$, —($C_{1-3}$ alkyl)N($R^{10}$)$_2$ and —$OCF_3$;

In some embodiments of Formula Ia, $R^{13}$ is 1-3 substituents attached to the heterocyclyl ring and each is independently selected from the group consisting of H, $C_{1-3}$ alkyl, —$CF_3$, halide, —CN, —O($R^{10}$), —($C_{1-3}$ alkyl)$OR^{10}$, —N($R^{10}$)$_2$, —($C_{1-3}$ alkyl)N($R^{10}$)$_2$ and —$OCF_3$;

In some embodiments of Formula Ia, $R^{14}$ is 1-3 substituents attached to the aryl ring and each is independently selected from the group consisting of H, $C_{1-3}$ alkyl, —$CF_3$, halide, —CN, —O($R^{10}$), —($C_{1-3}$ alkyl)$OR^{10}$, —N($R^{10}$)$_2$, —($C_{1-3}$ alkyl)N($R^{10}$)$_2$ and —$OCF_3$;

In other embodiments of Formula Ia, there is the proviso that a compound of Formula Ia is not a compound selected from the group consisting of:

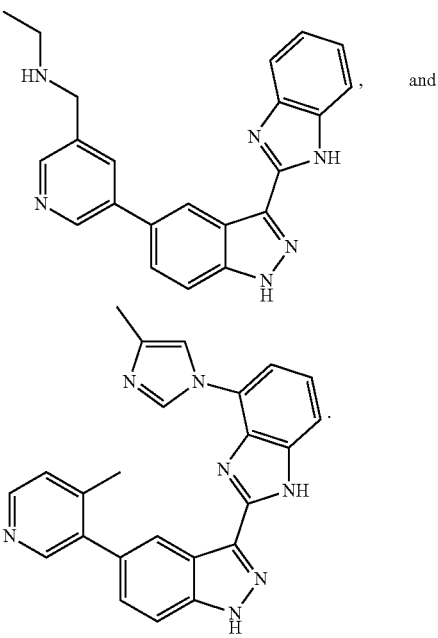

In some embodiments of Formula I, $R^1$ is pyridine$R^3R^4$.

In some embodiments of Formulas I and/or Ia, $R^1$ is pyridin-3-yl$R^3R^4$.

In some embodiments of Formulas I and/or Ia, $R^3$ and $R^4$ are both H.

In some embodiments of Formulas I and/or Ia, $R^3$ is —$C_{1-2}$ alkyl and $R^4$ is H.

In some embodiments of Formulas I and/or Ia, $R^3$ is methyl.

In some embodiments of Formulas I and/or Ia, $R^3$ is ethyl.

In some embodiments of Formulas I and/or Ia, $R^3$ is —$CH_2NR^9R^{10}$.

In some embodiments of Formula I, $R^4$ is H.

In some embodiments of Formulas I and/or Ia, $R^9$ is —$C_{1-2}$ alkyl; $R^{10}$ is —($C_{1-2}$ alkyl); and $R^4$ is H.

In some embodiments of Formulas I and/or Ia, $R^4$ and $R^9$ are both H;

and $R^{10}$ is selected from the group consisting of —$C_{1-2}$ alkyl, —$CH_2$phenyl and —$CH_2$carbocyclyl.

In some embodiments of Formulas I and/or Ia, $R^9$ is —$CH_2$cyclopropyl.

In some embodiments of Formulas I and/or Ia, $R^9$ is —$CH_2$cyclobutyl.

In some embodiments of Formulas I and/or Ia, $R^9$ is —$CH_2$cyclopentyl.

In some embodiments of Formulas I and/or Ia, $R^9$ is —$CH_2$cyclohexyl.

In some embodiments of Formulas I and/or (Ia), $R^9$ and $R^{10}$ are linked to form a five or six membered heterocyclyl ring and $R^4$ is H.

In some embodiments of Formulas I and/or Ia, $R^9$ and $R^{10}$ are linked to form a morpholine ring.

In some embodiments of Formulas I and/or Ia, $R^9$ and $R^{10}$ are linked to form a piperidine ring.

In some embodiments of Formulas I and/or Ia, $R^9$ and $R^{10}$ are linked to form a pyrrolidine ring.

In some embodiments of Formulas I and/or Ia, $R^9$ and $R^{10}$ are linked to form a piperazine ring.

In some embodiments of Formulas I and/or Ia, $R^3$ is —NHC(=O)$R^8$.

In some embodiments of Formulas I and/or Ia, $R^4$ is H; and $R^8$ is selected from the group consisting of —$C_{1-5}$ alkyl, —CH$_2$phenyl, phenyl and -carbocyclyl.

In another aspect of embodiments of Formulas I and/or Ia, $R^8$ is a —$C_{1-5}$ alkyl. For example, the —$C_{1-5}$ alkyl can be selected from the group consisting of methyl, ethyl, n-propyl, iso-propyl, n-butyl, iso-butyl, sec-butyl, tert-butyl, n-pentyl, iso-pentyl and neo-pentyl. In certain embodiments, $R^8$ is methyl. In another embodiment, $R^8$ is ethyl. In another embodiment, $R^8$ is n-propyl. In another embodiment, $R^8$ is iso-propyl. In another embodiment, $R^8$ is n-butyl. In another embodiment, $R^8$ is iso-butyl. In another embodiment, $R^8$ is sec-butyl. In another embodiment, $R^8$ is tert-butyl. In another embodiment, $R^8$ is n-pentyl. In another embodiment, $R^8$ is iso-pentyl. In another embodiment, $R^8$ is neo-pentyl.

In some embodiments of Formulas I and/or Ia, $R^8$ is —CH$_2$phenyl.

In some embodiments of Formulas I and/or Ia, $R^8$ is phenyl.

In some embodiments of Formulas I and/or Ia, $R^8$ is a carbocyclyl. For example, the carbocyclyl can be selected from the group consisting of cyclopropyl, cyclobutyl, cyclopentyl and cyclohexyl. In certain embodiments, $R^8$ is cyclopropyl. In another embodiment, $R^8$ is cyclobutyl. In another embodiment, $R^8$ is cyclopentyl. In another embodiment, $R^8$ is cyclohexyl.

In some embodiments of Formulas I and/or Ia, $R^3$ is —NR$^9$R$^{10}$.

In some embodiments of Formulas I and/or Ia, $R^3$ is —NH$_2$ and $R^4$ is H.

In some embodiments of Formulas I and/or Ia, $R^9$ is —$C_{1-2}$ alkyl; $R^{10}$ is —$C_{1-2}$ alkyl; and $R^4$ is H.

In some embodiments of Formulas I and/or Ia, $R^9$ is methyl and $R^{10}$ is methyl.

In some embodiments of Formulas I and/or Ia, $R^9$ is methyl and $R^{10}$ is ethyl.

In some embodiments of Formulas I and/or Ia, $R^9$ is ethyl and $R^{10}$ is ethyl.

In some embodiments of Formulas I and/or Ia, $R^4$ and $R^9$ are both H; and $R^{10}$ is —$C_{1-4}$ alkyl.

In some embodiments of Formulas I and/or Ia, $R^{10}$ is a —$C_{1-4}$ alkyl. For example, the —$C_{1-4}$ alkyl can be selected from the group consisting of methyl, ethyl, n-propyl, iso-propyl, n-butyl, iso-butyl, sec-butyl and tert-butyl. In certain embodiments, $R^{10}$ is methyl. In another embodiment, $R^{10}$ is ethyl. In another embodiment, $R^{10}$ is n-propyl. In another embodiment, $R^{10}$ is iso-propyl. In another embodiment, $R^{10}$ is n-butyl. In another embodiment, $R^{10}$ is iso-butyl. In another embodiment, $R^{10}$ is sec-butyl. In another embodiment, $R^{10}$ is tert-butyl.

In some embodiments of Formulas I and/or Ia, $R^2$ is H.

In some embodiments of Formulas I and/or Ia, $R^2$ is -heteroaryl$R^5$.

In some embodiments of Formulas I and/or Ia, $R^5$ is H.

In some embodiments of Formulas I and/or Ia, $R^2$ is -pyridine.

In some embodiments of Formulas I and/or Ia, $R^2$ is -pyridin-2-yl.

In some embodiments of Formulas I and/or Ia, $R^2$ is -pyridin-3-yl.

In some embodiments of Formulas I and/or Ia, $R^2$ is -pyridin-4-yl.

In some embodiments of Formulas I and/or Ia, $R^2$ is thiophene.

In some embodiments of Formulas I and/or Ia, $R^2$ is furan.

In some embodiments of Formulas I and/or Ia, $R^2$ is -imidazolyl$R^5$; and $R^5$ is 1 substituent selected from the group consisting of H or —$C_{1-2}$ alkyl.

In some embodiments of Formulas I and/or Ia, $R^5$ is methyl.

In some embodiments of Formulas I and/or Ia, $R^5$ is ethyl.

In some embodiments of Formulas I and/or Ia, $R^2$ is a heterocyclyl. For example, the heterocyclyl can be selected from the group consisting of morpholinyl, piperazinyl, 1-methylpiperazinyl, piperidinyl and pyrrolidinyl. In certain embodiments, $R^2$ is piperidinyl. In another embodiment, $R^2$ is piperazinyl. In another embodiment, $R^2$ is 1-methylpiperazinyl.

In some embodiments of Formulas I and/or Ia, $R^2$ is -piperazine$R^6$; and $R^6$ is 1 substituent selected from the group consisting of H or —$C_{1-2}$ alkyl.

In some embodiments of Formulas I and/or Ia, $R^6$ is methyl.

In some embodiments of Formulas I and/or Ia, $R^6$ is ethyl.

In some embodiments of Formulas I and/or Ia, $R^2$ is -phenyl$R^7$.

In some embodiments of Formulas I and/or Ia, $R^7$ is 1 fluorine atom.

In some embodiments of Formulas I and/or Ia, $R^7$ is 2 fluorine atoms.

In some embodiments of Formulas I and/or Ia, $R^1$ is pyridin-3-yl$R^3R^4$; $R^2$ is -phenyl$R^7$; $R^3$ is selected from the group consisting of H, —$C_{1-2}$ alkyl, —CH$_2$NR$^9$R$^{10}$, —NR$^9$R$^{10}$ and —NHC(=O)$R^8$; $R^4$ is H; $R^7$ is 1-2 fluorine atoms; $R^8$ is selected from the group consisting of —$C_{1-5}$ alkyl, —CH$_2$phenyl, phenyl and -carbocyclyl; $R^9$ is selected from the group consisting of —$C_{1-3}$ alkyl, —CH$_2$phenyl and —CH$_2$carbocyclyl; $R^{10}$ is H or —$C_{1-2}$ alkyl; or $R^9$ and $R^{10}$ are optionally linked to form a piperidine or pyrrolidine ring.

In some embodiments of Formulas I and/or Ia, $R^1$ is pyridin-3-yl$R^3R^4$; $R^2$ is pyridine; $R^3$ is selected from the group consisting of —$C_{1-2}$ alkyl, —CH$_2$NR$^9$R$^{10}$, —NR$^9$R$^{10}$ and —NHC(=O)$R^8$; $R^4$ is H; $R^8$ is selected from the group consisting of —$C_{1-5}$ alkyl, —CH$_2$phenyl and -carbocyclyl; $R^9$ is selected from the group consisting of H, —$C_{1-3}$ alkyl, —CH$_2$phenyl and —CH$_2$carbocyclyl; $R^{10}$ is H or —$C_{1-2}$ alkyl; or $R^9$ and $R^{10}$ are optionally linked to form a pyrrolidine ring.

In some embodiments of Formulas I and/or Ia, $R^1$ is pyridin-3-yl$R^3R^4$; $R^2$ is 1-methylpiperazinyl- or piperidinyl-; $R^3$ is selected from the group consisting of H, —$C_{1-2}$ alkyl, —CH$_2$NR$^9$R$^{10}$, —NR$^9$R$^{10}$ and —NHC(=O)$R^8$; $R^4$ is H; $R^8$ is selected from the group consisting of —$C_{1-5}$ alkyl, —CH$_2$phenyl, phenyl and -carbocyclyl; $R^9$ is H or —$C_{1-2}$ alkyl; $R^{10}$ is —$C_{1-3}$ alkyl; or $R^9$ and $R^{10}$ are optionally linked to form a piperidine or pyrrolidine ring.

In some embodiments of Formulas I and/or Ia, $R^1$ is pyridin-3-yl$R^3R^4$; $R^2$ is selected from the group consisting of furan, thiophene and -imidazolyl$R^5$; $R^3$ is selected from the group consisting of —CH$_2$NR$^9$R$^{10}$, —NR$^9$R$^{10}$ and —NHC(=O)$R^8$; $R^4$ is H; $R^5$ is H or —$C_{1-2}$ alkyl; $R^8$ is selected from the group consisting of —$C_{1-5}$ alkyl, —CH$_2$phenyl and -carbocyclyl; $R^9$ is selected from the group consisting of H, —$C_{1-3}$ alkyl and —$CH_2$phenyl; $R^{10}$ is H or —$C_{1-2}$ alkyl; or $R^9$ and $R^{10}$ are optionally linked to form a piperidine or pyrrolidine ring.

In some embodiments of Formulas I and/or Ia, $R^1$ is pyridin-3-yl$R^3R^4$; $R^2$ is H; $R^3$ is selected from the group consisting of —$C_{1-2}$ alkyl, —$CH_2NR^9R^{10}$ and —NHC(=O)$R^8$; $R^4$ is H; $R^8$ is selected from the group consisting of —$C_{1-5}$ alkyl, phenyl and -carbocyclyl; $R^9$ is —$CH_2$phenyl; and $R^{10}$ is H.

In some embodiments of Formulas I and/or Ia, $R^2$ is selected from the group consisting of:

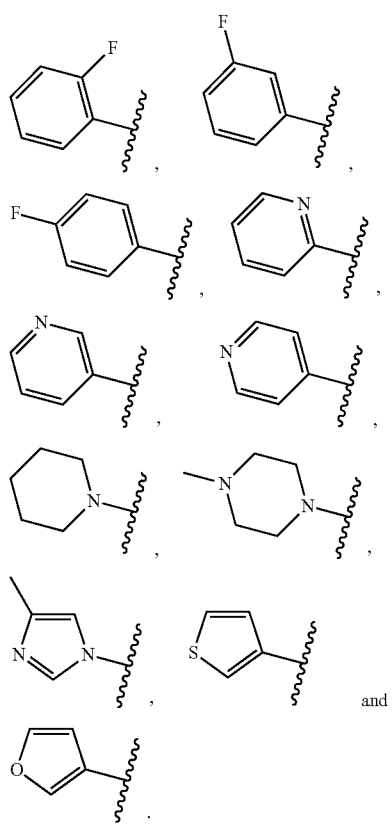

In some embodiments of Formulas I and/or Ia, R is selected from the group consisting of:

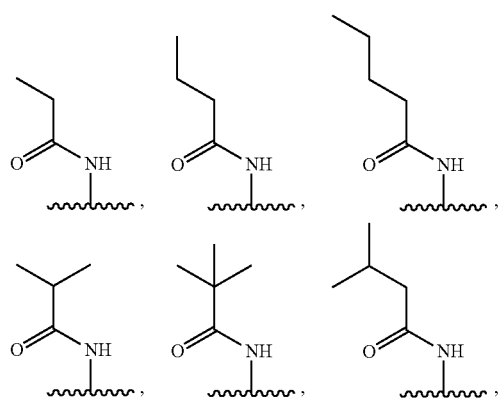

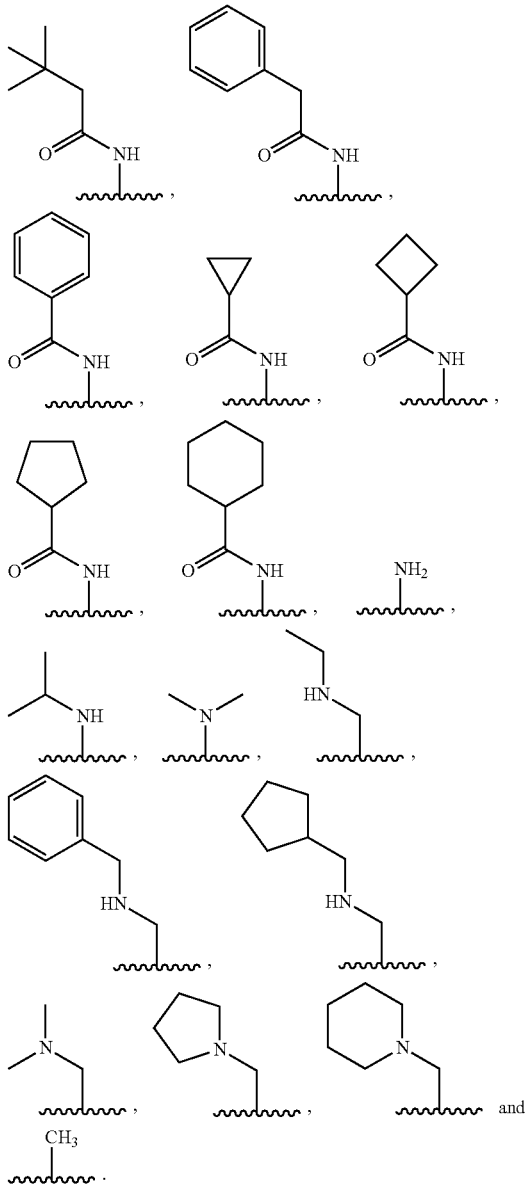

Illustrative compounds of Formulas I and/or Ia are shown in Table 1.

TABLE 1

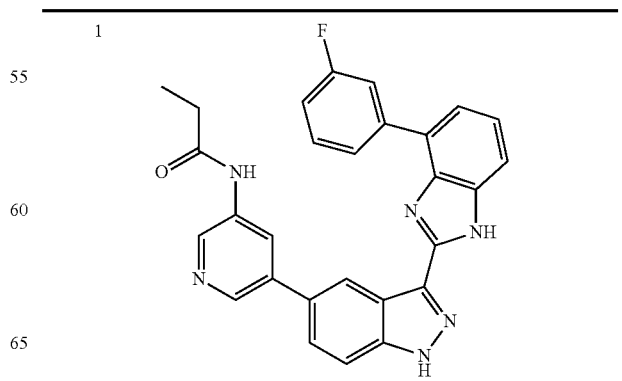

TABLE 1-continued
| 2 | 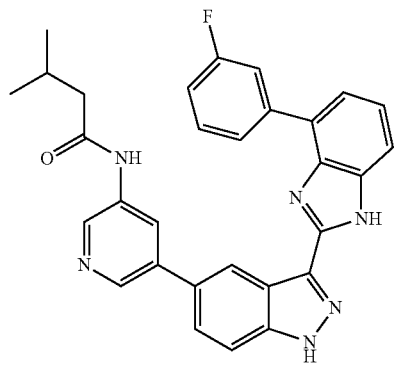 |
|---|---|
| 3 | 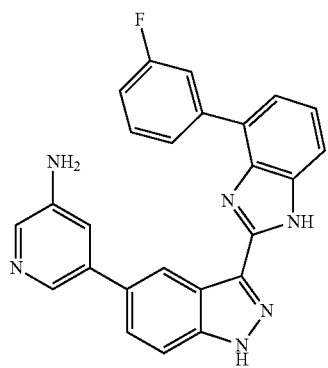 [SMILES: Nc1cncc(-c2ccc3[nH]nc(-c4nc5c(-c6cccc(F)c6)cccc5[nH]4)c3c2)c1] |
| 4 | 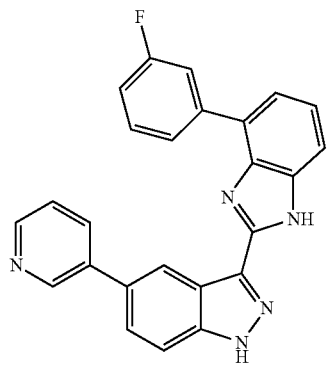 [SMILES: Fc1cccc(-c2cccc3[nH]c(-c4n[nH]c5ccc(-c6cccnc6)cc45)nc23)c1] |
| 5 | 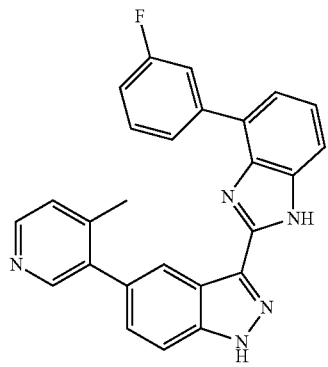 [SMILES: Cc1ccncc1-c1ccc2[nH]nc(-c3nc4c(-c5cccc(F)c5)cccc4[nH]3)c2c1] |
| 6 | 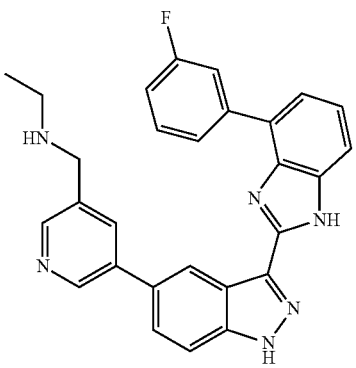 [SMILES: CCNCc1cncc(-c2ccc3[nH]nc(-c4nc5c(-c6cccc(F)c6)cccc5[nH]4)c3c2)c1] |
| 7 | 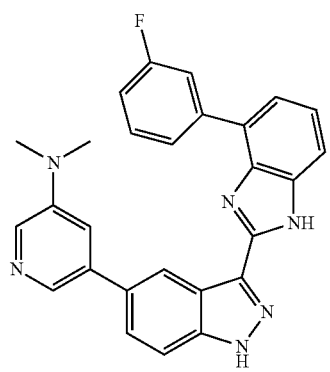 [SMILES: CN(C)c1cncc(-c2ccc3[nH]nc(-c4nc5c(-c6cccc(F)c6)cccc5[nH]4)c3c2)c1] |
| 8 | 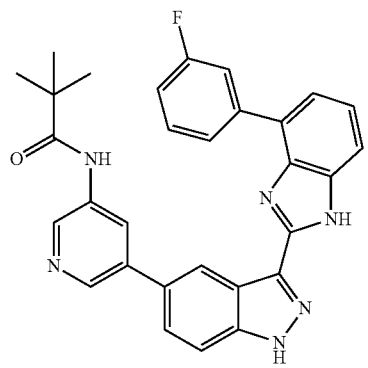 [SMILES: CC(C)(C)C(=O)Nc1cncc(-c2ccc3[nH]nc(-c4nc5c(-c6cccc(F)c6)cccc5[nH]4)c3c2)c1] |
| 9 | 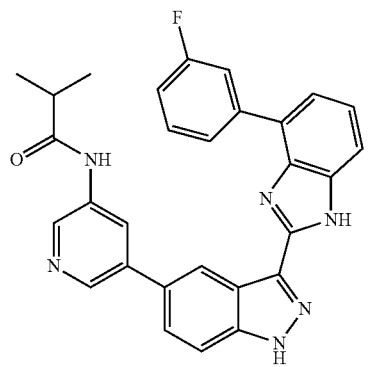 |

TABLE 1-continued
10
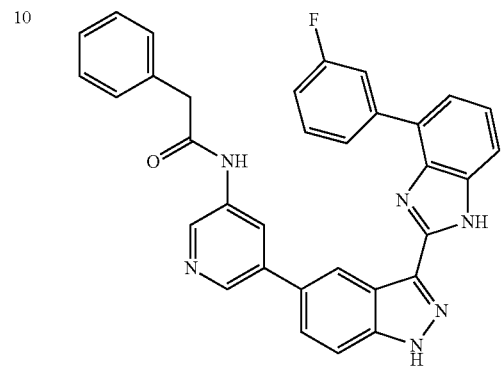
11
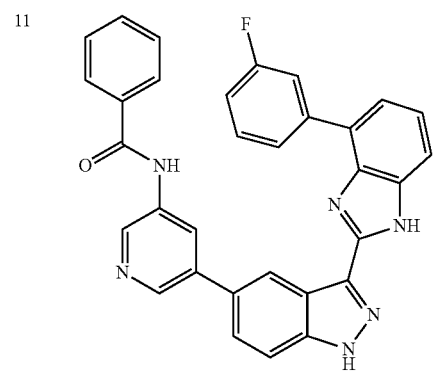
12
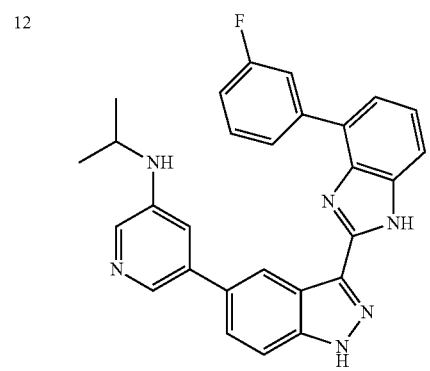
13
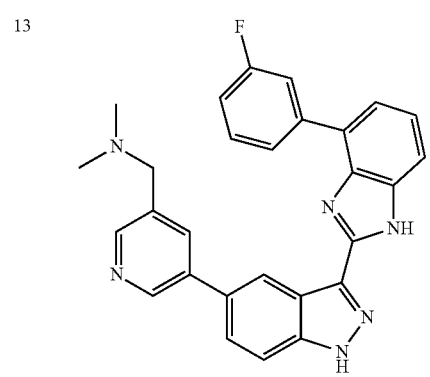
TABLE 1-continued
14
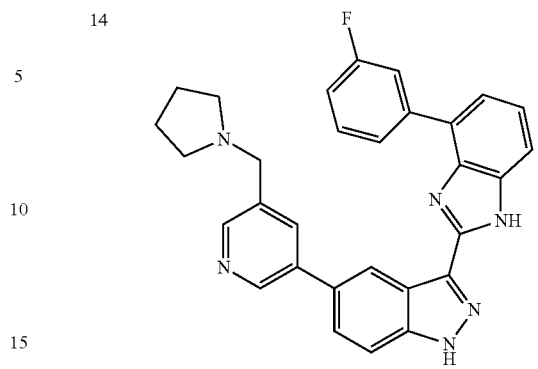
15
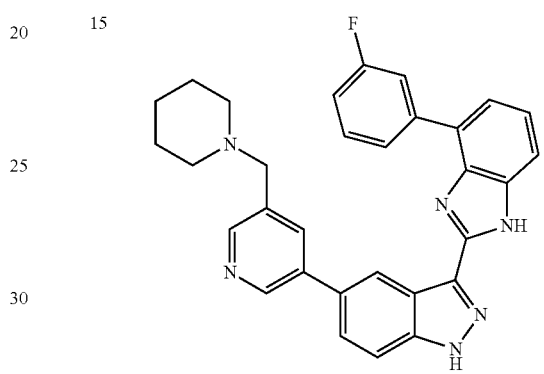
16
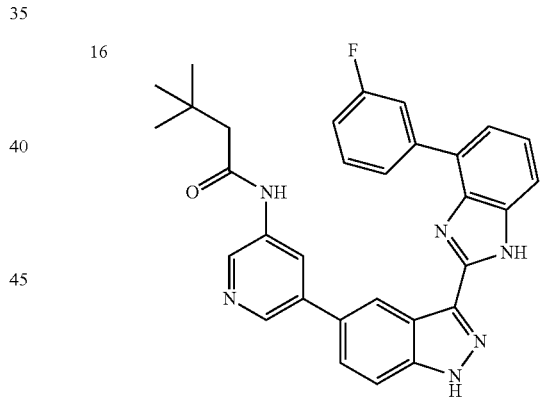
17
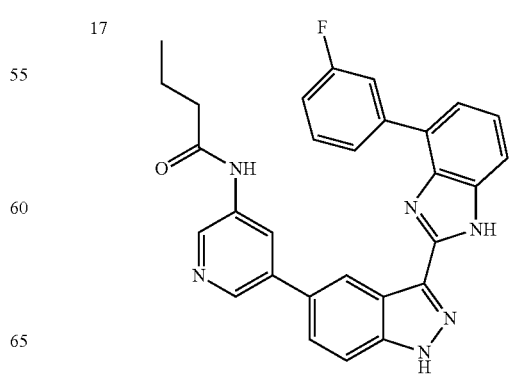

TABLE 1-continued
18
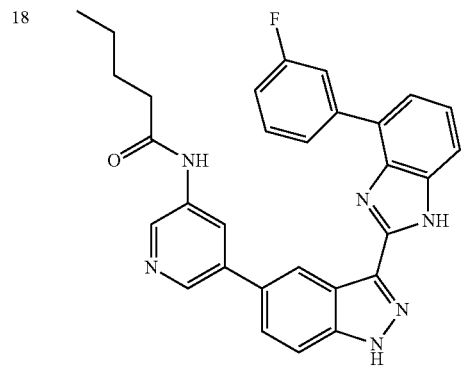
19
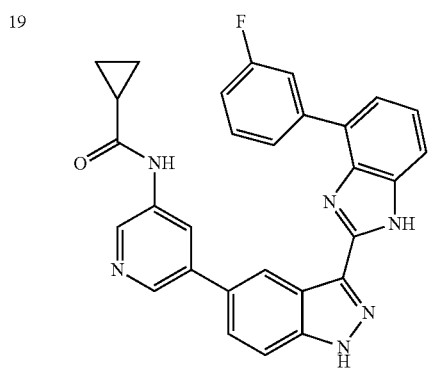
20
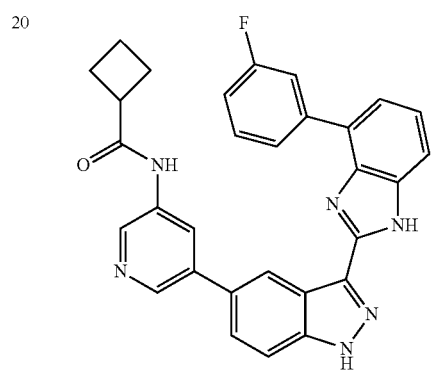
21
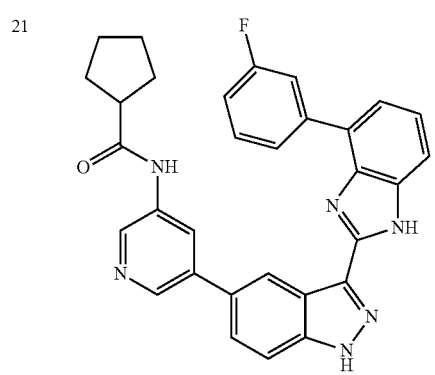
TABLE 1-continued
22
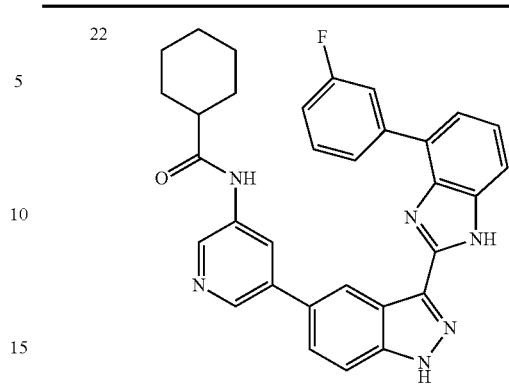
23
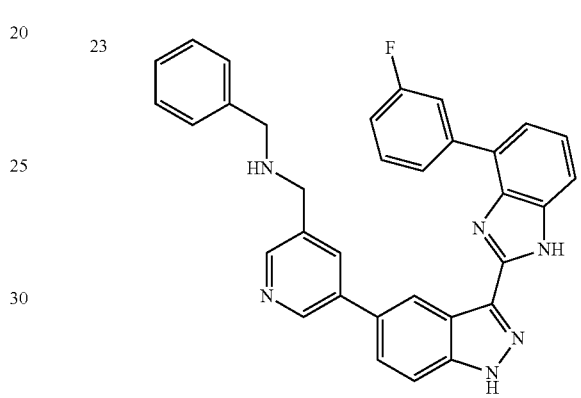
24
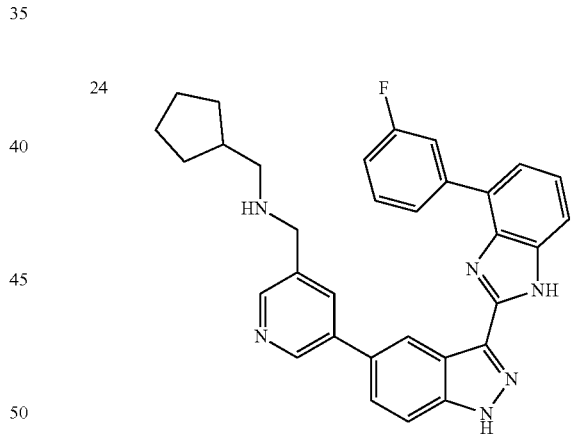
25
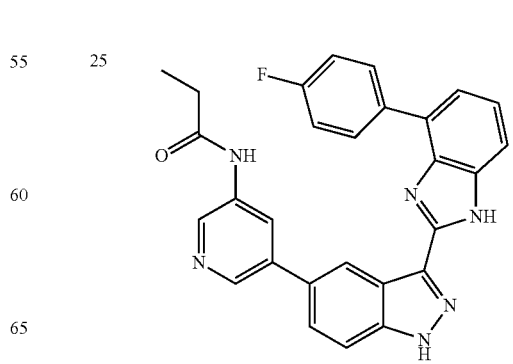

TABLE 1-continued
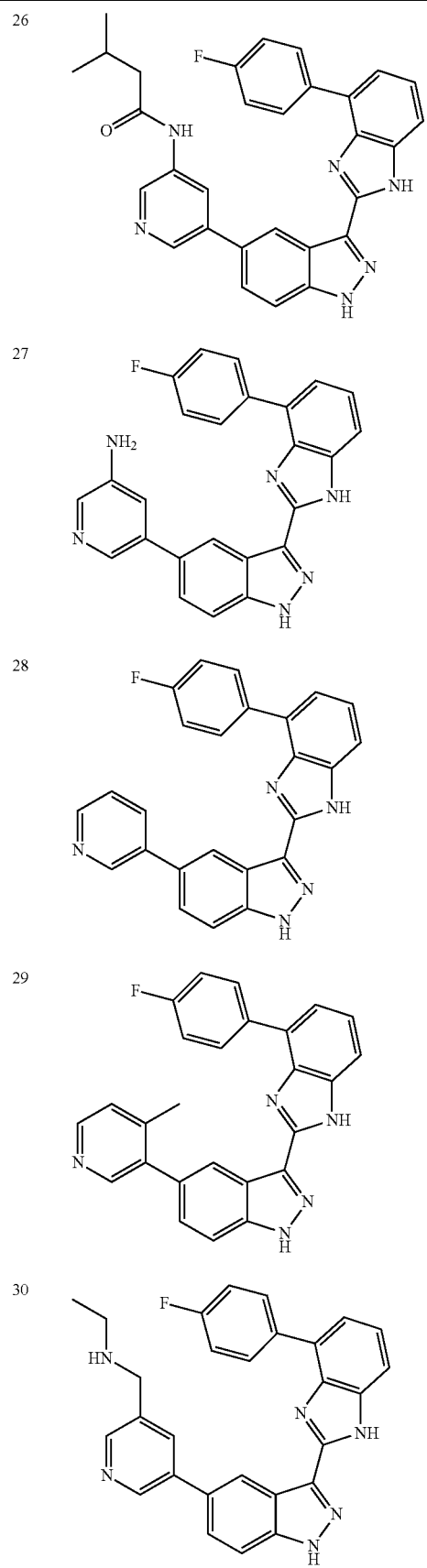
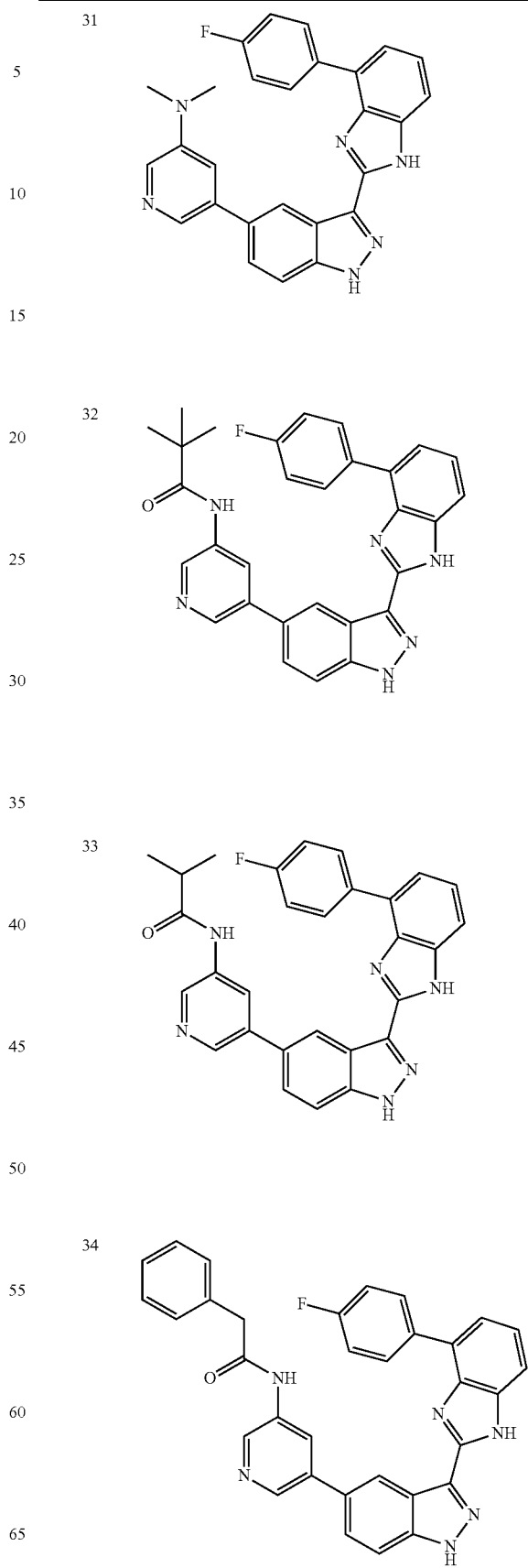

TABLE 1-continued
| 35 | 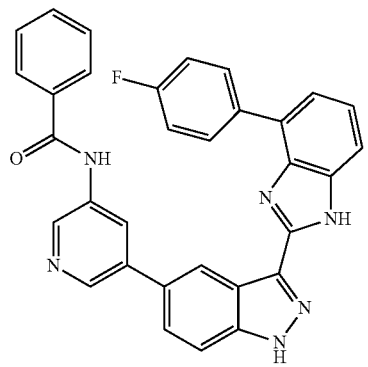 [SMILES: O=C(Nc1cncc(-c2ccc3[nH]nc(-c4nc5c(-c6ccc(F)cc6)cccc5[nH]4)c3c2)c1)c1ccccc1] | 40 | 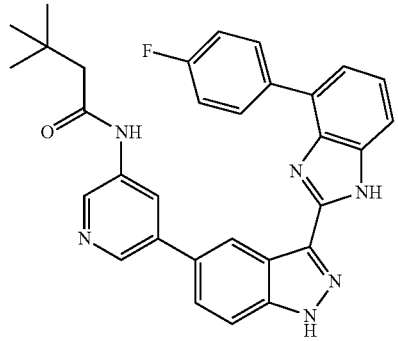 |
| 36 | 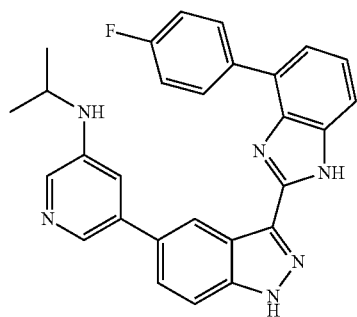 [SMILES: CC(C)Nc1cncc(-c2ccc3[nH]nc(-c4nc5c(-c6ccc(F)cc6)cccc5[nH]4)c3c2)c1] | 41 | 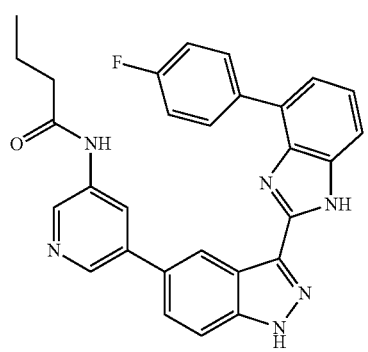 |
| 37 | 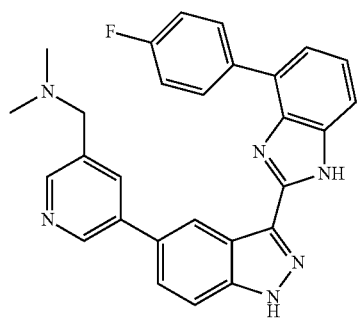 [SMILES: CN(C)Cc1cncc(-c2ccc3[nH]nc(-c4nc5c(-c6ccc(F)cc6)cccc5[nH]4)c3c2)c1] | 42 | 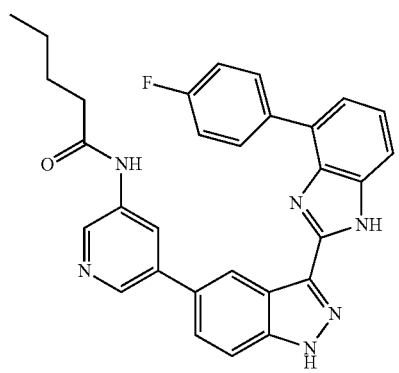 |
| 38 | 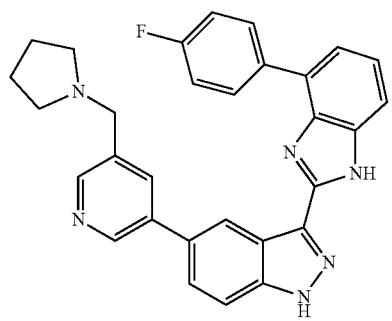 [SMILES: Fc1ccc(-c2cccc3[nH]c(-c4n[nH]c5ccc(-c6cncc(CN7CCCC7)c6)cc45)nc23)cc1] | 43 | 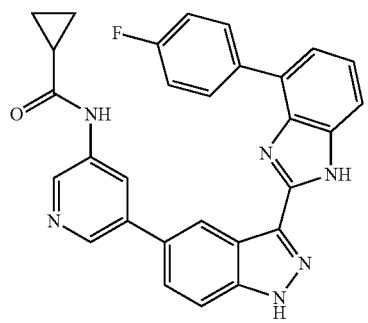 |
| 39 | 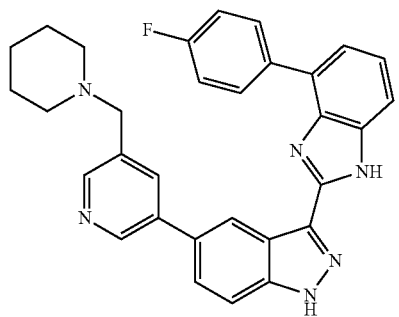 [SMILES: Fc1ccc(-c2cccc3[nH]c(-c4n[nH]c5ccc(-c6cncc(CN7CCCCC7)c6)cc45)nc23)cc1] | | |

TABLE 1-continued
| 44 | 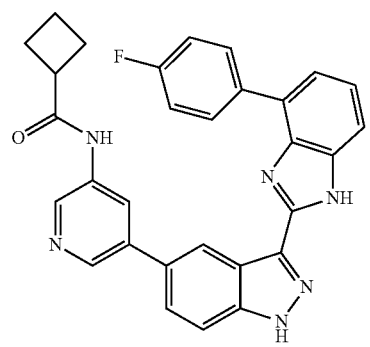 [SMILES: O=C(Nc1cncc(-c2ccc3[nH]nc(-c4nc5c(-c6ccc(F)cc6)cccc5[nH]4)c3c2)c1)C1CCC1] |
| 45 | 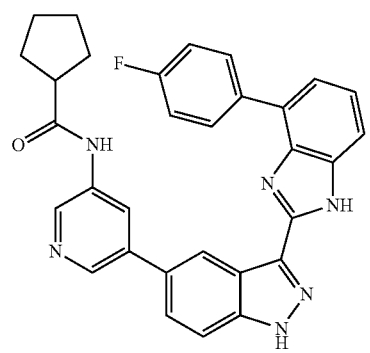 [SMILES: O=C(Nc1cncc(-c2ccc3[nH]nc(-c4nc5c(-c6ccc(F)cc6)cccc5[nH]4)c3c2)c1)C1CCCC1] |
| 46 | 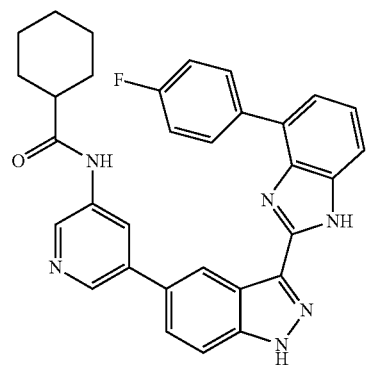 [SMILES: O=C(Nc1cncc(-c2ccc3[nH]nc(-c4nc5c(-c6ccc(F)cc6)cccc5[nH]4)c3c2)c1)C1CCCCC1] |
| 47 | 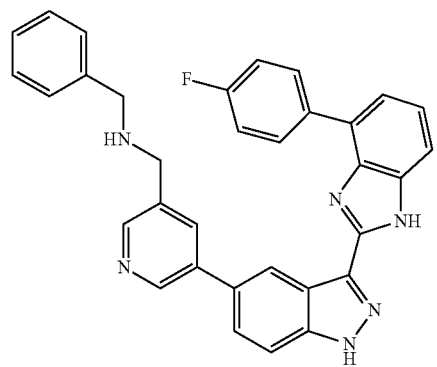 [SMILES: Fc1ccc(-c2cccc3[nH]c(-c4n[nH]c5ccc(-c6cncc(CNCc7ccccc7)c6)cc45)nc23)cc1] |
TABLE 1-continued
| 48 | 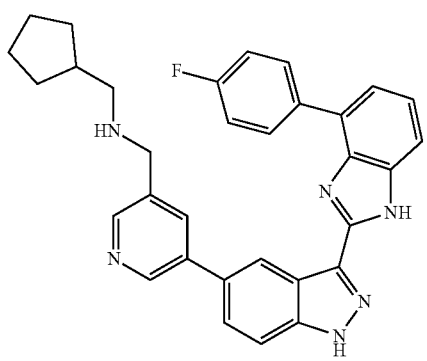 [SMILES: Fc1ccc(-c2cccc3[nH]c(-c4n[nH]c5ccc(-c6cncc(CNCC7CCCC7)c6)cc45)nc23)cc1] |
| 49 | 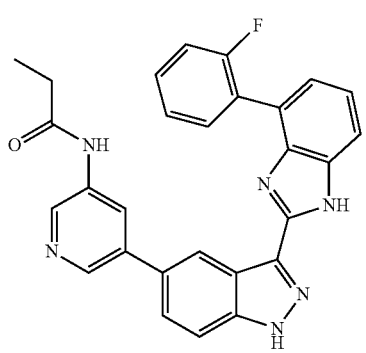 [SMILES: CCC(=O)Nc1cncc(-c2ccc3[nH]nc(-c4nc5c(-c6ccccc6F)cccc5[nH]4)c3c2)c1] |
| 50 | 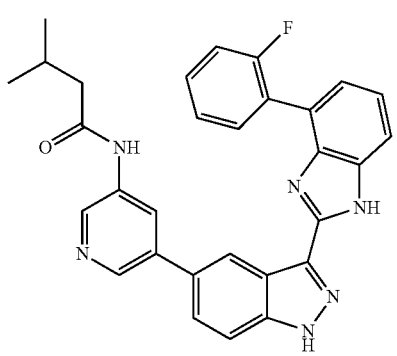 |
| 51 | 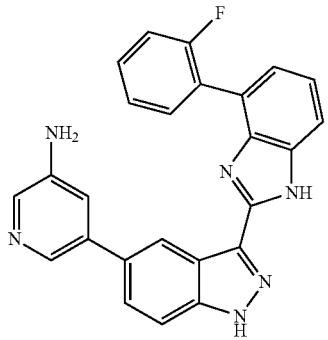 [SMILES: Nc1cncc(-c2ccc3[nH]nc(-c4nc5c(-c6ccccc6F)cccc5[nH]4)c3c2)c1] |

TABLE 1-continued
52 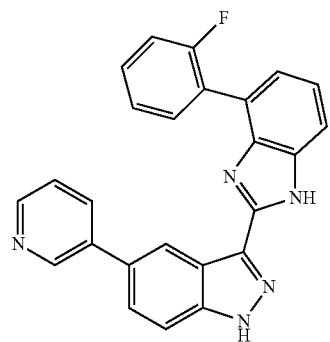 [SMILES: Fc1ccccc1-c1cccc2[nH]c(-c3n[nH]c4ccc(-c5cccnc5)cc34)nc12]
53 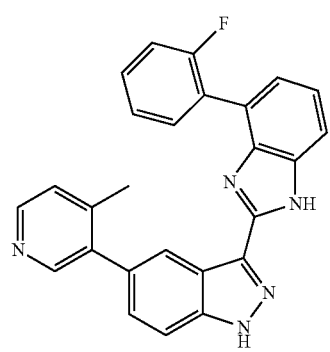 [SMILES: Cc1ccncc1-c1ccc2[nH]nc(-c3nc4c(-c5ccccc5F)cccc4[nH]3)c2c1]
54 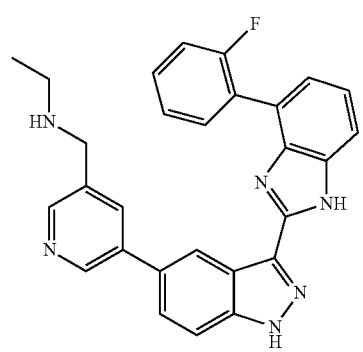 [SMILES: CCNCc1cncc(-c2ccc3[nH]nc(-c4nc5c(-c6ccccc6F)cccc5[nH]4)c3c2)c1]
55 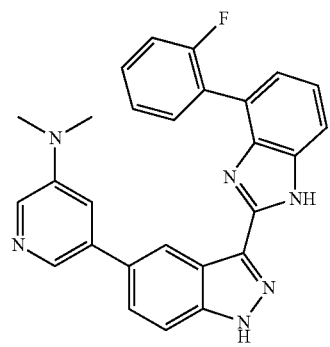 [SMILES: CN(C)c1cncc(-c2ccc3[nH]nc(-c4nc5c(-c6ccccc6F)cccc5[nH]4)c3c2)c1]
56 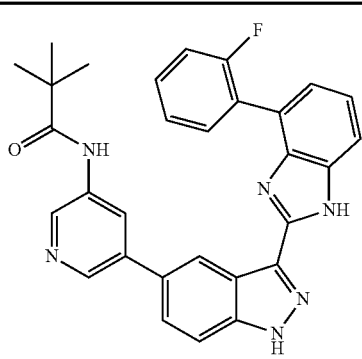
57 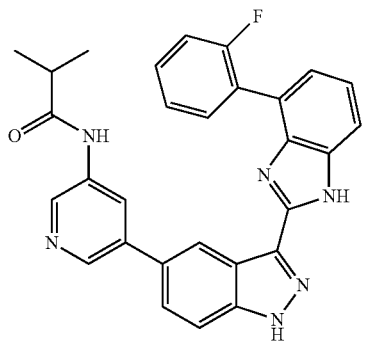 [SMILES: CC(C)C(=O)Nc1cncc(-c2ccc3[nH]nc(-c4nc5c(-c6ccccc6F)cccc5[nH]4)c3c2)c1]
58 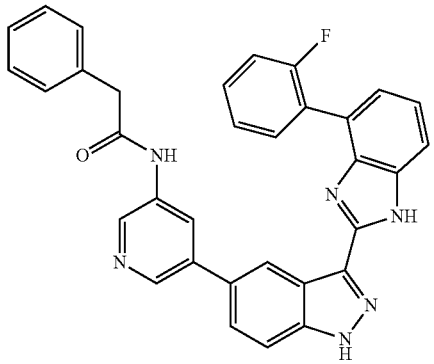 [SMILES: O=C(Cc1ccccc1)Nc1cncc(-c2ccc3[nH]nc(-c4nc5c(-c6ccccc6F)cccc5[nH]4)c3c2)c1]
59 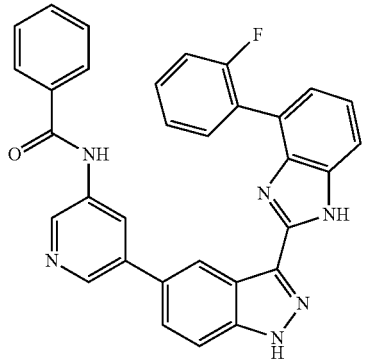 [SMILES: O=C(Nc1cncc(-c2ccc3[nH]nc(-c4nc5c(-c6ccccc6F)cccc5[nH]4)c3c2)c1)c1ccccc1]

TABLE 1-continued
60 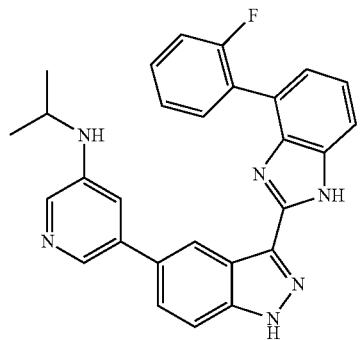 [SMILES: CC(C)Nc1cncc(-c2ccc3[nH]nc(-c4nc5c(-c6ccccc6F)cccc5[nH]4)c3c2)c1]
61 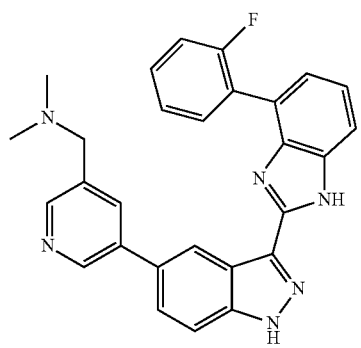 [SMILES: CN(C)Cc1cncc(-c2ccc3[nH]nc(-c4nc5c(-c6ccccc6F)cccc5[nH]4)c3c2)c1]
62 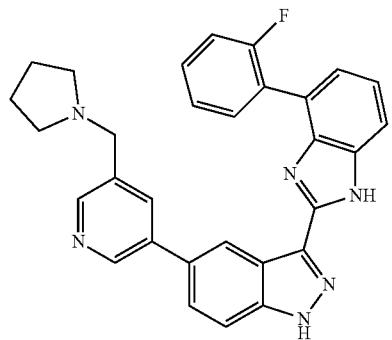 [SMILES: Fc1ccccc1-c1cccc2[nH]c(-c3n[nH]c4ccc(-c5cncc(CN6CCCC6)c5)cc34)nc12]
63 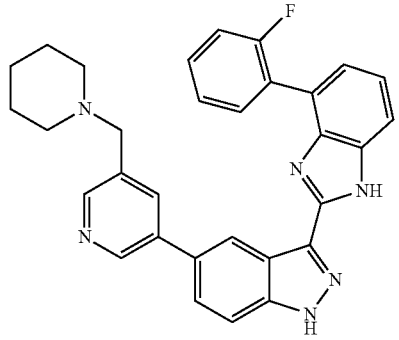 [SMILES: Fc1ccccc1-c1cccc2[nH]c(-c3n[nH]c4ccc(-c5cncc(CN6CCCCC6)c5)cc34)nc12]
TABLE 1-continued
64 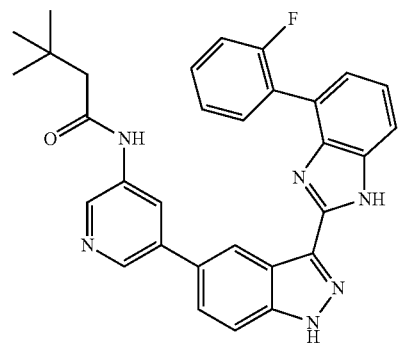 [SMILES: CC(C)(C)CC(=O)Nc1cncc(-c2ccc3[nH]nc(-c4nc5c(-c6ccccc6F)cccc5[nH]4)c3c2)c1]
65 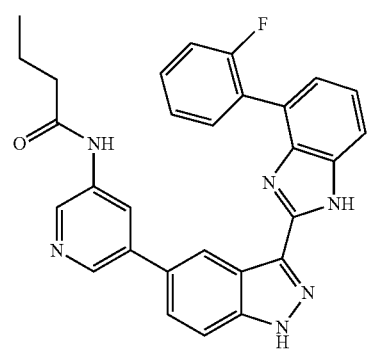 [SMILES: CCCC(=O)Nc1cncc(-c2ccc3[nH]nc(-c4nc5c(-c6ccccc6F)cccc5[nH]4)c3c2)c1]
66 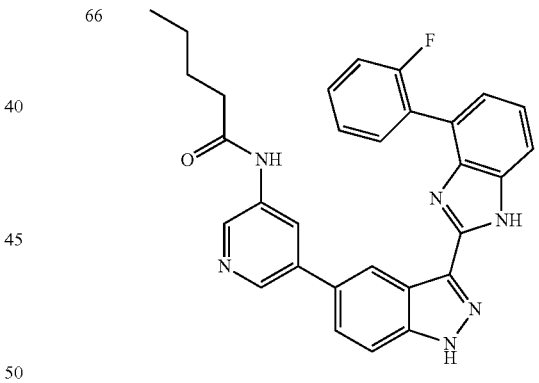
67 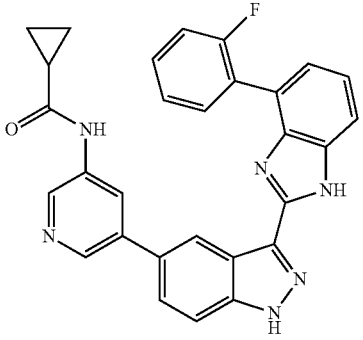 [SMILES: O=C(Nc1cncc(-c2ccc3[nH]nc(-c4nc5c(-c6ccccc6F)cccc5[nH]4)c3c2)c1)C1CC1]

TABLE 1-continued
| 68 | 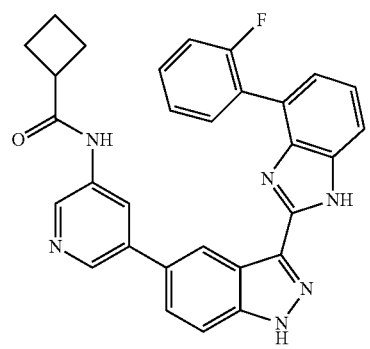 [SMILES: O=C(Nc1cncc(-c2ccc3[nH]nc(-c4nc5c(-c6ccccc6F)cccc5[nH]4)c3c2)c1)C1CCC1] |
| --- | --- |
| 69 | 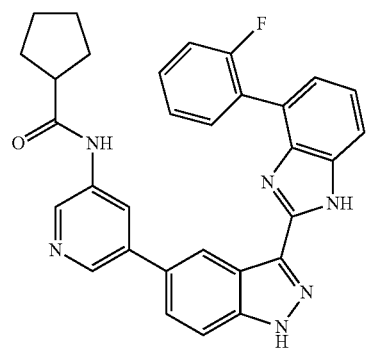 [SMILES: O=C(Nc1cncc(-c2ccc3[nH]nc(-c4nc5c(-c6ccccc6F)cccc5[nH]4)c3c2)c1)C1CCCC1] |
| 70 | 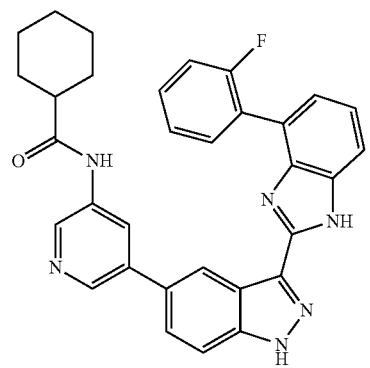 [SMILES: O=C(Nc1cncc(-c2ccc3[nH]nc(-c4nc5c(-c6ccccc6F)cccc5[nH]4)c3c2)c1)C1CCCCC1] |
| 71 | 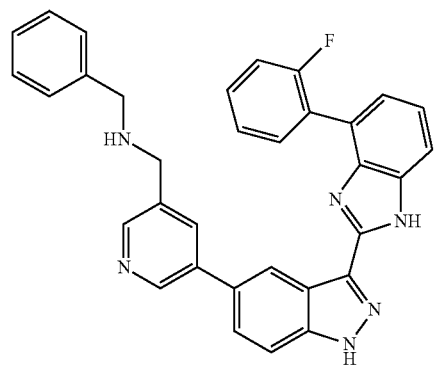 [SMILES: Fc1ccccc1-c1cccc2[nH]c(-c3n[nH]c4ccc(-c5cncc(CNCc6ccccc6)c5)cc34)nc12] |
| 72 | 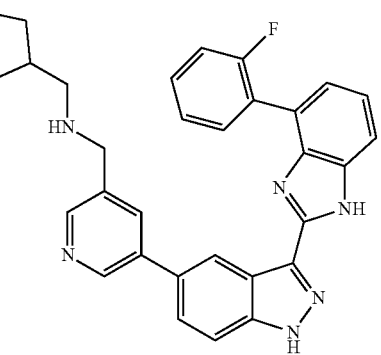 |
| 73 | 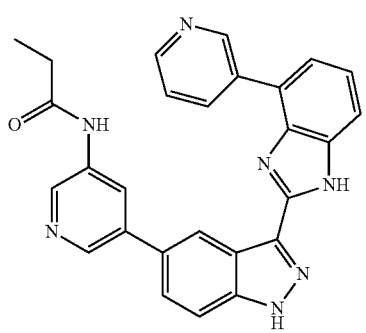 [SMILES: CCC(=O)Nc1cncc(-c2ccc3[nH]nc(-c4nc5c(-c6cccnc6)cccc5[nH]4)c3c2)c1] |
| 74 | 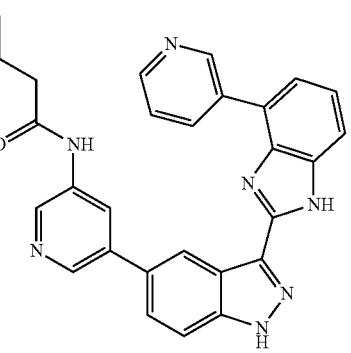 |
| 75 | 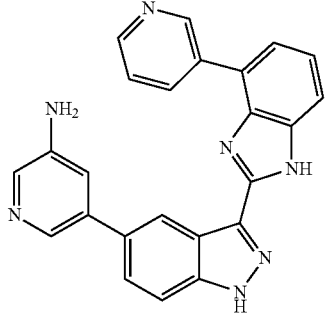 [SMILES: Nc1cncc(-c2ccc3[nH]nc(-c4nc5c(-c6cccnc6)cccc5[nH]4)c3c2)c1] |

TABLE 1-continued
| 76 | 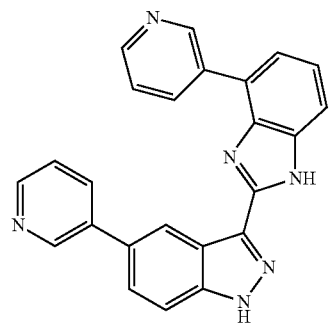 [SMILES: c1cncc(-c2ccc3[nH]nc(-c4nc5c(-c6cccnc6)cccc5[nH]4)c3c2)c1] |
| 77 | 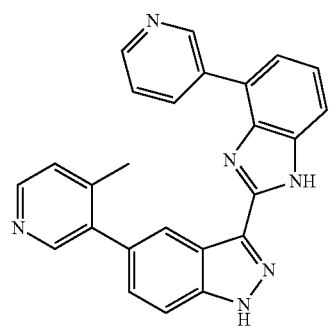 [SMILES: Cc1ccncc1-c1ccc2[nH]nc(-c3nc4c(-c5cccnc5)cccc4[nH]3)c2c1] |
| 78 | 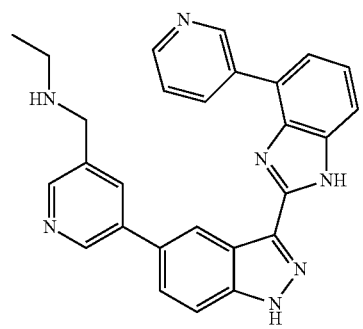 [SMILES: CCNCc1cncc(-c2ccc3[nH]nc(-c4nc5c(-c6cccnc6)cccc5[nH]4)c3c2)c1] |
| 79 | 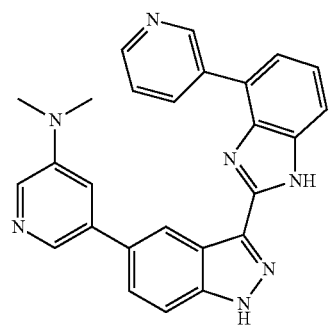 [SMILES: CN(C)c1cncc(-c2ccc3[nH]nc(-c4nc5c(-c6cccnc6)cccc5[nH]4)c3c2)c1] |
| 80 | 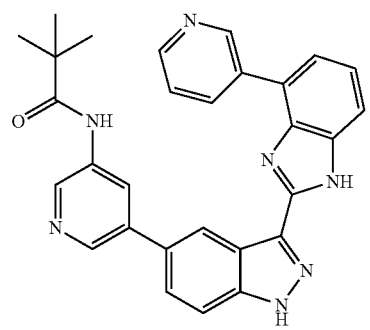 [SMILES: CC(C)(C)C(=O)Nc1cncc(-c2ccc3[nH]nc(-c4nc5c(-c6cccnc6)cccc5[nH]4)c3c2)c1] |
| 81 | 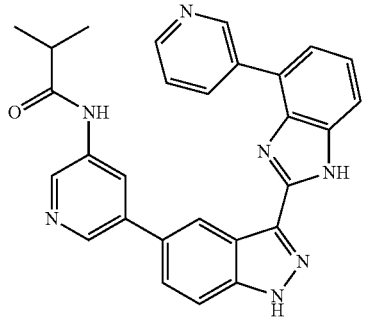 [SMILES: CC(C)C(=O)Nc1cncc(-c2ccc3[nH]nc(-c4nc5c(-c6cccnc6)cccc5[nH]4)c3c2)c1] |
| 82 | 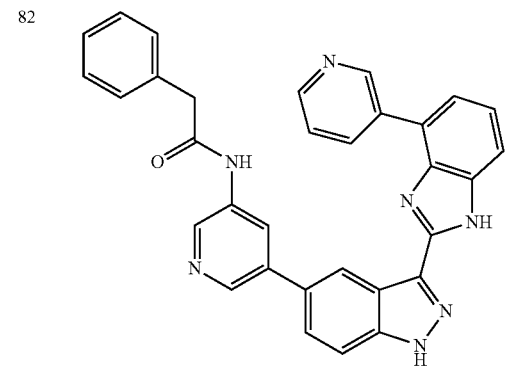 |
| 83 | 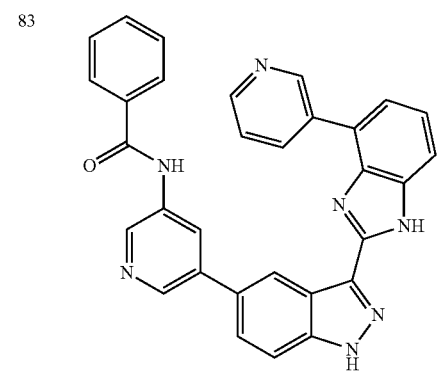 |
| 84 | 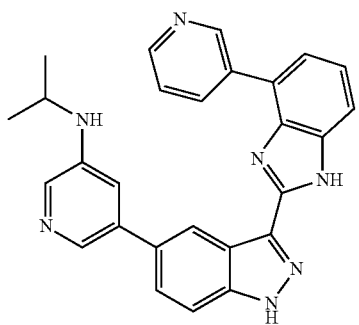 [SMILES: CC(C)Nc1cncc(-c2ccc3[nH]nc(-c4nc5c(-c6cccnc6)cccc5[nH]4)c3c2)c1] |

TABLE 1-continued
| 85 | 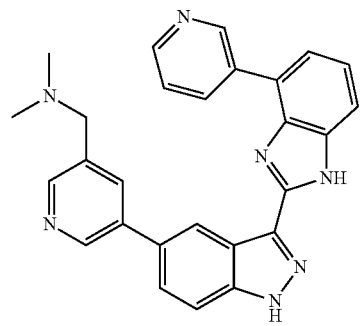 [SMILES: CN(C)Cc1cncc(-c2ccc3[nH]nc(-c4nc5c(-c6cccnc6)cccc5[nH]4)c3c2)c1] | 89 | 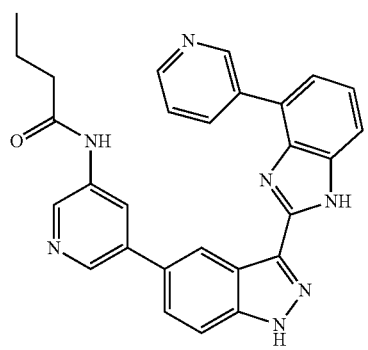 |
| 86 | 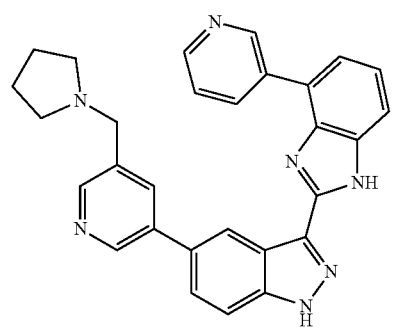 [SMILES: c1cncc(-c2cccc3[nH]c(-c4n[nH]c5ccc(-c6cncc(CN7CCCC7)c6)cc45)nc23)c1] | 90 | 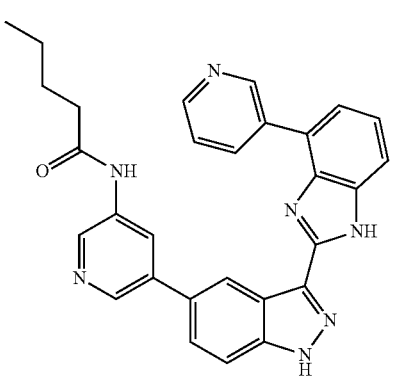 |
| 87 | 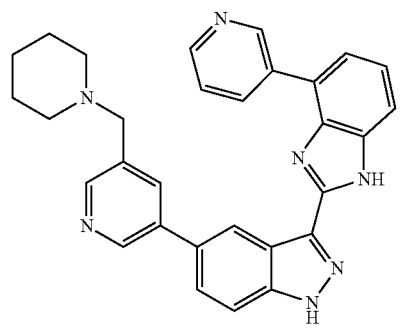 [SMILES: c1cncc(-c2cccc3[nH]c(-c4n[nH]c5ccc(-c6cncc(CN7CCCCC7)c6)cc45)nc23)c1] | 91 | 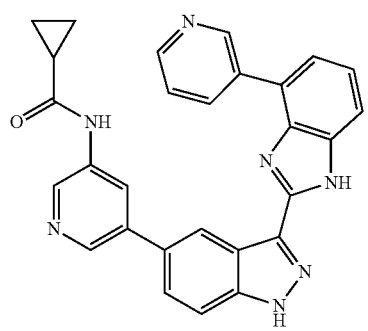 |
| 88 | 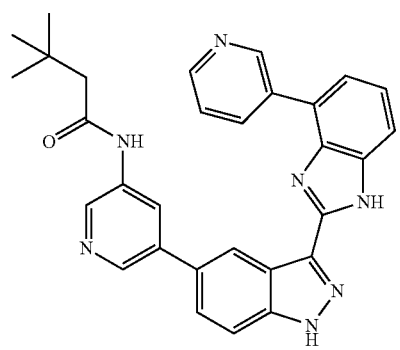 [SMILES: CC(C)(C)CC(=O)Nc1cncc(-c2ccc3[nH]nc(-c4nc5c(-c6cccnc6)cccc5[nH]4)c3c2)c1] | 92 | 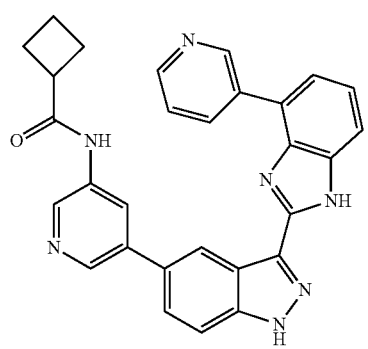 [SMILES: O=C(Nc1cncc(-c2ccc3[nH]nc(-c4nc5c(-c6cccnc6)cccc5[nH]4)c3c2)c1)C1CCC1] |

TABLE 1-continued
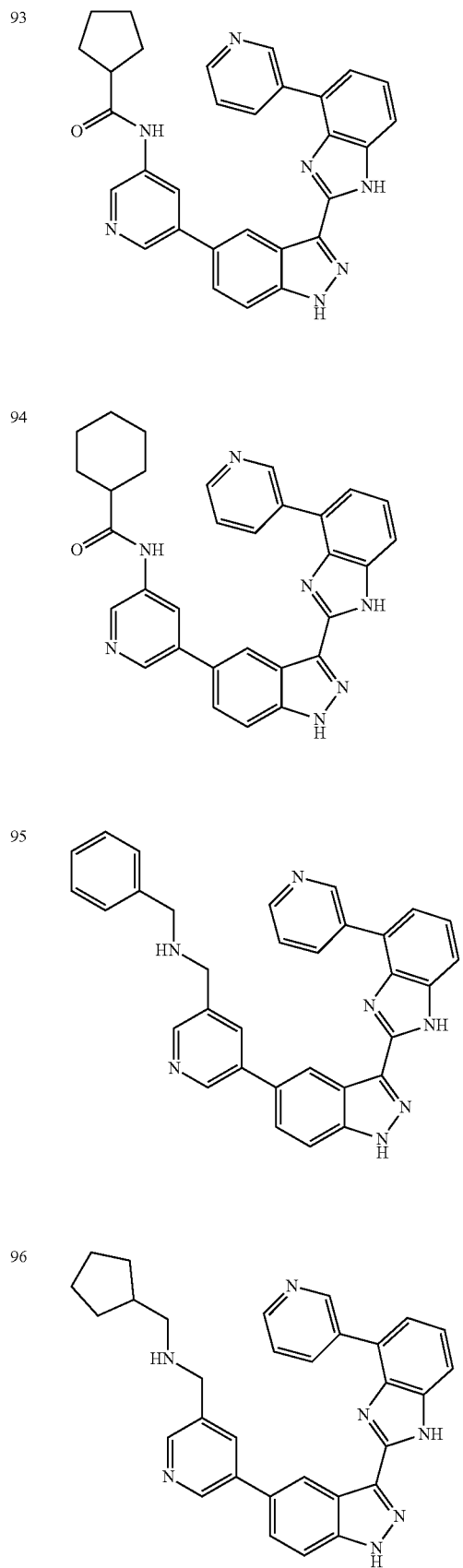
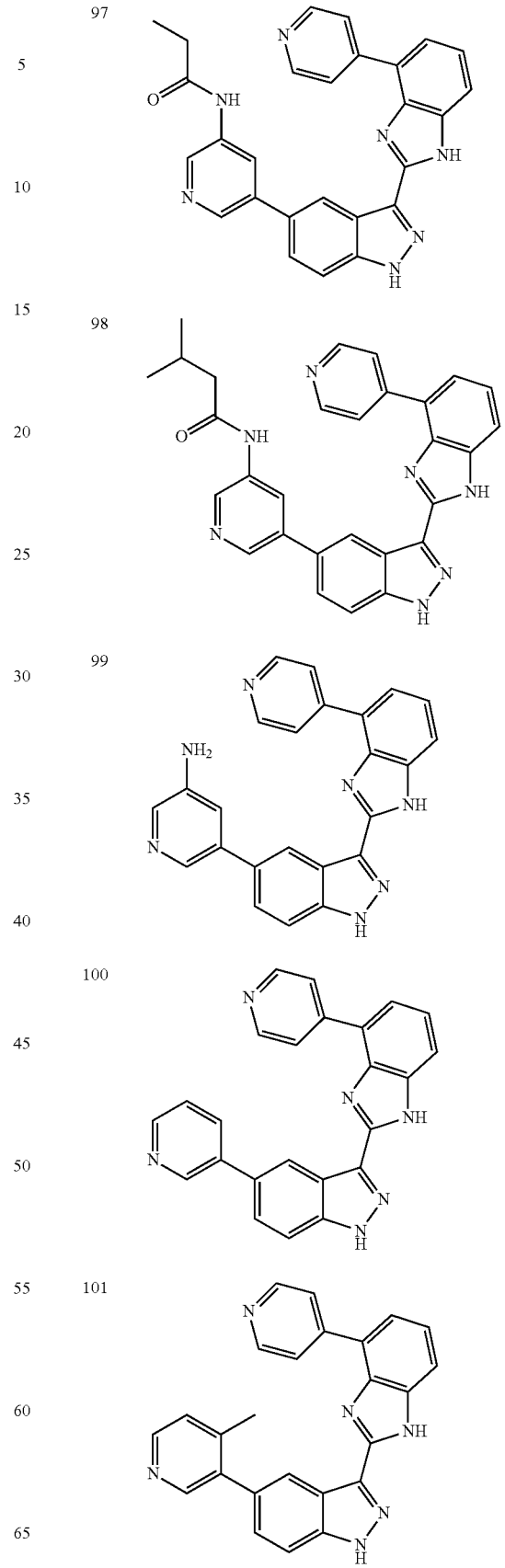

TABLE 1-continued
| | |
|---|---|
| 102 | 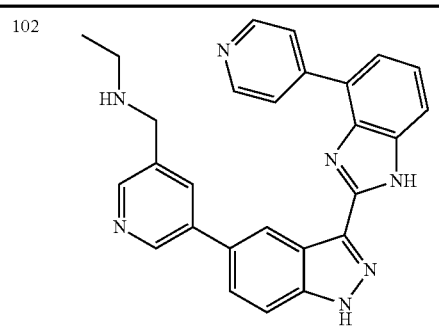 |
| 103 | 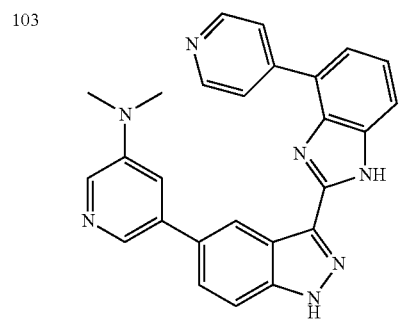 |
| 104 | 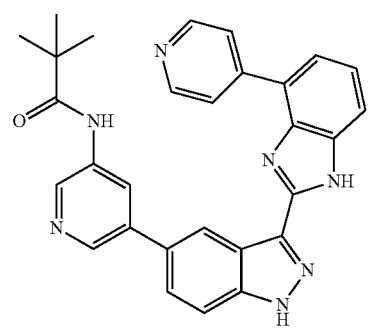 [SMILES: CC(C)(C)C(=O)Nc1cncc(-c2ccc3[nH]nc(-c4nc5c(-c6ccncc6)cccc5[nH]4)c3c2)c1] |
| 105 | 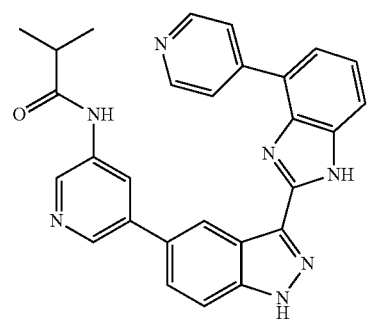 [SMILES: CC(C)C(=O)Nc1cncc(-c2ccc3[nH]nc(-c4nc5c(-c6ccncc6)cccc5[nH]4)c3c2)c1] |
| 106 | 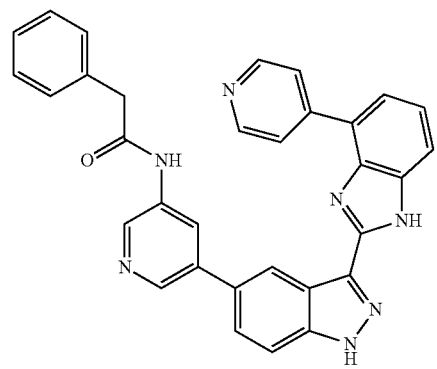 [SMILES: O=C(Cc1ccccc1)Nc1cncc(-c2ccc3[nH]nc(-c4nc5c(-c6ccncc6)cccc5[nH]4)c3c2)c1] |
| 107 | 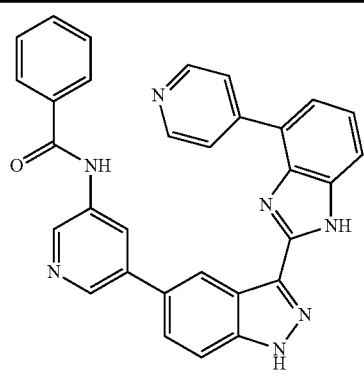 |
| 108 | 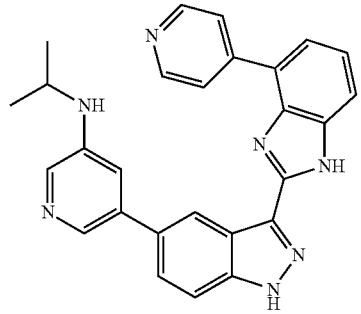 [SMILES: CC(C)Nc1cncc(-c2ccc3[nH]nc(-c4nc5c(-c6ccncc6)cccc5[nH]4)c3c2)c1] |
| 109 | 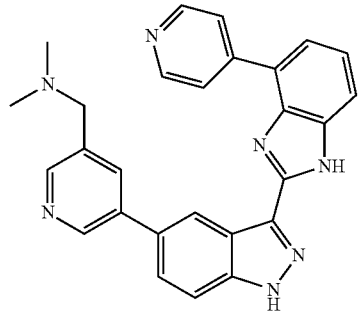 [SMILES: CN(C)Cc1cncc(-c2ccc3[nH]nc(-c4nc5c(-c6ccncc6)cccc5[nH]4)c3c2)c1] |
| 110 | 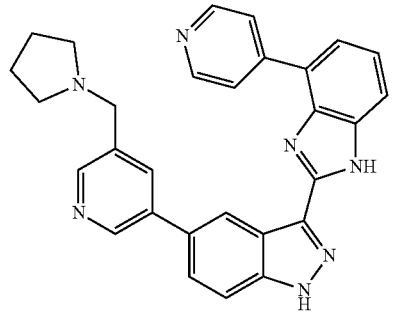 [SMILES: c1cc(-c2ccncc2)c2nc(-c3n[nH]c4ccc(-c5cncc(CN6CCCC6)c5)cc34)[nH]c2c1] |
| 111 | 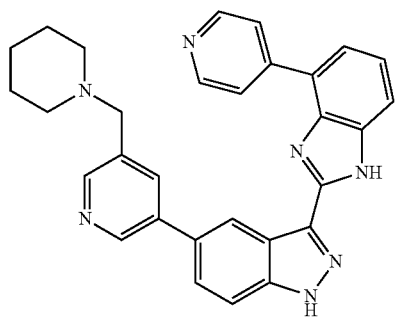 [SMILES: c1cc(-c2ccncc2)c2nc(-c3n[nH]c4ccc(-c5cncc(CN6CCCCC6)c5)cc34)[nH]c2c1] |

TABLE 1-continued
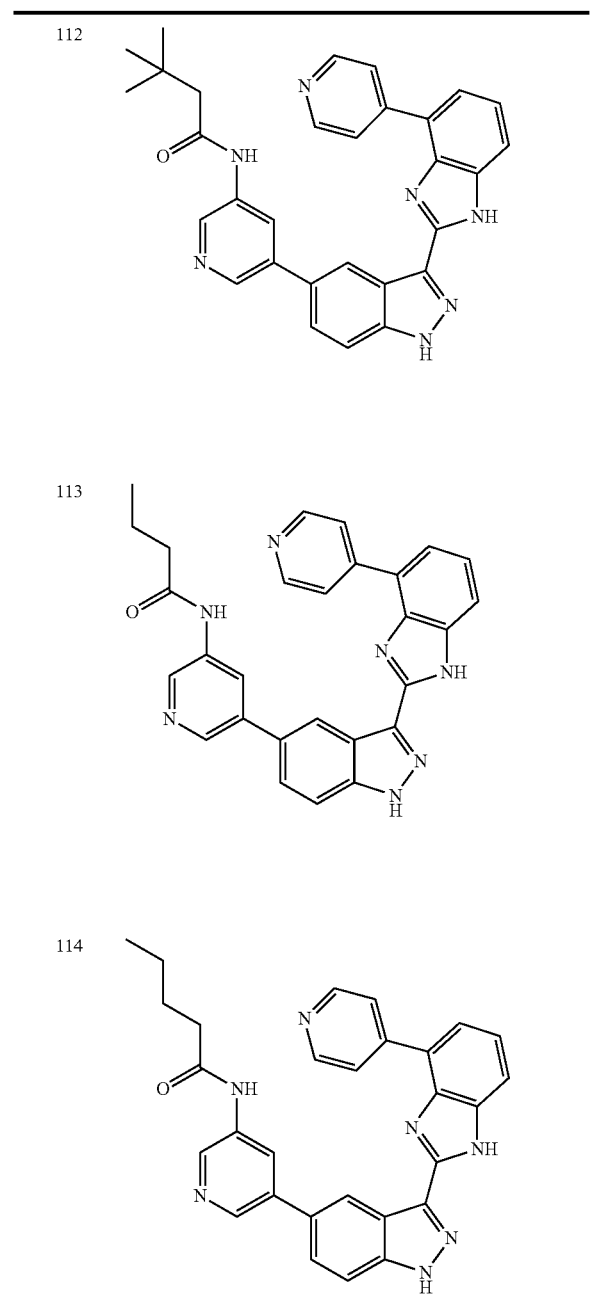
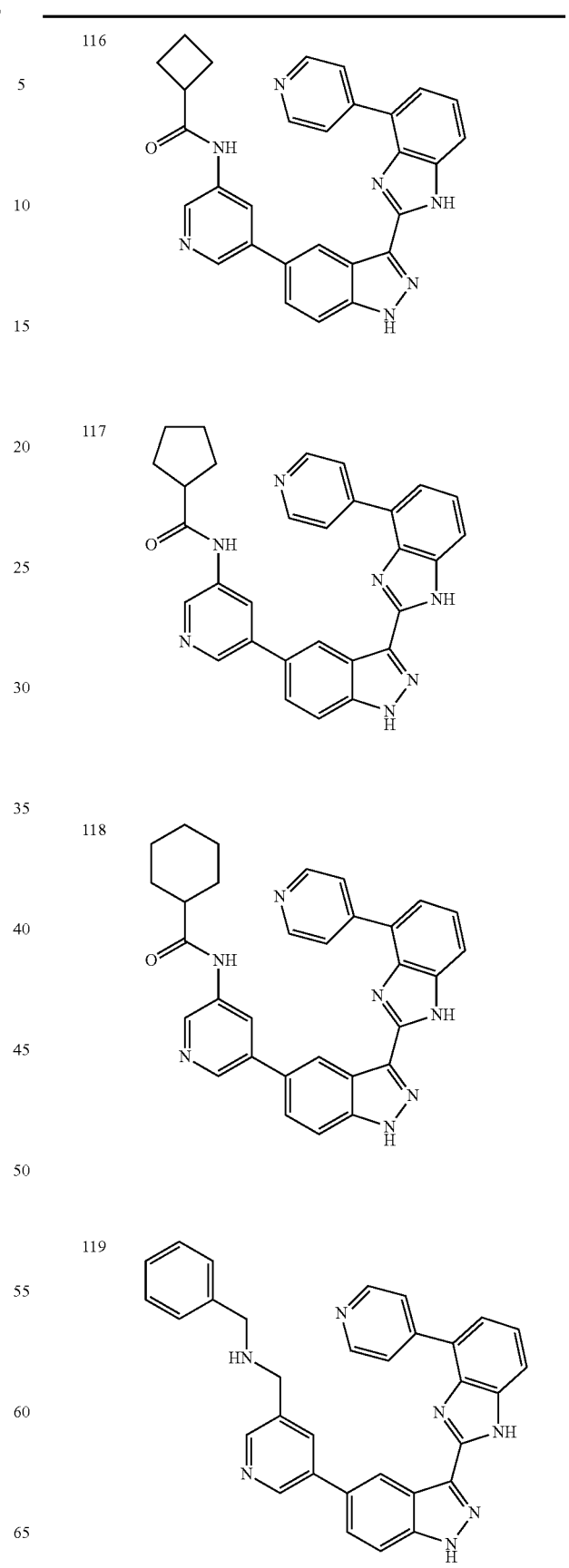

TABLE 1-continued
| 120 | 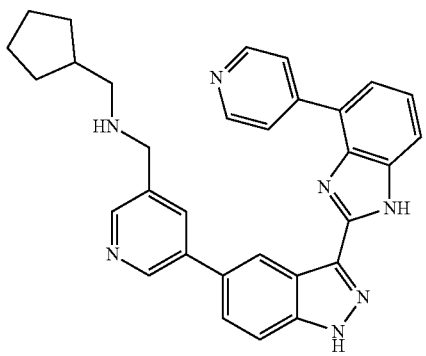 [SMILES: c1cc(-c2ccncc2)c2nc(-c3n[nH]c4ccc(-c5cncc(CNCC6CCCC6)c5)cc34)[nH]c2c1] |
| 121 | 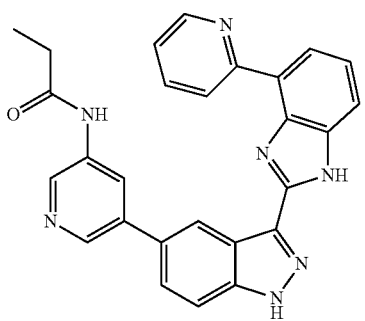 [SMILES: CCC(=O)Nc1cncc(-c2ccc3[nH]nc(-c4nc5c(-c6ccccn6)cccc5[nH]4)c3c2)c1] |
| 122 | 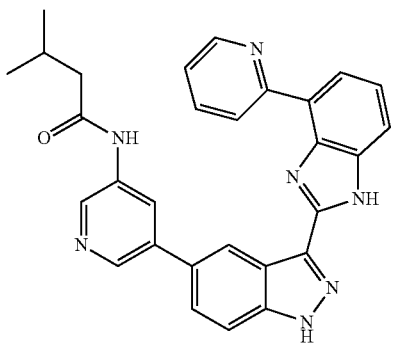 [SMILES: CC(C)CC(=O)Nc1cncc(-c2ccc3[nH]nc(-c4nc5c(-c6ccccn6)cccc5[nH]4)c3c2)c1] |
| 123 | 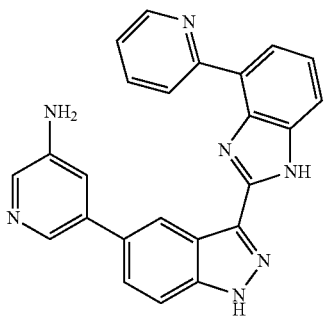 [SMILES: Nc1cncc(-c2ccc3[nH]nc(-c4nc5c(-c6ccccn6)cccc5[nH]4)c3c2)c1] |
TABLE 1-continued
| 124 | 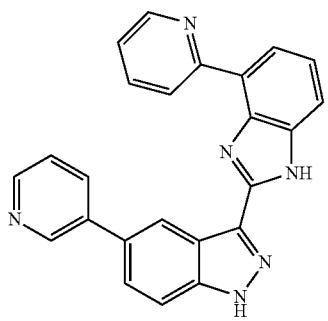 [SMILES: c1ccc(-c2cccc3[nH]c(-c4n[nH]c5ccc(-c6cccnc6)cc45)nc23)nc1] |
| 125 | 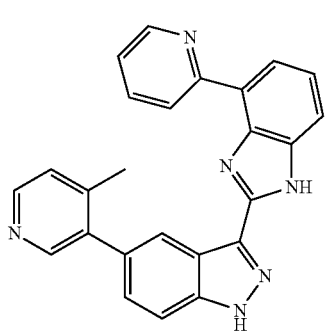 [SMILES: Cc1ccncc1-c1ccc2[nH]nc(-c3nc4c(-c5ccccn5)cccc4[nH]3)c2c1] |
| 126 | 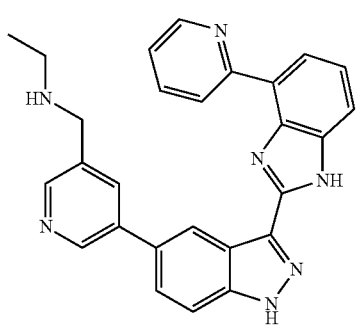 [SMILES: CCNCc1cncc(-c2ccc3[nH]nc(-c4nc5c(-c6ccccn6)cccc5[nH]4)c3c2)c1] |
| 127 | 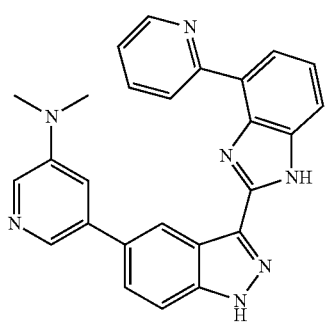 [SMILES: CN(C)c1cncc(-c2ccc3[nH]nc(-c4nc5c(-c6ccccn6)cccc5[nH]4)c3c2)c1] |
| 128 | 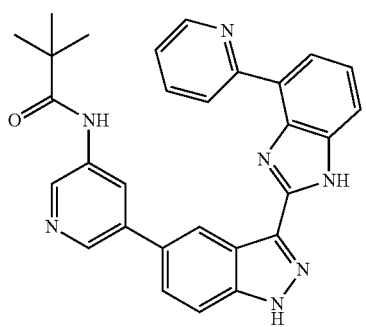 [SMILES: CC(C)(C)C(=O)Nc1cncc(-c2ccc3[nH]nc(-c4nc5c(-c6ccccn6)cccc5[nH]4)c3c2)c1] |

TABLE 1-continued
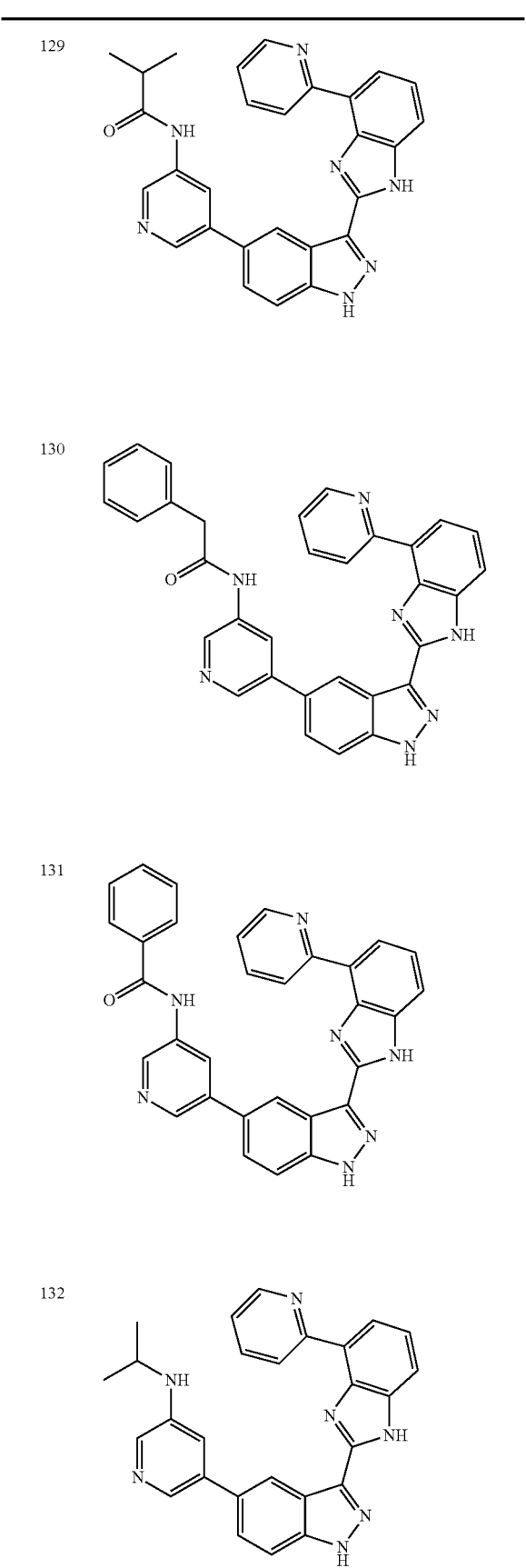
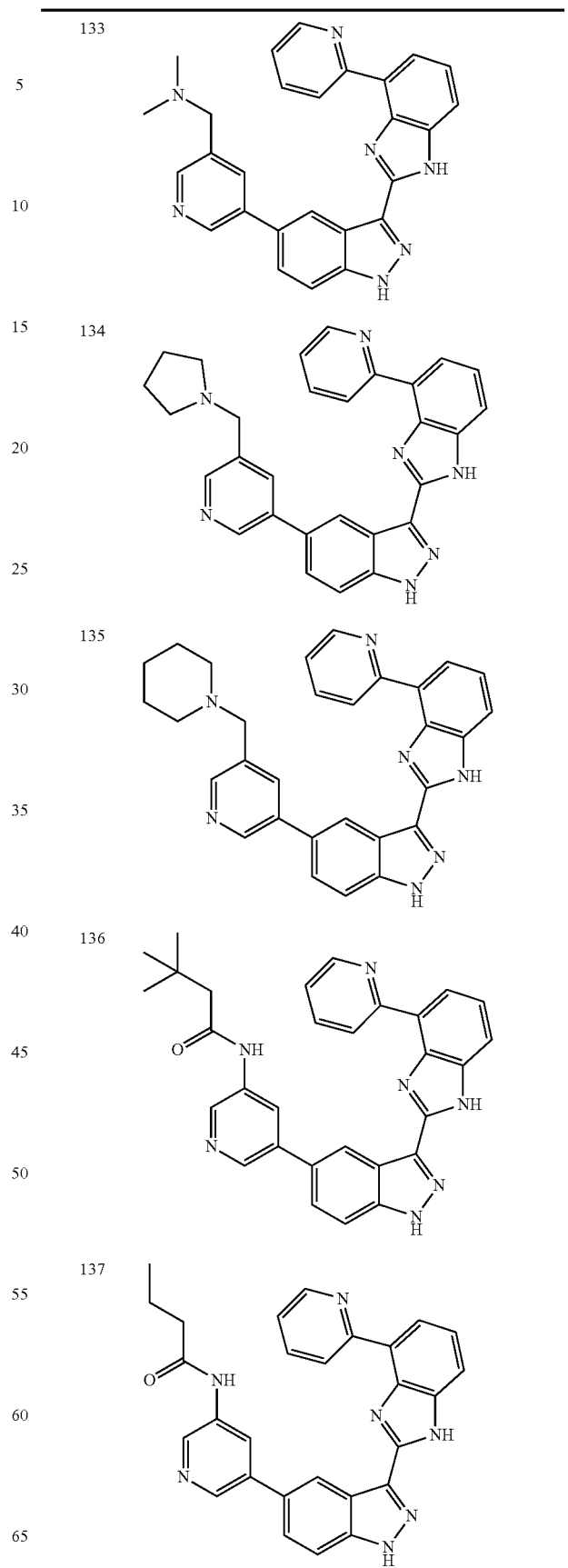

TABLE 1-continued
138 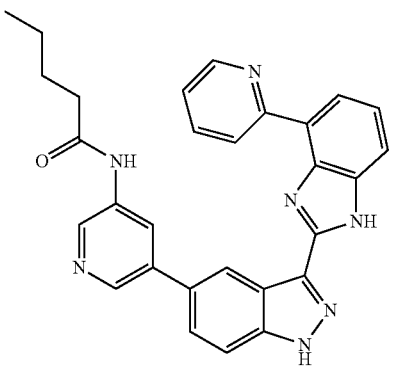 [SMILES: CCCCC(=O)Nc1cncc(-c2ccc3[nH]nc(-c4nc5c(-c6ccccn6)cccc5[nH]4)c3c2)c1]
139 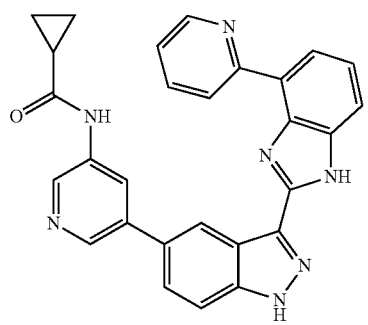 [SMILES: O=C(Nc1cncc(-c2ccc3[nH]nc(-c4nc5c(-c6ccccn6)cccc5[nH]4)c3c2)c1)C1CC1]
140 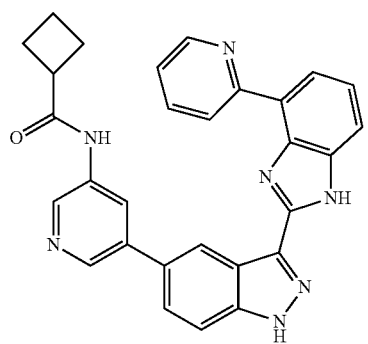 [SMILES: O=C(Nc1cncc(-c2ccc3[nH]nc(-c4nc5c(-c6ccccn6)cccc5[nH]4)c3c2)c1)C1CCC1]
141 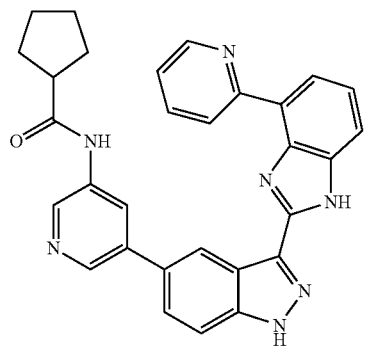 [SMILES: O=C(Nc1cncc(-c2ccc3[nH]nc(-c4nc5c(-c6ccccn6)cccc5[nH]4)c3c2)c1)C1CCCC1]
TABLE 1-continued
142 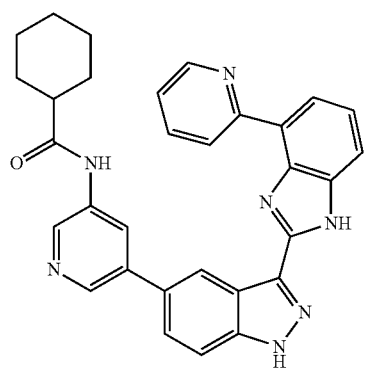 [SMILES: O=C(Nc1cncc(-c2ccc3[nH]nc(-c4nc5c(-c6ccccn6)cccc5[nH]4)c3c2)c1)C1CCCCC1]
143 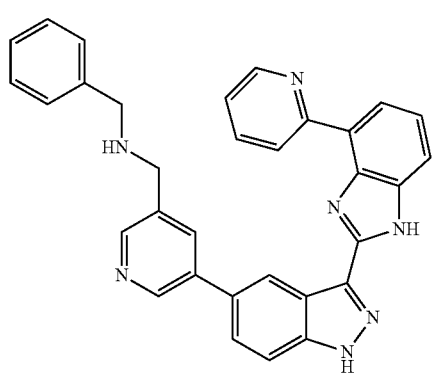 [SMILES: c1ccc(CNCc2cncc(-c3ccc4[nH]nc(-c5nc6c(-c7ccccn7)cccc6[nH]5)c4c3)c2)cc1]
144 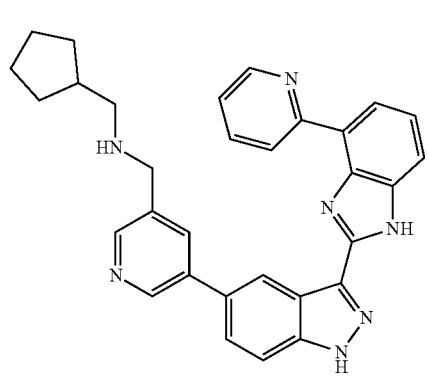 [SMILES: c1ccc(-c2cccc3[nH]c(-c4n[nH]c5ccc(-c6cncc(CNCC7CCCC7)c6)cc45)nc23)nc1]
145 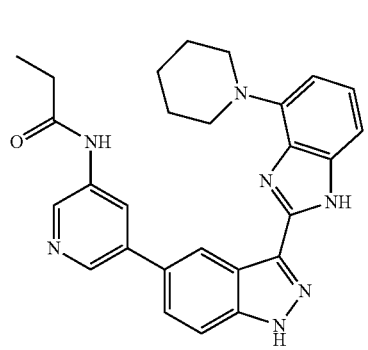 [SMILES: CCC(=O)Nc1cncc(-c2ccc3[nH]nc(-c4nc5c(N6CCCCC6)cccc5[nH]4)c3c2)c1]

TABLE 1-continued
| 146 | 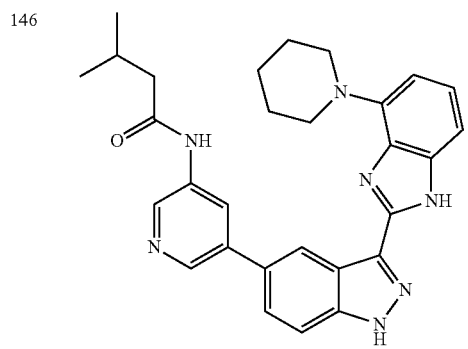 |
| --- | --- |
| 147 | 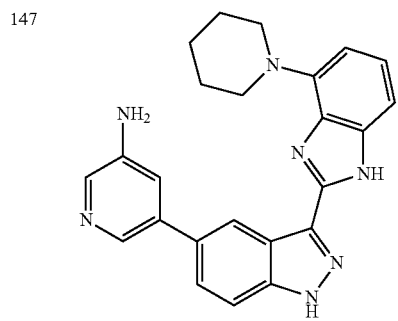 |
| 148 | 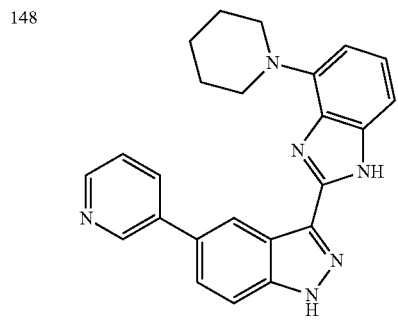 |
| 149 | 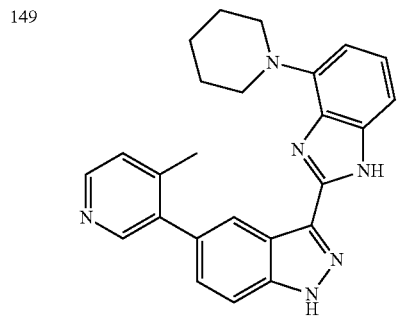 |
| 150 | 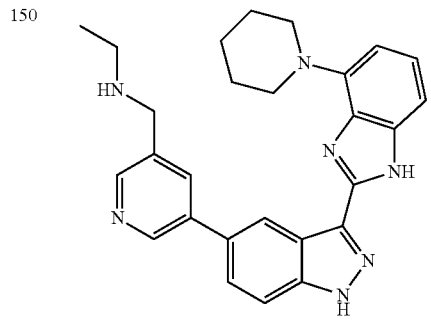 |
TABLE 1-continued
| 151 | 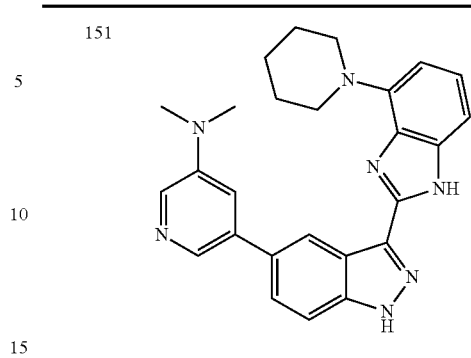 |
| --- | --- |
| 152 | 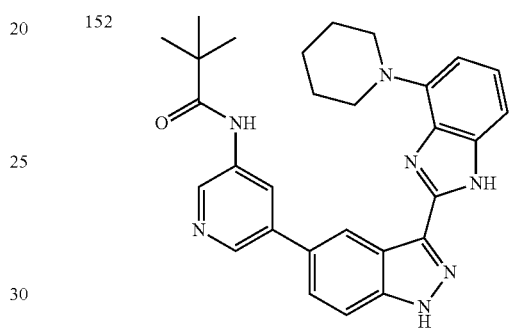 |
| 153 | 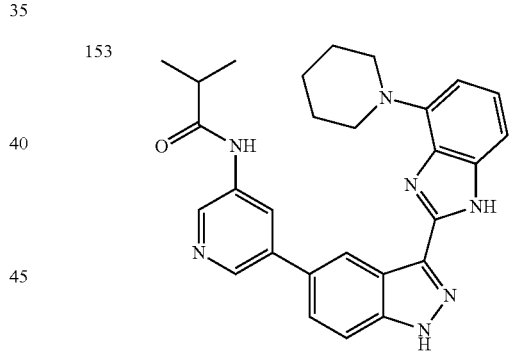 |
| 154 | 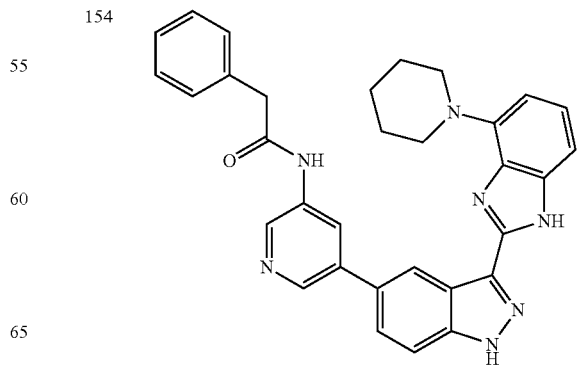 |

TABLE 1-continued
| 155 | 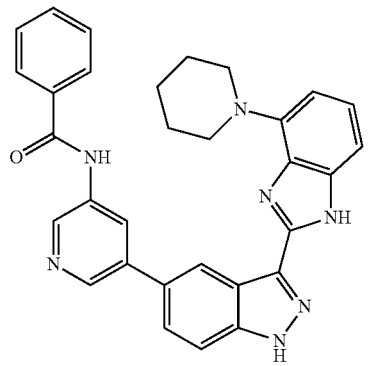 [SMILES: O=C(Nc1cncc(-c2ccc3[nH]nc(-c4nc5c(N6CCCCC6)cccc5[nH]4)c3c2)c1)c1ccccc1] |
| --- | --- |
| 156 | 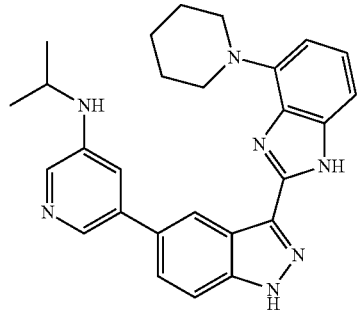 [SMILES: CC(C)Nc1cncc(-c2ccc3[nH]nc(-c4nc5c(N6CCCCC6)cccc5[nH]4)c3c2)c1] |
| 157 | 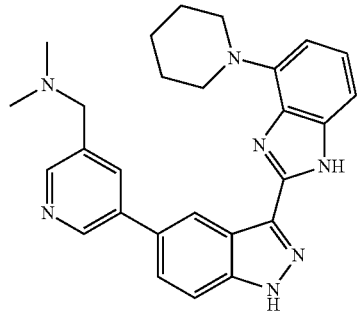 [SMILES: CN(C)Cc1cncc(-c2ccc3[nH]nc(-c4nc5c(N6CCCCC6)cccc5[nH]4)c3c2)c1] |
| 158 | 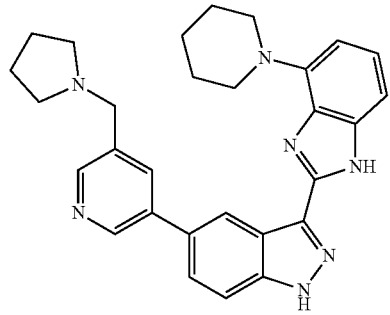 [SMILES: c1cc(N2CCCCC2)c2nc(-c3n[nH]c4ccc(-c5cncc(CN6CCCC6)c5)cc34)[nH]c2c1] |
| 159 | 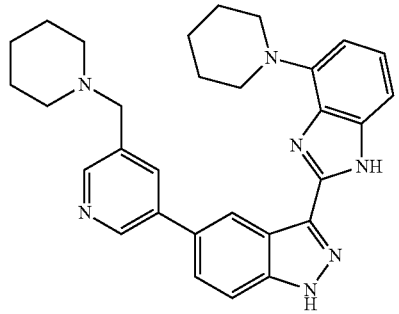 [SMILES: c1cc(N2CCCCC2)c2nc(-c3n[nH]c4ccc(-c5cncc(CN6CCCCC6)c5)cc34)[nH]c2c1] |
| 160 | 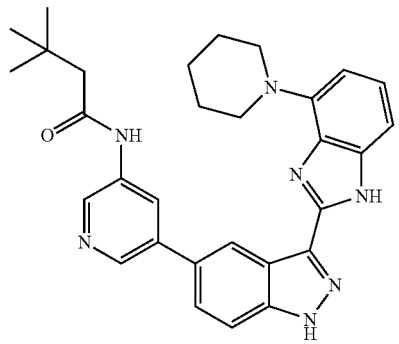 [SMILES: CC(C)(C)CC(=O)Nc1cncc(-c2ccc3[nH]nc(-c4nc5c(N6CCCCC6)cccc5[nH]4)c3c2)c1] |
| 161 | 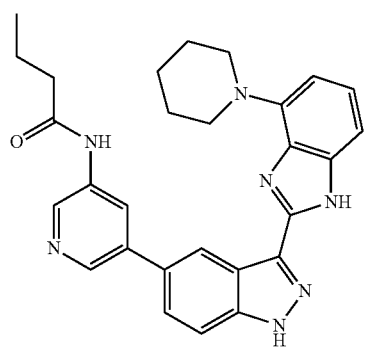 [SMILES: CCCC(=O)Nc1cncc(-c2ccc3[nH]nc(-c4nc5c(N6CCCCC6)cccc5[nH]4)c3c2)c1] |
| 162 | 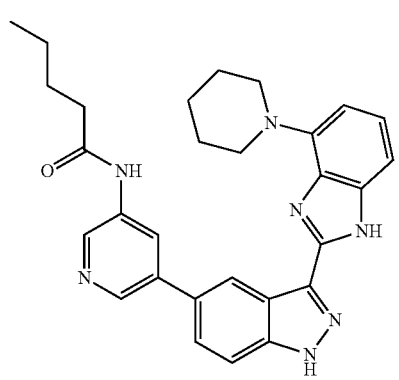 [SMILES: CCCCC(=O)Nc1cncc(-c2ccc3[nH]nc(-c4nc5c(N6CCCCC6)cccc5[nH]4)c3c2)c1] |
| 163 | 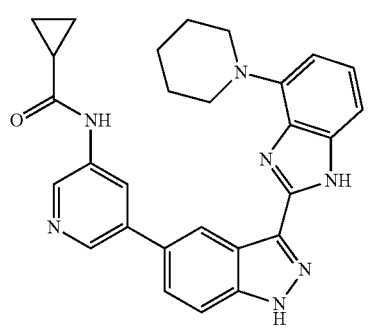 [SMILES: O=C(Nc1cncc(-c2ccc3[nH]nc(-c4nc5c(N6CCCCC6)cccc5[nH]4)c3c2)c1)C1CC1] |

TABLE 1-continued
164 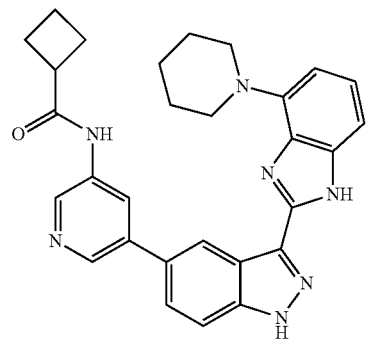 [SMILES: O=C(Nc1cncc(-c2ccc3[nH]nc(-c4nc5c(N6CCCCC6)cccc5[nH]4)c3c2)c1)C1CCC1]
165 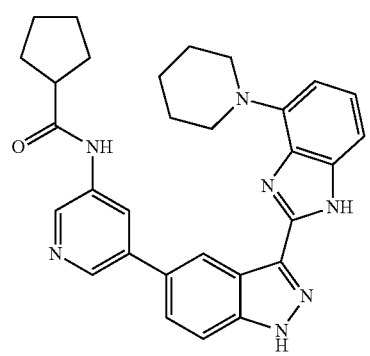 [SMILES: O=C(Nc1cncc(-c2ccc3[nH]nc(-c4nc5c(N6CCCCC6)cccc5[nH]4)c3c2)c1)C1CCCC1]
166 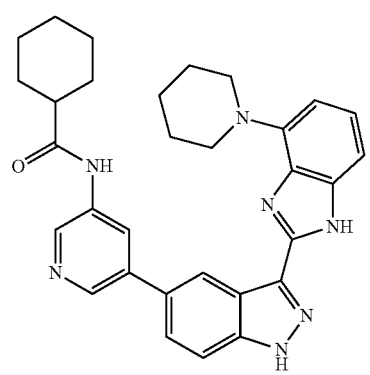 [SMILES: O=C(Nc1cncc(-c2ccc3[nH]nc(-c4nc5c(N6CCCCC6)cccc5[nH]4)c3c2)c1)C1CCCCC1]
167 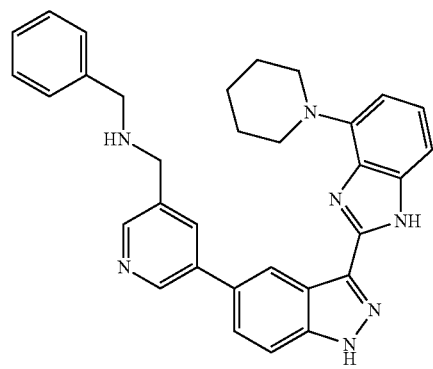 [SMILES: c1ccc(CNCc2cncc(-c3ccc4[nH]nc(-c5nc6c(N7CCCCC7)cccc6[nH]5)c4c3)c2)cc1]
TABLE 1-continued
168 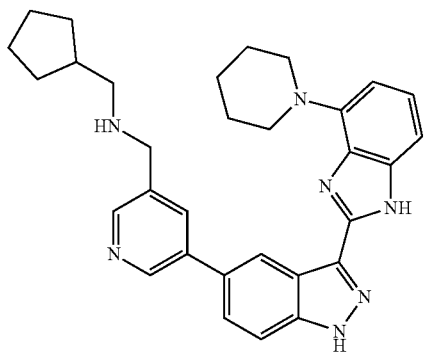 [SMILES: c1cc(N2CCCCC2)c2nc(-c3n[nH]c4ccc(-c5cncc(CNCC6CCCC6)c5)cc34)[nH]c2c1]
169 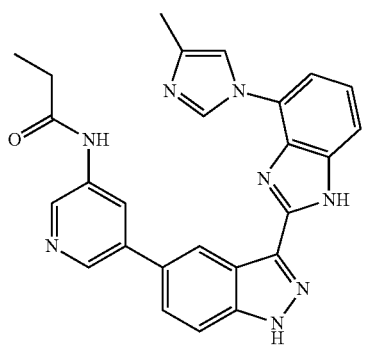 [SMILES: CCC(=O)Nc1cncc(-c2ccc3[nH]nc(-c4nc5c(-n6cnc(C)c6)cccc5[nH]4)c3c2)c1]
170 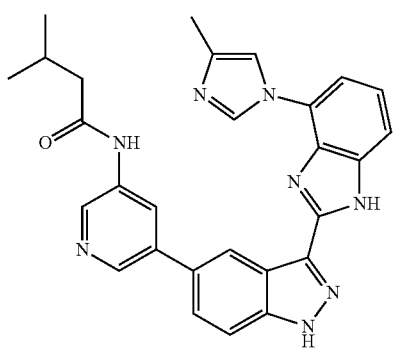 [SMILES: Cc1cn(-c2cccc3[nH]c(-c4n[nH]c5ccc(-c6cncc(NC(=O)CC(C)C)c6)cc45)nc23)cn1]
171 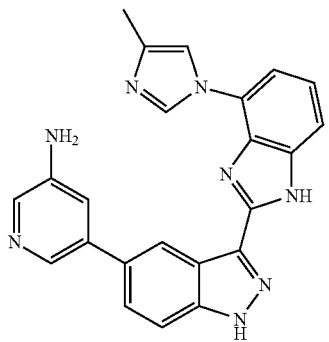 [SMILES: Cc1cn(-c2cccc3[nH]c(-c4n[nH]c5ccc(-c6cncc(N)c6)cc45)nc23)cn1]

TABLE 1-continued
172 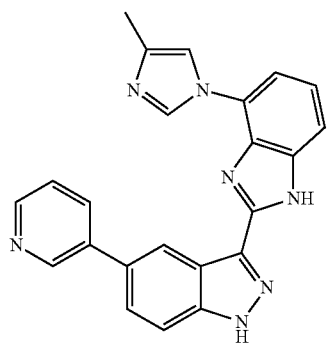 [SMILES: Cc1cn(-c2cccc3[nH]c(-c4n[nH]c5ccc(-c6cccnc6)cc45)nc23)cn1]
173 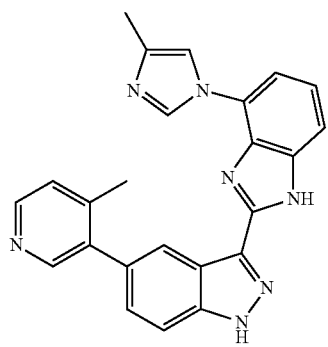 [SMILES: Cc1cn(-c2cccc3[nH]c(-c4n[nH]c5ccc(-c6cnccc6C)cc45)nc23)cn1]
174 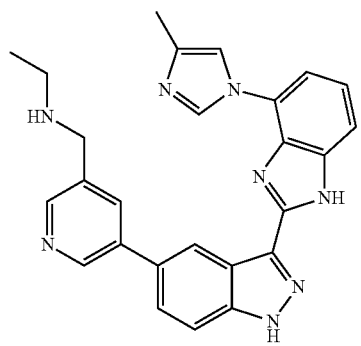 [SMILES: CCNCc1cncc(-c2ccc3[nH]nc(-c4nc5c(-n6cnc(C)c6)cccc5[nH]4)c3c2)c1]
175 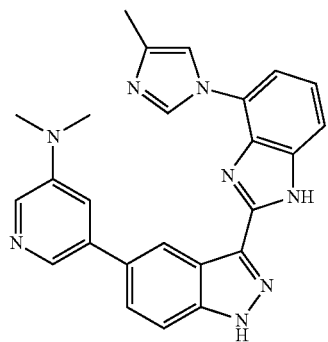 [SMILES: Cc1cn(-c2cccc3[nH]c(-c4n[nH]c5ccc(-c6cncc(N(C)C)c6)cc45)nc23)cn1]
TABLE 1-continued
176 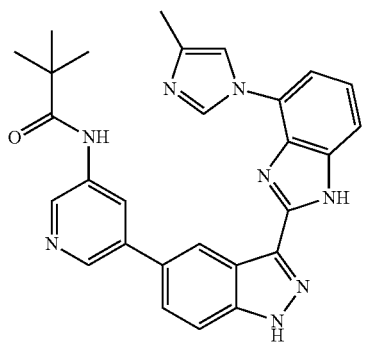 [SMILES: Cc1cn(-c2cccc3[nH]c(-c4n[nH]c5ccc(-c6cncc(NC(=O)C(C)(C)C)c6)cc45)nc23)cn1]
177 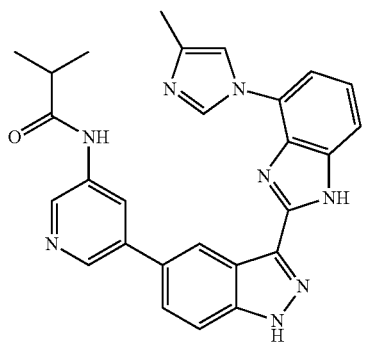 [SMILES: Cc1cn(-c2cccc3[nH]c(-c4n[nH]c5ccc(-c6cncc(NC(=O)C(C)C)c6)cc45)nc23)cn1]
178 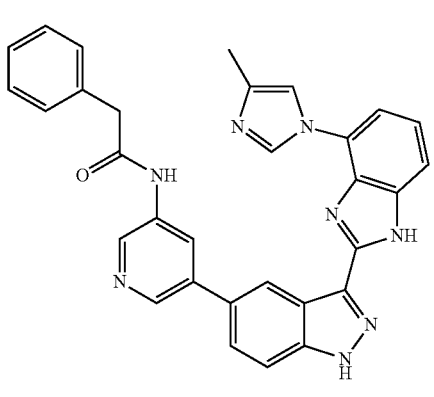 [SMILES: Cc1cn(-c2cccc3[nH]c(-c4n[nH]c5ccc(-c6cncc(NC(=O)Cc7ccccc7)c6)cc45)nc23)cn1]
179 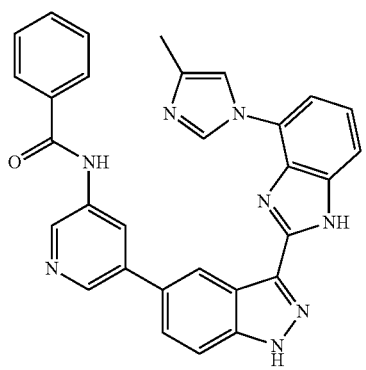 [SMILES: Cc1cn(-c2cccc3[nH]c(-c4n[nH]c5ccc(-c6cncc(NC(=O)c7ccccc7)c6)cc45)nc23)cn1]

TABLE 1-continued
180 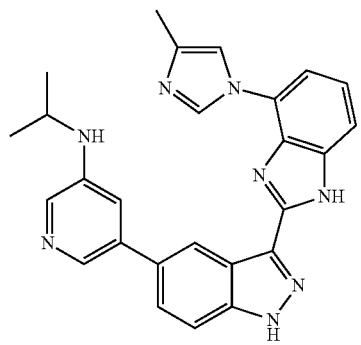 [SMILES: Cc1cn(-c2cccc3[nH]c(-c4n[nH]c5ccc(-c6cncc(NC(C)C)c6)cc45)nc23)cn1]
181 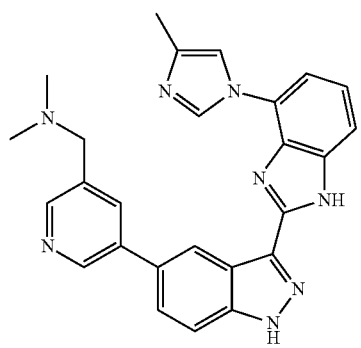 [SMILES: Cc1cn(-c2cccc3[nH]c(-c4n[nH]c5ccc(-c6cncc(CN(C)C)c6)cc45)nc23)cn1]
182 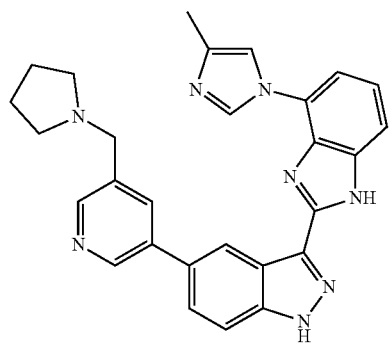 [SMILES: Cc1cn(-c2cccc3[nH]c(-c4n[nH]c5ccc(-c6cncc(CN7CCCC7)c6)cc45)nc23)cn1]
183 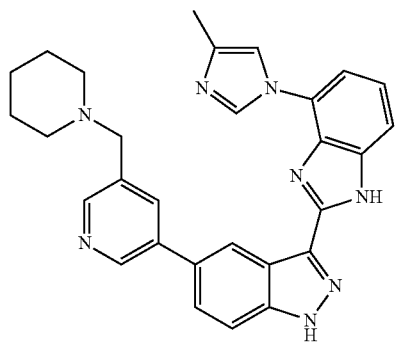 [SMILES: Cc1cn(-c2cccc3[nH]c(-c4n[nH]c5ccc(-c6cncc(CN7CCCCC7)c6)cc45)nc23)cn1]
184 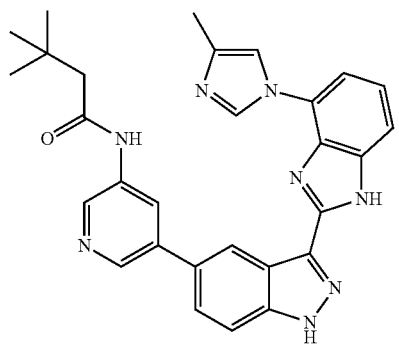 [SMILES: Cc1cn(-c2cccc3[nH]c(-c4n[nH]c5ccc(-c6cncc(NC(=O)CC(C)(C)C)c6)cc45)nc23)cn1]
185 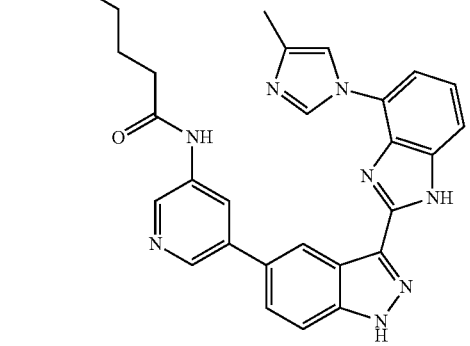
186 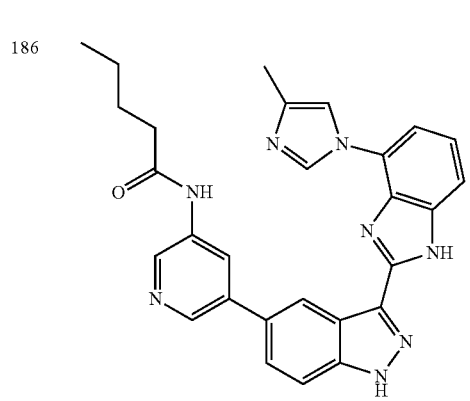
187 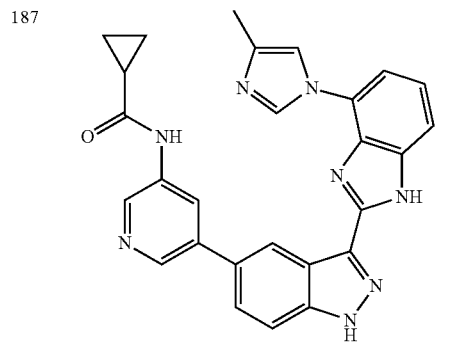

US 10,183,929 B2
TABLE 1-continued
| 188 | 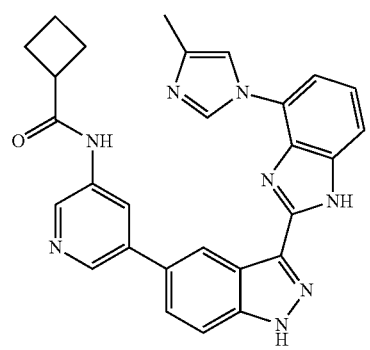 [SMILES: Cc1cn(-c2cccc3[nH]c(-c4n[nH]c5ccc(-c6cncc(NC(=O)C7CCC7)c6)cc45)nc23)cn1] |
| 189 | 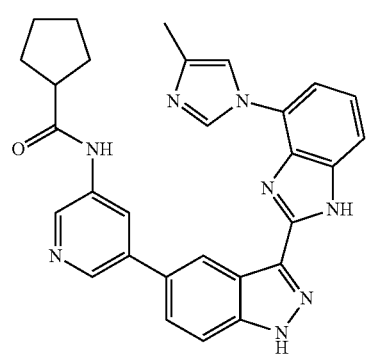 [SMILES: Cc1cn(-c2cccc3[nH]c(-c4n[nH]c5ccc(-c6cncc(NC(=O)C7CCCC7)c6)cc45)nc23)cn1] |
| 190 | 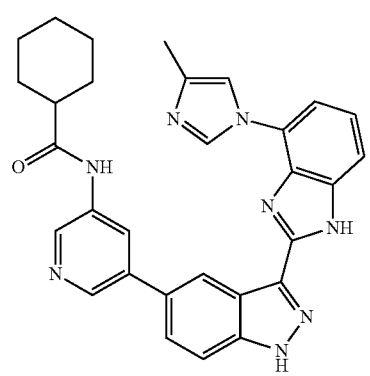 [SMILES: Cc1cn(-c2cccc3[nH]c(-c4n[nH]c5ccc(-c6cncc(NC(=O)C7CCCCC7)c6)cc45)nc23)cn1] |
| 191 | 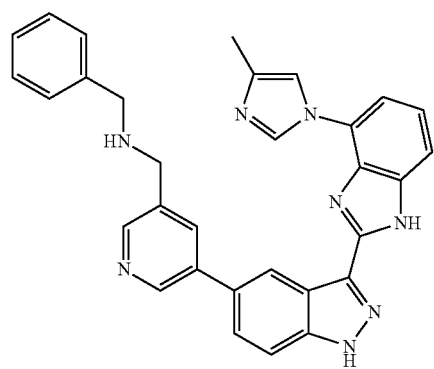 [SMILES: Cc1cn(-c2cccc3[nH]c(-c4n[nH]c5ccc(-c6cncc(CNCc7ccccc7)c6)cc45)nc23)cn1] |
TABLE 1-continued
| 192 | 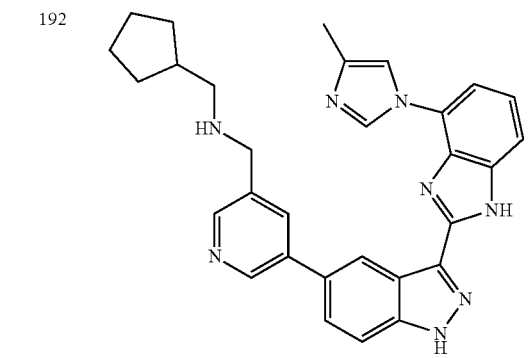 |
| 193 | 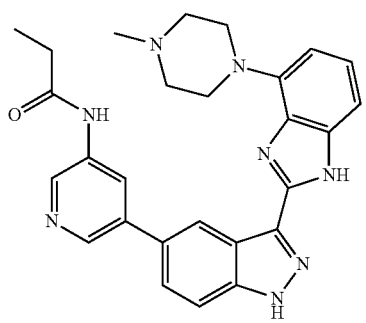 [SMILES: CCC(=O)Nc1cncc(-c2ccc3[nH]nc(-c4nc5c(N6CCN(C)CC6)cccc5[nH]4)c3c2)c1] |
| 194 | 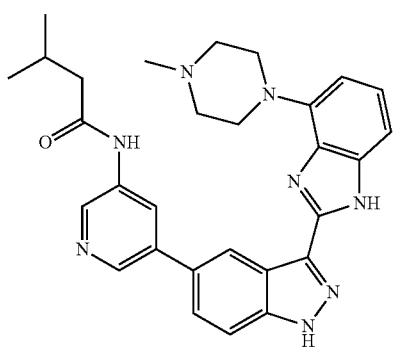 [SMILES: CC(C)CC(=O)Nc1cncc(-c2ccc3[nH]nc(-c4nc5c(N6CCN(C)CC6)cccc5[nH]4)c3c2)c1] |
| 195 | 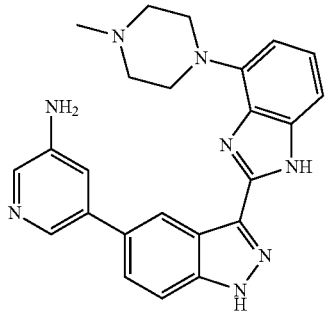 [SMILES: CN1CCN(c2cccc3[nH]c(-c4n[nH]c5ccc(-c6cncc(N)c6)cc45)nc23)CC1] |

TABLE 1-continued
196 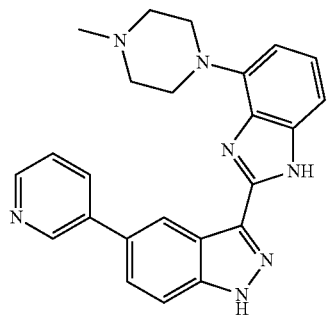 [SMILES: CN1CCN(c2cccc3[nH]c(-c4n[nH]c5ccc(-c6cccnc6)cc45)nc23)CC1]
197 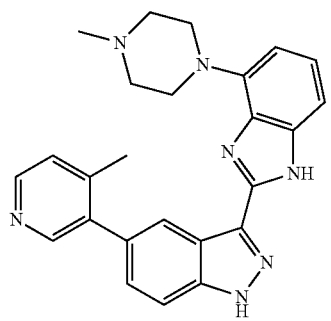 [SMILES: Cc1ccncc1-c1ccc2[nH]nc(-c3nc4c(N5CCN(C)CC5)cccc4[nH]3)c2c1]
198 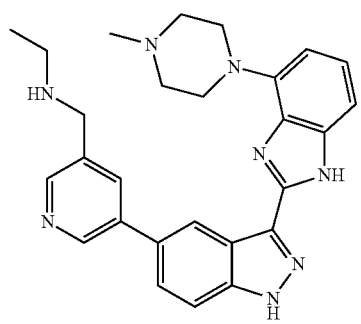 [SMILES: CCNCc1cncc(-c2ccc3[nH]nc(-c4nc5c(N6CCN(C)CC6)cccc5[nH]4)c3c2)c1]
199 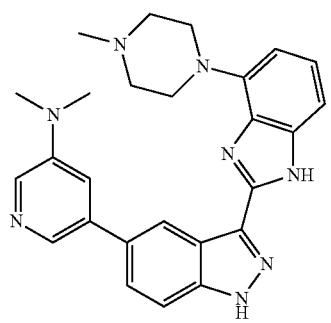 [SMILES: CN1CCN(c2cccc3[nH]c(-c4n[nH]c5ccc(-c6cncc(N(C)C)c6)cc45)nc23)CC1]
200 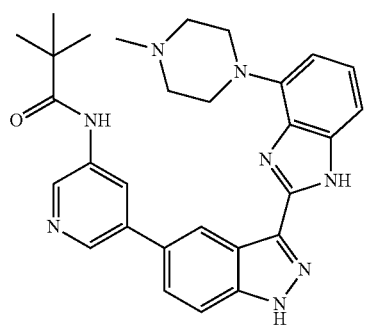
TABLE 1-continued
201 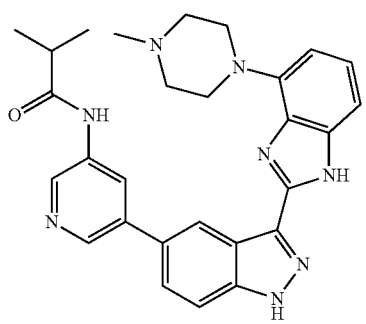 [SMILES: CC(C)C(=O)Nc1cncc(-c2ccc3[nH]nc(-c4nc5c(N6CCN(C)CC6)cccc5[nH]4)c3c2)c1]
202 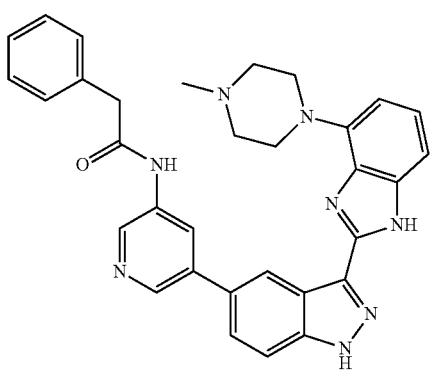 [SMILES: CN1CCN(c2cccc3[nH]c(-c4n[nH]c5ccc(-c6cncc(NC(=O)Cc7ccccc7)c6)cc45)nc23)CC1]
203 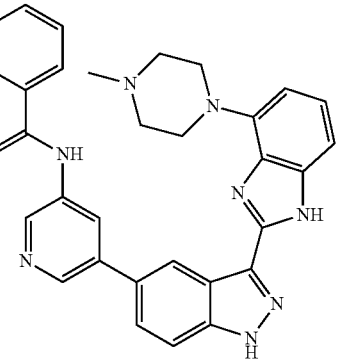
204 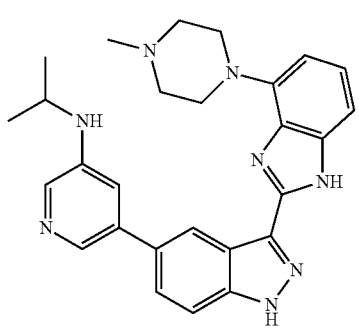 [SMILES: CC(C)Nc1cncc(-c2ccc3[nH]nc(-c4nc5c(N6CCN(C)CC6)cccc5[nH]4)c3c2)c1]

TABLE 1-continued
| 205 | 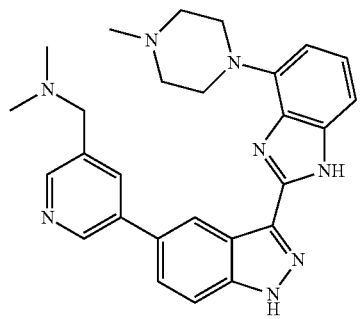 [SMILES: CN(C)Cc1cncc(-c2ccc3[nH]nc(-c4nc5c(N6CCN(C)CC6)cccc5[nH]4)c3c2)c1] |
| --- | --- |
| 206 | 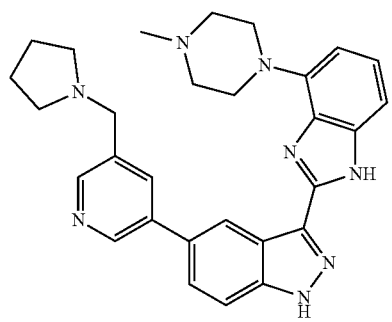 [SMILES: CN1CCN(c2cccc3[nH]c(-c4n[nH]c5ccc(-c6cncc(CN7CCCC7)c6)cc45)nc23)CC1] |
| 207 | 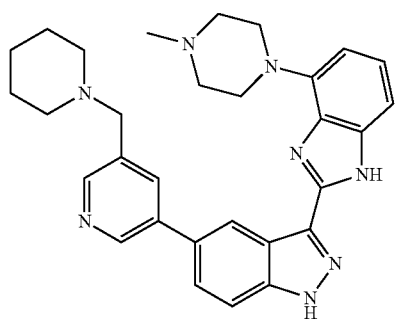 [SMILES: CN1CCN(c2cccc3[nH]c(-c4n[nH]c5ccc(-c6cncc(CN7CCCCC7)c6)cc45)nc23)CC1] |
| 208 | 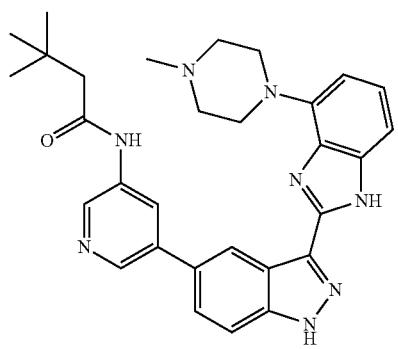 [SMILES: CN1CCN(c2cccc3[nH]c(-c4n[nH]c5ccc(-c6cncc(NC(=O)CC(C)(C)C)c6)cc45)nc23)CC1] |
| 209 | 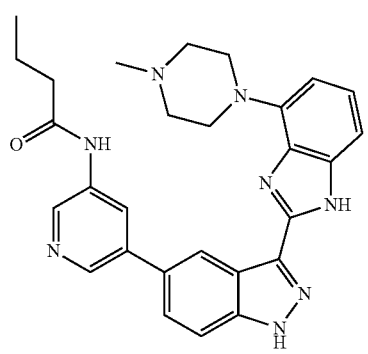 [SMILES: CCCC(=O)Nc1cncc(-c2ccc3[nH]nc(-c4nc5c(N6CCN(C)CC6)cccc5[nH]4)c3c2)c1] |
| 210 | 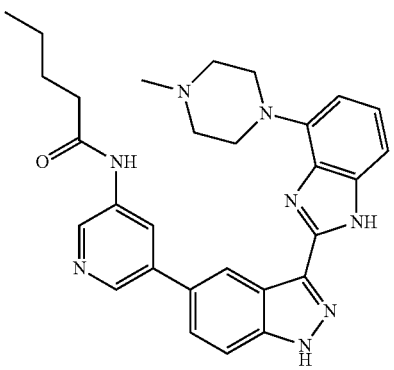 [SMILES: CCCCC(=O)Nc1cncc(-c2ccc3[nH]nc(-c4nc5c(N6CCN(C)CC6)cccc5[nH]4)c3c2)c1] |
| 211 | 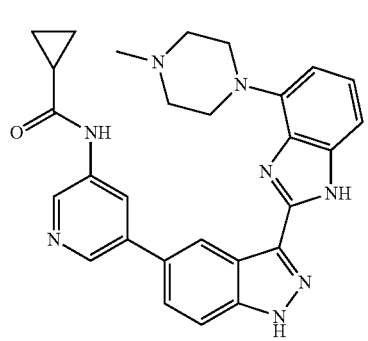 [SMILES: CN1CCN(c2cccc3[nH]c(-c4n[nH]c5ccc(-c6cncc(NC(=O)C7CC7)c6)cc45)nc23)CC1] |
| 212 | 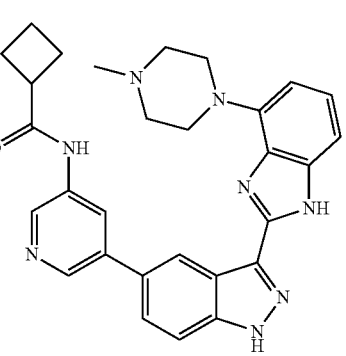 |
| 213 | 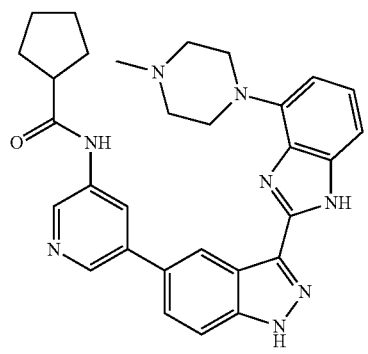 [SMILES: CN1CCN(c2cccc3[nH]c(-c4n[nH]c5ccc(-c6cncc(NC(=O)C7CCCC7)c6)cc45)nc23)CC1] |

TABLE 1-continued
214 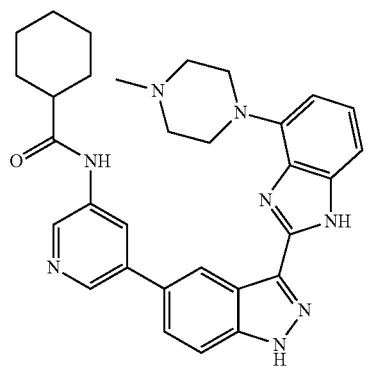 [SMILES: CN1CCN(c2cccc3[nH]c(-c4n[nH]c5ccc(-c6cncc(NC(=O)C7CCCCC7)c6)cc45)nc23)CC1]
215 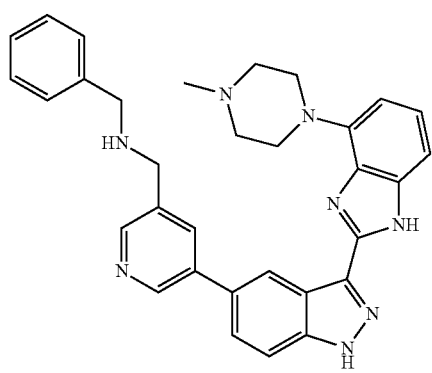 [SMILES: CN1CCN(c2cccc3[nH]c(-c4n[nH]c5ccc(-c6cncc(CNCc7ccccc7)c6)cc45)nc23)CC1]
216 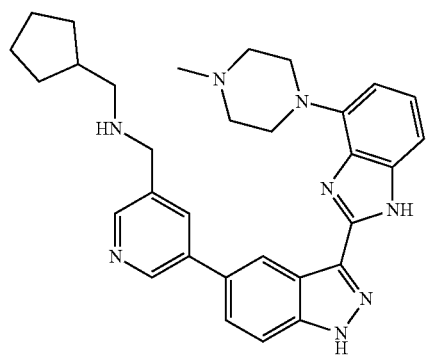 [SMILES: CN1CCN(c2cccc3[nH]c(-c4n[nH]c5ccc(-c6cncc(CNCC7CCCC7)c6)cc45)nc23)CC1]
217 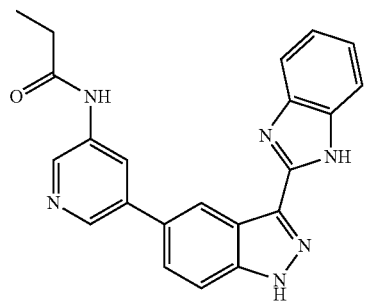 [SMILES: CCC(=O)Nc1cncc(-c2ccc3[nH]nc(-c4nc5ccccc5[nH]4)c3c2)c1]
TABLE 1-continued
218 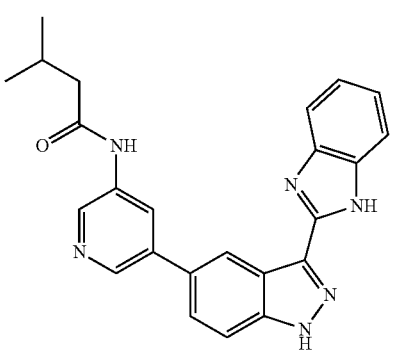 [SMILES: CC(C)CC(=O)Nc1cncc(-c2ccc3[nH]nc(-c4nc5ccccc5[nH]4)c3c2)c1]
219 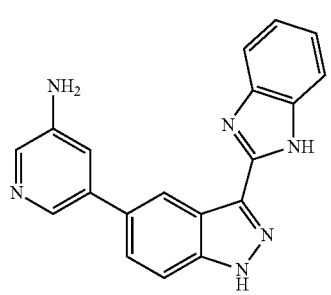 [SMILES: Nc1cncc(-c2ccc3[nH]nc(-c4nc5ccccc5[nH]4)c3c2)c1]
220 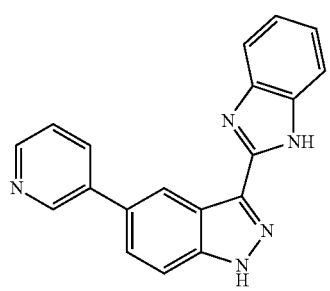 [SMILES: c1cncc(-c2ccc3[nH]nc(-c4nc5ccccc5[nH]4)c3c2)c1]
221 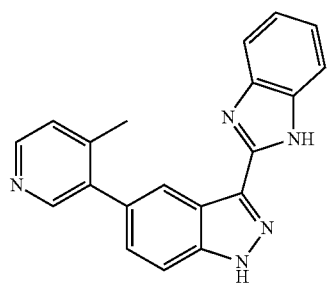 [SMILES: Cc1ccncc1-c1ccc2[nH]nc(-c3nc4ccccc4[nH]3)c2c1]
222 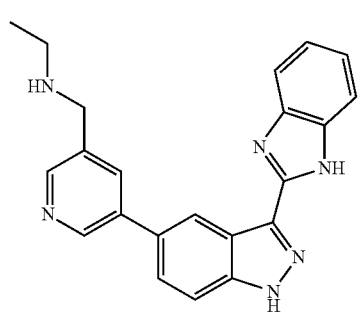 [SMILES: CCNCc1cncc(-c2ccc3[nH]nc(-c4nc5ccccc5[nH]4)c3c2)c1]

TABLE 1-continued
| 223 | 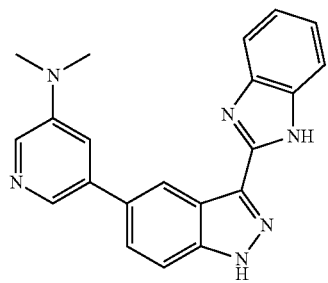 [SMILES: CN(C)c1cncc(-c2ccc3[nH]nc(-c4nc5ccccc5[nH]4)c3c2)c1] |
| 224 | 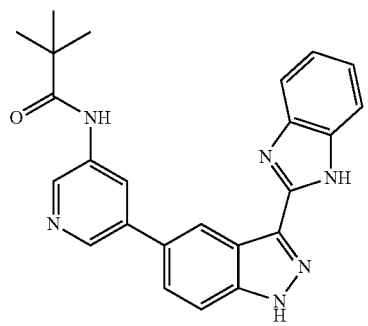 [SMILES: CC(C)(C)C(=O)Nc1cncc(-c2ccc3[nH]nc(-c4nc5ccccc5[nH]4)c3c2)c1] |
| 225 | 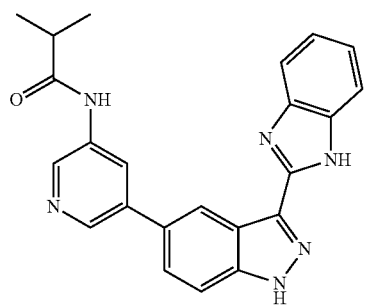 [SMILES: CC(C)C(=O)Nc1cncc(-c2ccc3[nH]nc(-c4nc5ccccc5[nH]4)c3c2)c1] |
| 226 | 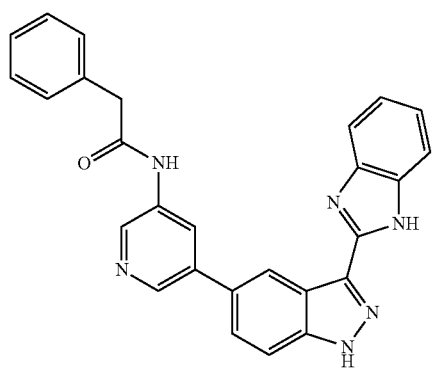 [SMILES: O=C(Cc1ccccc1)Nc1cncc(-c2ccc3[nH]nc(-c4nc5ccccc5[nH]4)c3c2)c1] |
| 227 | 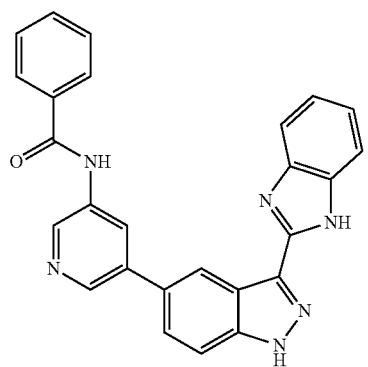 [SMILES: O=C(Nc1cncc(-c2ccc3[nH]nc(-c4nc5ccccc5[nH]4)c3c2)c1)c1ccccc1] |
| 228 | 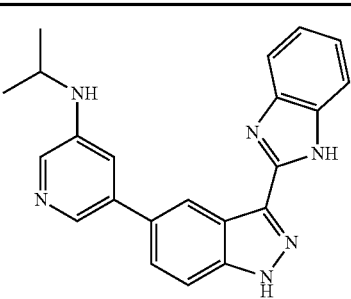 |
| 229 | 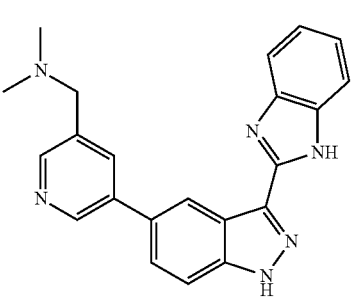 [SMILES: CN(C)Cc1cncc(-c2ccc3[nH]nc(-c4nc5ccccc5[nH]4)c3c2)c1] |
| 230 | 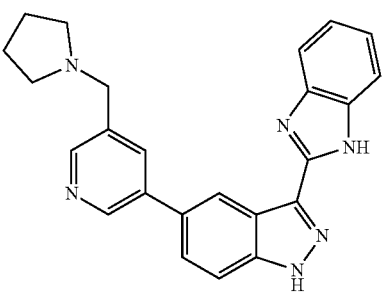 [SMILES: c1ccc2[nH]c(-c3n[nH]c4ccc(-c5cncc(CN6CCCC6)c5)cc34)nc2c1] |
| 231 | 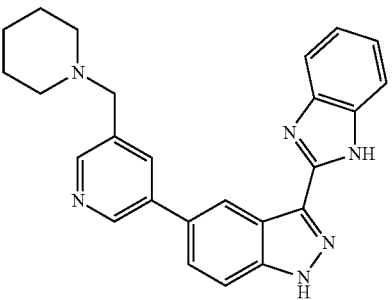 [SMILES: c1ccc2[nH]c(-c3n[nH]c4ccc(-c5cncc(CN6CCCCC6)c5)cc34)nc2c1] |
| 232 | 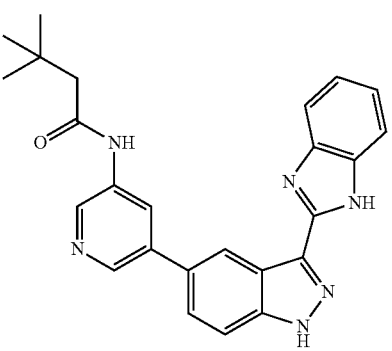 [SMILES: CC(C)(C)CC(=O)Nc1cncc(-c2ccc3[nH]nc(-c4nc5ccccc5[nH]4)c3c2)c1] |

TABLE 1-continued
233 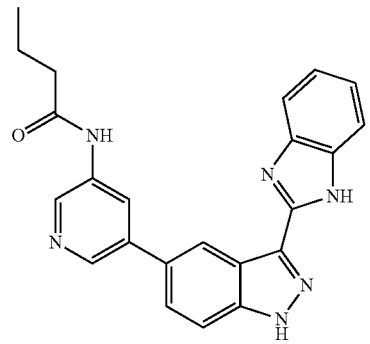 [SMILES: CCCC(=O)Nc1cncc(-c2ccc3[nH]nc(-c4nc5ccccc5[nH]4)c3c2)c1]
234 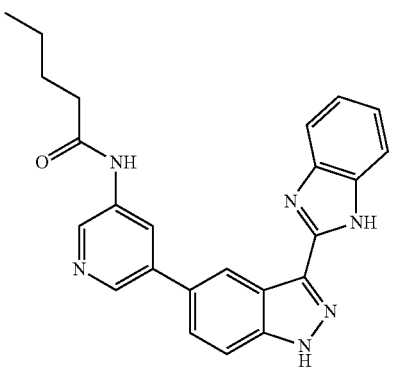 [SMILES: CCCCC(=O)Nc1cncc(-c2ccc3[nH]nc(-c4nc5ccccc5[nH]4)c3c2)c1]
235 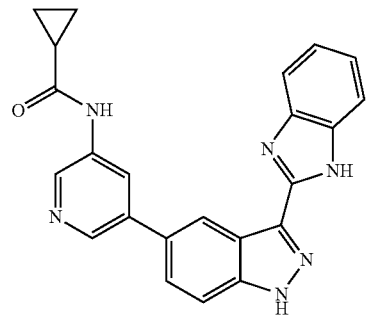 [SMILES: O=C(Nc1cncc(-c2ccc3[nH]nc(-c4nc5ccccc5[nH]4)c3c2)c1)C1CC1]
236 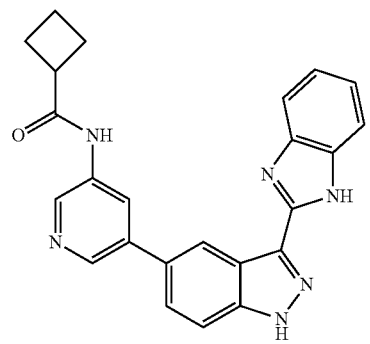 [SMILES: O=C(Nc1cncc(-c2ccc3[nH]nc(-c4nc5ccccc5[nH]4)c3c2)c1)C1CCC1]
TABLE 1-continued
237 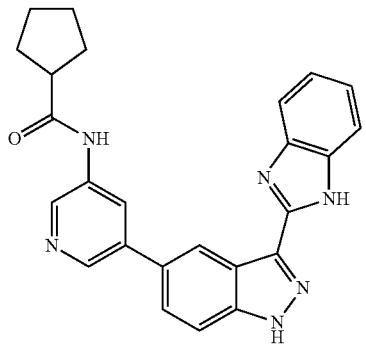 [SMILES: O=C(Nc1cncc(-c2ccc3[nH]nc(-c4nc5ccccc5[nH]4)c3c2)c1)C1CCCC1]
238 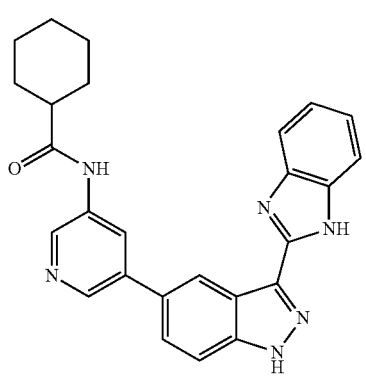 [SMILES: O=C(Nc1cncc(-c2ccc3[nH]nc(-c4nc5ccccc5[nH]4)c3c2)c1)C1CCCCC1]
239 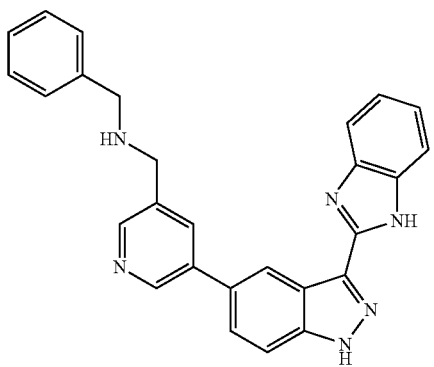 [SMILES: c1ccc(CNCc2cncc(-c3ccc4[nH]nc(-c5nc6ccccc6[nH]5)c4c3)c2)cc1]
240 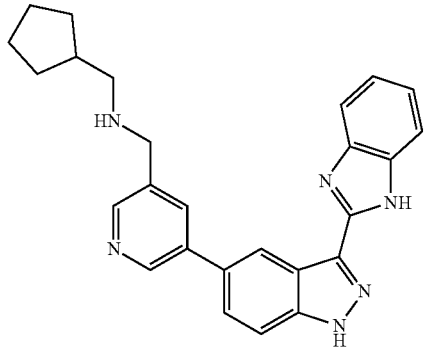 [SMILES: c1ccc2[nH]c(-c3n[nH]c4ccc(-c5cncc(CNCC6CCCC6)c5)cc34)nc2c1]

TABLE 1-continued
| | | | | |
|---|---|---|---|---|
| 241 | 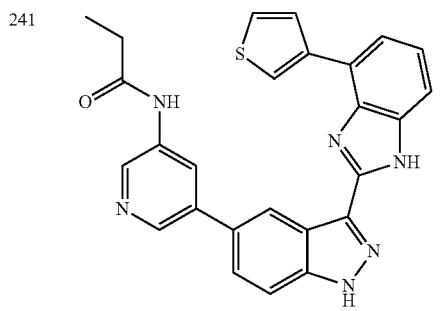 | | 246 | 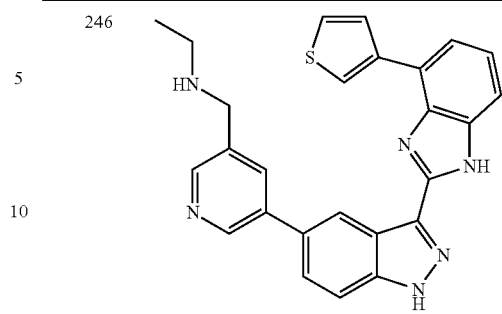 |
| 242 | 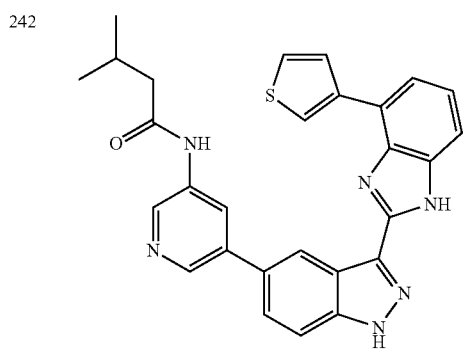 | | 247 | 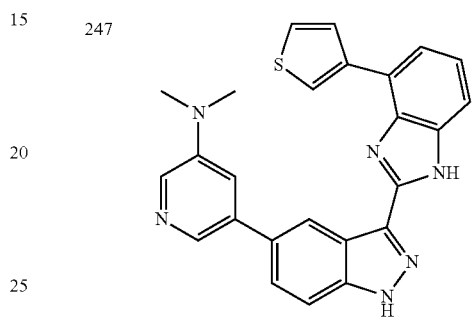 |
| 243 | 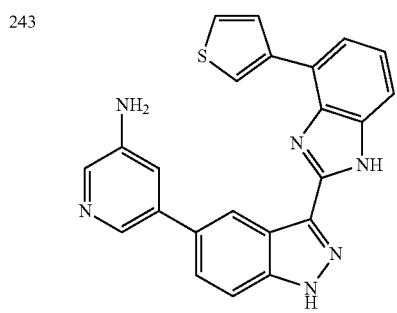 | | 248 | 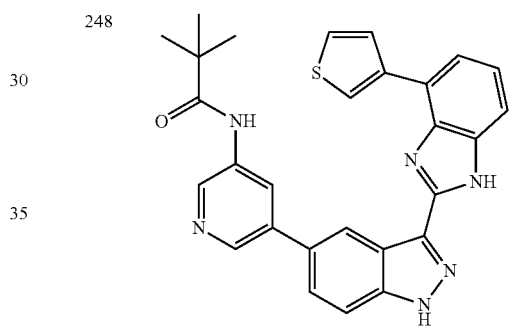 |
| 244 | 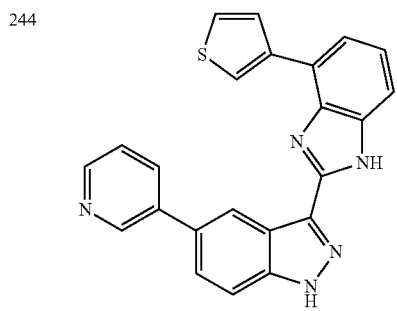 | | 249 | 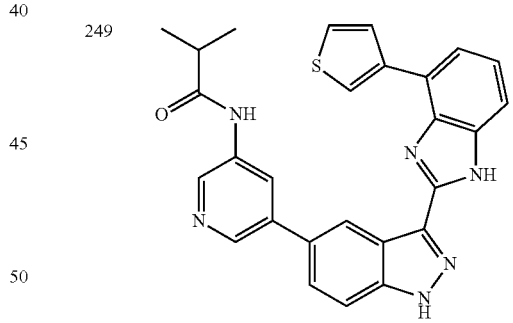 |
| 245 | 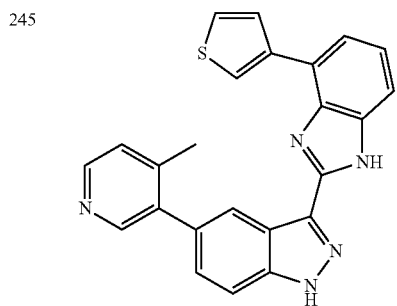 | | 250 | 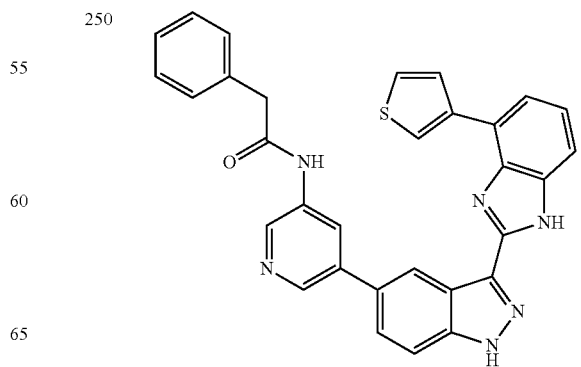 |

TABLE 1-continued
| 251 | 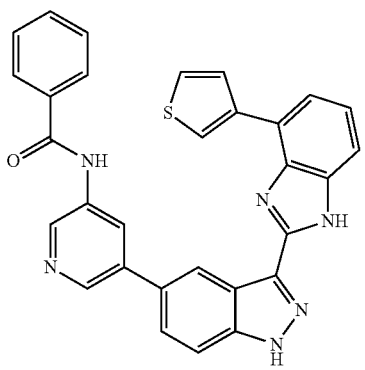 |
| --- | --- |
| 252 | 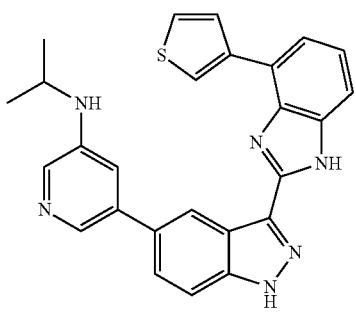 |
| 253 | 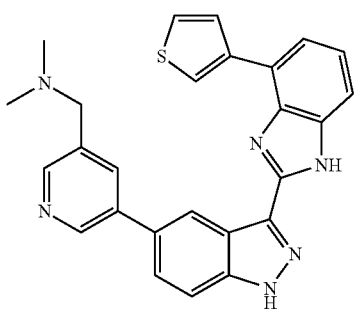 |
| 254 | 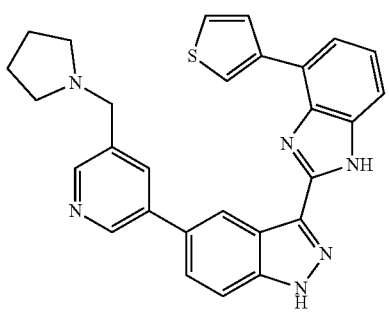 |
| 255 | 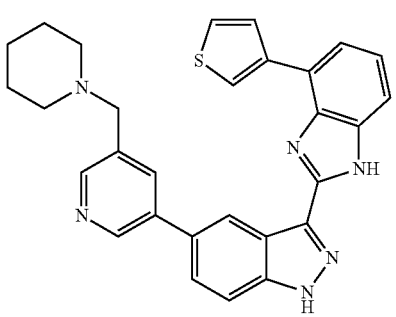 [SMILES: c1cc(-c2ccsc2)c2nc(-c3n[nH]c4ccc(-c5cncc(CN6CCCCC6)c5)cc34)[nH]c2c1] |
| 256 | 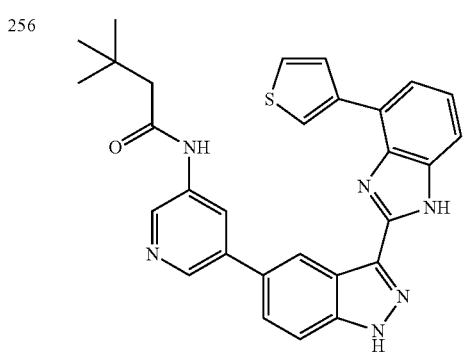 |
| 257 | 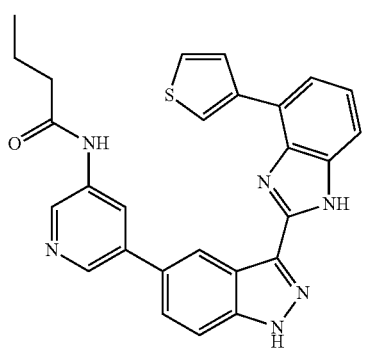 [SMILES: CCCC(=O)Nc1cncc(-c2ccc3[nH]nc(-c4nc5c(-c6ccsc6)cccc5[nH]4)c3c2)c1] |
| 258 | 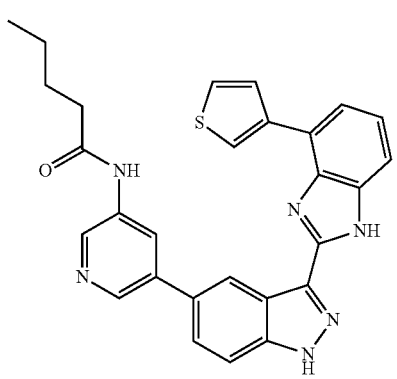 [SMILES: CCCCC(=O)Nc1cncc(-c2ccc3[nH]nc(-c4nc5c(-c6ccsc6)cccc5[nH]4)c3c2)c1] |
| 259 | 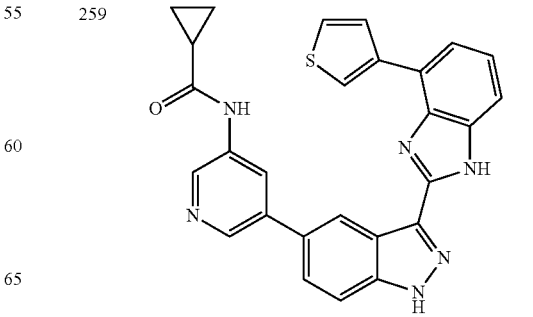 |

TABLE 1-continued
| 260 | 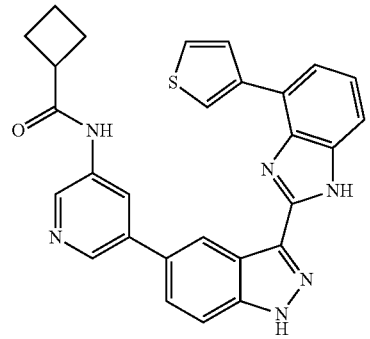 |
| --- | --- |
| 261 | 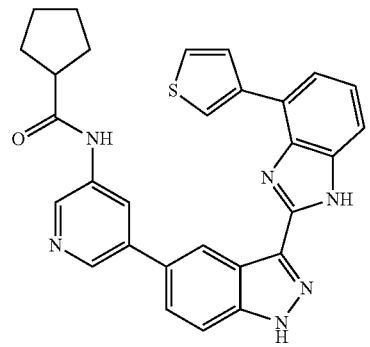 |
| 262 | 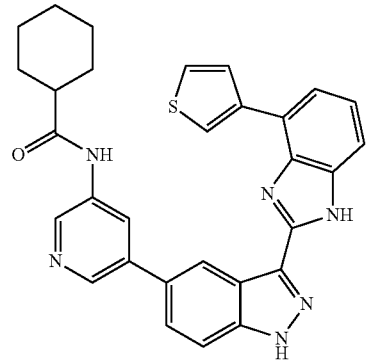 |
| 263 | 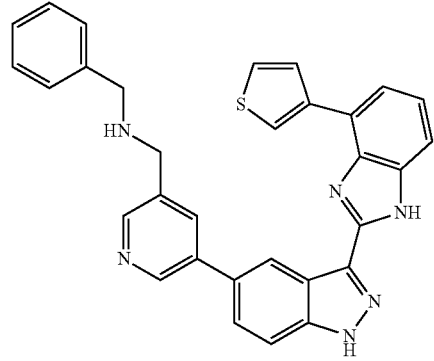 [SMILES: c1ccc(CNCc2cncc(-c3ccc4[nH]nc(-c5nc6c(-c7ccsc7)cccc6[nH]5)c4c3)c2)cc1] |
TABLE 1-continued
| 264 | 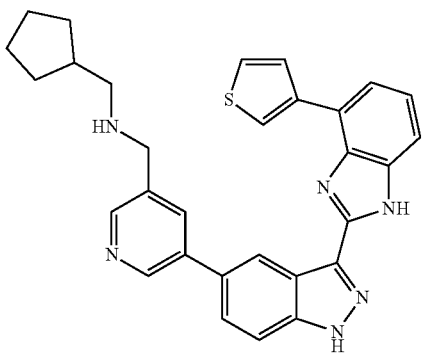 [SMILES: c1cc(-c2ccsc2)c2nc(-c3n[nH]c4ccc(-c5cncc(CNCC6CCCC6)c5)cc34)[nH]c2c1] |
| --- | --- |
| 265 | 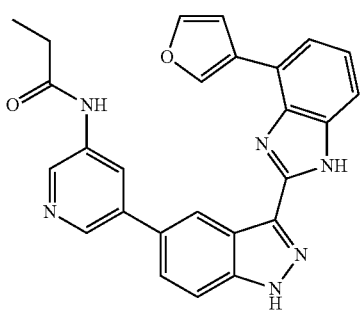 [SMILES: CCC(=O)Nc1cncc(-c2ccc3[nH]nc(-c4nc5c(-c6ccoc6)cccc5[nH]4)c3c2)c1] |
| 266 | 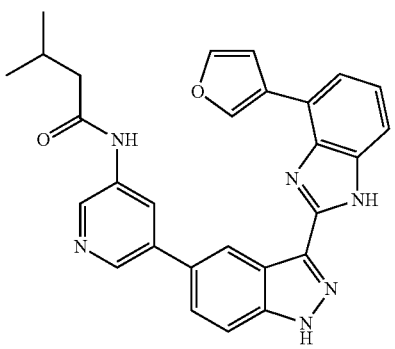 [SMILES: CC(C)CC(=O)Nc1cncc(-c2ccc3[nH]nc(-c4nc5c(-c6ccoc6)cccc5[nH]4)c3c2)c1] |
| 267 | 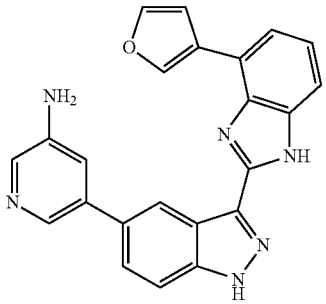 [SMILES: Nc1cncc(-c2ccc3[nH]nc(-c4nc5c(-c6ccoc6)cccc5[nH]4)c3c2)c1] |
| 268 | 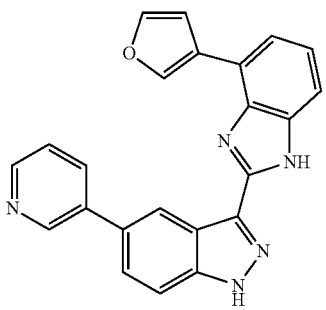 |

TABLE 1-continued
269
270
271
272
273
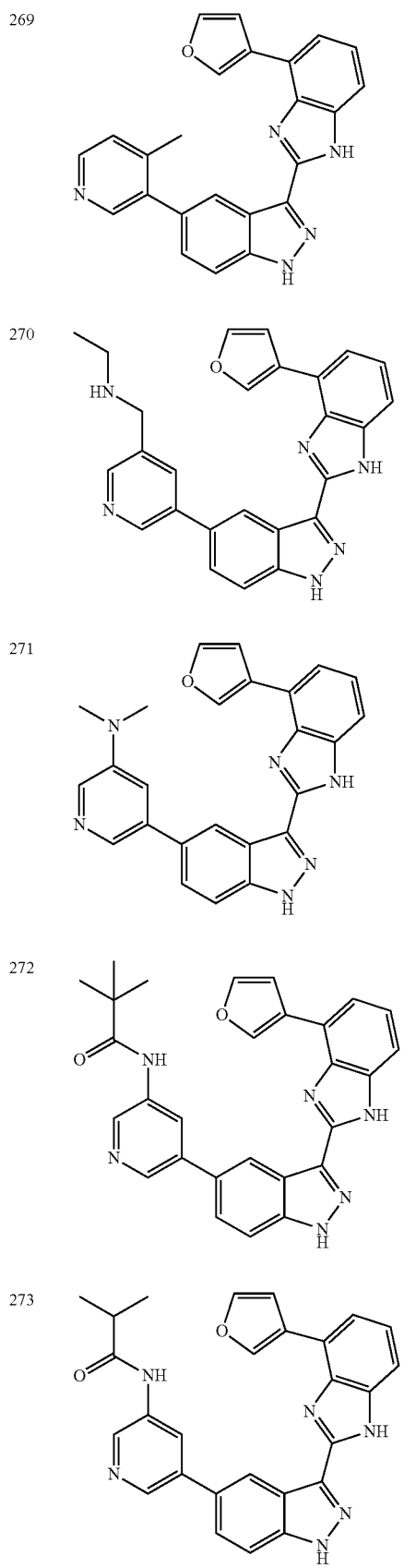
TABLE 1-continued
274
275
276
277
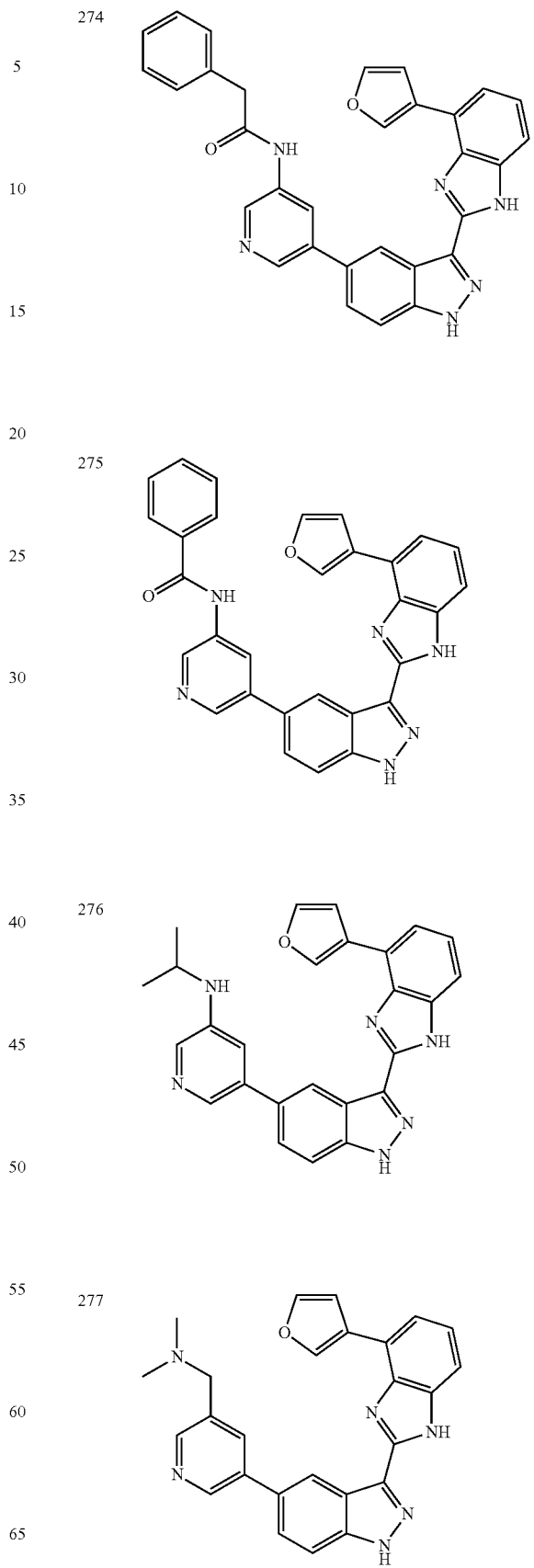

TABLE 1-continued
| | |
|---|---|
| 278 | 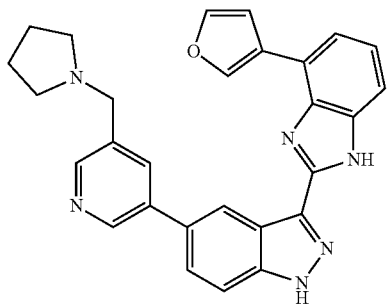 [SMILES: c1cc(-c2ccoc2)c2nc(-c3n[nH]c4ccc(-c5cncc(CN6CCCC6)c5)cc34)[nH]c2c1] |
| 279 | 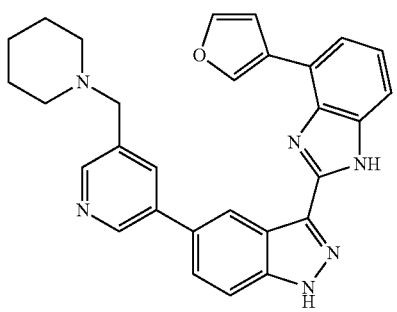 [SMILES: c1cc(-c2ccoc2)c2nc(-c3n[nH]c4ccc(-c5cncc(CN6CCCCC6)c5)cc34)[nH]c2c1] |
| 280 | 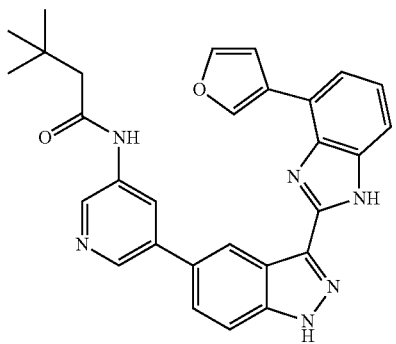 |
| 281 | 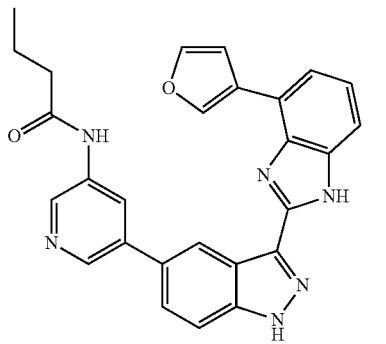 |
| 282 | 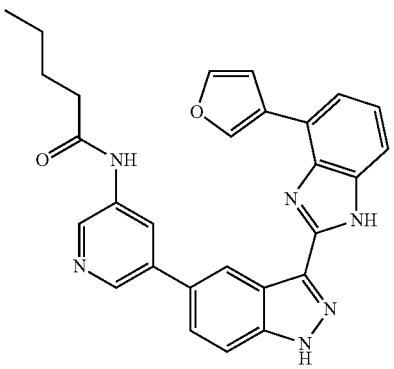 [SMILES: CCCCC(=O)Nc1cncc(-c2ccc3[nH]nc(-c4nc5c(-c6ccoc6)cccc5[nH]4)c3c2)c1] |
| 283 | 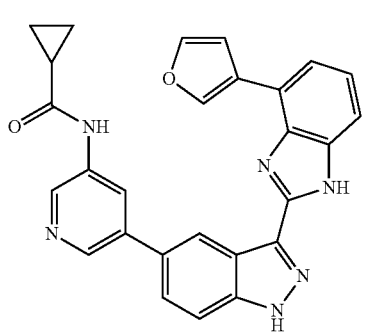 [SMILES: O=C(Nc1cncc(-c2ccc3[nH]nc(-c4nc5c(-c6ccoc6)cccc5[nH]4)c3c2)c1)C1CC1] |
| 284 | 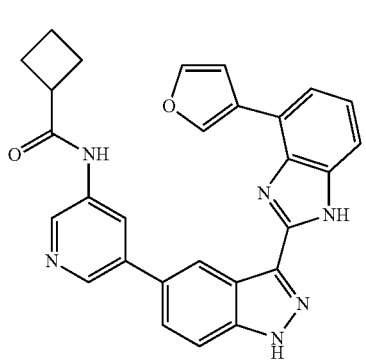 |
| 285 | 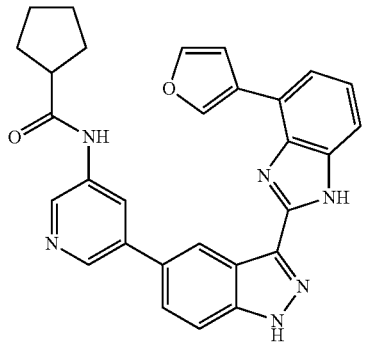 |

TABLE 1-continued

286
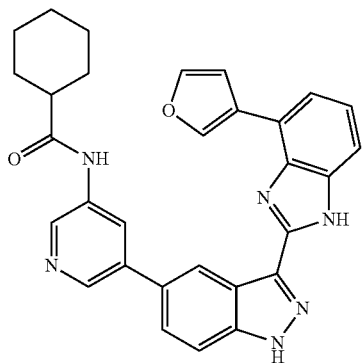 [SMILES: O=C(Nc1cncc(-c2ccc3[nH]nc(-c4nc5c(-c6ccoc6)cccc5[nH]4)c3c2)c1)C1CCCCC1]

287
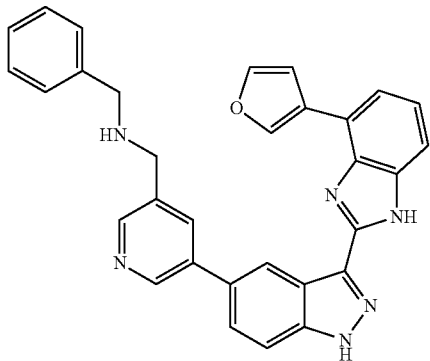

288
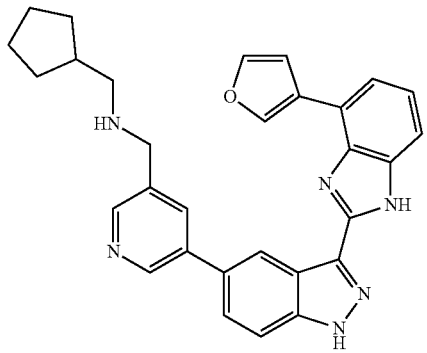

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other known agents.

Non-limiting examples of diseases which can be treated with a combination of a compound of Formula (I) or (Ia) and other known agents are colorectal cancer, ovarian cancer, diabetic retinopathy, pulmonary fibrosis, and osteoarthritis.

In some embodiments, colorectal cancer can be treated with a combination of a compound of either Formula (I) or (Ia) and one or more of the following drugs: 5-Fluorouracil (5-FU), which can be administered with the vitamin-like drug leucovorin (also called folinic acid); capecitabine (Xeloda®), irinotecan (Camptosar®), oxaliplatin (Eloxatin®). Examples of combinations of these drugs which could be further combined with a compound of either Formula (I) or (Ia) are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of either Formula (I) or (Ia) and one or more of the following drugs: Topotecan, Liposomal doxorubicin (Doxil®), Gemcitabine (Gemzar®), Cyclophosphamide (Cytoxan®), Vinorelbine (Navelbine®), Ifosfamide (Ifex®), Etoposide (VP-16), Altretamine (Hexalen®), Capecitabine (Xeloda®), Irinotecan (CPT-11, Camptosar®), Melphalan, Pemetrexed (Alimta®) and Albumin bound paclitaxel (nab-paclitaxel, Abraxane®). Examples of combinations of these drugs which could be further combined with a compound of either Formula (I) or (Ia) are TIP (paclitaxel [Taxol], ifosfamide, and cisplatin), VeIP (vinblastine, ifosfamide, and cisplatin) and VIP (etoposide [VP-16], ifosfamide, and cisplatin).

In some embodiments, a compound of either Formula (I) or (Ia) can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as *vinca* alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (Gleevec®, also known as STI-571), Gefitinib (Iressa, also known as ZD1839), Erlotinib (marketed as Tarceva®), Bortezomib (Velcade®), tamoxifen, tofacitinib, crizotinib, Bcl-2 inhibitors (e.g. obatoclax in clinical trials, ABT-263, and Gossypol), PARP inhibitors (e.g. Iniparib, Olaparib in clinical trials), PI3K inhibitors (eg. perifosine in a phase III trial), VEGF Receptor 2 inhibitors (e.g. Apatinib), AN-152, (AEZS-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MabThera® or Rituxan®), Trastuzumab (Herceptin also known as ErbB2), Cetuximab (marketed as Erbitux®), and Bevacizumab (marketed as Avastin®); and (k) radiation therapy.

In some embodiments, diabetic retinopathy can be treated with a combination of a compound of either Formula (I) or (Ia) and one or more of the following natural supplements: Bilberry, Butcher's broom, Ginkgo, Grape seed extract, and Pycnogenol (Pine bark).

In some embodiments, a compound of either Formula (I) or (Ia) can be used to treat pulmonary fibrosis in combination with any of the following methods: oxygen therapy, pulmonary rehabilitation, and surgery.

In some embodiments, a compound of either Formula (I) or (Ia) can be used to treat osteoarthritis in combination with any of the following methods: (a) Nonsteroidal anti-inflammatory drugs (NSAIDs) such as ibuprofen, naproxen and acetaminophen; (b) physical therapy; (c) injections of corticosteroid medications; and (d) injections of hyaluronic acid derivatives (e.g. Hyalgan, Synvisc).

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intramenin-geally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may be solid, semi-solid, liquid, solutions, colloidal, liposomes, emulsions, suspensions, complexes, coacervates, and aerosols. Dosage forms, such as, e.g., tablets, capsules, powders, liquids, suspensions, suppositories, aerosols, implants, controlled release or the like are provided herein. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants, and the like, for prolonged and/or timed, pulsed administration at a predetermined rate.

The compounds can be administered either alone or in combination with a conventional pharmaceutical carrier, excipient or the like. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, $22^{nd}$ Edition (Pharmaceutical Press, London, U K. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrine derivatives, sorbitan monolaurate, triethanolamine acetate, triethanolamine oleate, and the like).

In some embodiments, the unit dosage of compounds of Formulas (I) and/or (Ia) is about 0.25 mg/Kg to about 50 mg/Kg in humans.

In some embodiments, the unit dosage of compounds of Formulas (I) and/or (Ia) is about 0.25 mg/Kg to about 20 mg/Kg in humans.

In some embodiments, the unit dosage of compounds of Formulas (I) and/or (Ia) is about 0.50 mg/Kg to about 19 mg/Kg in humans.

In some embodiments, the unit dosage of compounds of Formulas (I) and/or (Ia) is about 0.75 mg/Kg to about 18 mg/Kg in humans.

In some embodiments, the unit dosage of compounds of Formulas (I) and/or (Ia) is about 1.0 mg/Kg to about 17 mg/Kg in humans.

In some embodiments, the unit dosage of compounds of Formulas (I) and/or (Ia) is about 1.25 mg/Kg to about 16 mg/Kg in humans.

In some embodiments, the unit dosage of compounds of Formulas (I) and/or (Ia) is about 1.50 mg/Kg to about 15 mg/Kg in humans.

In some embodiments, the unit dosage of compounds of Formulas (I) and/or (Ia) is about 1.75 mg/Kg to about 14 mg/Kg in humans.

In some embodiments, the unit dosage of compounds of Formulas (I) and/or (Ia) is about 2.0 mg/Kg to about 13 mg/Kg in humans.

In some embodiments, the unit dosage of compounds of Formulas (I) and/or (Ia) is about 3.0 mg/Kg to about 12 mg/Kg in humans.

In some embodiments, the unit dosage of compounds of Formulas (I) and/or (Ia) is about 4.0 mg/Kg to about 11 mg/Kg in humans.

In some embodiments, the unit dosage of compounds of Formulas (I) and/or (Ia) is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient of 0.01% to 10% in solution are employable, and could be higher if the composition is a solid or suspension, which could be subsequently diluted to the above percentages.

In some embodiments, the composition will comprise about 0.1-10% of the active agent in solution.

In some embodiments, the composition will comprise about 0.1-5% of the active agent in solution.

In some embodiments, the composition will comprise about 0.1-4% of the active agent in solution.

In some embodiments, the composition will comprise about 0.15-3% of the active agent in solution.

In some embodiments, the composition will comprise about 0.2-2% of the active agent in solution.

In some embodiments, the compositions are provided in dosage forms suitable for continuous dosage by intravenous infusion over a period of about 1-96 hours.

In some embodiments, the compositions are provided in dosage forms suitable for continuous dosage by intravenous infusion over a period of about 1-72 hours.

In some embodiments, the compositions are provided in dosage forms suitable for continuous dosage by intravenous infusion over a period of about 1-48 hours.

In some embodiments, the compositions are provided in dosage forms suitable for continuous dosage by intravenous infusion over a period of about 1-24 hours.

In some embodiments, the compositions are provided in dosage forms suitable for continuous dosage by intravenous infusion over a period of about 1-12 hours.

In some embodiments, the compositions are provided in dosage forms suitable for continuous dosage by intravenous infusion over a period of about 1-6 hours.

In some embodiments, these compositions can be administered by intravenous infusion to humans at doses of about 5 mg/m$^2$ to about 300 mg/m$^2$.

In some embodiments, these compositions can be administered by intravenous infusion to humans at doses of about 5 mg/m$^2$ to about 200 mg/m$^2$.

In some embodiments, these compositions can be administered by intravenous infusion to humans at doses of about 5 mg/m$^2$ to about 100 mg/m$^2$.

In some embodiments, these compositions can be administered by intravenous infusion to humans at doses of about 10 mg/m$^2$ to about 50 mg/m$^2$.

In some embodiments, these compositions can be administered by intravenous infusion to humans at doses of about 50 mg/m$^2$ to about 200 mg/m$^2$.

In some embodiments, these compositions can be administered by intravenous infusion to humans at doses of about 75 mg/m$^2$ to about 175 mg/m$^2$.

In some embodiments, these compositions can be administered by intravenous infusion to humans at doses of about 100 mg/m$^2$ to about 150 mg/m$^2$.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one preferred embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 μm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formulas (I) and/or (Ia) disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formulas (I) and/or (Ia) disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the disclosure can be incorporated into a gel formulation (e.g., U.S. Pat. Nos. 4,474,752 and 6,911,211).

In some embodiments, compounds of Formulas (I) and/or (Ia) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments, the acidic or basic solid gacyclidine can be delivered from the reservoir of an external or internal implanted pumping system.

Formulations of the disclosure also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formulas (I) and/or (Ia) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, diabetic retinopathy, pulmonary fibrosis, rheumatoid arthritis, sepsis, anklyosing spondylitis, psoriasis, scleroderma, mycotic and viral infections, bone and cartilage diseases, Alzheimer's disease, lung disease, osteoarthritis, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease, and Rett syndrome.

Methods of Treatment

The compounds and compositions provided herein can be used as inhibitors and/or modulators of one or more components of the Wnt pathway, which may include one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation, to correct a genetic disorder, and/or to treat a neurological condition/disorder/disease due to mutations or dysregulation of the Wnt pathway and/or of one or more of Wnt signaling components. Non-limiting examples of diseases which can be treated with the compounds and compositions provided herein include a variety of cancers, diabetic retinopathy, pulmonary fibrosis, rheumatoid arthritis, sepsis, anklyosing spondylitism, psoriasis, scleroderma, mycotic and viral infections, bone and cartilage diseases, neurological conditions/diseases such as Alzheimer's disease, amyotrophic lateral sclerosis (ALS), motor neurone disease, multiple sclerosis or autism, lung disease, osteoarthritis, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease, and Rett syndrome.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL and T-ALL. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compound, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative ($her2^-$). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia.

11) Skin cancers and skin disorders, including, for example, malignant melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. Accordingly, provided herein is a method of treating cancer or preventing or reducing angiogenesis through kinase inhibition.

In addition, and including treatment of cancer, the compounds and compositions described herein can function as cell-cycle control agents for treating proliferative disorders in a patient. Disorders associated with excessive proliferation include, for example, cancers, scleroderma, immunological disorders involving undesired proliferation of leukocytes, and restenosis and other smooth muscle disorders. Furthermore, such compounds may be used to prevent de-differentiation of post-mitotic tissue and/or cells.

Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma, and Kaposi's sarcoma.

a disease process which features abnormal cellular proliferation, e.g., benign prostatic hyperplasia, familial adenomatosis polyposis, neurofibromatosis, atherosclerosis, arthritis, glomerulonephritis, restenosis following angioplasty or vascular surgery, inflammatory bowel disease, transplantation rejection, endotoxic shock, and fungal infections. Fibrotic disorders such as skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; adhesions, such as those occurring in the abdomen, pelvis, spine or tendons; chronic obstructive pulmonary disease; fibrosis following myocardial infarction; pulmonary fibrosis; fibrosis and scarring associated with diffuse/interstitial lung disease; central nervous system fibrosis, such as fibrosis following stroke; fibrosis associated with neuro-degenerative disorders such as Alzheimer's Disease or multiple sclerosis; fibrosis associated with proliferative vitreoretinopathy (PVR); restenosis; endometriosis; ischemic disease and radiation fibrosis.

defective apoptosis-associated conditions, such as cancers (including but not limited to those types mentioned herein), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, sepsis, anklyosing spondylitism, psoriasis, scleroderma, autoimmune mediated glomerulonephritis, inflammatory bowel disease and autoimmune diabetes mellitus), neuro-degenerative disorders (including but not limited to Alzheimer's disease, lung disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteroporosis and arthritis), aspirin-sensitive rhinosinusitis, cystic fibrosis, multiple sclerosis, kidney diseases and cancer pain.

genetic diseases due to mutations in Wnt signaling components, such as polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease and Rett syndrome.

Furthermore, the compounds and compositions described herein can be used to treat neurological conditions, disorders and/or diseases caused by dysfunction in the Wnt signaling pathway. Non-limiting examples of neurological conditions/disorders/diseases which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, De Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barre syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Menieres disease, meningitis, Menkes disease, etachromatic leukodystrophy, microcephaly, micropsia, Miller Fisher syndrome, misophonia, mitochondrial myopathy, Mobius syndrome, monomelic amyotrophy, motor neurone disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia Congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina bifida, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease, and Zellweger syndrome.

The compounds and compositions may also be useful in the inhibition of the development of invasive cancer, tumor angiogenesis and metastasis.

In some embodiments, the disclosure provides a method for treating a disease or disorder associated with aberrant cellular proliferation by administering to a patient in need of such treatment an effective amount of one or more of the compounds of Formulas (I) and/or (Ia), in combination (simultaneously or sequentially) with at least one other agent.

In some embodiments, the pharmaceutical composition comprises a therapeutically effective amount of a compound of Formulas (I) and/or (Ia), or a pharmaceutically acceptable salt thereof, and a pharmaceutically acceptable excipient.

In some embodiments, the method of treating a disorder or disease in which aberrant Wnt signaling is implicated in a patient is provided herein, the method comprises administering to the patient a therapeutically effective amount of a compound of Formulas (I) and/or (Ia), or a pharmaceutically acceptable salt thereof.

In some embodiments, the disorder or disease is cancer.

In some embodiments, the disorder or disease is diabetic retinopathy.

In some embodiments, the disorder or disease is pulmonary fibrosis.

In some embodiments, the disorder or disease is rheumatoid arthritis.

In some embodiments, the disorder or disease is scleroderma.

In some embodiments, the disorder or disease is a mycotic or viral infection.

In some embodiments, the disorder or disease is a bone or cartilage disease.

In some embodiments, the disorder or disease is Alzheimer's disease.

In some embodiments, the disorder or disease is osteoarthritis.

In some embodiments, the disorder or disease is lung disease

In some embodiments, the disorder or disease is a genetic disease caused by mutations in Wnt signaling components, wherein the genetic disease is selected from: polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma, and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, rhabdomyosarcoma, salivary gland cancer, skin cancer—basal and squamous cell, skin cancer—melanoma, small intestine cancer, stomach cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer, and adrenal cortical cancer.

In some embodiments, the cancer is hepatocellular carcinoma.

In some embodiments, the cancer is colon cancer.

In some embodiments, the cancer is breast cancer.

In some embodiments, the cancer is pancreatic cancer.

In some embodiments, the cancer is chronic myeloid leukemia (CML).

In some embodiments, the cancer is chronic myelomonocytic leukemia.

In some embodiments, the cancer is chronic lymphocytic leukemia (CLL).

In some embodiments, the cancer is acute myeloid leukemia.

In some embodiments, the cancer is acute lymphocytic leukemia.

In some embodiments, the cancer is Hodgkin lymphoma.

In some embodiments, the cancer is lymphoma.

In some embodiments, the cancer is sarcoma.

In some embodiments, the cancer is ovarian cancer.

In some embodiments, the cancer is lung cancer—non-small cell.

In some embodiments, the cancer is lung cancer—small cell.

In some embodiments, the cancer is multiple myeloma.

In some embodiments, the cancer is nasopharyngeal cancer.

In some embodiments, the cancer is neuroblastoma.

In some embodiments, the cancer is osteosarcoma.

In some embodiments, the cancer is penile cancer.

In some embodiments, the cancer is pituitary tumors.

In some embodiments, the cancer is prostate cancer.

In some embodiments, the cancer is retinoblastoma.

In some embodiments, the cancer is rhabdomyosarcoma.

In some embodiments, the cancer is salivary gland cancer.

In some embodiments, the cancer is skin cancer—basal and squamous cell.

In some embodiments, the cancer is skin cancer—melanoma.

In some embodiments, the cancer is small intestine cancer.

In some embodiments, the cancer is stomach cancers.

In some embodiments, the cancer is testicular cancer.

In some embodiments, the cancer is thymus cancer.

In some embodiments, the cancer is thyroid cancer.

In some embodiments, the cancer is uterine sarcoma.

In some embodiments, the cancer is vaginal cancer.

In some embodiments, the cancer is vulvar cancer.

In some embodiments, the cancer is Wilms tumor.

In some embodiments, the cancer is laryngeal or hypopharyngeal cancer.

In some embodiments, the cancer is kidney cancer.

In some embodiments, the cancer is Kaposi sarcoma.

In some embodiments, the cancer is gestational trophoblastic disease.

In some embodiments, the cancer is gastrointestinal stromal tumor.

In some embodiments, the cancer is gastrointestinal carcinoid tumor.

In some embodiments, the cancer is gallbladder cancer.

In some embodiments, the cancer is eye cancer (melanoma and lymphoma).

In some embodiments, the cancer is Ewing tumor.

In some embodiments, the cancer is esophagus cancer.

In some embodiments, the cancer is endometrial cancer.

In some embodiments, the cancer is colorectal cancer.

In some embodiments, the cancer is cervical cancer.

In some embodiments, the cancer is brain or spinal cord tumor.

In some embodiments, the cancer is bone metastasis.

In some embodiments, the cancer is bone cancer.

In some embodiments, the cancer is bladder cancer.

In some embodiments, the cancer is bile duct cancer.

In some embodiments, the cancer is anal cancer.

In some embodiments, the cancer is adrenal cortical cancer.

In some embodiments, the disorder or disease is a neurological condition, disorder or disease, wherein the neurological condition/disorder/disease is selected from: Alzheimer's disease, frontotemporal dementias, dementia with lewy bodies, prion diseases, Parkinson's disease, Huntington's disease, progressive supranuclear palsy, corticobasal degeneration, multiple system atrophy, amyotrophic lateral sclerosis (ALS), inclusion body myositis, autism, degenerative myopathies, diabetic neuropathy, other metabolic neuropathies, endocrine neuropathies, orthostatic hypotension, multiple sclerosis, and Charcot-Marie-Tooth disease.

In some embodiments, the compound of Formulas (I) and/or (Ia) inhibits one or more proteins in the Wnt pathway.

In some embodiments, the compound of Formulas (I) and/or (Ia) inhibits signaling induced by one or more Wnt proteins.

In some embodiments, the Wnt proteins are chosen from: WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, and WNT16.

In some embodiments, the compounds of Formulas (I) and/or (Ia) inhibit a kinase activity.

In some embodiments, a method for treating a disease or disorder mediated by the Wnt pathway in a patient is provided, the method comprises administering to the patient a therapeutically effective amount of a compound (or compounds) of Formulas (I) and/or (Ia), or a pharmaceutically acceptable salt thereof.

In some embodiments, the compounds of Formulas (I) and/or (Ia) inhibit one or more Wnt proteins.

In some embodiments, a method for treating a disease or disorder mediated by kinase activity in a patient is provided, the method comprises administering to the patient a therapeutically effective amount of a compound (or compounds) of Formulas (I) and/or (Ia), or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds) of Formulas (I) and/or (Ia), or a pharmaceutically acceptable salt thereof.

In some embodiments, a method for treating a disease or disorder associated with aberrant cellular proliferation in a patient is provided, the method comprises administering to the patient a therapeutically effective amount of a compound (or compounds) of Formulas (I) and/or (Ia), or a pharmaceutically acceptable salt thereof.

In some embodiments, the method prevents or reduces angiogenesis in a patient; the method comprises administering to the patient a therapeutically effective amount of a compound (or compounds) of Formulas (I) and/or (Ia), or a pharmaceutically acceptable salt thereof.

In some embodiments, the method prevents or reduces abnormal cellular proliferation in a patient; the method comprises administering to the patient a therapeutically effective amount of a compound (or compounds) of Formulas (I) and/or (Ia), or a pharmaceutically acceptable salt thereof.

In some embodiments, a method for treating a disease or disorder associated with aberrant cellular proliferation in a patient is provided, the method comprises administering to the patient a pharmaceutical composition comprising one or more of the compounds of Formulas (I) and/or (Ia) in combination with a pharmaceutically acceptable carrier and one or more other agents.

Moreover, the compounds and compositions, for example, as inhibitors of the cyclin-dependent kinases (CDKs), can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus, and the like.

Compounds and compositions described herein can inhibit the kinase activity of, for example, CDK/cyclin complexes, such as those active in the $G_0$ or $G_1$ stage of the cell cycle, e.g., CDK2, CDK4, and/or CDK6 complexes.

Evaluation of Biological Activity

The biological activity of the compounds described herein can be tested using any suitable assay known to those of skill in the art, see e.g., WO 2001/053268 or WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, in vitro assays for Wnt biological activity may be used, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a Wnt composition in the presence of a candidate inhibitor with cells, e.g. mouse L cells. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin.

In a further example, the activity of a candidate compound can be measured in a *Xenopus* secondary axis bioassay [Leyns, L. et al. *Cell* (1997), 88(6), 747-756].

To further illustrate this disclosure, the following examples are included. The examples should not, of course, be construed as specifically limiting the disclosure. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Compound Preparation

The starting materials used in preparing the compounds of the disclosure are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* 7$^{th}$ Ed., John Wiley & Sons (2013), Carey and Sundberg, *Advanced Organic Chemistry* 5$^{th}$ Ed., Springer (2007), *Comprehensive Organic Transformations: A Guide to Functional Group Transformations*, 2$^{nd}$ Ed., John Wiley & Sons (1999) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protective Groups in Organic Synthesis,* 4th Ed., John Wiley & Sons (2007).

Trademarks used herein are examples only and reflect illustrative materials used at the time of filing the present disclosure. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the disclosure.

($^1$H) nuclear magnetic resonance spectra (NMR) were measured in the indicated solvents on a Bruker NMR spectrometer (Avance™ DRX300, 300 MHz for $^1$H or Avance™ DRX500, 500 MHz for $^1$H) or Varian NMR spectrometer (Mercury 400BB, 400 MHz for $^1$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; d/ABq, doublet of AB quartet; dt, doublet of triplets; td, triplet of doublets; dq, doublet of quartets; m, multiplet.

The following abbreviations have the indicated meanings:
brine=saturated aqueous sodium chloride
CDCl$_3$=deuterated chloroform
CsCO$_3$=cesium carbonate
DCE=dichloroethane
DCM=dichloromethane
DHP=3,4-dihydro-2H-pyran
DMF=N,N-dimethylformamide
DMSO-d$_6$=deuterated dimethylsulfoxide
ESIMS=electron spray mass spectrometry
EtOAc=ethyl acetate
Et$_3$SiH=triethylsilane
HCl=hydrochloric acid
HOAc=acetic acid
KOAc=potassium acetate
KOH=potassium hydroxide
K$_3$PO$_4$=potassium phosphate
LAH=lithium aluminum hydride
MeOH=methanol
MgSO$_4$=magnesium sulfate
NaBH(OAc)$_3$=sodium triacetoxy borohydride
Na$_2$CO$_3$=sodium carbonate
NaHCO$_3$=sodium bicarbonate
NaHSO$_3$=sodium bisulfite
NaOAc=sodium acetate
NMR=nuclear magnetic resonance
Pd/C=palladium on carbon
Pd$_2$(dba)$_3$=tris(dibenzylideneacetone)dipalladium(0)
PdClz$_2$(dppf)$_2$=1,1'-bis(diphenylphosphino)ferrocene-palladium(II)dichloride
Pd(PPh$_3$)$_2$Cl$_2$=dichloro-bis(triphenylphosphine)palladium (II)
Pd(PPh$_3$)$_4$=tetrakis(triphenylphosphine)palladium(0)
PE=petroleum ether
PPTS=pyridinium p-toluenesulfonate
rt=room temperature
SEM=2-(trimethylsilyl)ethoxymethyl
TFA=trifluoroacetic acid
THF=tetrahydrofuran
TLC=thin layer chromatography The following example schemes are provided for the guidance of the reader, and collectively represent an example method for making the compounds provided herein. Furthermore, other methods for preparing compounds of the disclosure will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedures

Compounds of Formulas (I) and/or (Ia) of the present disclosure can be prepared as depicted in Scheme 1.

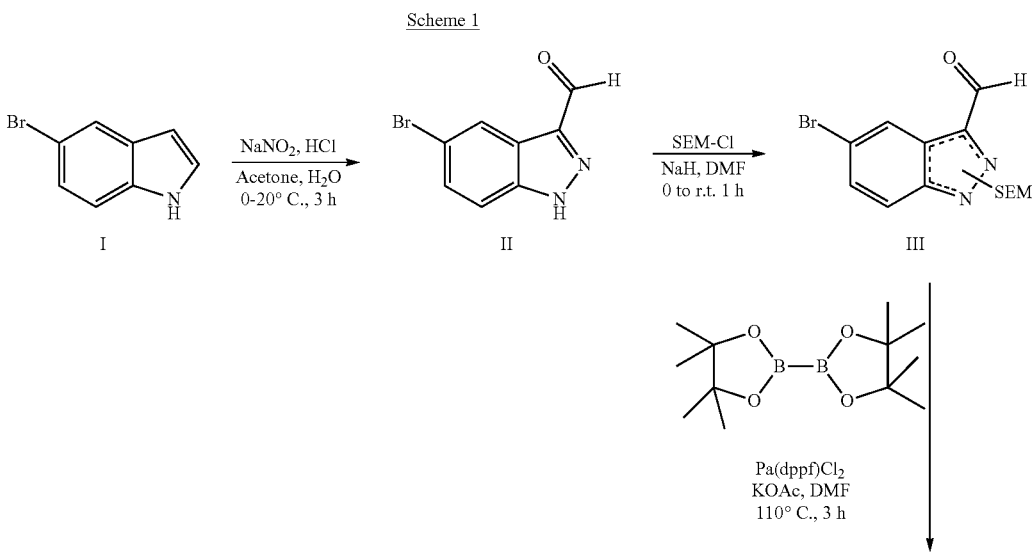

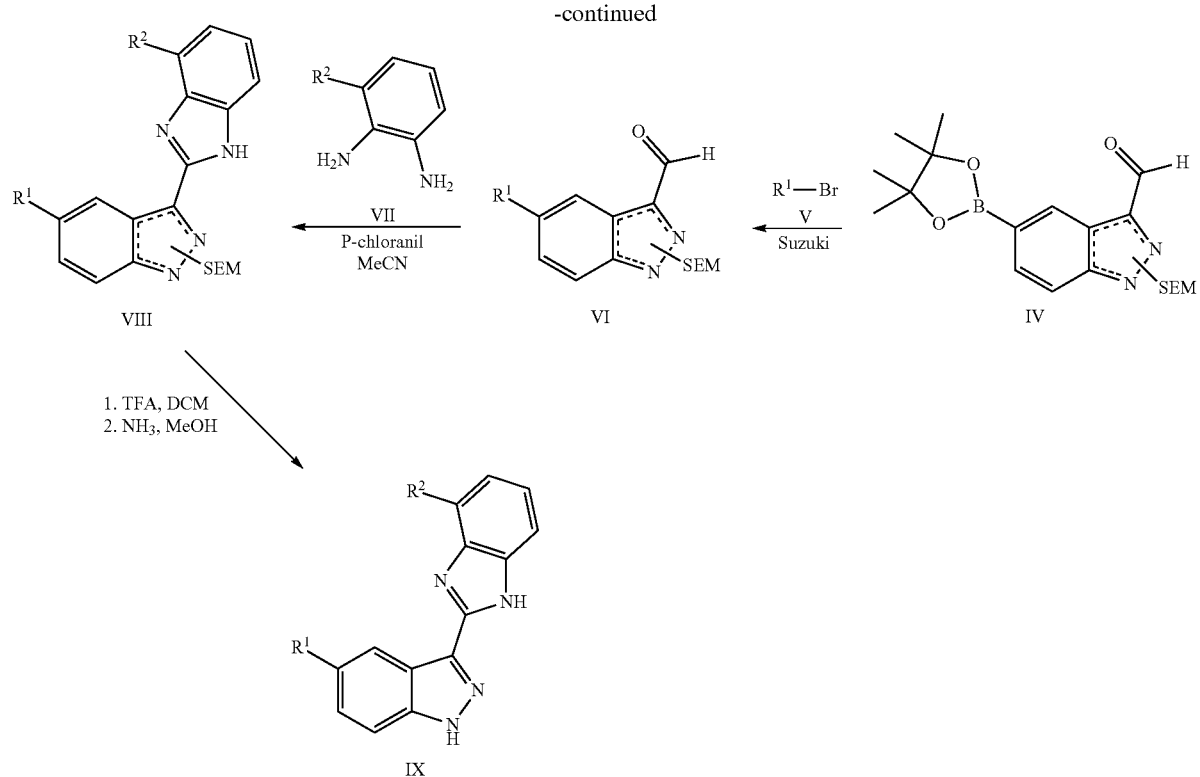

Scheme 1 describes a method for preparation of indazole derivatives (IX) by first formylating 5-bromo-1H-indole (I) to produce 5-bromo-1H-indazole-3-carbaldehyde (II) followed by protection with SEM-Cl to give 5-bromo-1-((2-(trimethylsilyl)ethoxy)methyl)-1H-indazole-3-carbaldehyde (III). Bromide (III) is then reacted with bis(pinacolato) diboron to form the borate ester (IV). Suzuki coupling with various bromides (V) yields indazole derivatives (VI). Aldehyde (VI) is reacted with various 1,2-diamines (VII) to produce (VIII). Final deprotection of the pyrazole nitrogen yields the desired indazole derivatives (IX).

Illustrative Compound Examples

Preparation of intermediate (IV) is depicted below in Scheme 2.

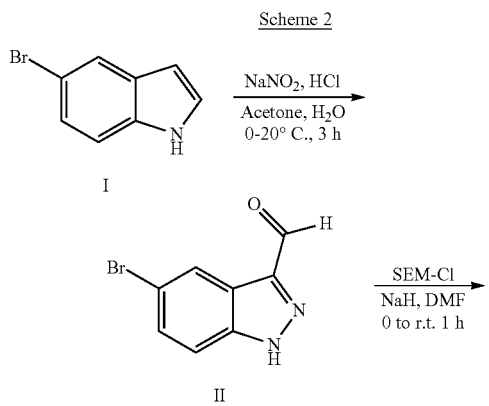

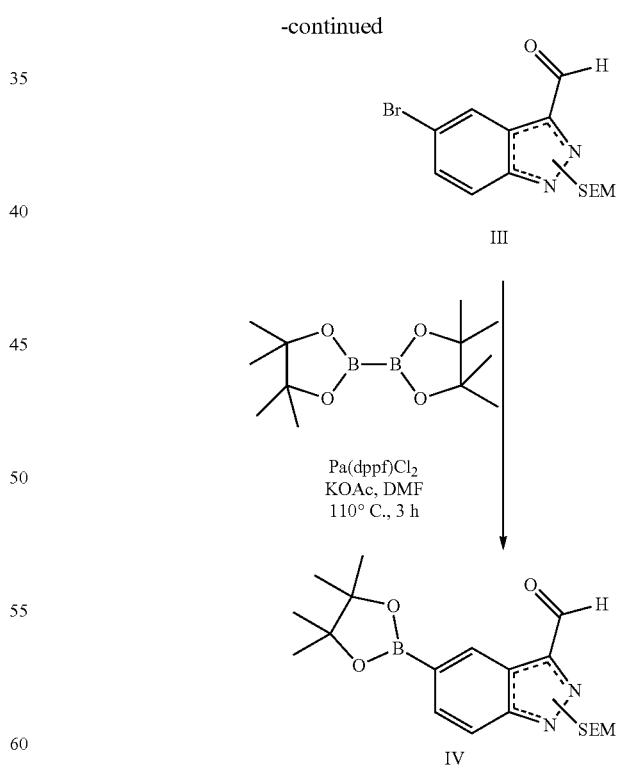

Step 1

A solution of NaNO$_2$ (110.4 g, 1.6 mol, 8 eq) in water (200 mL) was added dropwise to a solution of 5-bromoindole (I) (39.2 g, 0.2 mol, 1 eq) in acetone (1000 mL) stirred at −10--0° C., while adding NaNO$_2$ the solution temperature was maintained below 20° C. An aqueous 2N HCl solution (480 mL) was added slowly to the solution with vigorously stirring while keeping the internal temperature between 0 and 20° C. The solution was further stirred at 20° C. for 3 h after the addition. The solution was concentrated under reduced pressure to remove acetone while keeping the temperature below 35° C. The solid was collected by filtration and transferred to a flask. Cold (−10° C.) DCM (200 mL) was added and stirred for 30 min at −5° C., the solids were filtered and dried under vacuum at 40° C. to get 5-bromo-1H-indazole-3-carbaldehyde (II) (34.0 g, 151 mmol, 76% yield) as a brown solid. ESIMS found for $C_8H_5BrN_2O$ m/z 225 (M+H).

Step 2

To a suspension of NaH (6.6 g, 166 mmol, 1.10 eq) in DMF (500 mL) was added a solution of 5-bromo-1H-indazole-3-carbaldehyde (II) (34.0 g, 151 mmol, 1.00 eq) in DMF (50 mL) dropwise at 0° C. over a period of 30 min. The mixture was stirred at room temperature for 2 h, then SEM-Cl (26.4 g, 159 mmol, 1.08 eq) was added dropwise and the mixture was stirred at room temperature for another 3 h. Then the mixture was poured into an ice-water mixture (1000 mL) and extracted with EtOAc (300 mL×3), the organic phases were combined, dried over $Na_2SO_4$, filtered and concentrated in vacuo, the resultant residue was purified by flash chromatography on silica gel (PE:EtOAc=20:1-10:1) to afford 5-bromo-1-((2-(trimethylsilyl)ethoxy)methyl)-1H-indazole-3-carbaldehyde (III) as a mixture of regioisomers (53.0 g, 151 mmol, 100% yield) as a yellow oil. ESIMS found for $C_{14}H_{19}BrN_2O_2Si$ m/z 355 (M+H).

Step 3

To a solution of the mixed 5-bromo-1-((2-(trimethylsilyl)ethoxy)methyl)1H-indazole-3-carbaldehyde (III) (53.0 g, 151 mmol, 1.0 eq), bis(pinacolato)diboron (38.0 g, 150 mmol, 1.0 eq) and KOAc (44.0 g, 450 mmol, 3.00 eq) in DMF (1000 mL) was added $Pd(dppf)Cl_2$ (7.7 g, 10.5 mmol, 0.07 eq). The mixture was stirred at 90° C. under nitrogen for 10 h. The mixture was filtered; the filtrate was poured onto water (1000 mL) and extracted with EtOAc (500 mL×3). The combined organic phases were dried, filtered and concentrated in vacuo. The resultant residue was purified by flash chromatography on silica gel (PE:EtOAc=10:1-1:1) to give the 5-(4,4,5,5-tetramethyl-1,3,2-dioxaborolan-2-yl)-1-((2-(trimethylsilyl)ethoxy)methyl)-1H-indazole-3-carbaldehyde (IV) as a mixture of regioisomers (42.9 g, 106 mmol, 71% yield) as a yellow oil. ESIMS found for $C_{20}H_{31}BN_2O_4Si$ m/z 403 (M+H).

Preparation of intermediate N-(5-bromopyridin-3-yl) isobutyramide (VII) is depicted below in Scheme 3.

Scheme 3

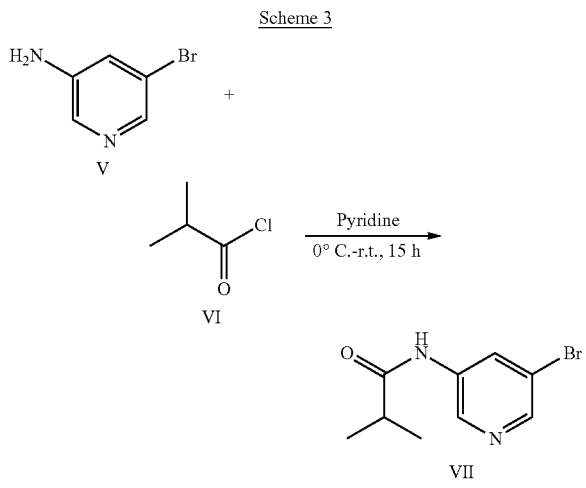

Step 1

3-Amino-5-bromo pyridine (V) (1 eq) was dissolved in DCM and cooled to 0° C. before adding pyridine (2.2 eq) and isobutyryl chloride (VI) (1.1 eq). The reaction mixture was stirred at r.t. for 15 h until TLC showed the reaction was complete. The reaction mixture was diluted with DCM and washed with water. The organic extract was dried, concentrated and purified by column chromatography using silica gel (100-200 mesh) to afford N-(5-bromopyridin-3-yl)isobutyramide (VII) as an off-white solid, (71% yield). $^1$H NMR (CDCl$_3$) δ ppm 8.55-8.35 (m, 3H), 7.32 (s, 1H), 2.59-2.48 (m, 1H), 1.28-1.27 (d, 6H); ESIMS found $C_9H_{11}BrN_2O$ m/z 243.05 (M+H).

The following compounds were prepared in accordance with the procedure described in the above Scheme 3.

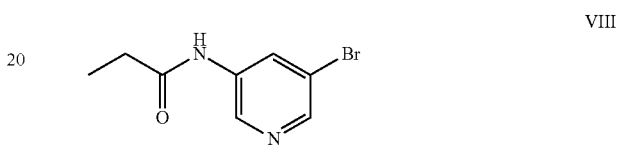

VIII

N-(5-Bromopyridin-3-yl)propionamide (VIII): Off white solid (92% yield). $^1$H NMR (DMSO-d$_6$) δ ppm 1.09 (t, J=7.54 Hz, 3H), 2.36 (q, J=7.54 Hz, 2H), 8.36 (m, 2H), 8.65 (d, J=2.07 Hz, 1H), 10.26 (s, 1H); ESIMS found $C_8H_9BrN_2O$ m/z 231 (M+H).

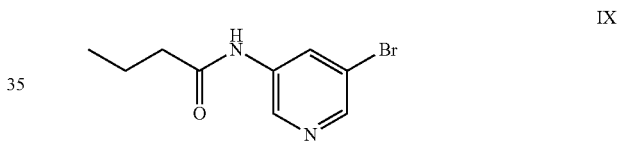

IX

N-(5-Bromopyridin-3-yl)butyramide (IX): Yellow solid (2.1 g, 8.64 mmol, 88.8% yield). ESIMS found $C_9H_{11}BrN_2O$ m/z 243 (M+H).

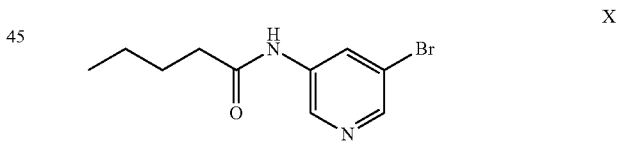

X

N-(5-Bromopyridin-3-yl)pentanamide (X): Yellow solid (2.0 g, 7.78 mmol, 85.3% yield). ESIMS found $C_{10}H_{13}BrN_2O$ m/z 257 (M+H).

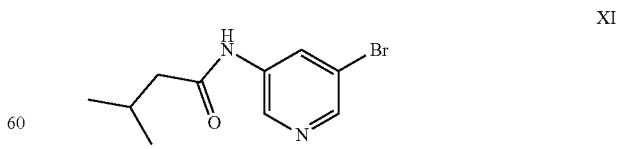

XI

N-(5-Bromopyridin-3-yl)-3-methylbutanamide (XI): Off white solid, (67% yield), $^1$H NMR (CDCl$_3$, 400 MHz) δ ppm 8.55-8.42 (m, 3H), 7.62 (s, 1H), 2.31-2.18 (m, 3H), 1.02-1.01 (d, J=6 Hz, 6H); ESIMS found $C_{10}H_{13}BrN_2O$ m/z 258.80 (M+H).

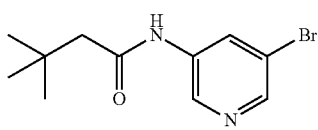

XII

N-(5-Bromopyridin-3-yl)-3,3-dimethylbutanamide (XII): Yellow solid (1.7 g, 6.27 mmol, 78.6% yield). ESIMS found $C_{11}H_{15}BrN_2O$ m/z 271 (M+H).

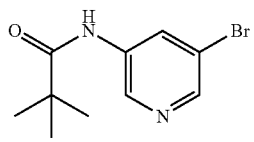

XIII

N-(5-Bromopyridin-3-yl)pivalamide (XIII): Off-white solid (1.082 g, 4.22 mmol, 73.1% yield). $^1$H NMR (DMSO-$d_6$, 500 MHz) δ ppm 1.23 (s, 9H), 8.37 (d, J=2 Hz, 1H), 8.39 (t, J=2 Hz, 1H), 8.80 (d, J=2 Hz, 1H), 9.58 (brs, 1H); ESIMS found $C_{10}H_{13}BrN_2O$ m/z 257.0 (M+H).

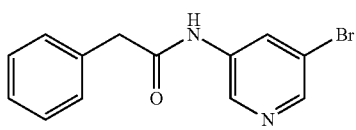

XIV

N-(5-Bromopyridin-3-yl)-2-phenylacetamide (XIV): White solid (2.5 g, 8.59 mmol, 77.9% yield). ESIMS found $C_{13}H_{11}BrN_2O$ m/z 291 (M+H).

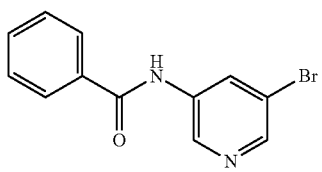

XV

N-(5-Bromopyridin-3-yl)benzamide (XV): White solid (2.7 g, 9.74 mmol, 60% yield). ESIMS found $C_{12}H_9BrN_2O$ m/z 277 (M+H).

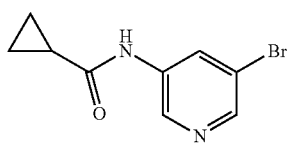

XVI

N-(5-Bromopynridin-3-yl)cyclopropanecarboxamide (XVI): Off-white solid, (83% yield), $^1$H NMR (CDCl$_3$, 400 MHz) δ ppm 8.46-8.39 (m, 3H), 7.54 (bs, 1H), 1.56-1.50 (m, 1H), 1.13-1.07 (m, 2H), 0.96-0.90 (m, 2H); ESIMS found for $C_9H_9BrN_2O$ m/z 240.9 (M+H).

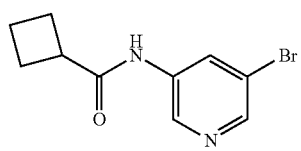

XVII

N-(5-Bromopyridin-3-yl)cyclobutanecarboxamide (XVII): Yellow solid (2.1 g, 6.27 mmol, 86.6% yield). ESIMS found $C_{10}H_{11}BrN_2O$ m/z 255 (M+H).

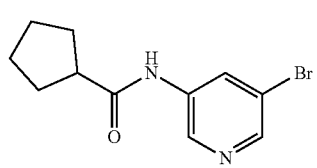

XVIII

N-(5-Bromopyridin-3-yl)cyclopentanecarboxamide (XVIII): Yellow solid (1.9 g, 7.06 mmol, 80.2% yield). ESIMS found $C_{11}H_{13}BrN_2O$ m/z 269 (M+H).

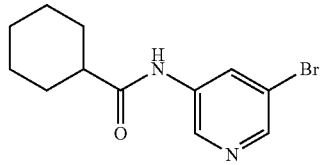

XIX

N-(5-bromopyridin-3-yl)cyclohexanecarboxamide (XIX): Yellow solid (2.0 g, 7.06 mmol, 84.3% yield). ESIMS found $C_{12}H_{15}BrN_2O$ m/z 283 (M+H).

Preparation of intermediate 5-bromo-N,N-dimethylpyridin-3-amine (XXI) is depicted below in Scheme 4.

Scheme 4

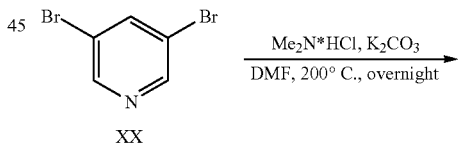

XX

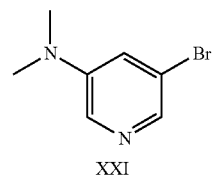

XXI

Step 1

To a solution of 3,5-dibromopyridine (XX) (2.37 g, 10.0 mmol) in dry DMF (20.0 mL) was added K$_2$CO$_3$ (4.5 g, 33 mmol) and dimethylamino hydrochloride (1.79 g, 22 mmol). The mixture was heated overnight at 200° C. in a sealed tube. The solution was cooled to room temperature and excess DMF was removed under vacuum. The residue was partitioned between EtOAc and water. The organic phase was separated. The aqueous phase was washed with EtOAc and the combined organic phases were dried over MgSO$_4$, and concentrated to afford 5-bromo-N,N-dimethylpyridin-3-amine (XXI) as an off-white solid (1.78 g, 8.85 mmol, 88% yield). $^1$H NMR (DMSO-$d_6$, 500 MHz) δ ppm 2.94 (s, 6H), 7.25 (t, J=2 Hz, 1H), 7.91 (d, J=2 Hz, 1H), 8.07 (d, J=2 Hz, 1H); ESIMS found $C_7H_9BrN_2$ m/z 201.1 (M+H).

Preparation of intermediate 5-bromo-N-isopropylpyridin-3-amine (XXIII) is depicted below in Scheme 5.

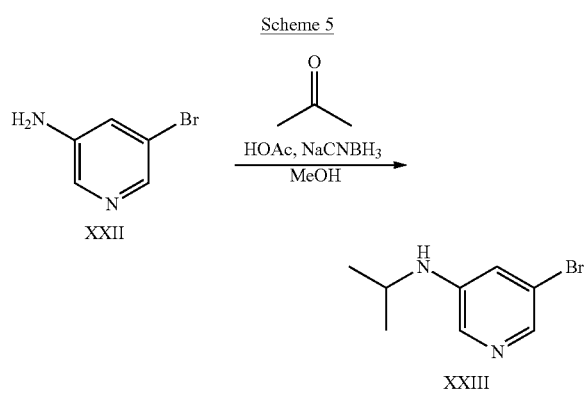

Steps 1

To a solution of 5-bromopyridin-3-amine (XXII) (535 mg, 3.09 mmol) in MeOH (62 mL) was added acetone (296 µL, 4.02 mL). The pH was adjusted to 4 using HOAc and stirred for 30 min. NaCNBH$_3$ (272 mg, 4.33 mmol) was added and stirred at room temperature overnight. The MeOH was removed under vacuum and the residue was partitioned between EtOAc and saturated aqueous NaHCO$_3$. The organic layer was dried over MgSO$_4$ and evaporated under vacuum. The crude product was purified on a silica gel column (100% hexane→90:10 hexane:EtOAc) to produce 5-bromo-N-isopropylpyridin-3-amine (XXIII) as an oil which slowly solidified into an off-white solid (309 mg, 1.44 mmol, 47% yield). $^1$H NMR (DMSO-$d_6$, 500 MHz) δ ppm 1.12 (d, J=6.3 Hz, 6H), 3.55-3.59 (m, 1H), 6.03 (d, J=7.9 Hz, 1H), 7.05-7.06 (m, 1H), 7.75 (d, J=2 Hz, 1H), 7.90 (d, J=2 Hz, 1H); ESIMS found $C_8H_{11}BrN_2$ m/z 215 (M+H).

Preparation of intermediate 1-(5-bromopyridin-3-yl)-N,N-dimethyl methanamine (XXV) is depicted below in Scheme 6.

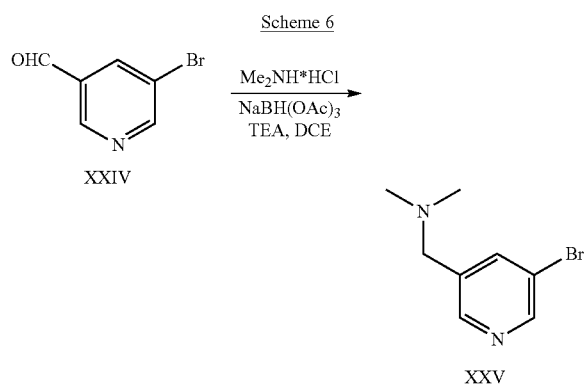

Step 1

To a solution of 5-bromonicotinaldehyde (XXIV) (5.0 g, 26.9 mmol) in DCE (108 mL) was added dimethylamine-HC (4.39 g, 53.8 mmol) and TEA (7.5 g, 53.8 mmol). The reaction was stirred at room temperature for 1 h. NaBH(OAc)$_3$ was added and the reaction was stirred overnight at room temperature. The reaction was diluted with DCM and sat. aq. NaHCO$_3$. The organic layer was separated, washed with water, brine, dried and concentrated under vacuum to produce 1-(5-bromopyridin-3-yl)-N,N-dimethylmethanamine (XXV) as a brown liquid (5.36 g, 24.9 mmol, 92.6% yield). $^1$H NMR (CDCl$_3$) δ ppm 2.15 (s, 6H), 3.43 (s, 2H), 7.94 (s, 1H), 8.47 (d, J=1.1 Hz, 1H), 8.59 (d, J=2.2 Hz, 1H); ESIMS found $C_8H_{11}BrN_2$ m/z 215 ($M^{Br79}$+H) and 217 ($M^{Br81}$+H).

The following intermediates were prepared in accordance with the procedure described in the above Scheme 6.

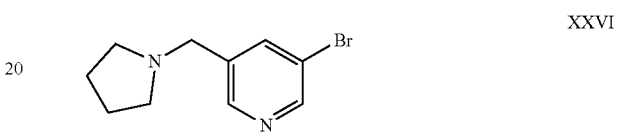

3-Bromo-5-(pyrrolidin-1-ylmethyl)pyridine (XXVI): Golden liquid (1.35 g, 97% yield). $^1$H NMR (DMSO-$d_6$) 1.68-1.71 (m, 4H), 2.42-2.44 (m, 4H), 3.60 (s, 2H), 7.96 (s, 1H), 8.48 (d, J=2 Hz, 1H), 8.58 (d, J=3 Hz, 1H); ESIMS found for $C_{10}H_{13}BrN_2$ m/z 242 (M+H).

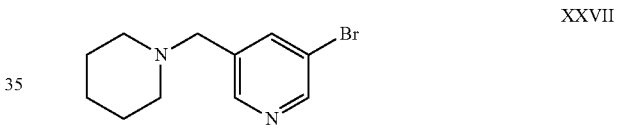

3-Bromo-5-(piperidin-1-ylmethyl)pyridine (XXVII): Brown liquid (13.1 g, 94% yield). $^1$H NMR (DMSO-$d_6$) 1.36-1.39 (m, 2H), 1.46-1.51 (m, 4H), 2.31-2.32 (m, 4H), 3.46 (s, 2H), 7.94 (s, 1H), 8.47 (d, J=2 Hz, 1H), 8.58 (d, J=3 Hz, 1H); ESIMS found for $C_{11}H_{15}BrN_2$ m/z 257 (M+H).

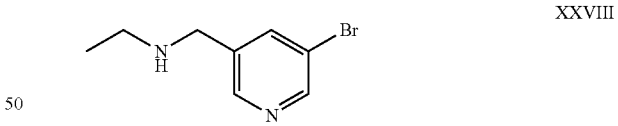

N-((5-Bromopyridin-3-yl)methyl)ethanamine (XXVIII): Golden liquid (1.29 g, 6.00 mmol, 60% yield ESIMS found for $C_8H_{11}Br_2N_2$ m/z 215 (M+H).

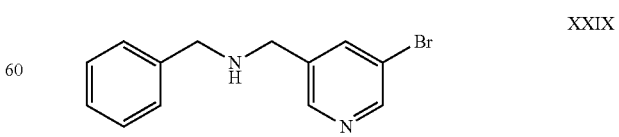

N-Benzyl-1-(5-bromopyridin-3-yl)methanamine (XXIX): Golden liquid (77 mg, 0.28 mmol, 25% yield). ESIMS found for $C_{13}H_{13}BrN_2$ m/z 277 (M+H).

Preparation of intermediate tert-butyl(5-bromopyridin-3-yl)methyl(cyclopentylmethyl)carbamate (XXXIV) is depicted below in Scheme 7.

($D_2O$, 400 MHz) δ ppm 4.34 (s, 2H), 8.56 (s, 1H), 8.75 (d, J=1.2 Hz, 1H), 8.91 (d, J=1.6 Hz, 1H). ESIMS found for $C_6H_7BrN_2$ m/z 187 (M+H).

Scheme 7

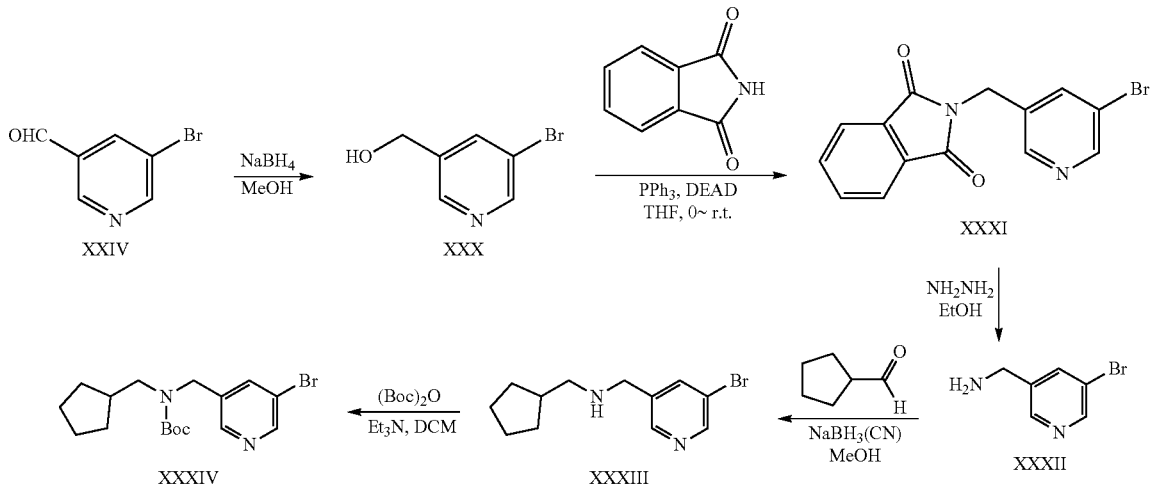

Step 1

To a solution of 5-bromonicotinaldehyde (XXIV) (2.0 g, 10.8 mmol, 1 eq) in MeOH (20 mL) was added $NaBH_4$ (2.4 g, 64.9 mmol, 6 eq) and the reaction mixture was stirred at room temperature for 3 h. The mixture was concentrated in vacuo and the residue was diluted in water (15 mL), the aqueous phase was extracted with DCM (10 mL×3). The combined organic layers were dried over $MgSO_4$, filtered and concentrated in vacuo to afford (5-bromopyridin-3-yl)methanol (XXX) (1.8 g, 9.57 mmol, 90.0% yield) as a colorless oil. $^1$H NMR ($CDCl_3$, 400 MHz) δ ppm 4.73 (s, 2H), 7.90 (s, 1H), 8.47 (s, 1H), 8.57 (s, 1H). ESIMS found for $C_6H_6BrNO$ m/z 188 (M+H).

Step 2

To a stirred solution of (5-bromopyridin-3-yl)methanol (XXX) (1.60 g, 8.5 mmol, 1 eq), phthalimide (1.24 g, 8.5 mmol, 1 eq) and $PPh_3$ (3.33 g, 12.75 mmol, 1.5 eq) in anhydrous THF (15 mL) was added DEAD (2.21 g, 12.75 mmol, 1.5 eq) dropwise at 0° C. under $N_2$. Then the reaction mixture was stirred at room temperature for 6 h. The mixture was washed with saturated $NaHCO_3$ solution (15 mL), water (15 mL) and brine (15 mL) subsequently. The organic layers were dried over $MgSO_4$, concentrated under reduced pressure, the resultant residue was purified by flash chromatography on silica gel (PE:EtOAc=4:1) to give 2-((5-bromopyridin-3-yl)methyl)isoindoline-1,3-dione (XXXI) (2.5 g, 7.88 mmol, 82.3% yield) as a white solid. ESIMS found for $C_{14}H_9BrN_2O_2$ m/z 317 (M+H).

Step 3

A solution of 2-((5-bromopyridin-3-yl)methyl)isoindoline-1,3-dione (XXXI) (1.9 g, 6.0 mmol, 1 eq) and hydrazine hydrate (2.0 g, 40 mmol, 6 eq) in EtOH (20 mL) was heated at 70° C. for 3 h. The mixture was filtered through a Celite pad and the filtrate was concentrated in vacuo, the crude product was dissolved in 1N HCl solution (15 mL) and concentrated to dryness, then it was washed with acetone (10 mL×3), the precipitate was collected by filtration, dried in vacuo to give (5-bromopyridin-3-yl)methanamine (XXXII) (1.3 g, 6.95 mmol, 97.7% yield) as a white solid. $^1$H NMR Step 4

A solution of (5-bromopyridin-3-yl)methanamine (XXXII) (1.30 g, 5.8 mmol, 1.0 eq), cyclopentanecarbaldehyde (0.57 g, 5.8 mmol, 1.0 eq) and TEA (0.60 g, 5.8 mmol, 1.0 eq) in MeOH (15 mL) was stirred at room temperature for 2 h. Then $NaBH_3CN$ (1.98 g, 34.6 mmol, 6.0 eq) was added and the mixture was stirred at the same temperature for another 3 h. The solvent was removed under reduced pressure and the residue was diluted in water (20 mL) and extracted with DCM (10 mL×3), combined organic layers were dried over $MgSO_4$ and concentrated in vacuo to give 1-(5-bromopyridin-3-yl)-N-(cyclopentylmethyl)methanamine (XXXIII) (1.23 g, 4.57 mmol, 79.3% yield) as a brown oil. ESIMS found for $C_{12}H_{17}BrN_2$ m/z 269 (M+H).

Step 5

To a solution of 1-(5-bromopyridin-3-yl)-N-(cyclopentylmethyl) methanamine (XXXIII) (1.00 g, 3.7 mmol, 1 eq) and TEA (0.93 g, 9.2 mmol, 2.5 eq) in DCM (20 mL) was added portionwise $(Boc)_2O$ (0.85 g, 4.0 mmol, 1.1 eq) at 0° C., the reaction mixture was stirred at room temperature for 1 h. The mixture was washed with water (10 mL), brine (10 mL), the organic layer was separated, dried over $MgSO_4$ and concentrated in vacuo to give tert-butyl (5-bromopyridin-3-yl)methyl (cyclopentylmethyl)carbamate (XXXIV) (1.25 g, 3.38 mmol, 91.9% yield) as a white solid. ESIMS found for $C_{17}H_{25}BrN_2O_2$ m/z 369 (M+H).

Preparation of intermediate 3-(4-methyl-imidazol-1-yl)-benzene-1,2-diamine (XXXVII) is depicted below in Scheme 8.

Scheme 8

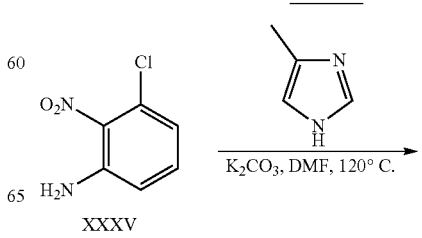

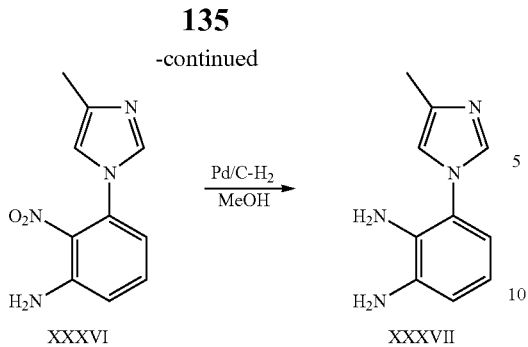

Step 1

A solution of 3-chloro-2-nitro-aniline (XXXV) (1.0 g, 5.8 mmol), potassium carbonate (2.4 g, 17.4 mmol), and 4-methylimidazole in dry DMF was heated overnight at 120° C. under nitrogen. The reaction was cooled and the solvent was evaporated in vacuo. The residue was suspended in a saturated NaHCO$_3$ solution and extracted with CH$_2$Cl$_2$. The combined organic phases were dried over MgSO$_4$ and concentrated in vacuo. The crude product was purified by flash chromatography to provide 3-(4-methyl-imidazol-1-yl)-2-nitro-phenylamine (XXXVI). $^1$H NMR (CDCl$_3$, 400 MHz) δ ppm 2.19 (s, 3H), 6.53 (m, 1H), 6.79 (m, 1H), 6.93 (m, 1H), 7.32 (m, 1H), 7.60 (m, 1H).

Step 2

To a solution of 3-(4-methyl-imidazol-1-yl)-2-nitro-phenylamine (XXXVI) in MeOH was added with 5% Pd/C. The combination was stirred under a hydrogen filled balloon at 40° C. for 6 h. The solution was then filtered through a pad of Celite. The filtrate was concentrated in vacuo to get 3-(4-methyl-imidazol-1-yl)-benzene-1,2-diamine (XXXVII). $^1$H NMR (CDCl$_3$, 400 MHz) δ ppm 2.17 (s, 3H), 6.54 (m, 1H), 6.80 (m, 1H), 6.97 (m, 1H), 7.28 (m, 1H), 7.56 (m, 1H).

Preparation of intermediate 2'-fluorobiphenyl-2,3-diamine (XLI) is depicted below in Scheme 9.

Scheme 9

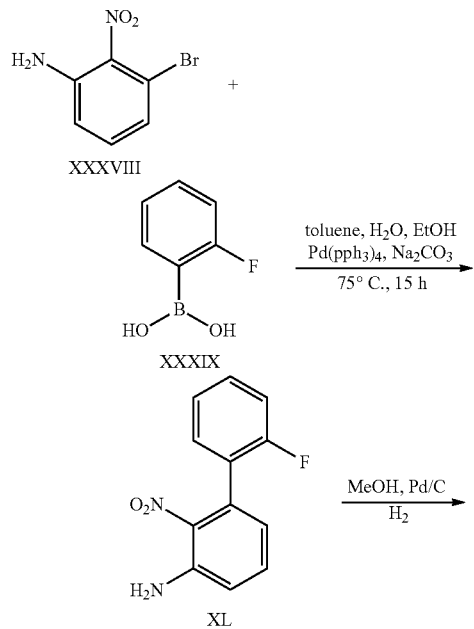

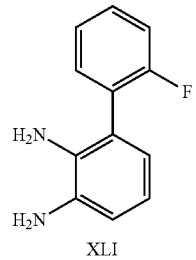

XLI

Step 1

A solution of 3-bromo-2-nitroaniline (XXXVIII) (2.00 g, 9.30 mmol, 1 eq), 2-fluorophenylboronic acid (XXXIX) (1.42 g, 10.14 mmol, 1.1 eq), Pd(PPh$_3$)$_4$ (0.35 g, 0.03 mmol, 0.03 eq), Na$_2$CO$_3$ (1.95 g, 18.40 mmol, 2 eq) in a mixed solvent of toluene (15 mL), H$_2$O (9 mL) and EtOH (3 ml) was stirred at 75° C. for 15 h under nitrogen atmosphere. Then the reaction mixture was washed with brine (20 mL) and dried over anhydrous Na$_2$SO$_4$, filtered and concentrated in vacuo, the resultant residue was purified by chromatography on silica gel (PE:EtOAc=3:1) to afford 2'-fluoro-2-nitrobiphenyl-3-amine (XL) (1.0 g, 4.30 mmol, 46.6% yield) as a yellow solid. $^1$H NMR (DMSO-d$_6$, 400 MHz) δ ppm 6.54 (d, J=6.4 Hz, 1H), 6.64 (s, 2H), 7.04 (dd, J=8.8 Hz, J=1.2 Hz, 1H), 7.18-7.31 (m, 2H), 7.33-7.47 (m, 3H); ESIMS found for C$_{12}$H$_9$FN$_2$O$_2$ m/z 233 (M+H).

Step 2

To a solution of 2'-fluoro-2-nitrobiphenyl-3-amine (XL) (1.0 g, 3.45 mmol, 1 eq) in MeOH (50 mL) was added Pd/C (0.5 g) under nitrogen atmosphere, the mixture was stirred under 50 psi of H$_2$ for 6 h at room temperature. Then the mixture was filtered and concentrated in vacuo to afford 2'-fluorobiphenyl-2,3-diamine (XLI) (0.8 g, 3.96 mmol, 92% yield) as a black solid. $^1$H NMR (DMSO-d$_6$, 400 MHz) δ ppm 3.99 (s, 2H), 4.62 (s, 2H), 6.32 (d, J=7.6 Hz, 1H), 6.49 (t, J=7.6 Hz, 1H), 6.60 (d, J=7.6 Hz, 1H), 7.21-7.35 (m, 3H), 7.35-7.45 (m, 1H); ESIMS found for C$_{12}$H$_{11}$FN$_2$ m/z 203 (M+H).

The following intermediates were prepared in accordance with the procedure described in the above Scheme 9.

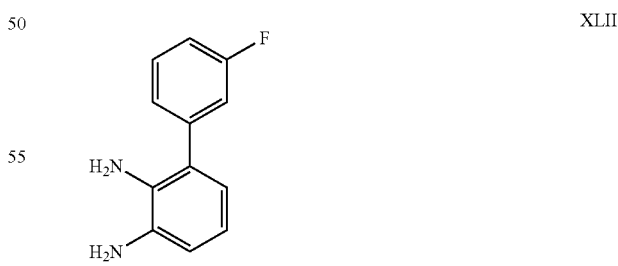

XLII

3'-Fluorobiphenyl-2,3-diamine (XLII): White solid (2.0 g, 9.89 mmol, 81% yield). $^1$H NMR (DMSO-d$_6$, 400 MHz) δ ppm 4.16 (s, 2H), 4.64 (s, 2H), 6.38 (dd, J=7.6 Hz, J=1.6 Hz, 1H), 6.51 (t, J=7.6 Hz, 1H), 6.60 (d, J=6 Hz, 1H), 7.11-7.26 (m, 3H), 7.48 (q, J=6.4 Hz, 1H); ESIMS found for C$_{12}$H$_{11}$FN$_2$ m/z 203 (M+H).

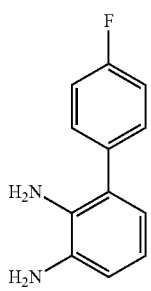

4'-Fluorobiphenyl-2,3-diamine (XLIII): White solid (2.4 g, 11.87 mmol, 98% yield). $^1$H NMR (DMSO-$d_6$, 400 MHz) δ ppm 4.07 (s, 2H), 4.60 (s, 2H), 6.34 (dd, J=7.6 Hz, J=1.6 Hz, 1H), 6.50 (t, J=7.6 Hz, 1H), 6.58 (dd, J=7.6 Hz, J=1.6 Hz, 1H), 7.26 (t, J=7.6 Hz, 2H), 7.40 (q, J=5.6 Hz, 2H); ESIMS found for $C_{12}H_{11}FN_2$ m/z 203 (M+H).

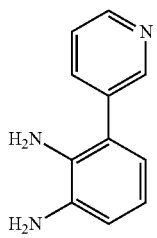

3-(Pyridin-3-yl)benzene-1,2-diamine (XLIV): White solid (1.36 g, 7.34 mmol, 92.5% yield). $^1$H NMR (CDCl$_3$, 400 MHz) δ ppm 1.57 (brs, 2H), 3.42 (brs, 2H), 6.66 (dd, J=6 Hz, J=3.2 Hz, 1H), 6.68-6.72 (m, 2H), 7.31 (dd, J=8 Hz, J=4.8 Hz, 1H), 7.71 (td, J=8 Hz, J=2 Hz, 1H), 8.54 (dd, J=4.8 Hz, J=1.6 Hz, 1H), 8.64 (d, J=1.6 Hz, 1H); ESIMS found for $C_{11}H_{11}N_3$ m/z 186 (M+H).

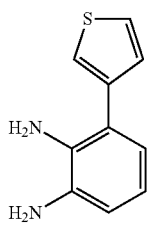

3-(Thiophen-3-yl)benzene-1,2-diamine (XLV): White solid (1.2 g, 6.31 mmol, mmol, 94% yield). $^1$H NMR (DMSO-$d_6$, 400 MHz) δ ppm 4.19 (s, 2H), 4.59 (s, 2H), 6.47 (dd, J=4.8 Hz, J=1 Hz, 2H), 6.55 (q, J=4.8 Hz, 1H), 7.24 (dd, J=4.8 Hz, J=1 Hz, 1H), 7.50 (t, J=1.6 Hz, 1H), 7.63 (dd, J=4.8 Hz, J=2.8 Hz, 1H); ESIMS found for $C_{10}H_{10}N_2S$ m/z 191 (M+H).

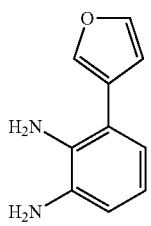

3-(Furan-3-yl)benzene-1,2-diamine (XLVI): White solid (1.3 g, 7.46 mmol, mmol, 85% yield). $^1$H NMR (DMSO-$d_6$, 400 MHz) δ ppm 4.24 (brs, 2H), 4.57 (brs, 2H), 6.46-6.50 (m, 1H), 6.50-6.56 (m, 2H), 6.72 (s, 1H), 7.74 (t, J=1.6 Hz, 1H), 7.87 (s, 1H); ESIMS found for $C_{10}H_{10}N_2O$ m/z 175 (M+H).

Preparation of intermediate (XLIX) is depicted below in Scheme 10.

Scheme 10

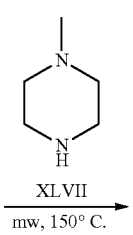
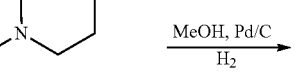
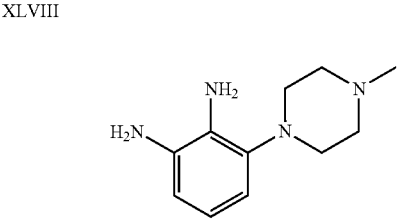

Step 1

A mixture of 1-methylpiperazine (XLVII) (20 mL) and 3-chloro-2-nitroaniline (XXXV) (1.5 g, 8.7 mmol, 1 eq) was stirred at 50° C. for 1 h under microwave irradiation. The reaction mixture was diluted with water (100 mL) and filtered, the cake washed with water (30 mL×3), dried in vacuo to give the 3-(4-methylpiperazin-1-yl)-2-nitroaniline (XLVIII) (1.64 g, 6.94 mmol, 80% yield) as a yellow solid. ESIMS found for $C_{11}H_{16}N_4O_2$ m/z 237 (M+H).

Step 2

A mixture of 3-(4-methylpiperazin-1-yl)-2-nitroaniline (XLVIII) (1.64 g, 6.9 mmol, 1 eq) and Pd/C (0.2 g) in MeOH (20 mL) was stirred under 30 psi of $H_2$ at room temperature overnight. The reaction was monitored by TLC. The mixture was filtered and the filtrate was concentrated in vacuo to give the 3-(4-methylpiperazin-1-yl)benzene-1,2-diamine (XLIX) (1.31 g, 6.35 mmol, 92% yield) as a black solid. $^1$H NMR (CDCl$_3$, 400 MHz) δ ppm 2.30 (s, 3H), 3.30 (brs, 2H), 3.68 (brs, 2H), 6.46 (dd, J=7.2 Hz, J=2 Hz, 1H), 6.54-6.63 (m, 2H); ESIMS found for $C_{11}H_{18}N_4$ m/z 207 (M+H).

Preparation of intermediate 3-(piperidin-1-yl)benzene-1,2-diamine (LI) is depicted below in Scheme 11.

Scheme 11

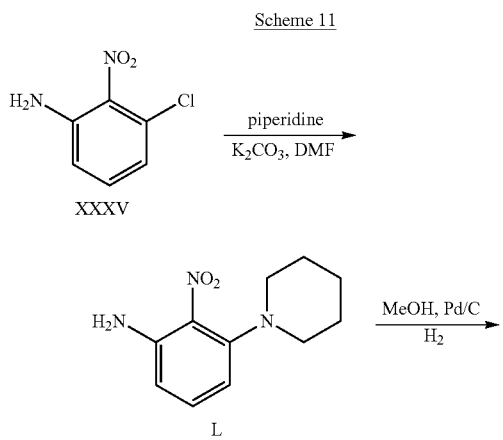

Preparation of intermediate 3-(pyridin-4-yl)benzene-1,2-diamine (LVII) is depicted below in Scheme 12.

Scheme 12

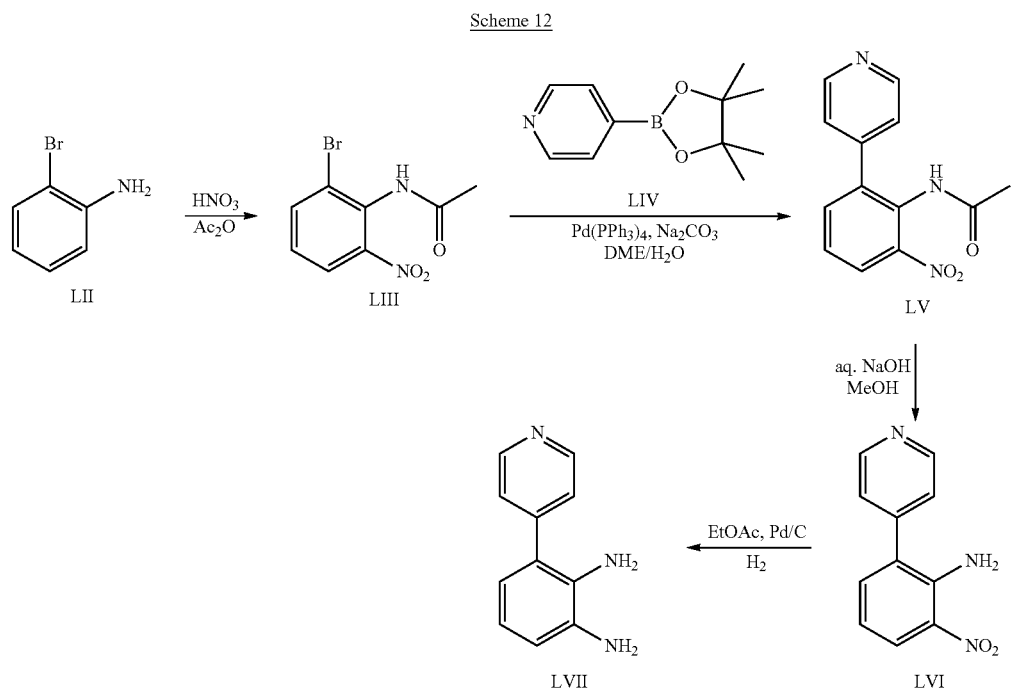

-continued

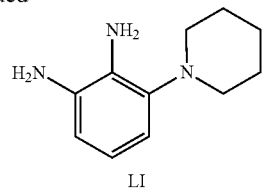

LI

Step 1

To a solution of 3-chloro-2-nitroaniline (XXXV) (2.00 g, 11.6 mmol, 1 eq) and piperidine (2.95 g, 34.7 mmol, 3 eq) in DMF (60 ml) was added K$_2$CO$_3$ (4.78 g, 34.4 mmol, 3 eq) in one portion and the mixture was stirred at 120° C. under nitrogen overnight. The reaction mixture was diluted with EtOAc (60 ml) and washed with saturated NaHCO$_3$ solution (50 mL). The organic phases were dried over Na$_2$SO$_4$ and concentrated in vacuo, the resultant residue was purified by silica gel column chromatography (PE:EtOAc=5:1→1:1) to give 2-nitro-3-(piperidin-1-yl)aniline (L) (1.8 g, 8.14 mmol, 70.3% yield) as a black solid. ESIMS found for C$_{11}$H$_{15}$N$_3$O$_2$ m/z 222 (M+H).

Step 2

A mixture of 2-nitro-3-(piperidin-1-yl)aniline (L) (1.64 g, 6.9 mmol, 1 eq) and Pd/C (0.50 g) in MeOH (20 mL) was stirred at room temperature under 30 psi H$_2$ overnight. After the starting material was consumed completely, the mixture was filtered through a Celite pad and the filtrate was concentrated in vacuo to give the 3-(piperidin-1-yl)benzene-1,2-diamine (LI) (1.1 g, 5.75 mmol, 76% yield) as a yellow solid. $^1$H NMR (CDCl$_3$, 400 MHz) δ ppm 1.59 (brs, 2H), 1.73 (quin, J=5.6 Hz, 4H), 2.84 (brs, 4H), 3.50 (brs, 4H), 6.52 (dd, J=6.4 Hz, J=1.6 Hz, 1H), 6.59-6.75 (m, 2H); ESIMS found for C$_{11}$H$_{17}$N$_3$ m/z 192 (M+H).

Step 1

To a solution of 2-bromoaniline (LII) (50 g, 0.29 mol, 1 eq) in acetic anhydride (265 mL) was added dropwise nitric acid (fuming) (36.75 mL, 0.93 mol, 3.2 eq) at 0° C. and then stirred at that temperature, when the starting material was consumed, the mixture was filtered, the filtrate was poured into ice water. The aqueous phase was basified with aqueous solution of sodium bicarbonate to pH=7, then the mixture was extracted with EtOAc (30 mL×3). The organic layers were combined, dried and concentrated in vacuo to give the N-(2-bromo-6-nitrophenyl)acetamide (LIII) (12.6 g, 48.6 mmol, 16.7% yield) as a white solid. $^1$H NMR (DMSO-d$_6$, 400 MHz) δ ppm 2.06 (s, 3H), 7.43 (t, J=8 Hz, 1H), 7.94 (d, J=8 Hz, 1H), 8.05 (d, J=8 Hz, 1H); ESIMS found for C$_8$H$_7$BrN$_2$O$_3$ m/z 259 (M+H).

Step 2

A degassed mixture of N-(2-bromo-6-nitrophenyl)acetamide (LIII) (2.59 g, 10 mmol, 1.0 eq), 4-(4,4,5,5-tetramethyl-1,3,2-dioxaborolan-2-yl)pyridine (LIV) (2.05 g, 10 mmol, 1.3 eq), Na$_2$CO$_3$ (2.12 g, 20 mmol, 2 eq) and Pd(PPh$_3$)$_4$ (1.16 g, 1 mmol, 0.1 eq) in a mixed solvent of DME (30 mL) and H$_2$O (10 mL) was heated to reflux under nitrogen overnight, the mixture was poured onto water (40 ml) and extracted with EtOAc (30 mL×3). The combined organic layers were dried over Na$_2$SO$_4$, filtered and concentrated in vacuo, purification the resultant residue was purified by column chromatography (EtOAc:PE=1: 4→100% EtOAc) to afford N-(2-nitro-6-(pyridin-4-yl)phenyl)acetamide (LV) (1.42 g, 5.52 mmol, 55% yield) as a yellow solid. $^1$H NMR (DMSO-d$_6$, 400 MHz) δ ppm 1.92 (s, 3H), 7.46 (d, J=5.6 Hz, 2H), 7.69 (t, J=8 Hz, 1H), 7.80 (dd, J=7.6 Hz, J=1.2 Hz, 1H), 8.06 (dd, J=8 Hz, J=1.6 Hz, 1H), 8.73 (d, J=6 Hz, 2H), 9.96 (s, 1H); ESIMS found for C$_{13}$H$_{11}$N$_3$O$_3$ m/z 258 (M+H).

Step 3

To a solution of N-(2-nitro-6-(pyridin-4-yl)phenyl)acetamide (LV) (3.94 g, 15 mmol, 1 eq) in MeOH (20 mL) was added 2 N aqueous NaOH solution (50 mL) and the mixture was refluxed until the starting material was consumed completely, the precipitate was collected by filtration to afford the 2-nitro-6-(pyridin-4-yl)aniline (LVI) (3.0 g, 13.9 mmol, 91% yield) as yellow solid. ESIMS found for C$_{11}$H$_9$N$_3$O$_2$ m/z 216 (M+H).

Step 4

To a solution of 2-nitro-6-(pyridin-4-yl)aniline (LVI) (3 g, 14 mmol, 1 eq) in EtOAc (350 mL) was added Pd/C (0.3 g) and the mixture was stirred at room temperature under 1 atm of H$_2$ atmosphere overnight, the mixture was filtered and concentrated in vacuo to give the product 3-(pyridin-4-yl)benzene-1,2-diamine (LVII) (2.4 g, 13.0 mmol, 93% yield) as a white solid. $^1$H NMR (DMSO-d$_6$, 400 MHz) δ ppm 4.35 (s, 2H), 4.75 (s, 2H), 6.45 (dd, J=7.6 Hz, J=1 Hz, 1H), 6.58 (t, J=7.6 Hz, 1H), 6.67 (d, J=6.8 Hz, 1H), 7.47 (d, J=6 Hz, 2H), 8.65 (d, J=6 Hz, 2H); ESIMS found for C$_{11}$H$_{11}$N$_3$ m/z 186 (M+H).

Preparation of intermediate 3-(pyridin-2-yl)benzene-1,2-diamine 3HCl (LXII) is depicted below in Scheme 13.

Scheme 13

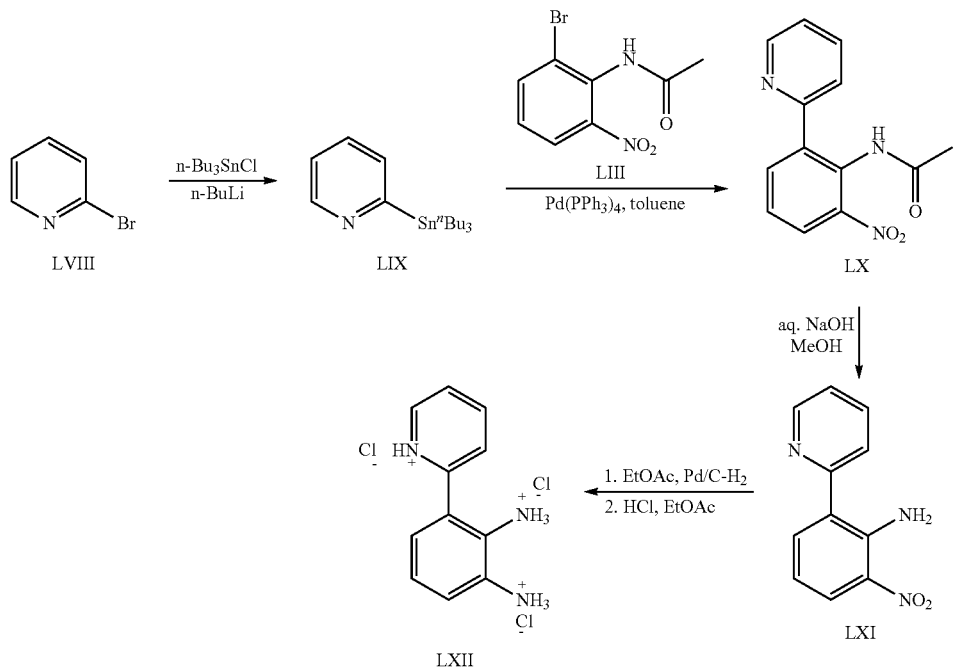

Scheme 13

To a solution of 2-bromopyridine (LVIII) (10 g, 63 mmol, 1.00 eq) in THF (150 mL) was added n-BuLi (25.3 mL, 63 mmol, 1.00 eq) and the mixture was stirred at −70° C. for 30 min under nitrogen atmosphere. Then n-Bu$_3$SnCl (21.7 g, 67 mmol, 1.06 eq) was added and the mixture was stirred at the same temperature for another 2 h. Saturated ammonium chloride solution (150 mL) was added to the solution and extracted with EtOAc (150 mL×3). The combined organic layers were dried over Na$_2$SO$_4$, filtered and concentrated in vacuo to afford the crude 2-(tributylstannyl)pyridine (LIX) (25.9 g, 63 mmol, 100% yield) as a yellow oil. The crude product was used without further purification.

Step 2

A degassed mixture of N-(2-bromo-6-nitrophenyl)acetamide (LIII) (4.8 g, 19 mmol, 1.00 eq), 2-(tributylstannyl)pyridine (LIX) (7.5 g, 20 mmol, 1.05 eq) and Pd(PPh$_3$)$_4$ (2.1 g, 1.8 mmol, 0.01 eq) in toluene (60 mL) was heated to reflux under nitrogen overnight. Saturated sodium bicarbonate solution (50 mL) was then added to the mixture and it was extracted with EtOAc (50 mL×3). The combined organic layers were dried over Na$_2$SO$_4$, filtered and concentrated in vacuo, the residue was purified by column chromatography on silica gel (EtOAc:PE=1:2→100% EtOAc) to afford N-(2-nitro-6-(pyridin-2-yl)phenyl)acetamide (LX) (4.4 g, 17.1 mmol, 92% yield) as a white-off solid. $^1$H NMR (DMSO-d$_6$, 400 MHz) δ ppm 1.93 (s, 3H), 7.43-7.51 (m, 1H), 7.51-7.65 (m, 1H), 7.67 (d, J=7.6 Hz, 1H), 7.97 (dd, J=7.6 Hz, J=2.4 Hz, 3H), 8.75 (d, J=4.4 Hz, 1H), 10.52 (s, 1H); ESIMS found for $C_{13}H_{11}N_3O_3$ m/z 258 (M+H).

Step 3

To a solution of N-(2-nitro-6-(pyridin-2-yl)phenyl)acetamide (LX) (4.41 g, 17 mmol, 1 eq) in MeOH (20 mL) was added 2N NaOH aqueous (50 mL) and the mixture was refluxed until the stirring material was consumed completely. The mixture was concentrated in vacuo to remove the MeOH and the precipitate was collected by filtration to afford 2-nitro-6-(pyridin-2-yl)aniline (LXI) (2.4 g, 11.2 mmol, 65% yield) as a yellow solid. ESIMS found for $C_{11}H_9N_3O_2$ m/z 216 (M+H).

Step 4

To a solution of 2-nitro-6-(pyridin-2-yl)aniline (LXI) (2.4 g, 0.01 mmol, 1 eq) in EtOAc (350 mL) was added Pd/C (1 g) and the mixture was stirred at room temperature under 1 atm of $H_2$ atmosphere overnight, filtered and then concentrated in vacuo, to give 3-(pyridin-2-yl)benzene-1,2-diamine (1.9 g, 10.3 mmol, 89% yield) as a yellow oil. ESIMS found for $C_{11}H_{11}N_3$ m/z 186 (M+H).

Step 5

To a solution of 3-(pyridin-2-yl)benzene-1,2-diamine (1.86 g, 0.01 mmol) in EtOAc (200 mL) was added HCl in EtOAc (40 mL) and the mixture was stirred at 0° C. for 20 min. The precipitate was collected by filtration to give 3-(pyridin-2-yl)benzene-1,2-diamine-3HCl (LXII) as a yellow solid. $^1$H NMR (DMSO-$d_6$, 400 MHz) δ ppm 6.89 (t, J=7.6 Hz, 1H), 7.33 (brs, 1H), 7.51 (d, J=7.2 Hz, 1H), 7.54-7.66 (m, 2H), 7.97 (d, J=8 Hz, 1H), 8.16 (brs, 1H), 8.75 (brs, 1H).

Example 1

Preparation of N-(5-(3-(4-(4-methylpiperazin-1-yl)-1H-benzo[d]imidazol-2-yl)-1H-indazol-5-yl)pyridin-3-yl)-2-phenylacetamide (202) is depicted below in Scheme 14.

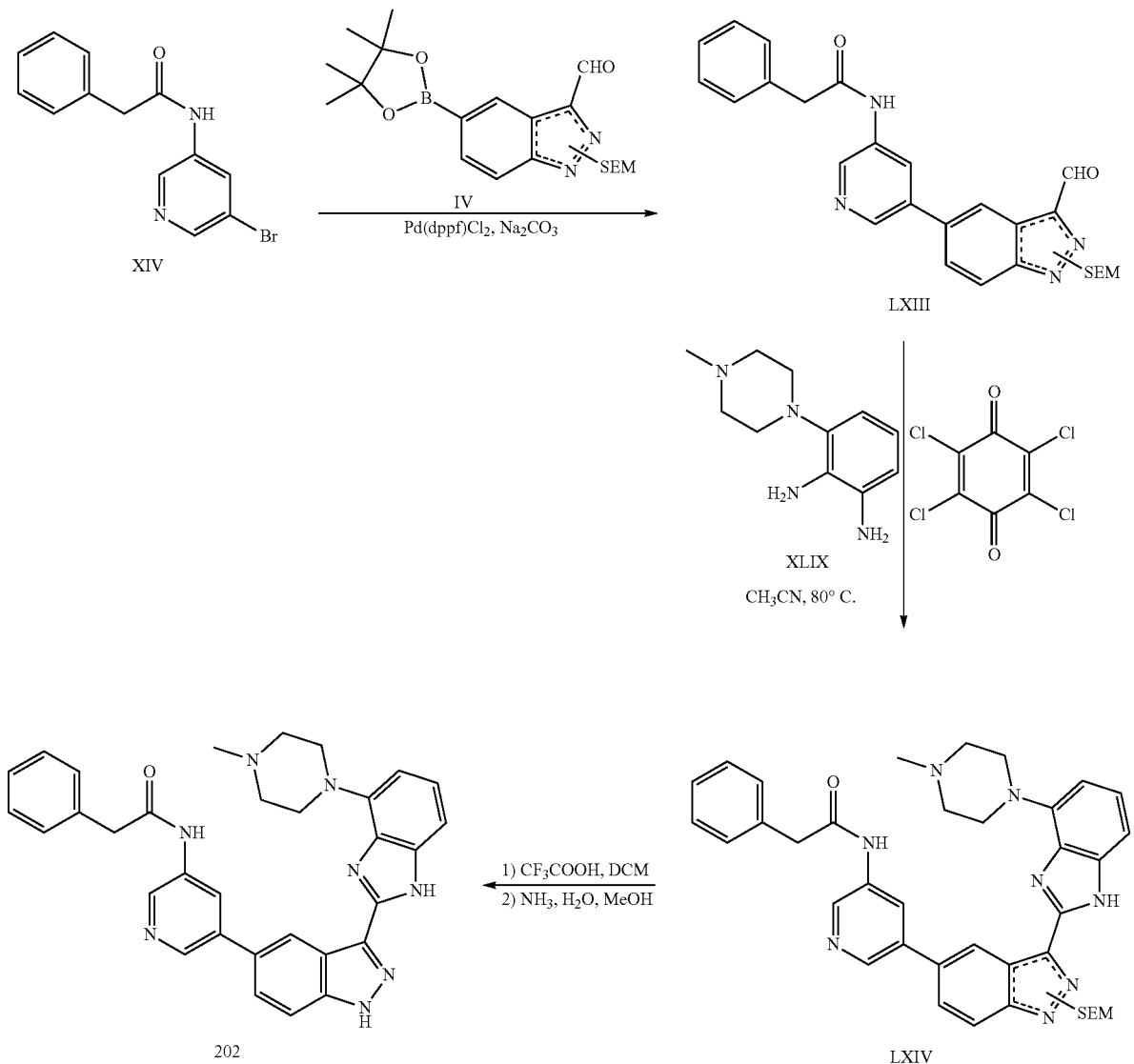

Step 1

A solution of N-(5-bromopyridin-3-yl)-2-phenylacetamide (XIV) (2.2 g, 5.5 mmol, 1.00 eq), 5-bromo-1-((2-(trimethylsilyl)ethoxy)methyl)-1H-indazole-3-carbaldehyde (IV) (1.5 g, 5.5 mmol, 1.00 eq), Pd(dppf)Cl$_2$ (0.28 g, 0.39 mmol, 0.07 eq) and Na$_2$CO$_3$ (0.8 g, 16.5 mmol, 3.00 eq) in a mixed solvent of 1,2-dimethoxyethane (30 mL) and H$_2$O (5 mL) was refluxed for 3 h under nitrogen atmosphere. The reaction mixture was diluted in water (30 mL) and extracted with EtOAc (20 mL×3). The combined organic layers were dried over Na$_2$SO$_4$, filtered and concentrated in vacuo, the resultant residue was purified by flash chromatography on silica gel (PE/EtOAc=10:1-3:1) to give N-(5-(3-formyl-1-((2-(trimethylsilyl)ethoxy)methyl)-1H-indazol-5-yl)pyridin-3-yl)-2-phenylacetamide (LXIII) (2.3 g, 4.73 mmol, 51% yield) as a brown oil. ESIMS found C$_{27}$H$_{30}$N$_4$O$_3$Si m/z 487 (M+H).

Step 2

To a well stirred solution of N-(5-(3-formyl-1-((2-(trimethylsilyl)ethoxy)methyl)-1H-indazol-5-yl)pyridin-3-yl)-2-phenylacetamide (LXIII) (100 mg, 0.205 mmol, 1.0 eq), 3-(4-methylpiperazin-1-yl)benzene-1,2-diamine (XLIX) (46 mg, 0.223 mmol, 1.09 eq) in CH$_3$CN (2 mL) was added compound 2,3,5,6-tetrachlorocyclohexa-2,5-diene-1,4-dione (60 mg, 1.1 eq). The reaction mixture was refluxed for 3 h, TLC analysis (1:1, PE/EtOAc) showed complete consumption of starting material (LXIII). The precipitate was collected by filtration, washed with CH$_3$CN and dried under reduced pressure to give N-(5-(3-(4-(4-methylpiperazin-1-yl)-1H-benzo[d]imidazol-2-yl)-1-((2-(trimethylsilyl)ethoxy)methyl)-1H-indazol-5-yl)pyridin-3-yl)-2-phenylacetamide (LXIV) (41 mg, 0.061 mmol, 29.6% yield). ESIMS found for C$_{38}$H$_{44}$N$_8$O$_2$Si m/z 673 (M+H).

Step 3

To a well stirred solution of N-(5-(3-(4-(4-methylpiperazin-1-yl)-1H-benzo[d]imidazol-2-yl)-1-((2-(trimethylsilyl)ethoxy)methyl)-1H-indazol-5-yl)pyridin-3-yl)-2-phenylacetamide (LXIV) (40 mg, 0.06 mmol, 1.0 eq) in DCM (5 mL) was added TFA (0.3 mL) at room temperature for 2 h, TLC analysis (10:1, DCM/MeOH) showed complete consumption of compound (LXIV). Then the reaction mixture was added NH$_4$OH (2 mL) and washed with EtOAc and water, dried over Na$_2$SO$_4$, filtration, and concentration, the crude product was obtained as a solid, which was purified by preparative HPLC to give N-(5-(3-(4-(4-methylpiperazin-1-yl)-1H-benzo[d]imidazol-2-yl)-1H-indazol-5-yl)pyridin-3-yl)-2-phenylacetamide 202 (20 mg, 0.037 mmol, 60.9% yield) as a white solid. $^1$H NMR (CD$_3$OD, 400 MHz) δ ppm 2.98 (s, 3H), 3.22-3.31 (m, 2H), 3.51-3.61 (m, 2H), 3.67-3.76 (m, 2H), 3.88 (s, 2H), 4.11-4.20 (m, 2H), 7.03 (d, J=7.6 Hz, 1H), 7.27-7.51 (m, 7H), 7.91 (ABq, 2H), 8.84 (s, 1H), 8.88 (s, 1H), 8.93 (s, 1H), 9.06 (s, 1H); ESIMS found for C$_{32}$H$_{30}$N$_8$O m/z 543.3 (M+H).

The following compounds were prepared in accordance with the procedure described in the above Example 1.

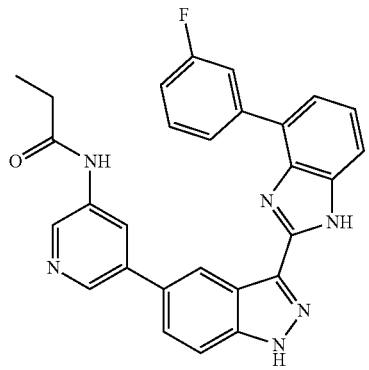

N-(5-(3-(4-(3-Fluorophenyl)-1H-benzo[d]imidazol-2-yl)-1H-indazol-5-yl)pyridin-3-yl)propionamide 1

$^1$H NMR (CD$_3$OD, 400 MHz) δ ppm 1.29 (t, J=7.2 Hz, 3H), 2.60 (q, J=7.6 Hz, 2H), 7.23-7.40 (m, 2H), 7.61-7.77 (m, 5H), 7.94 (d, J=8 Hz, 1H), 7.99 (s, 1H), 8.87 (s, 1H), 8.95 (s, 1H), 9.04 (s, 1H), 9.33 (s, 1H); ESIMS found for C$_{28}$H$_{21}$FN$_6$O m/z 477.2 (M+H).

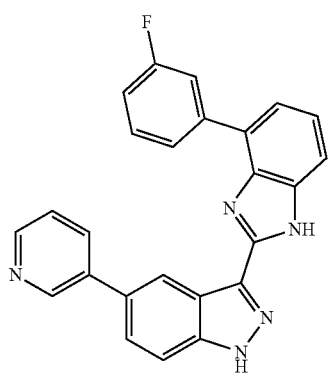

3-(4-(3-Fluorophenyl)-1H-benzo[d]imidazol-2-yl)-5-(pyridin-3-yl)-1H-indazole 4

$^1$H NMR (CD$_3$OD, 400 MHz) δ ppm 7.32 (t, J=8 Hz, 1H), 7.59-7.73 (m, 4H), 7.78 (t, J=7.6 Hz, 1H), 8.02 (d, J=8.4 Hz, 2H), 8.09 (d, J=8.4 Hz, 1H), 8.29 (brs, 1H), 8.93 (d, J=5.2 Hz, 2H), 9.18 (d, J=7.6 Hz, 1H), 9.46 (s, 1H); ESIMS found for C$_{25}$H$_{16}$FN$_5$ m/z 406.1 (M+H).

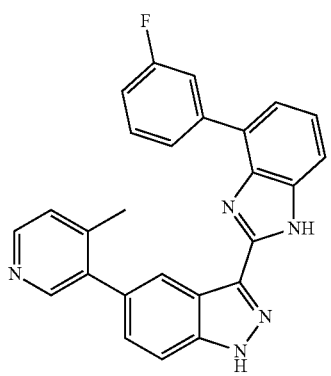

3-(4-(3-Fluorophenyl)-1H-benzo[d]imidazol-2-yl)-5-(4-methylpyridin-3-yl)-1H-indazole 5

$^1$H NMR (CD$_3$OD, 400 MHz) δ ppm 2.45 (s, 3H), 7.08 (dt, 1H), 7.36 (t, J=7.6 Hz, 1H), 7.41-7.53 (m, 4H), 7.62 (d, J=8 Hz, 1H), 7.74 (d, J=8.4 Hz, 1H), 7.97 (d, 1H), 8.43 (brs, 1H), 8.51 (brs, 1H), 8.60 (s, 1H); ESIMS found for C$_{26}$H$_{18}$FN$_5$ m/z 420.1 (M+H).

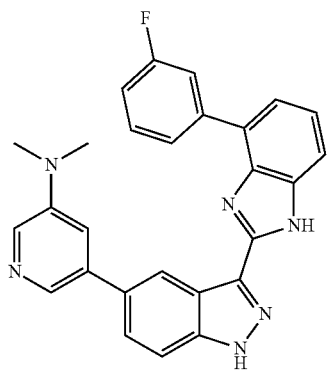

5-(3-(4-(3-Fluorophenyl)-1H-benzo[d]imidazol-2-yl)-1H-indazol-5-yl)-N,N-dimethylpyridin-3-amine 7

$^1$H NMR (CD$_3$OD, 400 MHz) δ ppm 1.30 (s, 6H), 7.32 (t, 1H), 7.58-7.68 (m, 3H), 7.70 (d, J=7.6 Hz, 1H), 7.78 (t, J=7.6 Hz, 1H), 7.94-8.08 (m, 3H), 8.17 (s, 1H), 8.21 (s, 1H), 8.51 (s, 1H), 8.82 (s, 1H); ESIMS found for C$_{27}$H$_{21}$FN$_6$ m/z 449.1 (M+H).

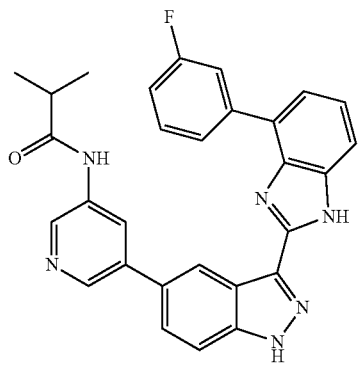

N-(5-(3-(4-(3-Fluorophenyl)-1H-benzo[d]imidazol-2-yl)-1H-indazol-5-yl)pyridin-3-yl)isobutyramide 9

$^1$H NMR (CD$_3$OD, 400 MHz) δ ppm 1.31 (d, J=6.8 Hz, 6H), 2.83 (sep, J=6.8 Hz, 1H), 7.24-7.33 (m, 1H), 7.62-7.71 (m, 4H), 7.72 (t, J=8 Hz, 1H), 7.97 (d, 1H), 8.00 (s, 2H), 8.86 (s, 1H), 9.01 (s, 1H), 9.06 (s, 1H), 9.36 (s, 1H); ESIMS found for C$_{29}$H$_{23}$FN$_6$O m/z 491.2 (M+H).

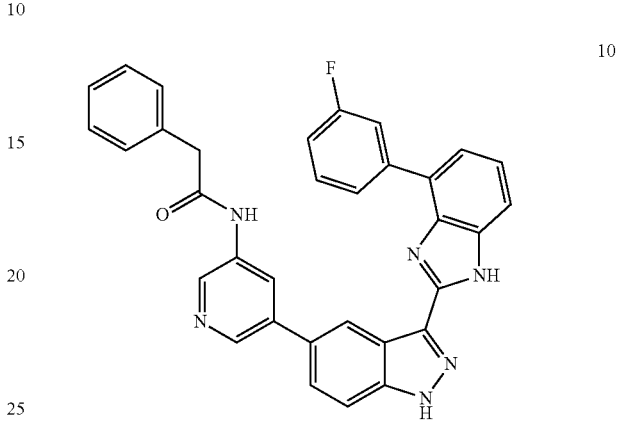

N-(5-(3-(4-(3-Fluorophenyl)-1H-benzo[d]imidazol-2-yl)-1H-indazol-5-yl)pyridin-3-yl)-2-phenylacetamide 10

$^1$H NMR (CD$_3$OD, 400 MHz) δ ppm 3.89 (s, 2H), 7.22-7.46 (m, 6H), 7.60-7.77 (m, 5H), 7.95 (d, J=8 Hz, 1H), 8.00 (s, 2H), 8.81 (s, 1H), 9.01 (s, 1H), 9.03 (s, 1H), 9.29 (s, 1H); ESIMS found for C$_{33}$H$_{23}$FN$_6$O m/z 539.1 (M+H).

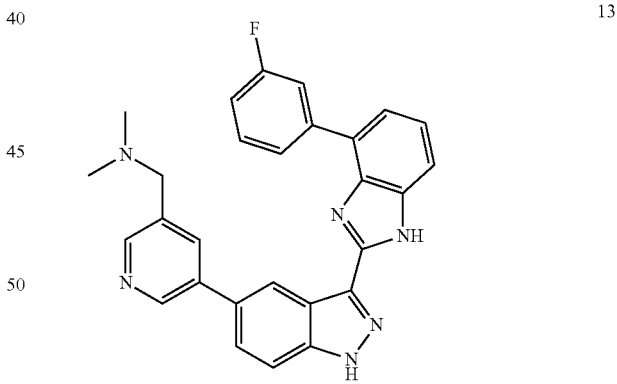

1-(5-(3-(4-(3-Fluorophenyl)-1H-benzo[d]imidazol-2-yl)-1H-indazol-5-yl)pyridin-3-yl)-N,N-dimethylmethanamine 13

$^1$H NMR (CD$_3$OD, 400 MHz) δ ppm 3.12 (s, 6H), 4.80 (s, 2H), 7.36 (dt, J=8.8 Hz, J=2 Hz, 1H), 7.64-7.77 (m, 4H), 7.83 (t, J=7.2 Hz, 1H), 8.06 (d, J=8.8 Hz, 1H), 8.12 (d, J=8 Hz, 1H), 8.20 (d, J=8.4 Hz, 1H), 9.11 (s, 1H), 9.41 (s, 1H), 9.51 (s, 1H); ESIMS found for C$_{28}$H$_{23}$FN$_6$ m/z 463.2 (M+H).

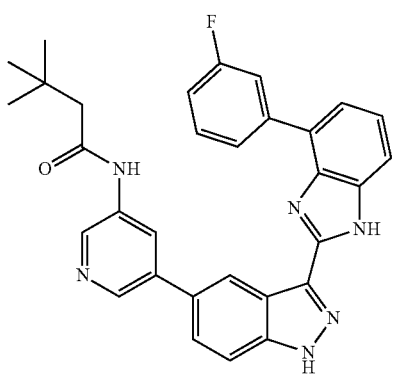

N-(5-(3-(4-(3-Fluorophenyl)-1H-benzo[d]imidazol-2-yl)-1H-indazol-5-yl)pyridin-3-yl)-3,3-dimethylbutanamide 16

¹H NMR (CD₃OD, 400 MHz) δ ppm 1.04 (s, 9H), 2.30 (s, 2H), 7.09 (t, J=8 Hz, 1H), 7.41-7.52 (m, 3H), 7.57 (d, J=7.6 Hz, 1H), 7.60-7.71 (m, 2H), 7.76 (Abq, 2H), 8.69 (s, 1H), 8.71 (s, 1H), 8.83 (brs, 1H), 9.17 (brs, 1H); ESIMS found for $C_{31}H_{27}FN_6O$ m/z 519.2 (M+H).

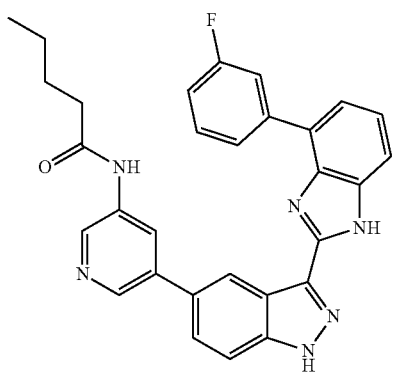

N-(5-(3-(4-(3-Fluorophenyl)-1H-benzo[d]imidazol-2-yl)-1H-indazol-5-yl)pyridin-3-yl)pentanamide 18

¹H NMR (CD₃OD, 400 MHz) δ ppm 0.90 (t, J=7.2 Hz, 3H), 1.36 (sex, J=7.2 Hz, 2H), 1.66 (quin, J=7.6 Hz, 2H), 2.47 (t, J=7.6 Hz, 2H), 7.13-7.22 (m, 1H), 7.50-7.59 (m, 4H), 7.63 (t, J=8 Hz, 1H), 7.82-7.93 (m, 3H), 8.72 (s, 1H), 8.88 (s, 1H), 8.95 (s, 1H), 9.24 (s, 1H); ESIMS found for $C_{30}H_{25}FN_6O$ m/z 505.2 (M+H).

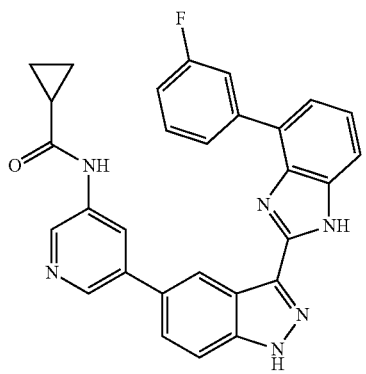

N-(5-(3-(4-(3-Fluorophenyl)-1H-benzo[d]imidazol-2-yl)-1H-indazol-5-yl)pyridin-3-yl)cyclopropanecarboxamide 19

¹H NMR (DMSO-d₆, 400 MHz) δ ppm 0.95 (d, J=7.6 Hz, 4H), 1.94-2.05 (m, 1H), 7.22 (dt, J=6.8 Hz, J=1.6 Hz, 1H), 7.31 (s, 1H), 7.42 (t, J=7.6 Hz, 2H), 7.55-7.71 (m, 3H), 7.91 (Abq, 2H), 8.10 (d, J=6.8 Hz, 1H), 8.22 (d, J=10.4 Hz, 1H), 8.92 (s, 1H), 8.97 (s, 1H), 9.02 (s, 1H), 9.17 (s, 1H); ESIMS found for $C_{29}H_{21}FN_6O$ m/z 489.2 (M+H).

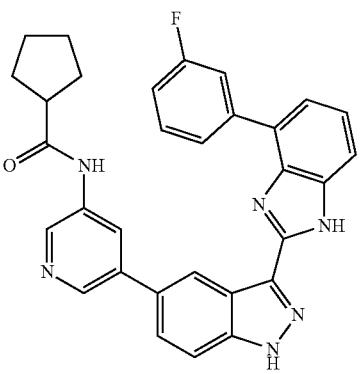

N-(5-(3-(4-(3-Fluorophenyl)-1H-benzo[d]imidazol-2-yl)-1H-indazol-5-yl)pyridin-3-yl)cyclopentanecarboxamide 21

¹H NMR (CD₃OD, 400 MHz) δ ppm 1.66-1.78 (m, 2H), 1.78-1.89 (m, 2H), 1.89-2.01 (m, 2H), 2.01-2.12 (m, 2H), 3.01 (quin, J=8 Hz, 1H), 7.26-7.35 (m, 1H), 7.62-7.73 (m, 4H), 7.76 (t, J=8 Hz, 1H), 7.98 (d, J=8 Hz, 1H), 8.02 (s, 2H), 8.83 (s, 1H), 9.03 (s, 1H), 9.05 (s, 1H), 9.35 (d, J=1.6 Hz, 1H); ESIMS found for $C_{31}H_{25}FN_6O$ m/z 517.2 (M+H).

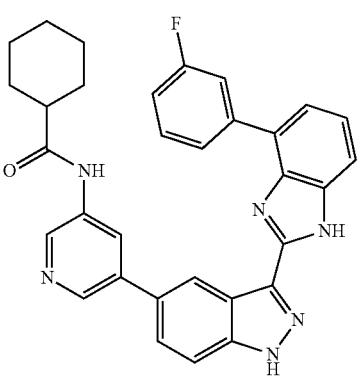

N-(5-(3-(4-(3-Fluorophenyl)-1H-benzo[d]imidazol-2-yl)-1H-indazol-5-yl)pyridin-3-yl)cyclohexanecarboxamide 22

¹H NMR (DMSO-d₆, 400 MHz) δ ppm 1.27 (d, J=14.8 Hz, 1H), 1.38 (q, J=13.6 Hz, 2H), 1.54 (q, J=10.4 Hz, 2H), 1.72 (d, J=12.4 Hz, 1H), 1.84 (d, J=13.6 Hz, 2H), 1.94 (d, J=12.4 Hz, 2H), 2.49 (q, J=10.8 Hz, 1H), 7.18-7.28 (m, 1H), 7.54-7.64 (m, 4H), 7.68 (t, J=8 Hz, 1H), 7.90 (d, J=8 Hz, 1H), 7.95 (s, 2H), 8.76 (s, 1H), 8.94 (s, 1H), 8.97 (s, 1H), 9.27 (s, 1H); ESIMS found for $C_{32}H_{27}FN_6O$ m/z 531.2 (M+H).

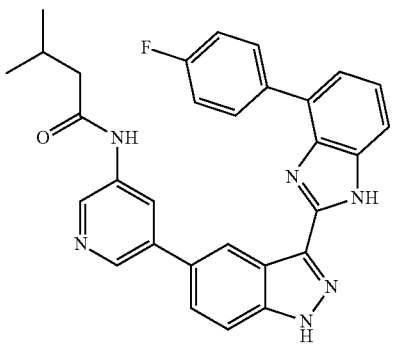

N-(5-(3-(4-(4-Fluorophenyl)-1H-benzo[d]imidazol-2-yl)-1H-indazol-5-yl)pyridin-3-yl)-3-methylbutanamide 26

$^1$H NMR (CD$_3$OD, 400 MHz) δ ppm 1.08 (d, J=6.4 Hz, 6H), 2.28 (non, J=6.8 Hz, 1H), 2.45 (d, J=7.2 Hz, 2H), 7.39 (t, J=8.4 Hz, 1H), 7.64 (d, 1H), 7.72 (t, 1H), 7.87 (dd, J=8.4 Hz, J=5.2 Hz, 2H), 7.94 (d, 1H), 8.00 (s, 2H), 8.84 (s, 1H), 9.02 (s, 1H), 9.06 (s, 1H), 9.32 (s, 1H); ESIMS found for $C_{30}H_{25}FN_6O$ m/z 5051 (M+H).

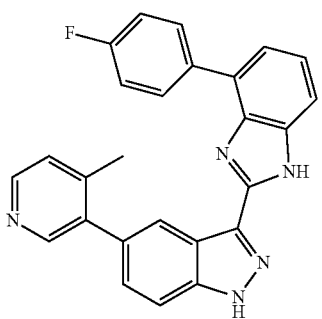

3-(4-(4-Fluorophenyl)-1H-benzo[d]imidazol-2-yl)-5-(4-methylpyridin-3-yl)-1H-indazole 29

$^1$H NMR (CD$_3$OD, 400 MHz) δ ppm 2.69 (s, 3H), 7.30-7.42 (m, 2H), 7.63 (d, J=6 Hz, 1H), 7.69-7.87 (m, 4H), 7.94-8.06 (m, 2H), 8.14 (brs, 1H), 8.56 (brrs, 1H), 8.80 (brs, 1H), 8.92 (brs, 1H); ESIMS found for $C_{26}H_{18}FN_5$ m/z 420.2 (M+H).

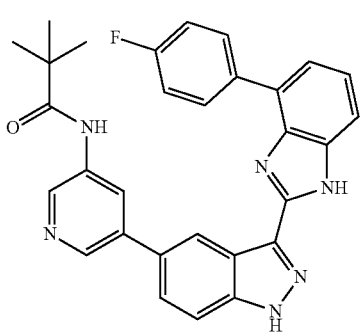

N-(5-(3-(4-(4-Fluorophenyl)-1H-benzo[d]imidazol-2-yl)-1H-indazol-5-yl)pyridin-3-yl)pivalamide 32

$^1$H NMR (CD$_3$OD, 400 MHz) δ ppm 1.42 (s, 9H), 7.39 (t, J=8.4 Hz, 2H), 7.65 (d, J=7.2 Hz, 1H), 7.74 (t, J=7.6 Hz, 1H), 7.80-7.91 (m, 2H), 7.98 (d, J=8 Hz, 1H), 8.02 (s, 2H), 8.87 (s, 1H), 9.10 (s, 1H), 9.26 (s, 1H), 9.39 (s, 1H); ESIMS found for $C_{30}H_{25}FN_6O$ m/z 505.2 (M+H).

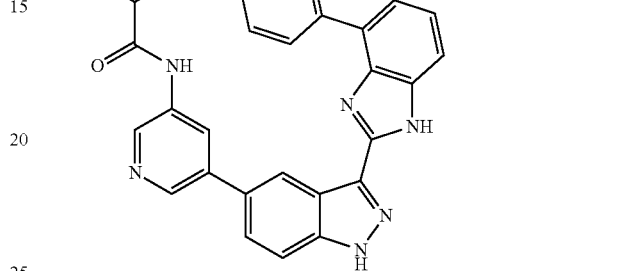

N-(5-(3-(4-(4-Fluorophenyl)-1H-benzo[d]imidazol-2-yl)-1H-indazol-5-yl)pyridin-3-yl)isobutyramide 33

$^1$H NMR (CD$_3$OD, 400 MHz) δ ppm 1.29 (d, J=6.8 Hz, 6H), 2.79 (sep, J=6.8 Hz, 1H), 7.37 (t, J=8.8 Hz, 2H), 7.62 (d, J=7.2 Hz, 1H), 7.70 (t, 1H), 7.82-7.93 (m, 3H), 7.98 (s, 2H), 8.78 (s, 1H), 8.98 (s, 1H), 9.00 (s, 1H), 9.23 (s, 1H); ESIMS found for $C_{29}H_{23}FN_6O$ m/z 491.2 (M+H).

N-(5-(3-(4-(4-Fluorophenyl)-1H-benzo[d]imidazol-2-yl)-1H-indazol-5-yl)pyridin-3-yl)benzamide 35

$^1$H NMR (CD$_3$OD, 400 MHz) δ ppm 7.43 (t, 2H), 7.61-7.82 (m, 5H), 7.92 (dd, 2H), 8.00 (d, 1H), 8.08 (Abq, J=5.6 Hz, 2H), 8.16 (d, J=7.6 Hz, 2H), 8.89 (s, 1H), 9.13 (s, 1H), 9.34 (s, 1H), 9.47 (s, 1H); ESIMS found for $C_{32}H_{21}FN_6O$ m/z 525.1 (M+H).

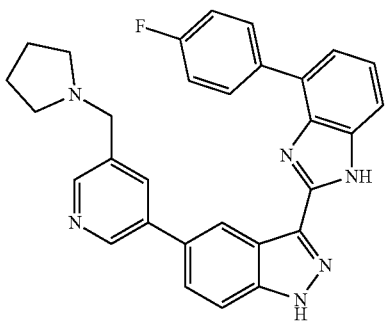

3-(4-(4-Fluorophenyl)-1H-benzo[d]imidazol-2-yl)-5-(5-(pyrrolidin-1-ylmethyl)pyridin-3-yl)-1H-indazole 38

¹H NMR (CD₃OD, 400 MHz) δ ppm 2.14 (brs, 2H), 2.26 (brs, 2H), 3.35 (brs, 4H), 3.70 (brs, 2H), 7.36 (t, J=8 Hz, 2H), 7.62 (d, J=7.2 Hz, 1H), 7.72 (t, 1H), 7.82 (brs, 2H), 7.98 (d, J=8.4 Hz, 1H), 8.03 (d, J=8 Hz, 1H), 8.12 (d, J=8.4 Hz, 1H), 9.02 (s, 1H), 9.03 (s, 1H), 9.32 (s, 1H), 9.38 (s, 1H); ESIMS found for C₃₀H₂₅FN₆ m/z 489.2 (M+H).

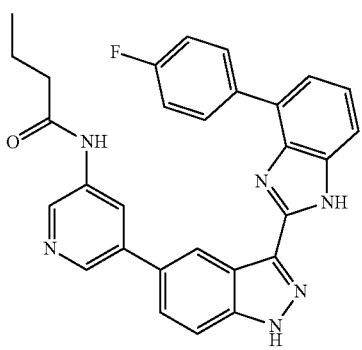

N-(5-(3-(4-(4-Fluorophenyl)-1H-benzo[d]imidazol-2-yl)-1H-indazol-5-yl)pyridin-3-yl)butyramide 41

¹H NMR (CD₃OD, 400 MHz) δ ppm 1.12 (t, J=7.2 Hz, 3H), 1.87 (sex, J=7.6 Hz, 2H), 2.62 (t, J=7.6 Hz, 2H), 7.45 (t, J=8.4 Hz, 2H), 7.73 (dd, J=6.8 Hz, J=1 Hz, 1H), 7.81 (t, J=8 Hz, 1H), 7.90 (dd, J=8.4 Hz, J=5.2 Hz, 2H), 8.02 (d, J=7.6 Hz, 1H), 8.07 (d, J=1 Hz, 2H), 8.87 (s, 1H), 9.11 (s, 1H), 9.12 (s, 1H), 9.37 (d, J=1.6 Hz, 1H); ESIMS found for C₂₉H₂₃FN₆O m/z 491.2 (M+H).

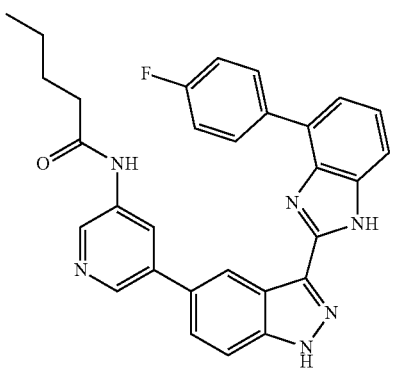

N-(5-(3-(4-(4-Fluorophenyl)-1H-benzo[d]imidazol-2-yl)-1H-indazol-5-yl)pyridin-3-yl)pentanamide 42

¹H NMR (DMSO-d₆, 400 MHz) δ ppm 0.92 (t, J=7.2 Hz, 3H), 1.38 (sex, J=7.6 Hz, 2H), 1.66 (quin, J=7.6 Hz, 2H), 2.72 (d, J=5.2 Hz, 2H), 7.34-7.46 (m, 3H), 7.50 (d, J=7.6 Hz, 1H), 7.63 (d, J=7.6 Hz, 1H), 7.90 (s, 2H), 8.29 (brs, 2H), 8.93 (s, 1H), 8.96 (s, 1H), 9.03 (s, 1H), 9.19 (s, 1H); ESIMS found for C₃₀H₂₅FN₆O m/z 505.2 (M+H).

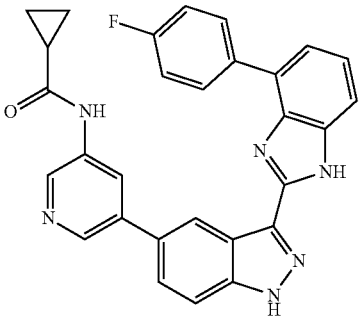

N-(5-(3-(4-(4-Fluorophenyl)-1H-benzo[d]imidazol-2-yl)-1H-indazol-5-yl)pyridin-3-yl)cyclopropanecarboxamide 43

¹H NMR (CD₃OD, 400 MHz) δ ppm 1.43 (d, J=7.2 Hz, 2H), 1.50 (brs, 2H), 1.59 (t, J=7.2 Hz, 1H), 7.78 (t, 2H), 8.03 (d, J=7.2 Hz, 1H), 8.11 (d, J=7.6 Hz, 1H), 8.14 (brs, 2H), 8.35 (d, J=7.6 Hz, 1H), 8.40 (s, 2H), 9.24 (s, 1H), 9.42 (brs, 2H), 9.69 (s, 1H); ESIMS found for C₂₉H₂₁FN₆O m/z 489.2 (M+H).

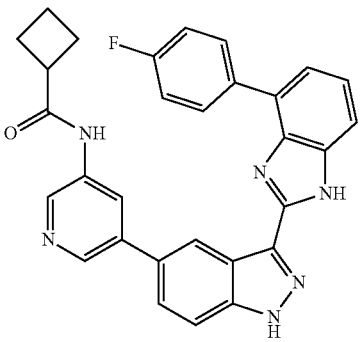

N-(5-(3-(4-(4-Fluorophenyl)-1H-benzo[d]imidazol-2-yl)-1H-indazol-5-yl)pyridin-3-yl)cyclobutanecarboxamide 44

¹H NMR (CD₃OD, 400 MHz) δ ppm 1.92-2.02 (m, 1H), 2.07-2.19 (m, 1H), 2.28-2.39 (m, 2H), 2.39-2.51 (m, 2H), 3.42-3.53 (m, 1H), 7.40 (t, J=8.4 Hz, 2H), 7.67 (d, J=7.6 Hz, 1H), 7.77 (t, J=8 Hz, 1H), 7.85 (Abq, J=8 Hz, J=4.8 Hz, 2H), 8.01 (d, J=8 Hz, 1H), 8.03 (s, 2H), 8.87 (s, 1H), 9.10 (s, 2H), 9.38 (s, 1H); ESIMS found for C₃₀H₂₃FN₆O m/z 503.2 (M+H).

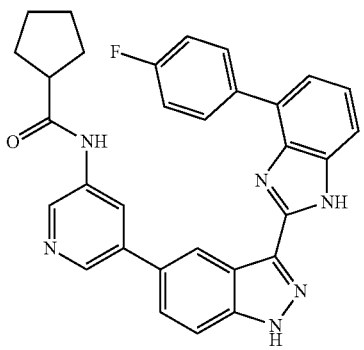

N-(5-(3-(4-(4-Fluorophenyl)-1H-benzo[d]imidazol-2-yl)-1H-indazol-5-yl)pyridin-3-yl)cyclopentanecarboxamide 45

$^1$H NMR (CD$_3$OD, 400 MHz) δ ppm 1.64-1.76 (m, 2H), 1.76-1.87 (m, 2H), 1.87-1.97 (m, 2H), 1.97-2.11 (m, 2H), 3.00 (quin, J=8 Hz, 1H), 7.36 (t, J=8.4 Hz, 2H), 7.61 (d, J=7.6 Hz, 1H), 7.69 (t, 1H), 7.86 (Abq, J=8 Hz, J=5.2 Hz, 2H), 7.91 (d, J=8 Hz, 1H), 7.97 (s, 2H), 8.80 (s, 1H), 9.00 (s, 2H), 9.26 (s, 1H); ESIMS found for C$_{31}$H$_{25}$FN$_6$O m/z 517.2 (M+H).

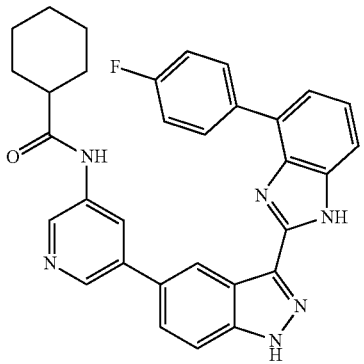

N-(5-(3-(4-(4-Fluorophenyl)-1H-benzo[d]imidazol-2-yl)-1H-indazol-5-yl)pyridin-3-yl)cyclohexanecarboxamide 46

$^1$H NMR (CD$_3$OD, 400 MHz) δ ppm 1.44 (q, J=12.8 Hz, 2H), 1.62 (q, J=14.8 Hz, 2H), 1.90 (d, J=12.8 Hz, 2H), 2.01 (d, J=16 Hz, 2H), 2.50-2.68 (m, 1H), 7.39 (t, J=8.8 Hz, 2H), 7.62 (d, 1H), 7.67 (t, 1H), 7.90 (t, 3H), 7.98 (s, 2H), 8.80 (s, 1H), 8.97 (s, 1H), 8.99 (s, 1H), 9.21 (s, 1H); ESIMS found for C$_{32}$H$_{27}$FN$_6$O m/z 531.2 (M+H).

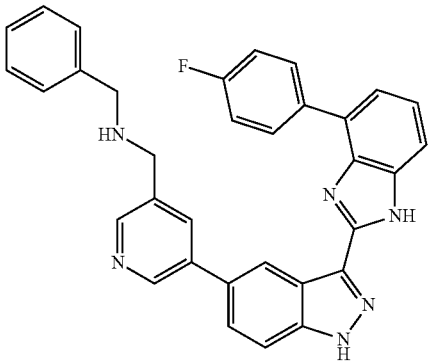

N-benzyl-1-(5-(3-(4-(4-Fluorophenyl)-1H-benzo[d]imidazol-2-yl)-1H-indazol-5-yl)pyridin-3-yl)methanamine 47

$^1$H NMR (CD$_3$OD, 400 MHz) δ ppm 4.47 (s, 2H), 4.64 (s, 2H), 7.38 (t, J=8.8 Hz, 2H), 7.48-7.53 (m, 3H), 7.62-7.69 (m, 3H), 7.76 (t, J=7.6 Hz, 1H), 7.85 (Abq, J=8.4 Hz, J=5.2 Hz, 2H), 8.02 (Abq, J=10.8 Hz, J=8.8 Hz, 2H), 8.09 (d, J=8.8 Hz, 1H), 8.96 (brs, 1H), 8.97 (s, 1H), 9.21 (s, 1H), 9.36 (brs, 1H); ESIMS found for C$_{33}$H$_{25}$FN$_6$ m/z 525.2 (M+H).

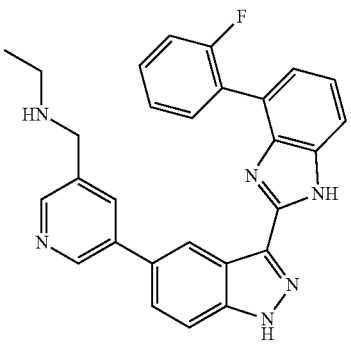

N-((5-(3-(4-(2-Fluorophenyl)-1H-benzo[d]imidazol-2-yl)-1H-indazol-5-yl)pyridin-3-yl)methyl)ethanamine 54

$^1$H NMR (CD$_3$OD, 400 MHz) δ ppm 1.49 (t, J=7.2 Hz, 3H), 3.29-3.38 (m, 2H), 4.62 (s, 2H), 7.36-7.49 (m, 2H), 7.57-7.73 (m, 3H), 7.79 (t, J=8 Hz, 1H), 8.02 (d, J=8.8 Hz, 1H), 8.14 (d, J=7.6 Hz, 2H), 9.05 (s, 1H), 9.08 (s, 1H), 9.41 (s, 1H), 9.45 (s, 1H); ESIMS found for C$_{28}$H$_{23}$FN$_6$ m/z 463.2 (M+H).

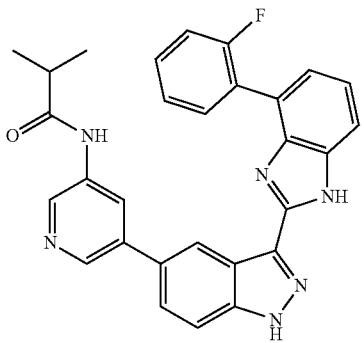

N-(5-(3-(4-(2-Fluorophenyl)-1H-benzo[d]imidazol-2-yl)-1H-indazol-5-yl)pyridin-3-yl)isobutyramide 57

$^1$H NMR (CD$_3$OD, 400 MHz) δ ppm 1.30 (d, J=6.8 Hz, 6H), 2.84 (sep, J=7.2 Hz, 1H), 7.36-7.49 (m, 2H), 7.61 (q, J=7.2 Hz, 1H), 6.65 (d, J=7.6 Hz, 1H), 7.71 (t, J=7.6 Hz, 1H), 7.77 (t, J=7.6 Hz, 1H), 8.00 (s, 2H), 8.05 (d, J=8 Hz, 1H), 8.85 (s, 1H), 9.02 (s, 1H), 9.08 (brs, 1H), 9.36 (br, 1H); ESIMS found for C$_{29}$H$_{23}$FN$_6$O m/z 491.2 (M+H).

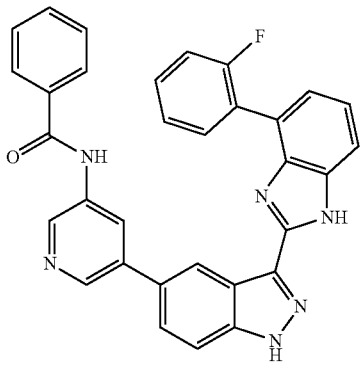

N-(5-(3-(4-(2-Fluorophenyl)-1H-benzo[d]imidazol-
2-yl)-1H-indazol-5-yl)pyridin-3-yl)benzamide 59

$^1$H NMR (CD$_3$OD, 400 MHz) δ ppm 7.36-7.47 (m, 2H), 7.56-7.65 (m, 3H), 7.65-7.76 (m, 3H), 7.78 (t, 1H), 8.00-8.11 (m, 2H), 8.13 (d, J=7.6 Hz, 3H), 8.91 (s, 1H), 9.18 (s, 1H), 9.34 (s, 1H), 9.53 (s, 1H); ESIMS found for C$_{32}$H$_{21}$FN$_6$O m/z 525.2 (M+H).

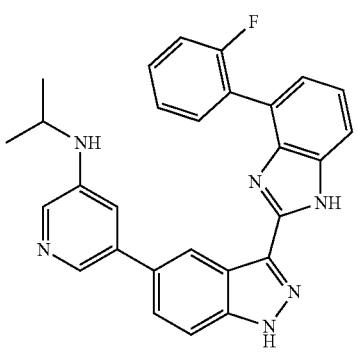

5-(3-(4-(2-Fluorophenyl)-1H-benzo[d]imidazol-2-
yl)-1H-indazol-5-yl)-N-isopropylpyridin-3-amine 60

$^1$H NMR (CD$_3$OD, 400 MHz) δ ppm 1.23 (d, J=5.6 Hz, 6H), 3.78 (sep, J=5.6 Hz, 1H), 7.22-7.35 (m, 2H), 7.49 (q, J=6.8 Hz, 1H), 7.53 (d, J=7.2 Hz, 1H), 7.59 (t, J=7.6 Hz, 1H), 7.67 (t, J=8 Hz, 1H), 7.83 (s, 2H), 7.93 (d, J=8 Hz, 3H), 8.30 (s, 1H), 8.65 (s, 1H); ESIMS found for C$_{28}$H$_{23}$FN$_6$ m/z 463.1 (M+H).

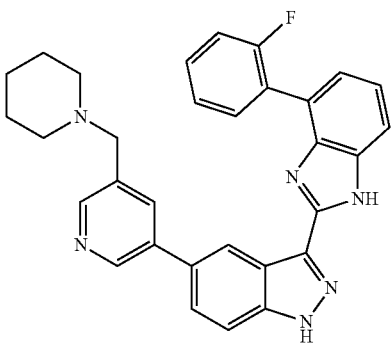

3-(4-(2-Fluorophenyl)-1H-benzo[d]imidazol-2-yl)-5-
(5-(piperidin-1-ylmethyl)pyridin-3-yl)-1H-indazole
63

$^1$H NMR (CD$_3$OD, 400 MHz) δ ppm 1.61 (brs, 1H), 1.83-2.07 (m, 5H), 2.17 (s, 1H), 2.69 (s, 1H), 3.13-3.29 (m, 2H), 3.65 (d, J=9.6 Hz, 2H), 7.42 (quin, J=8.8 Hz, 2H), 7.61 (q, J=6.8 Hz, 1H), 7.69 (q, J=8.4 Hz, 2H), 7.79 (t, J=8 Hz, 1H), H), 8.01 (d, J=8.4 Hz, 1H), 8.16 (t, J=7.6 Hz, 2H), 9.10 (s, 1H), 9.48 (s, 1H); ESIMS found for C$_{31}$H$_{27}$FN$_6$ m/z 503.2 (M+H).

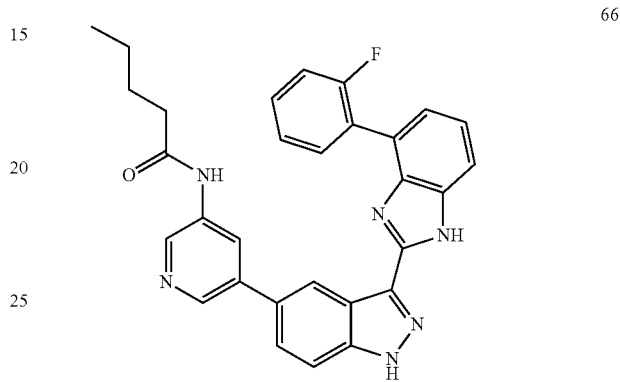

N-(5-(3-(4-(2-Fluorophenyl)-1H-benzo[d]imidazol-
2-yl)-1H-indazol-5-yl)pyridin-3-yl)pentanamide 66

$^1$H NMR (CD$_3$OD, 400 MHz) δ ppm 1.02 (t, J=7.6 Hz, 3H), 1.48 (sex, J=7.2 Hz, 2H), 1.77 (quin, J=7.6 Hz, 2H), 2.51 (t, J=8 Hz, 2H), 7.37 (quin, J=8.4 Hz, 3H), 7.46 (sex, J=7.6 Hz, 3H), 7.77-7.89 (m, 4H), 8.53 (s, 1H), 8.74 (s, 1H), 8.79 (s, 1H), 8.85 (s, 1H); ESIMS found for C$_{30}$H$_{25}$FN$_6$O m/z 505.2 (M+H).

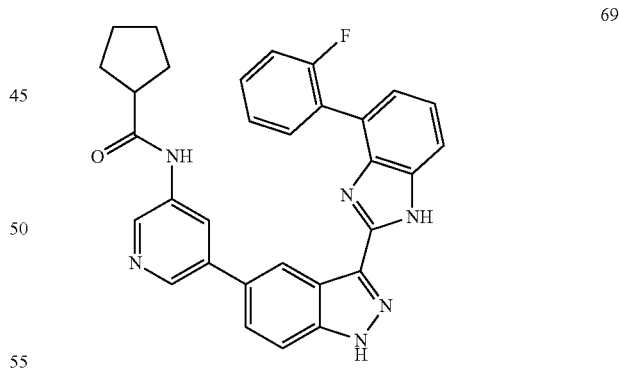

N-(5-(3-(4-(2-Fluorophenyl)-1H-benzo[d]imidazol-
2-yl)-1H-indazol-5-yl)pyridin-3-yl)cyclopentanecar-
boxamide 69

$^1$H NMR (DMSO-d$_6$, 400 MHz) δ ppm 1.57-1.69 (m, 2H), 1.66-1.76 (m, 2H), 1.73-1.86 (m, 2H), 1.90-2.02 (m, 2H), 2.95 (quin, J=8 Hz, 1H), 7.34-7.55 (m, 5H), 7.76 (brd, J=7.2 Hz, 1H), 7.82-8.00 (m, 3H), 8.78 (s, 1H), 8.84 (s, 1H), 8.92 (s, 1H), 9.09 (s, 1H); ESIMS found for C$_{31}$H$_{25}$FN$_6$O m/z 517.2 (M+H).

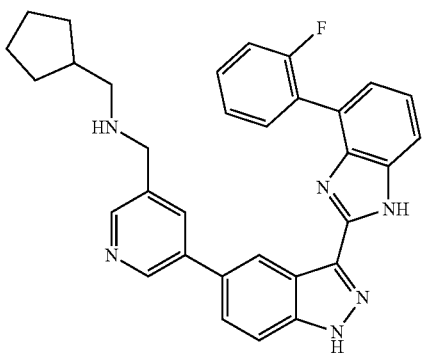

1-Cyclopentyl-N-((5-(3-(4-(2-fluorophenyl)-1H-benzo[d]imidazol-2-yl)-1H-indazol-5-yl)pyridin-3-yl)methyl)methanamine 72

$^1$H NMR (CD$_3$OD, 400 MHz) δ ppm 1.16-1.36 (m, 4H), 1.51-1.70 (m, 4H), 1.88 (brs, 2H), 2.80 (s, 1H), 3.10-3.17 (m, 2H), 7.23-7.36 (m, 2H), 7.45-7.55 (m, 1H), 7.54-7.64 (m, 2H), 7.64-7.73 (m, 1H), 7.92 (d, J=8 Hz, 1H), 8.04 (d, J=7.6 Hz, 2H), 9.00 (brs, 2H), 9.37 (brs, 1H), 9.43 (brs, 1H); ESIMS found for C$_{32}$H$_{29}$FN$_6$ m/z 517.2 (M+H).

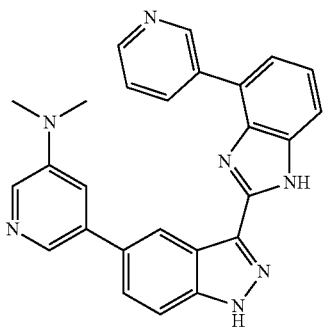

5-(3-(4-(Pyridin-3-yl)-1H-benzo[d]imidazol-2-yl)-1H-indazol-5-yl)pyridin-3-amine 75

$^1$H NMR (CD$_3$OD, 400 MHz) δ ppm 7.63 (t, J=8 Hz, 1H), 7.77 (d, J=7.6 Hz, 1H), 7.88 (s, 2H), 7.93 (d, J=8 Hz, 1H), 8.05 (d, J=2.4 Hz, 1H), 8.11 (s, 1H), 8.45 (s, 1H), 8.88 (s, 1H), 8.94 (d, J=5.6 Hz, 1H), 9.36 (d, J=8 Hz, 1H), 9.73 (s, 1H); ESIMS found for C$_{24}$H$_{17}$N$_7$ m/z 404.1 (M+H).

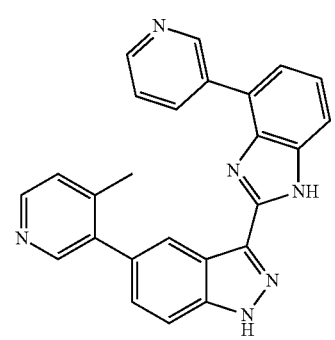

5-(4-Methylpyridin-3-yl)-3-(4-(pyridin-3-yl)-1H-benzo[d]imidazol-2-yl)-1H-indazole 77

$^1$H NMR (CD$_3$OD, 400 MHz) δ ppm 2.68 (s, 3H), 7.71 (d, J=8.8 Hz, 1H), 7.81 (Abq, J=6.8 Hz, J=4 Hz, 2H), 7.97 (d, J=8.8 Hz, 1H), 8.11-8.31 (m, 2H), 8.32 (dd, 1H), 8.69 (s, 1H), 8.78 (d, J=6.4 Hz, 1H), 8.92 (s, 1H), 9.01 (d, J=6 Hz, 1H), 9.11 (d, 1H), 9.50 (s, 1H); ESIMS found for C$_{25}$H$_{18}$N$_6$ m/z 403.2 (M+H).

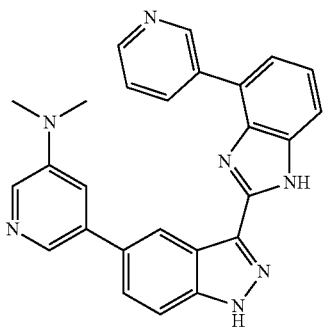

N,N-Dimethyl-5-(3-(4-(pyridin-3-yl)-1H-benzo[d]imidazol-2-yl)-1H-indazol-5-yl)pyridin-3-amine 79

$^1$H NMR (CD$_3$OD, 400 MHz) δ ppm 3.10 (s, 6H), 7.42 (t, J=8 Hz, 1H), 7.49 (d, J=7.2 Hz, 1H), 7.52 (s, 1H), 7.61 (dd, J=8 Hz, J=3.2 Hz, 1H), 7.67 (d, 1H), 7.73 (d, J=8.4 Hz, 1H), 7.79 (d, 1H), 8.07 (d, 1H), 8.23 (s, 1H), 8.30 (s, 1H), 8.57 (d, J=3.6 Hz, 1H), 8.61 (brs, 1H), 8.82 (s, 1H), 9.25 (brs, 1H); ESIMS found for C$_{26}$H$_{21}$N$_7$ m/z 432.2 (M+H).

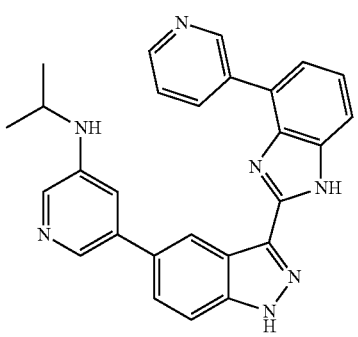

N-Isopropyl-5-(3-(4-(pyridin-3-yl)-1H-benzo[d]imidazol-2-yl)-1H-indazol-5-yl)pyridin-3-amine 84

$^1$H NMR (CD$_3$OD, 400 MHz) δ ppm 1.34 (d, J=6.4 Hz, 6H), 3.88 (sep, J=6.4 Hz, 1H), 7.68 (t, J=7.6 Hz, 1H), 7.79 (d, J=7.6 Hz, 1H), 7.91 (s, 2H), 7.99 (d, J=8.4 Hz, 1H), 8.02-8.07 (m, 2H), 8.32 (dd, J=8 Hz, J=5.6 Hz, 1H), 8.46 (s, 1H), 8.91 (s, 1H), 8.98 (d, J=5.6 Hz, 1H), 9.28 (d, J=8.4 Hz, 1H), 9.70 (s, 1H); ESIMS found for C$_{27}$H$_{23}$N$_7$ m/z 446.2 (M+H).

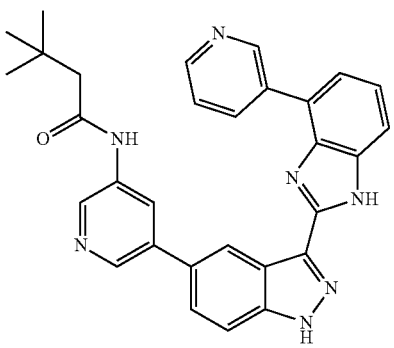

3,3-Dimethyl-N-(5-(3-(4-(pyridin-3-yl)-1H-benzo[d]imidazol-2-yl)-1H-indazol-5-yl)pyridin-3-yl)butanamide 88

¹H NMR (CD$_3$OD, 400 MHz) δ ppm 1.19 (s, 9H), 2.36 (s, 2H), 7.41 (t, J=7.6 Hz, 1H), 7.50 (d, J=7.2 Hz, 1H), 7.65 (quin, J=5.2 Hz, 2H), 7.76 (q, J=6.8 Hz, 2H), 8.22 (brs, 2H), 8.41 (s, 1H), 8.55 (d, J=4.4 Hz, 1H), 8.65 (s, 1H), 8.67 (brs, 1H), 8.82 (s, 1H), 8.85 (s, 1H), 9.31 (brs, 1H); ESIMS found for C$_{30}$H$_{27}$N$_7$O m/z 502.2 (M+H).

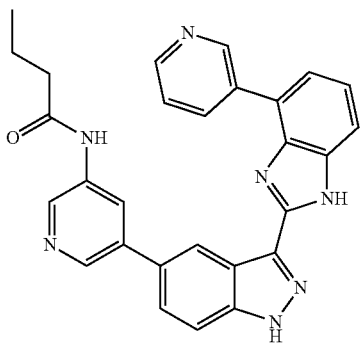

N-(5-(3-(4-(Pyridin-3-yl)-1H-benzo[d]imidazol-2-yl)-1H-indazol-5-yl)pyridin-3-yl)butyramide 89

¹H NMR (CD$_3$OD, 400 MHz) δ ppm 1.09 (t, J=7.6 Hz, 3H), 1.84 (sex, J=7.2 Hz, 2H), 2.59 (t, J=7.6 Hz, 2H), 7.64 (t, J=8 Hz, 1H), 7.81 (d, J=7.2 Hz, 1H), 7.88-7.99 (m, 3H), 8.33 (dd, J=8 Hz, J=5.6 Hz, 1H), 8.94 (d, J=5.6 Hz, 1H), 8.98 (s, 1H), 9.08 (t, J=1.8 Hz, 2H), 9.29 (d, J=1.6 Hz, 1H), 9.36 (d, J=8.4 Hz, 1H), 9.90 (s, 1H); ESIMS found for C$_{28}$H$_{23}$N$_7$O m/z 474.1 (M+H).

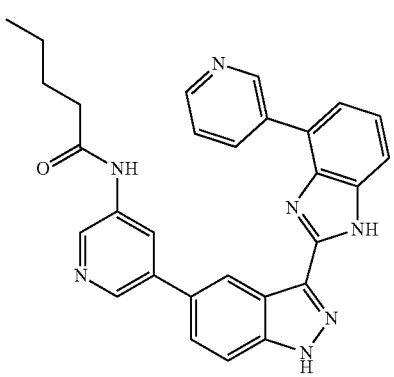

N-(5-(3-(4-(Pyridin-3-yl)-1H-benzo[d]imidazol-2-yl)-1H-indazol-5-yl)pyridin-3-yl)pentanamide 90

¹H NMR (CD$_3$OD, 400 MHz) δ ppm 1.02 (t, J=7.6 Hz, 3H), 1.48 (sex, J=7.6 Hz, 2H), 1.77 (quin, J=7.2 Hz, 2H), 2.61 (t, J=7.6 Hz, 2H), 7.83 (d, J=6 Hz, 2H), 8.00 (s, 2H), 8.14 (d, J=6 Hz, 1H), 8.38 (t, J=7.2 Hz, 1H), 9.05 (t, J=7.6 Hz, 3H), 9.14 (d, J=7.6 Hz, 1H), 9.18 (s, 1H), 9.43 (s, 1H), 9.57 (s, 1H); ESIMS found for C$_{29}$H$_{25}$N$_7$O m/z 488.1 (M+H).

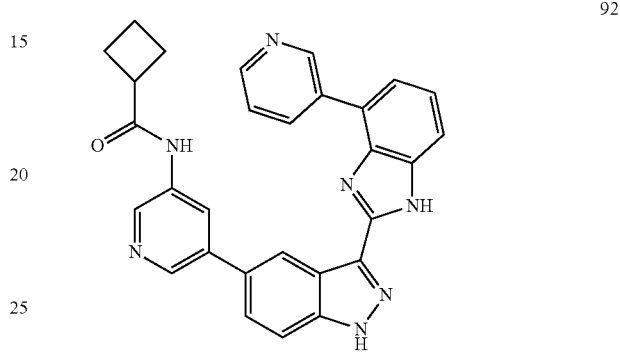

N-(5-(3-(4-(Pyridin-3-yl)-1H-benzo[d]imidazol-2-yl)-1H-indazol-5-yl)pyridin-3-yl)cyclobutanecarboxamide 92

¹H NMR (CD$_3$OD, 400 MHz) δ ppm 1.86-1.98 (m, 1H), 2.06 (sex, J=9.6 Hz, 1H), 2.19-2.31 (m, 2H), 2.38 (quin, J=9.2 Hz, 2H), 3.34 (quin, J=8.4 Hz, 1H), 7.31 (t, J=8 Hz, 1H), 7.41 (d, J=7.2 Hz, 1H), 7.52-7.60 (m, 1H), 7.60 (d, J=8.4 Hz, 1H), 7.66 (d, J=8.4 Hz, 1H), 8.12 (s, 1H), 8.35 (s, 1H), 8.47 (d, J=4.8 Hz, 1H), 8.53 (s, 1H), 8.61 (d, J=7.6 Hz, 1H), 8.69 (s, 1H), 8.76 (s, 1H), 9.25 (s, 1H); ESIMS found for C$_{29}$H$_{23}$N$_7$O m/z 486.2 (M+H).

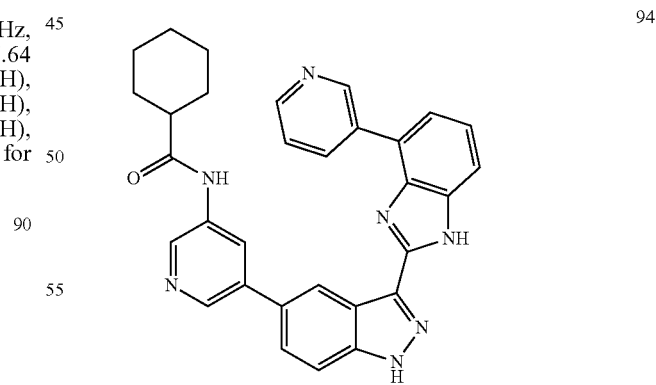

N-(5-(3-(4-(Pyridin-3-yl)-1H-benzo[d]imidazol-2-yl)-1H-indazol-5-yl)pyridin-3-yl)cyclohexanecarboxamide 94

¹H NMR (CD$_3$OD, 400 MHz) δ ppm 1.45 (q, J=12.8 Hz, 2H), 1.61 (q, J=13.2 Hz, 2H), 1.79 (d, J=12.8 Hz, 1H), 1.91

(d, J=12.8 Hz, 2H), 2.03 (d, J=11.6 Hz, 2H), 2.60 (t, J=11.2 Hz, 1H), 2.77 (d, J=4.4 Hz, 1H), 7.71 (t, J=7.6 Hz, 1H), 7.83 (d, J=7.6 Hz, 1H), 7.97 (s, 2H), 8.01 (d, J=8 Hz, 1H), 8.35 (t, J=6.4 Hz, 1H), 8.97 (d, J=5.2 Hz, 1H), 9.01 (s, 1H), 9.08 (s, 1H), 9.11 (s, 1H), 9.29 (d, J=8 Hz, 1H), 9.36 (s, 1H), 9.78 (s, 1H); ESIMS found for $C_{31}H_{27}N_7O$ m/z 514.3 (M+H).

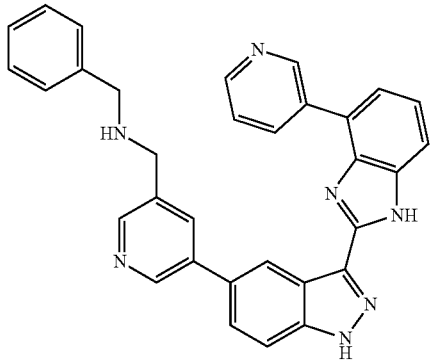

95

N-Benzyl-1-(5-(3-(4-(pyridin-3-yl)-1H-benzo[d]imidazol-2-yl)-1H-indazol-5-yl)pyridin-3-yl)methanamine 95

$^1$H NMR (CD$_3$OD, 400 MHz) δ ppm 4.39 (s, 2H), 4.62 (s, 2H), 7.34-7.42 (m, 3H), 7.58 (t, J=4.4 Hz, 2H), 7.62 (t, J=7.6 Hz, 1H), 7.71 (d, J=7.6 Hz, 1H), 7.85 (d, J=8.8 Hz, 1H), 7.96 (t, J=7.2 Hz, 2H), 8.21 (t, 1H), 8.85 (d, J=4.4 Hz, 1H), 8.93 (brs, 1H), 9.04 (s, 1H), 9.11 (s, 1H), 9.36 (s, 1H), 9.37 (brs, 1H), 9.65 (s, 1H); ESIMS found for $C_{32}H_{25}N_7$ m/z 508.2 (M+H).

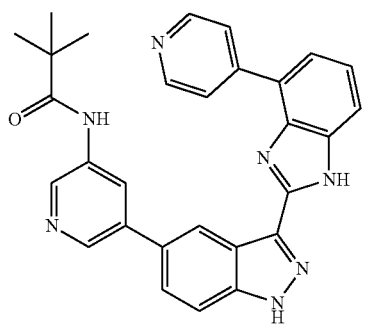

104

N-(5-(3-(4-(Pyridin-4-yl)-1H-benzo[d]imidazol-2-yl)-1H-indazol-5-yl)pyridin-3-yl)pivalamide 104

$^1$H NMR (CD$_3$OD, 400 MHz) δ ppm 1.42 (s, 9H), 7.72 (t, J=8 Hz, 1H), 7.92-8.00 (m, 3H), 8.07 (d, J=8 Hz, 1H), 8.95 (d, J=5.6 Hz, 2H), 9.02 (s, 1H), 9.06 (d, J=6 Hz, 2H), 9.12 (s, 1H), 9.28 (s, 1H), 9.41 (s, 1H); ESIMS found for $C_{29}H_{25}N_7O$ m/z 488.1 (M+H).

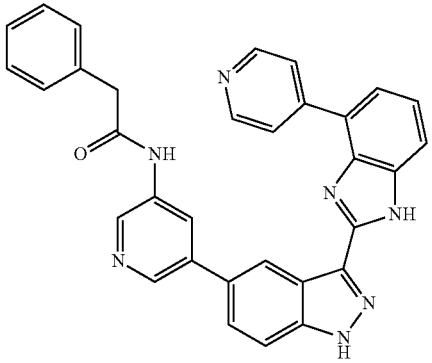

106

2-Phenyl-N-(5-(3-(4-(pyridin-4-yl)-1H-benzo[d]imidazol-2-yl)-1H-indazol-5-yl)pyridin-3-yl)acetamide 106

$^1$H NMR (CD$_3$OD, 400 MHz) δ ppm 3.92 (s, 2H), 7.25-7.45 (m, 6H), 7.59 (t, 1H), 7.87-7.98 (m, 4H), 8.92 (d, J=6.4 Hz, 2H), 8.98 (s, 1H), 9.03 (s, 1H), 9.12 (s, 2H), 9.15 (d, J=5.2 Hz, 1H); ESIMS found for $C_{32}H_{23}N_7O$ m/z 522.1 (M+H).

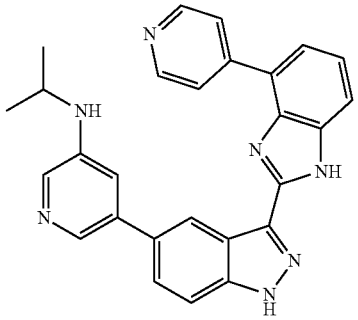

108

N-Isopropyl-5-(3-(4-(pyridin-4-yl)-1H-benzo[d]imidazol-2-yl)-1H-indazol-5-yl)pyridin-3-amindazole 108

$^1$H NMR (CD$_3$OD, 400 MHz) δ ppm 1.23 (d, J=6H), 3.78 (sep, J=6 Hz, 1H), 7.68 (t, J=8 Hz, 1H), 7.79-7.87 (m, 3H), 7.93 (s, 1H), 7.98 (s, 1H), 8.03 (d, J=8 Hz, 1H), 8.36 (s, 1H), 8.67 (d, J=6.4 Hz, 2H), 8.83 (s, 1H), 8.96 (d, J=6 Hz, 2H); ESIMS found for $C_{27}H_{23}N_7$ m/z 446.3 (M+H).

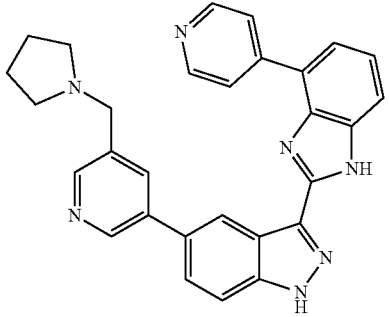

110

3-(4-(Pyridin-4-yl)-1H-benzo[d]imidazol-2-yl)-5-(5-(pyrrolidin-1-ylmethyl)pyridin-3-yl)-1H-indazole 110

$^1$H NMR (CD$_3$OD, 400 MHz) δ ppm 2.04-2.32 (m, 6H), 3.64 (brs, 2H), 4.67 (s, 2H), 7.56 (t, J=7.6 Hz, 1H), 7.82-8.01 (m, 4H), 8.72 (s, 1H), 8.87 (brs, 1H), 8.96 (d, J=6.8 Hz, 2H), 9.00 (s, 1H), 9.15 (d, J=6 Hz, 2H), 9.27 (brs, 1H); ESIMS found for C$_{29}$H$_{25}$N$_7$ m/z 472.1 (M+H).

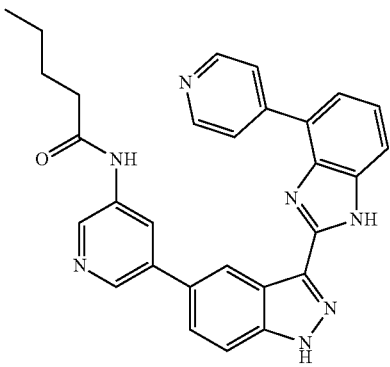

N-(5-(3-(4-(Pyridin-4-yl)-1H-benzo[d]imidazol-2-yl)-1H-indazol-5-yl)pyridin-3-yl)pentanamide 114

$^1$H NMR (CD$_3$OD, 400 MHz) δ ppm 1.00 (t, J=7.2 Hz, 3H), 1.47 (sex, J=7.2 Hz, 2H), 1.76 (quin, J=7.6 Hz, 2H), 2.58 (t, J=8 Hz, 2H), 7.58 (t, J=7.6 Hz, 1H), 7.86-7.98 (m, 4H), 8.97 (s, 1H), 8.98 (d, J=6.4 Hz, 2H), 9.01 (s, 1H), 9.05 (s, 1H), 9.14 (d, J=6.4 Hz, 2H), 9.22 (s, 1H); ESIMS found for C$_{29}$H$_{25}$N$_7$O m/z 488.1 (M+H).

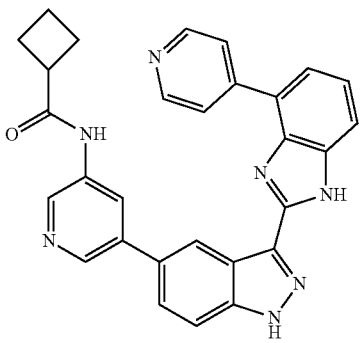

N-(5-(3-(4-(Pyridin-4-yl)-1H-benzo[d]imidazol-2-yl)-1H-indazol-5-yl)pyridin-3-yl)cyclobutanecarboxamide 116

$^1$H NMR (CD$_3$OD, 400 MHz) δ ppm 1.92-2.04 (m, 1H), 2.12 (sex, 1H), 2.27-2.37 (m, 2H), 2.43 (quin, 2H), 3.50 (quin, 1H), 7.81 (t, 1H), 7.94 (d, 1H), 7.99 (s, 2H), 8.16 (d, 1H), 8.75 (d, 2H), 9.01 (s, 1H), 9.06 (s, 1H), 9.10 (d, 2H), 9.12 (s, 1H), 9.41 (s, 1H); ESIMS found for C$_{29}$H$_{23}$N$_7$O m/z 486.2 (M+H).

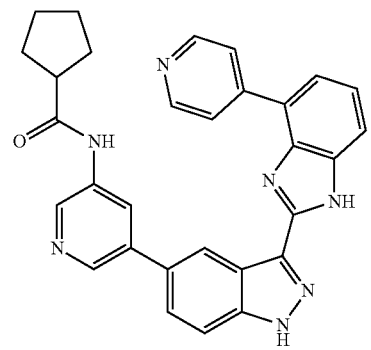

N-(5-(3-(4-(Pyridin-4-yl)-1H-benzo[d]imidazol-2-yl)-1H-indazol-5-yl)pyridin-3-yl)cyclopentanecarboxamide 117

$^1$H NMR (DMSO-d$_6$, 400 MHz) δ ppm 1.53-1.64 (m, 2H), 1.64-1.73 (m, 2H), 1.73-1.84 (m, 2H), 1.86-2.01 (m, 2H), 2.91 (quin, J=7.6 Hz, 1H), 7.47 (t, J=7.6 Hz, 1H), 7.75 (d, J=8 Hz, 1H), 7.85 (s, 3H), 8.65 (s, 1H), 8.75 (s, 1H), 8.79 (s, 1H), 8.83 (s, 4H), 8.90 (s, 1H), 10.38 (s, 1H); ESIMS found for C$_{30}$H$_{25}$N$_7$O m/z 500.1 (M+H).

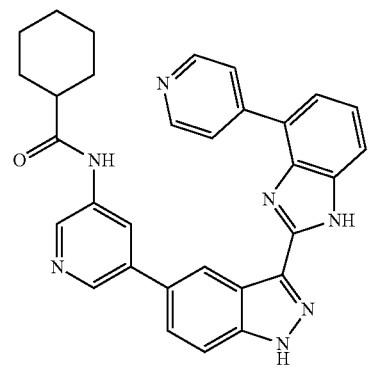

N-(5-(3-(4-(Pyridin-4-yl)-1H-benzo[d]imidazol-2-yl)-1H-indazol-5-yl)pyridin-3-yl)cyclohexanecarboxamide 118

$^1$H NMR (CD$_3$OD, 400 MHz) δ ppm 1.25-1.50 (m, 3H), 1.58 (q, J=14.4 Hz, 2H), 1.76 (d, J=12.4 Hz, 1H), 1.88 (d, J=12.8 Hz, 2H), 1.98 (d, J=12 Hz, 2H), 2.50 (quin, 1H), 7.53 (t, J=8 Hz, 1H), 7.78-7.89 (m, 3H), 7.93 (d, J=7.6 Hz, 1H), 8.82 (s, 2H), 8.88 (s, 1H), 8.93 (d, J=6 Hz, 3H), 9.16 (d, J=6 Hz, 2H); ESIMS found for C$_{31}$H$_{27}$N$_7$O m/z 514.2 (M+H).

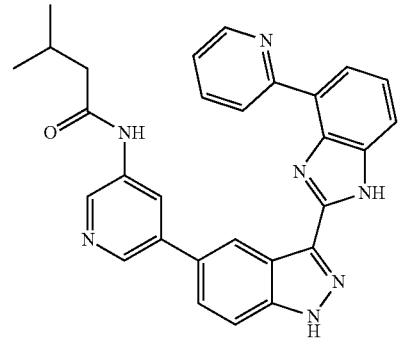

3-Methyl-N-(5-(3-(4-(pyridin-2-yl)-1H-benzo[d]imidazol-2-yl)-1H-indazol-5-yl)pyridin-3-yl)butanamide 122

$^1$H NMR (CD$_3$OD, 400 MHz) δ ppm 1.09 (d, J=6.8 Hz, 6H), 2.27 (non, J=6.8 Hz, 1H), 2.45 (d, J=7.6 Hz, 2H), 7.64 (t, J=8 Hz, 1H), 7.89 (q, J=8.8 Hz, 2H), 7.98 (d, J=8 Hz, 1H), 8.05 (brs, 1H), 8.10 (d, J=7.6 Hz, 1H), 8.68-8.79 (m, 2H), 8.96 (s, 1H), 9.08 (s, 1H), 9.16 (s, 2H), 9.33 (s, 1H); ESIMS found for C$_{29}$H$_{25}$N$_7$O m/z 488.2 (M+H).

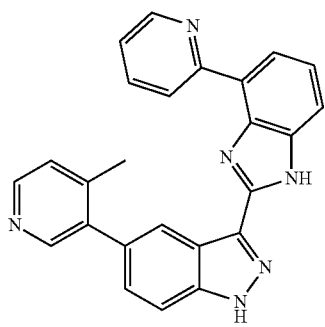

5-(4-Methylpyridin-3-yl)-3-(4-(pyridin-2-yl)-1H-benzo[d]imidazol-2-yl)-1H-indazole 125

$^1$H NMR (CD$_3$OD, 400 MHz) δ ppm 2.72 (s, 3H), 7.69-7.81 (m, 2H), 7.96 (d, J=8 Hz, 1H), 8.06 (d, J=6.8 Hz, 1H), 8.08-8.22 (m, 3H), 8.66 (brs, 1H), 8.70-8.80 (m, 3H), 9.01 (s, 1H), 9.05 (brs, 1H); ESIMS found for C$_{25}$H$_{18}$N$_6$ m/z 403.1 (M+H).

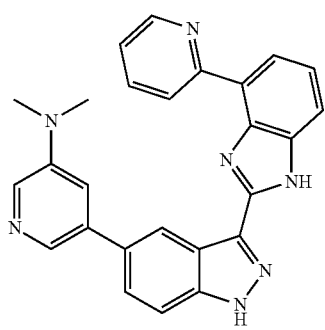

N,N-Dimethyl-5-(3-(4-(pyridin-2-yl)-1H-benzo[d]imidazol-2-yl)-1H-indazol-5-yl)pyridin-3-amine 127

$^1$H NMR (CD$_3$OD, 400 MHz) δ ppm 2.68 (s, 3H), 2.92 (s, 3H), 7.68 (t, 1H), 7.90 (d, J=8.8 Hz, 1H), 7.99 (d, 1H), 8.00-8.10 (m, 2H), 8.10-8.23 (m, 2H), 8.60 (s, 1H), 8.69 (t, J=8 Hz, 1H), 8.78 (d, J=8.4 Hz, 1H), 8.99 (s, 1H), 9.06 (d, J=4.8 Hz, 1H); ESIMS found for C$_{26}$H$_{21}$N$_7$ m/z 432.3 (M+H).

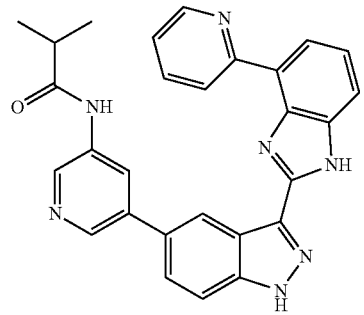

N-(5-(3-(4-(Pyridin-2-yl)-1H-benzo[d]imidazol-2-yl)-1H-indazol-5-yl)pyridin-3-yl)isobutyramide 129

$^1$H NMR (CD$_3$OD, 400 MHz) δ ppm 1.32 (d, J=6.8 Hz, 6H), 2.85 (sep, J=6.8 Hz, 1H), 7.63 (t, J=8 Hz, 1H), 7.91 (q, J=8.8 Hz, 2H), 7.97 (d, J=8 Hz, 1H), 8.04 (brs, 1H), 8.12 (d, J=7.2 Hz, 1H), 8.71 (t, J=7.2 Hz, 1H), 8.78 (d, J=8 Hz, 1H), 8.97 (s, 1H), 9.15 (s, 2H), 9.32 (s, 1H); ESIMS found for C$_{28}$H$_{23}$N$_7$O m/z 474.1 (M+H).

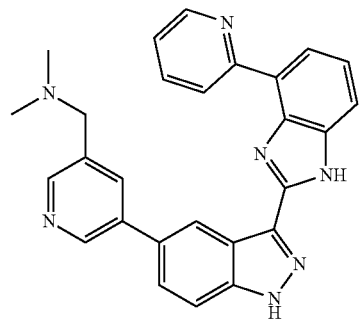

N,N-Dimethyl-1-(5-(3-(4-(pyridin-2-yl)-1H-benzo[d]imidazol-2-yl)-1H-indazol-5-yl)pyridin-3-yl)methanamine 133

$^1$H NMR (CD$_3$OD, 400 MHz) δ ppm 3.11 (brs, 6H), 4.87 (brs, 2H), 7.50 (brs, 1H), 7.72 (brs, 1H), 7.84 (brs, 2H), 7.99 (brs, 1H), 8.06 (brs, 1H), 8.52 (brs, 1H), 8.66 (brs, 1H), 8.96 (brs, 1H), 9.10 (brs, 1H), 9.15 (brs, 1H), 9.60 (brs, 1H), 9.64 (brs, 1H); ESIMS found for C$_{27}$H$_{23}$N$_7$ m/z 446.1 (M+H).

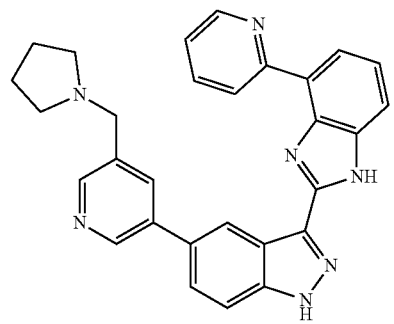

3-(4-(Pyridin-2-yl)-1H-benzo[d]imidazol-2-yl)-5-(5-(pyrrolidin-1-ylmethyl)pyridin-3-yl)-1H-indazole 134

$^1$H NMR (DMSO-d$_6$, 400 MHz) δ ppm 1.92 (brs, 2H), 2.07 (brs, 2H), 3.23 (brs, 2H), 3.48 (brs, 2H), 4.74 (brs, 2H), 7.53 (brs, 1H), 7.88 (brs, 2H), 8.02 (brs, 1H), 8.14 (brs, 2H), 8.75 (brs, 1H), 9.04 (brs, 1H), 9.12 (s, 1H), 9.17 (brs, 1H), 9.20 (brs, 1H), 9.41 (s, 1H), 9.60 (s, 1H), 12.01 (brs, 1H); ESIMS found for C$_{29}$H$_{25}$N$_7$ m/z 472.2 (M+H).

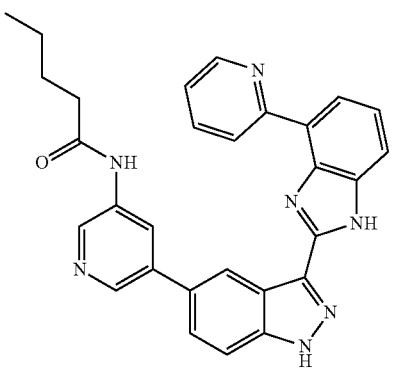

N-(5-(3-(4-(Pyridin-2-yl)-1H-benzo[d]imidazol-2-yl)-1H-indazol-5-yl)pyridin-3-yl)pentanamide 138

$^1$H NMR (DMSO-d$_6$, 400 MHz) δ ppm 0.94 (t, J=7.2 Hz, 3H), 1.20 (sex, J=7.2 Hz, 2H), 1.39 (quin, J=7.6 Hz, 2H), 2.52 (t, J=8 Hz, 2H), 7.21-7.42 (m, 2H), 7.56 (t, J=7.6 Hz, 1H), 7.65-7.98 (m, 4H), 8.16 (d, J=8 Hz, 1H), 8.62 (d, J=8.8 Hz, 1H), 8.95 (s, 1H), 9.01 (s, 1H), 9.03-9.17 (m, 2H); ESIMS found for C$_{29}$H$_{25}$N$_7$O m/z 488.2 (M+H).

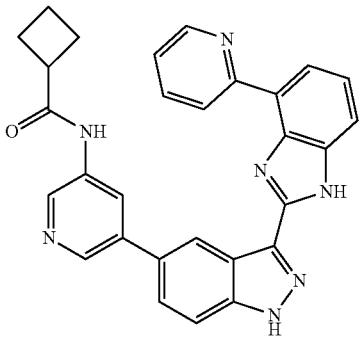

N-(5-(3-(4-(Pyridin-2-yl)-1H-benzo[d]imidazol-2-yl)-1H-indazol-5-yl)pyridin-3-yl)cyclobutanecarboxamide 140

$^1$H NMR (CD$_3$OD, 400 MHz) δ ppm 1.92-2.05 (m, 1H), 2.05-2.20 (m, 1H), 2.26-2.40 (m, 2H), 2.37-2.51 (m, 2H), 3.46 (quin, J=8.4 Hz, 1H), 7.55 (t, J=7.2 Hz, 1H), 7.72 (d, J=8 Hz, 1H), 7.78 (d, J=8.4 Hz, 1H), 7.87 (d, J=8 Hz, 1H), 7.96 (d, J=8 Hz, 1H), 8.06 (brs, 1H), 8.62 (d, J=7.6 Hz, 1H), 8.71 (brs, 1H), 8.80 (s, 1H), 8.98 (s, 1H), 9.10 (s, 2H), 9.28 (s, 1H); ESIMS found for C$_{29}$H$_{23}$N$_7$O m/z 486.2 (M+H).

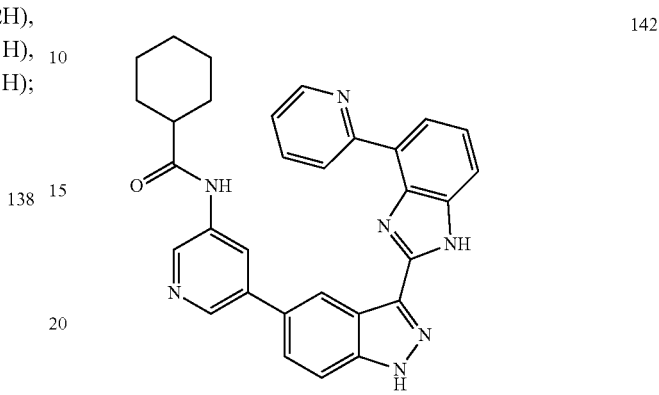

N-(5-(3-(4-(Pyridin-2-yl)-1H-benzo[d]imidazol-2-yl)-1H-indazol-5-yl)pyridin-3-yl)cyclohexanecarboxamide 142

$^1$H NMR (CD$_3$OD, 400 MHz) δ ppm 1.37-1.66 (m, 3H), 1.38 (d, J=12.4 Hz, 1H), 1.90 (d, J=12.8 Hz, 2H), 2.02 (d, J=11.2 Hz, 2H), 2.59 (s, 1H), 7.65 (t, J=8 Hz, 1H), 7.95 (s, 2H), 8.00 (d, J=7.6 Hz, 2H), 8.21 (d, J=7.5 Hz, 1H), 8.70 (t, J=7.6 Hz, 1H), 8.87 (d, J=8.4 Hz, 1H), 9.02 (s, 1H), 9.11 (s, 1H), 9.13-9.20 (m, 2H), 9.25 (s, 1H); ESIMS found for C$_{31}$H$_{27}$N$_7$O m/z 514.3 (M+H).

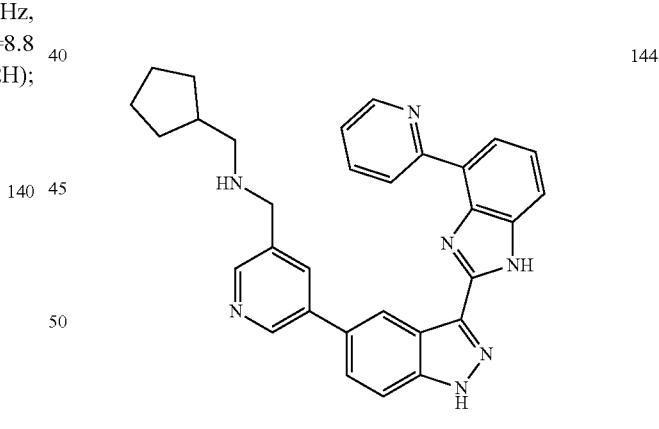

1-Cyclopentyl-N-((5-(3-(4-(pyridin-2-yl)-1H-benzo[d]imidazol-2-yl)-1H-indazol-5-yl)pyridin-3-yl)methyl)methanamine 144

$^1$H NMR (CD$_3$OD, 400 MHz) δ ppm 1.44 (brs, 2H), 1.68 (brs, 2H), 1.77 (brs, 2H), 2.01 (brs, 2H), 2.45 (brs, 1H), 3.30 (brs, 2H), 7.58 (brs, 1H), 7.86 (d, J=6 Hz, 1H), 7.96 (d, J=6.8 Hz, 1H), 8.05 (brs, 3H), 8.69 (brs, 2H), 9.13 (brs, 3H), 9.59 (brs, 1H), 9.61 (brs, 1H); ESIMS found for C$_{31}$H$_{29}$N$_7$ m/z 500.2 (M+H).

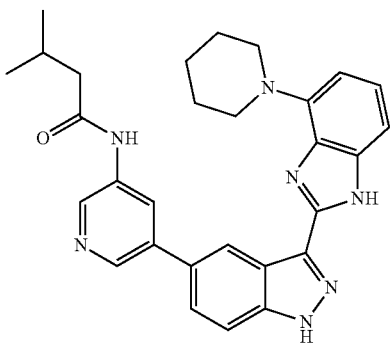

3-Methyl-N-(5-(3-(4-(piperidin-1-yl)-1H-benzo[d]imidazol-2-yl)-1H-indazol-5-yl)pyridin-3-yl)butanamide 146

$^1$H NMR (CD$_3$OD, 400 MHz) δ ppm 1.08 (d, J=6.8 Hz, 6H), 1.90 (brs, 2H), 2.16-2.33 (m, 5H), 2.44 (d, J=7.6 Hz, 2H), 4.21 (brs, 4H), 7.47 (t, J=8 Hz, 1H), 7.56 (d, J=8 Hz, 1H), 7.80 (d, J=8 Hz, 1H), 7.93 (s, 2H), 9.03 (s, 2H), 9.10 (s, 1H), 9.26 (s, 1H); ESIMS found for C$_{29}$H$_{31}$N$_7$O m/z 494.3 (M+H).

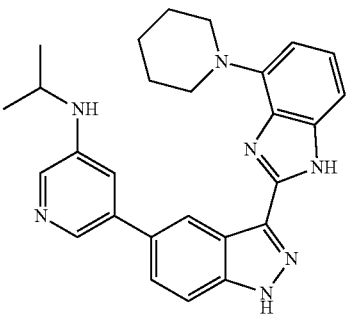

N,N-Dimethyl-5-(3-(4-(piperidin-1-yl)-1H-benzo[d]imidazol-2-yl)-1H-indazol-5-yl)pyridin-3-amine 151

$^1$H NMR (CD$_3$OD, 400 MHz) δ ppm 1.80 (brs, 2H), 2.10 (brs, 4H), 3.16 (s, 6H), 4.07 (brs, 4H), 7.22-7.29 (m, 1H), 7.31-7.41 (m, 1H), 7.47 (d, J=8 Hz, 1H), 7.68 (d, 1H), 7.78 (d, 1H), 8.01 (s, 1H), 8.10 (s, 1H), 8.38 (s, 1H), 8.87 (s, 1H); ESIMS found for C$_{26}$H$_{27}$N$_7$ m/z 438.2 (M+H).

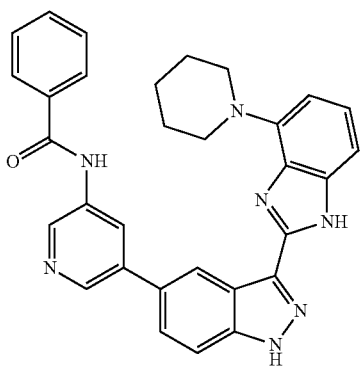

N-(5-(3-(4-(Piperidin-1-yl)-1H-benzo[d]imidazol-2-yl)-1H-indazol-5-yl)pyridin-3-yl)benzamide 155

$^1$H NMR (DMSO-d$_6$, 400 MHz) δ ppm 1.79 (brs, 2H), 2.17 (brs, 4H), 4.16 (brs, 4H), 7.46 (t, J=8 Hz, 1H), 7.52-7.63 (m, 3H), 7.70 (t, 1H), 7.79 (d, J=8 Hz, 1H), 7.92 (d, 1H), 7.98 (d, 1H), 8.12 (d, J=7.2 Hz, 2H), 9.11 (s, 2H), 9.37 (s, 1H), 9.49 (s, 1H); ESIMS found for C$_{31}$H$_{27}$N$_7$O m/z 514.0 (M+H).

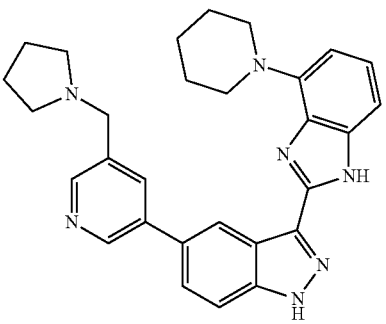

N-Isopropyl-5-(3-(4-(piperidin-1-yl)-1H-benzo[d]imidazol-2-yl)-1H-indazol-5-yl)pyridin-3-amine 156

$^1$H NMR (DMSO-d$_6$, 400 MHz) δ ppm 1.35 (d, J=6.4 Hz, 6H), 1.94 (brs, 2H), 2.25 (brs, 4H), 3.92 (sep, J=6.4 Hz, 1H), 4.18 (brs, 4H), 7.54 (t, J=7.6 Hz, 1H), 7.68 (d, J=7.6 Hz, 1H), 7.85 (d, J=8.4 Hz, 1H), 7.91 (s, 2H), 8.06 (s, 2H), 8.45 (s, 1H), 9.04 (s, 1H); ESIMS found for C$_{27}$H$_{29}$N$_7$ m/z 452.3 (M+H).

3-(4-(Piperidin-1-yl)-1H-benzo[d]imidazol-2-yl)-5-(5-(pyrrolidin-1-ylmethyl)pyridin-3-yl)-1H-indazole 158

$^1$H NMR (CD$_3$OD, 400 MHz) δ ppm 1.97 (brs, 3H), 2.16 (brs, 2H), 2.32 (brs, 6H), 2.70 (brs, 1H), 3.43 (d, J=5.2 Hz, 2H), 3.76 (brs, 2H), 4.11 (brs, 4H), 7.58 (d, J=6.8 Hz, 1H), 7.74 (d, J=7.2 Hz, 1H), 7.88 (d, J=7.6 Hz, 1H), 7.96 (s, 1H), 8.14 (d, J=4.4 Hz, 1H), 9.19 (brs, 1H), 9.37 (brs, 1H), 9.58 (brs, 1H), 9.62 (brs, 1H); ESIMS found for C$_{29}$H$_{31}$N$_7$ m/z 478.2 (M+H).

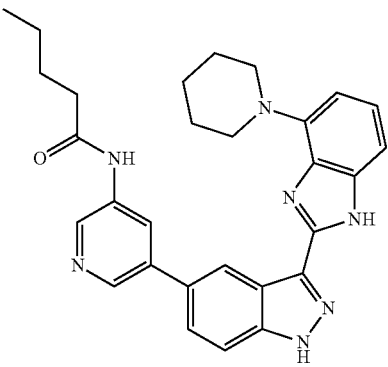

N-(5-(3-(4-(Piperidin-1-yl)-1H-benzo[d]imidazol-2-yl)-1H-indazol-5-yl)pyridin-3-yl)pentanamide 162

$^1$H NMR (CD$_3$OD, 400 MHz) δ ppm 1.02 (t, J=7.2 Hz, 3H), 1.48 (sex, J=7.6 Hz, 2H), 1.66-1.81 (m, 4H), 1.88-2.00 (m, 2H), 2.48 (t, J=7.6 Hz, 2H), 3.51 (brs, 4H), 4.63 (brs, 2H), 6.77 (d, 1H), 7.20 (q, J=7.6 Hz, 1H), 7.20-7.28 (m, 1H), 7.79 (dq, J=7.6 Hz, J=1.6 Hz, 2H), 8.51 (s, 1H), 8.71 (d, J=1.6 Hz, 1H), 8.77 (d, J=2.4 Hz, 1H), 8.93 (s, 1H); ESIMS found for C$_{29}$H$_{31}$N$_7$O m/z 494.2 (M+H).

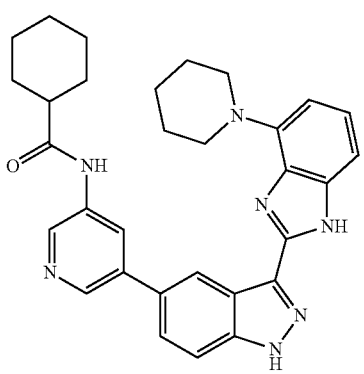

N-(5-(3-(4-(Piperidin-1-yl)-1H-benzo[d]imidazol-2-yl)-1H-indazol-5-yl)pyridin-3-yl)cyclohexanecarboxamide 166

$^1$H NMR (CD$_3$OD, 400 MHz) δ ppm 1.23 (m, 3H), 1.51 (q, J=10.8 Hz, 2H), 1.67 (d, J=11.6 Hz, 1H), 1.78 (d, J=10.8 Hz, 4H), 1.90 (d, J=11.6 Hz, 2H), 2.13 (brs, 4H), 2.46 (t, J=12 Hz, 1H), 4.08 (brs, 4H), 7.38 (t, J=8 Hz, 1H), 7.51 (d, J=7.6 Hz, 1H), 7.71 (d, J=8 Hz, 1H), 7.82 (s, 2H), 8.97 (d, J=2.4 Hz, 2H), 9.08 (s, 1H), 9.17 (s, 1H); ESIMS found for C$_{31}$H$_{33}$N$_7$O m/z 520.2 (M+H).

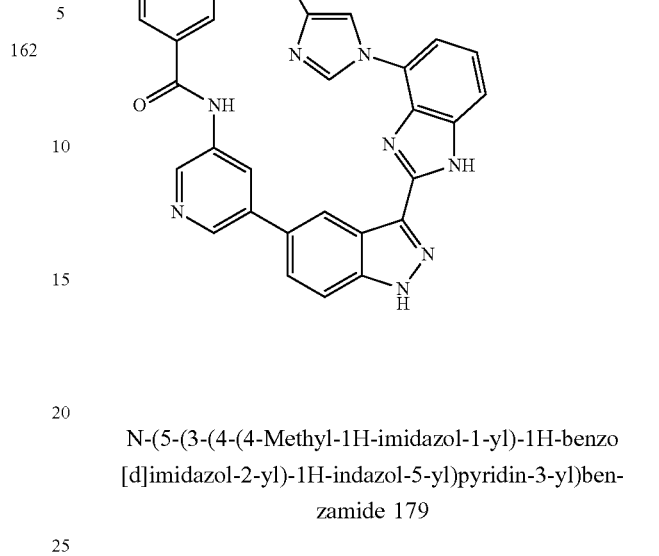

N-(5-(3-(4-(4-Methyl-1H-imidazol-1-yl)-1H-benzo[d]imidazol-2-yl)-1H-indazol-5-yl)pyridin-3-yl)benzamide 179

$^1$H NMR (CD$_3$OD, 400 MHz) δ ppm 2.38 (s, 3H), 7.52 (t, 1H), 7.56-7.66 (m, 3H), 7.71 (d, 1H), 7.77 (d, J=8 Hz, 1H), 7.83 (d, J=8.8 Hz, 1H), 7.91 (d, 1H), 8.15 (s, 1H), 8.20 (d, J=7.6 Hz, 2H), 8.93 (s, 1H), 9.07 (s, 1H), 9.14 (s, 1H), 9.51 (s, 1H), 10.12 (s, 1H); ESIMS found for C$_{30}$H$_{22}$N$_8$O m/z 511.2 (M+H).

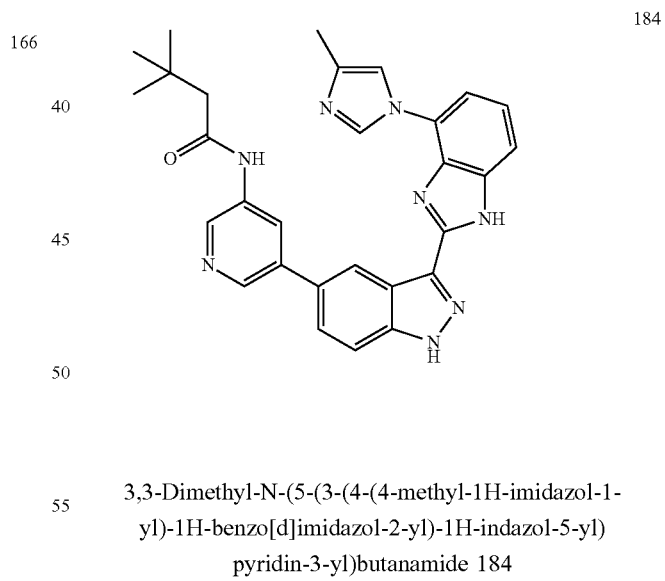

3,3-Dimethyl-N-(5-(3-(4-(4-methyl-1H-imidazol-1-yl)-1H-benzo[d]imidazol-2-yl)-1H-indazol-5-yl)pyridin-3-yl)butanamide 184

$^1$H NMR (DMSO-d$_6$, 400 MHz) δ ppm 1.07 (s, 9H), 2.34 (s, 2H), 2.45 (s, 3H), 7.49 (t, J=8 Hz, 1H), 7.69 (d, J=7.6 Hz, 1H), 7.75 (d, J=8 Hz, 1H), 7.87 (q, J=7.6 Hz, 2H), 8.46 (s, 1H), 8.63 (s, 1H), 8.84 (s, 1H), 8.86 (s, 1H), 8.97 (s, 1H), 9.99 (s, 1H), 10.68 (s, 1H); ESIMS found for C$_{29}$H$_{28}$N$_8$O m/z 505.2 (M+H).

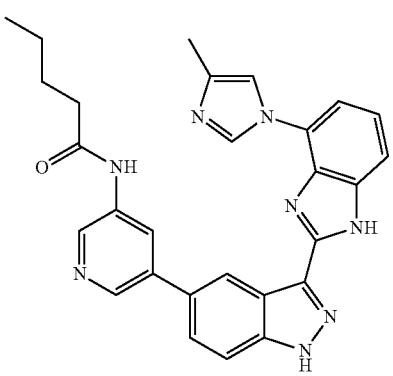

N-(5-(3-(4-(4-Methyl-1H-imidazol-1-yl)-1H-benzo[d]imidazol-2-yl)-1H-indazol-5-yl)pyridin-3-yl)pentanamide 186

$^1$H NMR (CD$_3$OD, 400 MHz) δ ppm 1.03 (t, J=7.2 Hz, 3H), 1.49 (sex, J=7.6 Hz, 2H), 1.75 (quin, J=8 Hz, 2H), 2.36 (s, 3H), 2.50 (t, J=7.6 Hz, 2H), 7.26-7.43 (m, 2H), 7.44-7.57 (1H), 7.64 (d, J=8.4 Hz, 1H), 7.70 (d, J=8.4 Hz, 1H), 7.89 (brs, 1H), 8.22 (s, 1H), 8.41 (d, J=10.4 Hz, 1H), 8.56 (s, 1H), 8.61 (s, 1H), 8.65 (s, 1H); ESIMS found for C$_{28}$H$_{26}$N$_8$O m/z 491.2 (M+H).

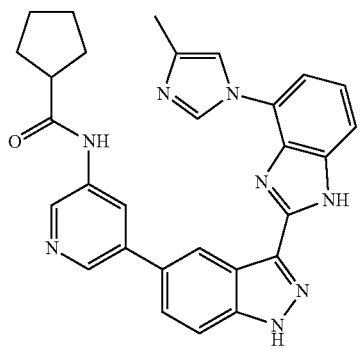

N-(5-(3-(4-(4-Methyl-1H-imidazol-1-yl)-1H-benzo[d]imidazol-2-yl)-1H-indazol-5-yl)pyridin-3-yl)cyclopentanecarboxamide 189

$^1$H NMR (CD$_3$OD, 400 MHz) δ ppm 1.66-1.80 (m, 2H), 1.78-1.87 (m, 2H), 1.87-2.00 (m, 2H), 2.01-2.12 (m, 2H), 2.55 (s, 3H), 3.04 (quin, J=8 Hz, 1H), 7.53 (t, J=8 Hz, 1H), 7.66 (d, J=7.6 Hz, 1H), 7.81 (d, J=8 Hz, 1H), 7.90 (Abq, J=13.2 Hz, J=8.8 Hz, 2H), 8.21 (s, 1H), 8.93 (s, 1H), 9.04 (s, 2H), 9.32 (s, 1H), 10.04 (d, J=1.2 Hz, 1H); ESIMS found for C$_{29}$H$_{26}$N$_8$O m/z 503.2 (M+H).

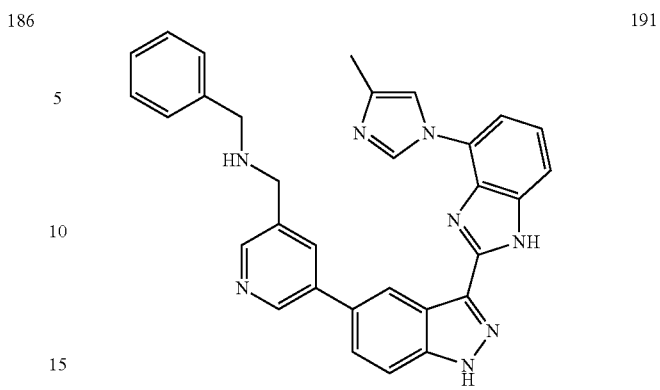

N-Benzyl-1-(5-(3-(4-(4-methyl-1H-imidazol-1-yl)-1H-benzo[d]imidazol-2-yl)-1H-indazol-5-yl)pyridin-3-yl)methanamine 191

$^1$H NMR (CD$_3$OD, 400 MHz) δ ppm 2.33 (s, 3H), 4.36 (s, 2H), 4.44 (s, 2H), 7.36-7.51 (m, 5H), 7.51-7.61 (m, 2H), 7.79 (d, J=8.8 Hz, 1H), 7.85 (d, J=9.2 Hz, 1H), 8.36 (s, 3H), 8.68 (d, J=1.6 Hz, 1H), 8.92 (s, 1H), 9.02 (d, J=1.6 Hz, 1H), 9.11 (brs, 1H); ESIMS found for C$_{31}$H$_{26}$N$_8$ m/z 511.2 (M+H).

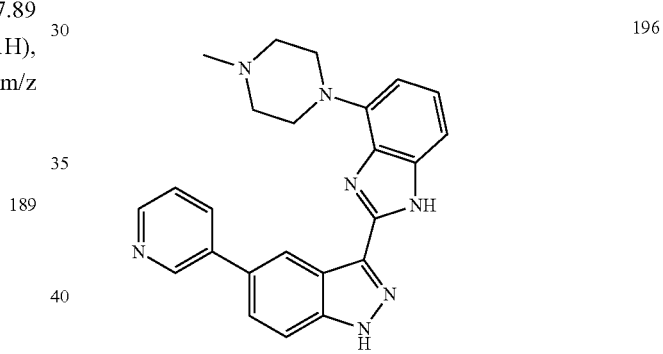

3-(4-(4-Methylpiperazin-1-yl)-1H-benzo[d]imidazol-2-yl)-5-(pyridin-3-yl)-1H-indazole 196

$^1$H NMR (CD$_3$OD, 400 MHz) δ ppm 3.02 (s, 3H), 3.58 (brs, 4H), 3.85 (brs, 4H), 6.78 (brs, 1H), 7.24 (t, J=8 Hz, 1H), 7.28 (brs, 1H), 7.62 (dd, J=7.6 Hz, J=4.8 Hz, 1H), 7.79 (d, J=8.8 Hz, 1H), 7.85 (d, J=8.8 Hz, 1H), 8.28 (d, J=7.6 Hz, 1H), 8.59 (d, J=4.4 Hz, 1H), 8.85 (s, 1H), 9.02 (s, 1H); ESIMS found for C$_{24}$H$_{23}$N$_7$ m/z 410.2 (M+H).

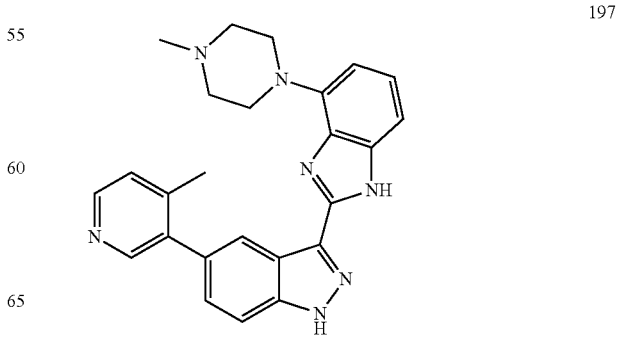

3N-(5-(4-(4-Methylpiperazin-1-yl)-1H-benzo[d]
imidazol-2-yl)-5-(4-methylpyridin-3-yl)-1H-indazole
197

¹H NMR (CD₃OD, 400 MHz) δ ppm 2.39 (s, 3H), 2.46 (s, 6H), 2.74 (brs, 5H), 7.18 (brs, 2H), 7.46 (d, J=4.8 Hz, 1H), 7.52 (d, J=8.4 Hz, 1H), 7.75 (d, J=8.8 Hz, 1H), 8.44 (d, J=5.6 Hz, 1H), 8.52 (s, 2H), 8.57 (s, 1H); ESIMIMS found for C₂₅H₂₅N₇ m/z 424.1 (M+H).

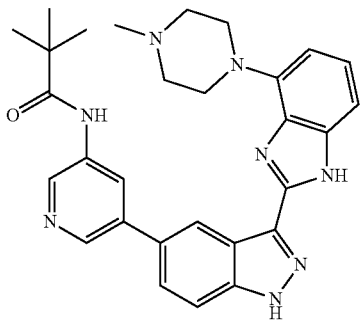

200

N-(5-(3-(4-(4-Methylpiperazin-1-yl)-1H-benzo[d]
imidazol-2-yl)-1H-indazol-5-yl)pyridin-3-yl)pival-
amide 200

¹H NMR (CD₃OD, 400 MHz) δ ppm 1.36 (s, 9H), 2.42 (s, 3H), 2.82 (s, 4H), 3.67 (brs, 4H), 6.68 (brs, 1H), 7.18 (brs, 2H), 7.22-7.33 (m, 2H), 8.50 (brs, 1H), 8.69 (brs, 1H), 8.77 (brs, 1H), 8.84 (brs, 1H); ESIMS found for C₂₉H₃₂N₈O m/z 509.2 (M+H).

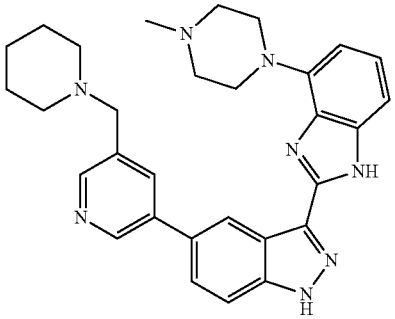

207

N-(5-(3-(7-(5-fluoropyridin-3-yl)-3H-imidazo[4,5-c]
pyridin-2-yl)-1H-indazol-5-yl)pyridin-3-yl)propiona-
mide 207

¹H NMR (CD₃OD, 400 MHz) δ ppm 1.52 (brs, 2H), 1.60-1.72 (m, 4H), 2.48 (s, 3H), 2.55 (brs, 5H), 2.87 (brs, 4H), 3.61-3.80 (m, 5H), 6.71 (brs, 1H), 7.21 (brs, 2H), 7.78 (d, 1H), 7.85 (d, 1H), 8.23 (brs, 1H), 8.54 (brs, 1H), 8.88 (brs, 1H), 8.91 (brs, 1H); ESIMS found for C₃₀H₃₄N₈O m/z 507.2 (M+H).

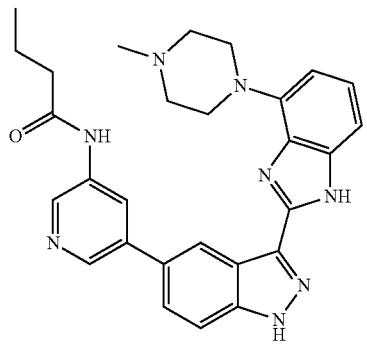

209

N-(5-(3-(4-(4-Methylpiperazin-1-yl)-1H-benzo[d]
imidazol-2-yl)-1H-indazol-5-yl)pyridin-3-yl)butyr-
amide 209

¹H NMR (CD₃OD, 400 MHz) δ ppm 1.05 (t, J=7.6 Hz, 3H), 1.78 (sex, J=7.6 Hz, 2H), 2.45 (t, J=7.6 Hz, 2H), 2.84 (s, 3H), 3.35 (brs, 4H), 3.85 (brs, 4H), 6.73 (brs, 1H), 7.17-7.28 (m, 2H), 7.77 (Abq, J=8.8 Hz, J=2.8 Hz, 2H), 8.54 (brs, 1H), 8.69 (brs, 2H), 8.81 (s, 1H); ESIMS found for C₂₈H₃₀N₈O m/z 495.2 (M+H).

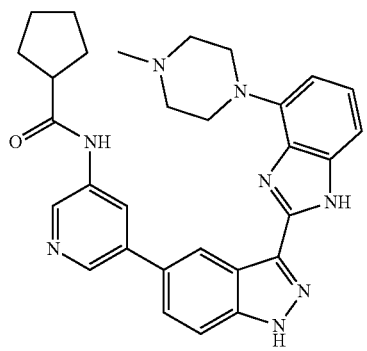

213

N-(5-(3-(4-(4-Methylpiperazin-1-yl)-1H-benzo[d]
imidazol-2-yl)-1H-indazol-5-yl)pyridin-3-yl)cyclo-
pentanecarboxamide 213

¹H NMR (CD₃OD, 400 MHz) δ ppm 1.25 (d, J=8.8 Hz, 1H), 1.50-1.62 (m, 2H), 1.62-1.83 (m, 6H), 1.82-1.95 (m, 2H), 2.31 (s, 3H), 2.70 (brs, 4H), 2.77 (quin, 1H), 3.53 (brs, 1H), 6.55 (brs, 1H), 7.05 (brs, 2H), 7.60 (Abq, J=5.6 Hz, 2H), 8.35 (s, 1H), 8.53 (s, 1H), 8.65 b (s, 1H), 8.68 (s, 1H); ESIMS found for C₃₀H₃₂N₈O m/z 521.2 (M+H).

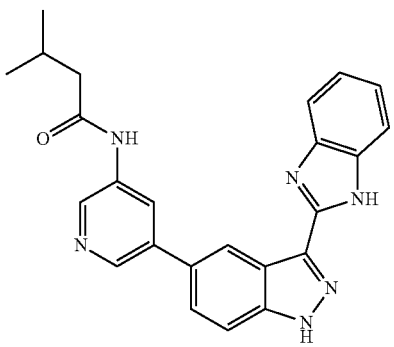

N-(5-(3-(1H-Benzo[d]imidazol-2-yl)-1H-indazol-5-yl)pyridin-3-yl)-3-methylbutanamide 218

¹H NMR (CD₃OD, 400 MHz) δ ppm 1.07 (d, J=6.4 Hz, 6H), 2.26 (sep, J=6.8 Hz, 1H), 2.43 (d, J=7.6 Hz, 2H), 7.68 (dd, J=6 Hz, J=2.8 Hz, 2H), 7.95 (dd, J=6.4 Hz, J=3.2 Hz, 2H), 8.01 (s, 2H), 8.98 (s, 2H), 9.09 (s, 1H), 9.35 (s, 1H); ESIMS found for C$_{24}$H$_{22}$N$_6$O m/z 411.2 (M+H).

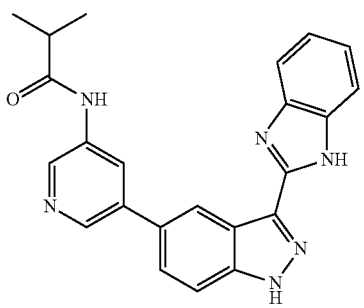

3-(1H-Benzo[d]imidazol-2-yl)-5-(4-methylpyridin-3-yl)-1H-indazole 221

¹H NMR (CD₃OD, 400 MHz) δ ppm 2.41 (s, 3H), 7.29 (dd, J=6 Hz, J=3.2 Hz, 2H), 7.42 (d, J=4.8 Hz, 1H), 7.48 (d, 1H), 7.67 (brd, J=3.2 Hz, 2H), 7.75 (d, J=8.4 Hz, 1H), 8.42 (d, J=5.2 Hz, 1H), 8.50 (s, 2H); ESIMS found for C$_{20}$H$_{15}$N$_5$ m/z 326.1 (M+H).

N-(5-(3-(1H-Benzo[d]imidazol-2-yl)-1H-indazol-5-yl)pyridin-3-yl)isobutyramide 225

¹H NMR (CD₃OD, 400 MHz) δ ppm 1.29 (d, J=6.8 Hz, 6H), 2.81 (sep, J=6.8 Hz, 1H), 7.69 (dd, J=6.4 Hz, J=3.2 Hz, 2H), 7.96 (dd, J=6 Hz, J=3.2 Hz, 2H), 8.03 (d, J=1 Hz, 2H), 9.01 (s, 1H), 9.04 (t, J=2 Hz, 1H), 9.13 (d, J=1.6 Hz, 1H), 9.39 (d, J=2 Hz, 1H); ESIMS found for C$_{23}$H$_{20}$N$_6$O m/z 397.1 (M+H).

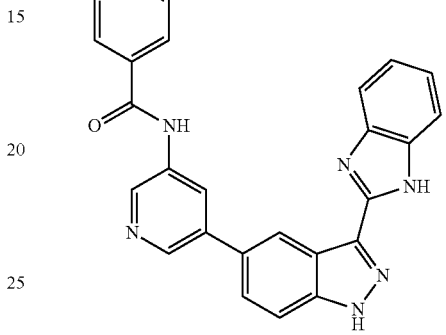

N-(5-(3-(1H-Benzo[d]imidazol-2-yl)-1H-indazol-5-yl)pyridin-3-yl)benzamide 227

¹H NMR (CD₃OD, 400 MHz) δ ppm 7.31 (dd, J=6 Hz, J=3.2 Hz, 2H), 7.57 (t, J=7.6 Hz, 2H), 7.64 (t, 1H), 7.70 (brs, 2H), 7.78 (d, J=8.4 Hz, 1H), 7.85 (d, J=8.4 Hz, 1H), 8.04 (d, J=7.6 Hz, 2H), 8.59 (s, 1H), 8.79 (d, J=1.6 Hz, 1H), 8.84 (s, 1H), 9.01 (d, J=2 Hz, 1H); ESIMS found for C$_{26}$H$_{18}$N$_6$O m/z 431.1 (M+H).

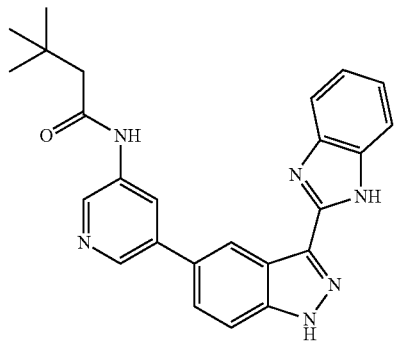

N-(5-(3-(1H-Benzo[d]imidazol-2-yl)-1H-indazol-5-yl)pyridin-3-yl)-3,3-dimethylbutanamide 232

¹H NMR (CD₃OD, 400 MHz) δ ppm 1.05 (s, 9H), 2.34 (s, 2H), 7.56 (dd, J=6 Hz, J=2.8 Hz, 2H), 7.85 (dd, J=6 Hz, J=3.2 Hz, 2H), 7.90 (s, 2H), 8.89 (d, J=2 Hz, 1H), 8.93 (s, 1H), 9.04 (s, 1H), 9.31 (s, 1H); ESIMS found for C$_{25}$H$_{24}$N$_6$O m/z 425.2 (M+H).

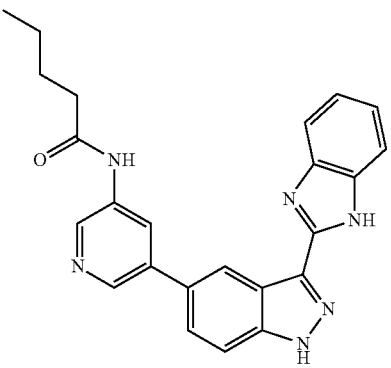

N-(5-(3-(1H-Benzo[d]imidazol-2-yl)-1H-indazol-5-yl)pyridin-3-yl)pentanamide 234

$^1$H NMR (CD$_3$OD, 400 MHz) δ ppm 1.02 (t, J=7.2 Hz, 3H), 1.49 (sex, J=7.2 Hz, 2H), 1.78 (quin, J=7.6 Hz, 2H), 2.59 (t, J=7.2 Hz, 2H), 7.70 (dd, J=6 Hz, J=3.2 Hz, 2H), 7.98 (dd, J=6 Hz, J=3.2 Hz, 2H), 8.04 (s, 2H), 9.02 (s, 1H), 9.05 (s, 1H), 9.15 (s, 1H), 9.42 (d, J=2 Hz, 1H); ESIMS found for C$_{24}$H$_{22}$N$_6$O m/z 411.1 (M+H).

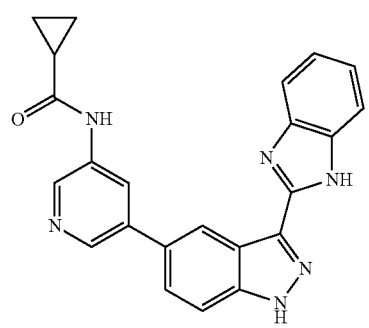

N-(5-(3-(1H-Benzo[d]imidazol-2-yl)-1H-indazol-5-yl)pyridin-3-yl)cyclopropanecarboxamide 235

$^1$H NMR (CD$_3$OD, 400 MHz) δ ppm 0.90-0.98 (m, 2H), 1.01-1.07 (m, 2H), 1.87 (quin, 1H), 7.32 (dd, J=6.4 Hz, J=3.2 Hz, 2H), 7.71 (dd, J=6 Hz, J=3.2 Hz, 2H), 7.80 (q, J=8.8 Hz, 2H), 8.46 (t, J=0.4 Hz, 1H), 8.74 (d, J=2 Hz, 1H), 8.82 (s, 1H), 8.83 (d, J=2.4 Hz, 1H); ESIMS found for C$_{23}$H$_{18}$N$_6$O m/z 395.1 (M+H).

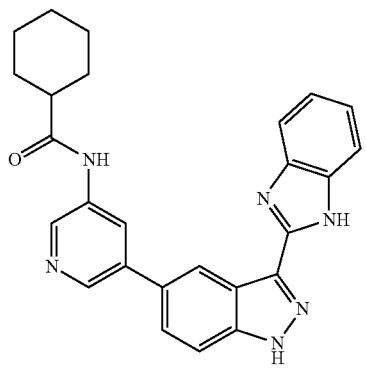

N-(5-(3-(1H-Benzo[d]imidazol-2-yl)-1H-indazol-5-yl)pyridin-3-yl)cyclohexanecarboxamide 238

$^1$H NMR (CD$_3$OD, 400 MHz) δ ppm 1.14-1.40 (m, 3H), 1.48 (q, J=12 Hz, 2H), 1.66 (d, J=11.6 Hz, 1H), 1.78 (d, J=12.8 Hz, 2H), 1.89 (d, J=12.4 Hz, 2H), 2.60 (t, J=11.6 Hz, 1H), 7.57 (dd, J=6.4 Hz, J=3.2 Hz, 2H), 7.85 (dd, J=6 Hz, J=3.6 Hz, 2H), 7.90 (s, 2H), 8.91 (s, 2H), 9.01 (s, 1H), 9.26 (s, 1H); ESIMS found for C$_{26}$H$_{24}$N$_6$O m/z 437.1 (M+H).

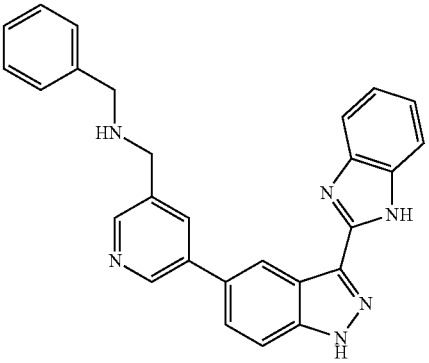

1-(5-(3-(1H-Benzo[d]imidazol-2-yl)-1H-indazol-5-yl)pyridin-3-yl)-N-benzylmethanamine 239

$^1$H NMR (CD$_3$OD, 400 MHz) δ ppm 4.25 (s, 2H), 4.32 (s, 2H), 7.33 (dd, J=6 Hz, J=3.2 Hz, 2H), 7.40-7.58 (m, 5H), 7.71 (dd, J=6 Hz, J=3.2 Hz, 2H), 7.81 (d, J=8.8 Hz, 1H), 7.88 (dd, J=8.8 Hz, J=1.6 Hz, 1H), 8.40 (s, 1H), 8.65 (d, J=1.6 Hz, 1H), 8.87 (s, 1H), 9.06 (d, J=2 Hz, 1H); ESIMS found for C$_{27}$H$_{22}$N$_6$ m/z 431.2 (M+H).

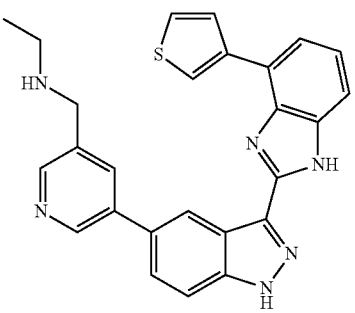

N-((5-(3-(4-(Thiophen-3-yl)-1H-benzo[d]imidazol-2-yl)-1H-indazol-5-yl)pyridin-3-yl)methyl)ethanamine 246

$^1$H NMR (DMSO-d$_6$, 400 MHz) δ ppm 1.12 (t, J=7.2 Hz, 3H), 2.74 (q, J=7.2 Hz, 2H), 4.00 (s, 2H), 7.31 (t, J=7.6 Hz, 1H), 7.49 (d, J=7.6 Hz, 1H), 7.65 (d, J=7.2 Hz, 1H), 7.71 (dd, J=5.2 Hz, J=3.2 Hz, 1H), 7.84 (d, J=8.4 Hz, 1H), 7.92 (d, J=7.2 Hz, 1H), 8.23 (s, 1H), 8.27 (s, 1H), 8.62 (d, J=1.6 Hz, 1H), 8.77 (d, J=1.6 Hz, 1H), 8.96 (d, J=2 Hz, 1H), 8.99 (s, 1H); ESIMS found for C$_{26}$H$_{22}$N$_6$S m/z 451.1 (M+H).

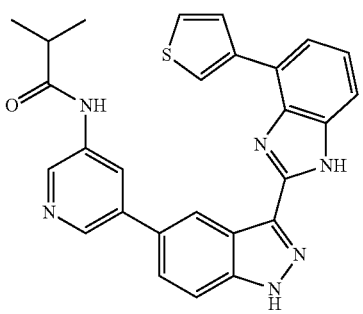

N-(5-(3-(4-(Thiophen-3-yl)-1H-benzo[d]imidazol-2-yl)-1H-indazol-5-yl)pyridin-3-yl)isobutyramide 249

$^1$H NMR (DMSO-d$_6$, 400 MHz) δ ppm 1.19 (d, J=6.8 Hz, 6H), 2.71 (sep, J=7.2 Hz, 1H), 7.31 (t, J=8 Hz, 1H), 7.49 (d, J=7.6 Hz, 1H), 7.64 (d, J=7.2 Hz, 2H), 7.84 (s, 2H), 8.16 (d, J=4.4 Hz, 1H), 8.60 (brs, 1H), 8.72 (brs, 2H), 8.79 (brs, 1H), 8.93 (brs, 1H); ESIMS found for C$_{27}$H$_{22}$N$_6$OS m/z 479.1 (M+H).

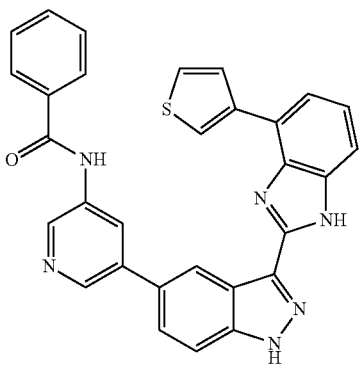

2-Phenyl-N-(5-(3-(4-(thiophen-3-yl)-1H-benzo[d]imidazol-2-yl)-1H-indazol-5-yl)pyridin-3-yl)acetamide 250

$^1$H NMR (DMSO-d$_6$, 400 MHz) δ ppm 3.86 (s, 2H), 7.24-7.46 (m, 8H), 7.52 (d, 1H), 7.63 (d, J=6 Hz, 2H), 7.89 (s, 2H), 8.11 (brs, 1H), 8.61 (brs, 1H), 8.94 (brs, 2H); ESIMS found for C$_{31}$H$_{22}$N$_6$OS m/z 527.1 (M+H).

N,N-Dimethyl-1-(5-(3-(4-(thiophen-3-yl)-1H-benzo[d]imidazol-2-yl)-1H-indazol-5-yl)pyridin-3-yl)methanamine 253

$^1$H NMR (DMSO-d$_6$, 400 MHz) δ ppm 3.02 (s, 6H), 4.62 (d, J=2.8 Hz, 2H), 7.42 (t, J=7.6 Hz, 1H), 7.66 (t, J=7.2 Hz, 2H), 7.78 (dd, J=4.8 Hz, J=3.2 Hz, 1H), 7.94 (d, J=8.8 Hz, 1H), 8.02 (d, J=4.8 Hz, 1H), 8.10 (d, J=8.8 Hz, 1H), 8.56 (s, 1H), 9.10 (s, 2H), 9.23 (s, 1H), 9.47 (s, 1H), 11.77 (brs, 1H); ESIMS found for C$_{26}$H$_{22}$N$_6$S m/z 451.1 (M+H).

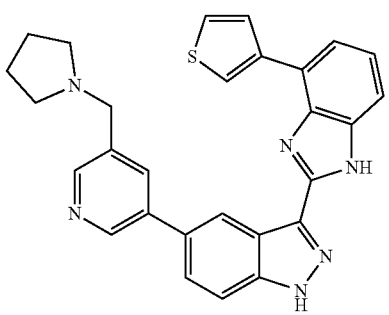

5-(5-(Pyrrolidin-1-ylmethyl)pyridin-3-yl)-3-(4-(thiophen-3-yl)-1H-benzo[d]imidazol-2-yl)-1H-indazole 254

$^1$H NMR (CD$_3$OD, 400 MHz) δ ppm 2.17 (brs, 2H), 2.30 (brs, 2H), 3.33 (s, 2H), 3.39 (brs, 2H), 3.60 (brs, 2H), 7.61 (d, J=4 Hz, 1H), 7.67-7.79 (m, 3H), 7.97-8.10 (m, 3H), 8.18 (d, J=8.4 Hz, 1H), 9.13 (s, 1H), 9.15 (s, 1H), 9.52 (s, 1H), 9.61 (s, 1H); ESIMS found for C$_{28}$H$_{24}$N$_6$S m/z 477.1 (M+H).

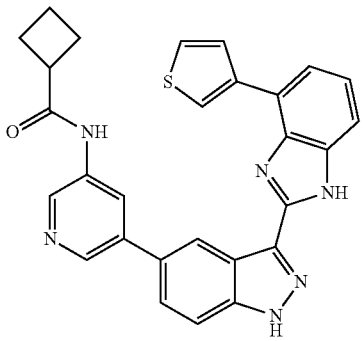

N-(5-(3-(4-(Thiophen-3-yl)-1H-benzo[d]imidazol-2-yl)-1H-indazol-5-yl)pyridin-3-yl)cyclobutanecarboxamide 260

ESIMS found for C$_{28}$H$_{22}$N$_6$OS m/z 491.1 (M+H).

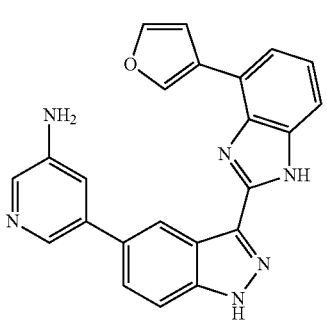

5-(3-(4-(Furan-3-yl)-1H-benzo[d]imidazol-2-yl)-1H-indazol-5-yl)pyridin-3-amine 267

¹H NMR (CD₃OD, 400 MHz) δ ppm 7.03 (s, 1H), 7.57-7.69 (m, 2H), 7.75 (s, 1H), 7.81 (d, 1H), 7.93 (Abq, 2H), 8.05 (d, J=2 Hz, 1H), 8.10 (s, 1H), 8.33 (s, 1H), 8.43 (s, 1H), 8.77 (s, 1H); ESIMS found for C₂₃H₁₆N₆O m/z 393.0 (M+H).

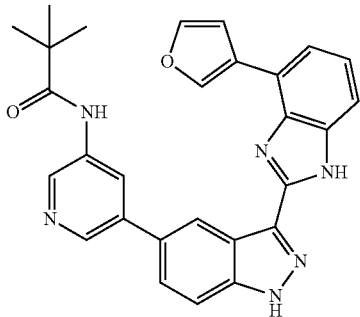

N-(5-(3-(4-(Furan-3-yl)-1H-benzo[d]imidazol-2-yl)-1H-indazol-5-yl)pyridin-3-yl)pivalamide 272

¹H NMR (CD₃OD, 400 MHz) δ ppm 1.40 (s, 9H), 7.20 (brs, 1H), 7.33 (t, J=7.6 Hz, 1H), 7.49 (d, J=6.8 Hz, 1H), 7.53 (brs, 1H), 7.66 (s, 1H), Abq (7.80 [d, J=9.2 Hz, 1H], 7.86 [dd, J=8.4 Hz, J=1.6 Hz, 1H]), 8.58 (s, 1H), 8.75 (d, J=2 Hz, 2H), 8.84 (d, J=6.4 Hz, 1H), 8.96 (s, 1H); ESIMS found for C₂₈H₂₄N₆O₂ m/z 477.2 (M+H).

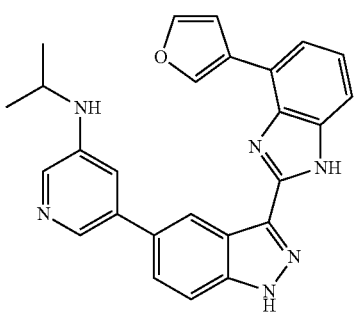

5-(3-(4-(Furan-3-yl)-1H-benzo[d]imidazol-2-yl)-1H-indazol-5-yl)-N-isopropylpyridin-3-amine 276

¹H NMR (CD₃OD, 400 MHz) δ ppm 1.32 (d, J=6.4 Hz, 6H), 3.83 (sep, J=6 Hz, 1H), 7.20 (brs, 1H), 7.32 (t, J=7.6 Hz, 1H), 7.41 (t, J=2.4 Hz, 1H), 7.49 (d, J=6.8 Hz, 1H), 7.50 (brs, 1H), 7.66 (s, 1H), Abq (7.74 [d, J=8.4 Hz, 1H], 7.80 [dd, J=8.4 Hz, J=1.6 Hz, 1H]), 7.95 (d, J=2.4 Hz, 1H), 7.17 (d, J=2 Hz, 1H), 8.78 (brs, 1H), 8.88 (brs, 1H); ESIMS found for C₂₆H₂₂N₆O m/z 435.1 (M+H).

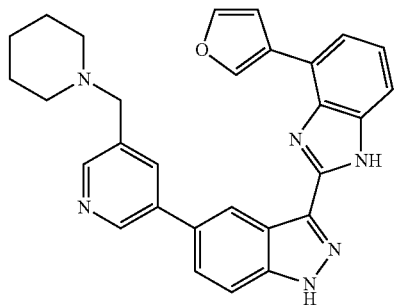

3-(4-(Furan-3-yl)-1H-benzo[d]imidazol-2-yl)-5-(5-(piperidin-1-ylmethyl)pyridin-3-yl)-1H-indazole 279

¹H NMR (CD₃OD, 400 MHz) δ ppm 1.85-2.03 (m, 4H), 2.90 (s, 4H), 3.62 (d, J=10.4, 2H), 4.64 (s, 2H), 7.01 (s, 1H), 7.63-7.73 (m, 2H), 7.76 (s, 1H), 7.92 (d, J=5.2 Hz, 1H), Abq (7.99 [d, J=9.2 Hz, 1H], 8.11 [d, J=8.8 Hz, 1H]), 8.33 (s, 1H), 8.97 (s, 1H), 9.01 (s, 1H), 9.24 (s, 1H), 9.36 (s, 1H); ESIMS found for C₂₉H₂₆N₆O m/z 475.2 (M+H).

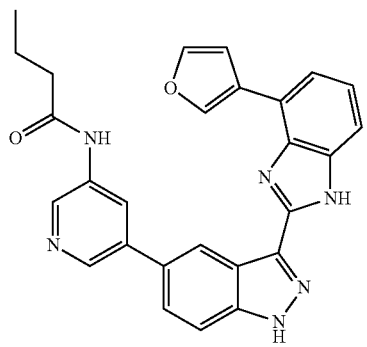

N-(5-(3-(4-(Furan-3-yl)-1H-benzo[d]imidazol-2-yl)-1H-indazol-5-yl)pyridin-3-yl)butyramide 281

¹H NMR (CD₃OD, 400 MHz) δ ppm 1.08 (t, J=7.6 Hz, 3H), 1.82 (sex, J=7.2 Hz, 2H), 2.48 (t, J=7.6 Hz, 2H), 7.20 (brs, 1H), 7.33 (t, J=7.6 Hz, 1H), 7.66 (s, 1H), 7.82 (q, J=8.8 Hz, 2H), 8.57 (s, 1H), 7.73 (s, 1H), 8.80 (s, 1H), 8.94 (s, 1H); ESIMS found for C₂₇H₂₂N₆O₂ m/z 463.2 (M+H).

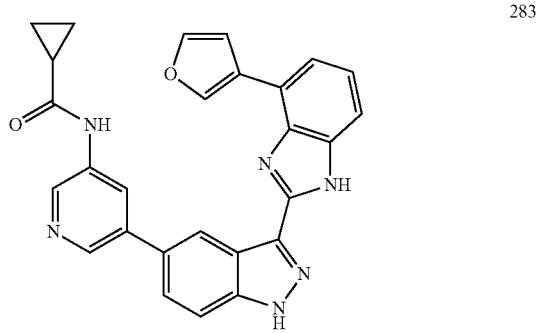 [SMILES: O=C(Nc1cncc(-c2ccc3[nH]nc(-c4nc5c(-c6ccoc6)cccc5[nH]4)c3c2)c1)C1CC1]

N-(5-(3-(4-(Furan-3-yl)-1H-benzo[d]imidazol-2-yl)-1H-indazol-5-yl)pyridin-3-yl)cyclopropanecarboxamide 283

$^1$H NMR (CD$_3$OD, 400 MHz) δ ppm 0.73-0.87 (m, 2H), 0.87-0.99 (m, 2H), 1.76 (quin, J=4 Hz, 1H), 7.08 (brs, 1H), 7.20 (t, J=7.6 Hz, 1H), 7.37 (d, J=7.6 Hz, 1H), 7.54 (s, 1H), 7.68 (q, J=8.8 Hz, 2H), 8.46 (s, 1H), 8.59 (s, 1H), 8.65 (s, 1H), 8.81 (s, 1H); ESIMS found for C$_{27}$H$_{20}$N$_6$O$_2$ m/z 461.1 (M+H).

Example 2

The above synthesized compounds were screened using the assay procedure for Wnt activity described below.

Reporter cell lines were generated by stably transducing cells of cancer cell lines (e.g., colon cancer) with a lentiviral construct that include a wnt-responsive promoter driving expression of the firefly luciferase gene.

Lentiviral constructs were made in which the SP5 promoter, a promoter having eight TCF/LEF binding sites derived from the SP5 promoter, was linked upstream of the firefly luciferase gene. The lentiviral constructs included a hygromycin resistance gene as a selectable marker. The SP5 promoter construct was used to transduce SW480 cells, a colon cancer cell line having a mutated APC gene that generates a truncated APC protein, leading to de-regulated accumulation of β-catenin. A control cell line was generated using another lentiviral construct containing the luciferase gene under the control of the SV40 promoter which does not require (β-catenin for activation.

Cultured SW480 cells bearing a reporter construct were distributed at approximately 10,000 cells per well into 384 well multiwell plates. Compounds were then added to the wells in half-log dilutions using a three micromolar top concentration. A series of control wells for each cell type received only buffer and compound solvent. Twenty-four hours after the addition of compound, reporter activity for luciferases was assayed, for example, by addition of the BrightGlo luminescence reagent (Promega) and the Victor3 plate reader (Perkin Elmer). Readings were normalized to DMSO only treated cells, and normalized activities were then used for the IC$_{50}$ calculations. Table 2 shows the activity of selected compounds as provided herein.

TABLE 2

| Compound | Wnt inhibition (μM) |
|---|---|
| 1 | 0.002 |
| 4 | 0.004 |
| 5 | 0.034 |
| 7 | 0.008 |
| 9 | 0.25 |
| 10 | 0.069 |
| 13 | 0.011 |
| 16 | 0.031 |
| 18 | 0.03 |
| 19 | 0.005 |
| 21 | 0.05 |
| 22 | 0.18 |
| 26 | 0.179 |
| 29 | 0.1 |
| 32 | 0.035 |
| 33 | 0.034 |
| 35 | 0.161 |
| 38 | 0.153 |
| 41 | 0.015 |
| 42 | 0.033 |

TABLE 2-continued

| Compound | Wnt inhibition (μM) |
|---|---|
| 43 | 0.043 |
| 44 | 0.14 |
| 45 | 0.11 |
| 46 | 0.225 |
| 47 | 0.45 |
| 54 | 0.046 |
| 57 | 0.006 |
| 57 | 0.116 |
| 59 | 0.332 |
| 63 | 0.01 |
| 66 | 4 |
| 69 | 0.023 |
| 72 | 1.14 |
| 75 | 0.006 |
| 77 | 0.063 |
| 79 | 0.045 |
| 84 | 0.013 |
| 88 | 0.135 |
| 89 | 0.004 |
| 90 | 0.011 |
| 92 | 0.008 |
| 94 | 0.121 |
| 95 | 0.163 |
| 104 | 0.065 |
| 106 | 1.93 |
| 108 | 0.016 |
| 110 | 0.205 |
| 114 | 0.067 |
| 116 | 0.023 |
| 117 | 0.054 |
| 118 | 1.46 |
| 122 | 0.011 |
| 125 | 0.054 |
| 127 | 0.032 |
| 129 | 0.021 |
| 133 | 0.127 |
| 134 | 0.219 |
| 138 | 0.018 |
| 140 | 0.008 |
| 142 | 0.155 |
| 144 | 1.18 |
| 146 | 0.058 |
| 151 | 0.041 |
| 155 | 0.289 |
| 156 | 0.066 |
| 158 | 0.116 |
| 162 | 0.14 |
| 166 | 0.445 |
| 173 | 0.046 |
| 179 | 0.01 |
| 184 | 0.115 |
| 186 | 0.006 |
| 189 | 0.013 |
| 191 | 0.138 |
| 196 | 0.028 |
| 197 | 0.249 |
| 200 | 0.076 |
| 202 | 0.248 |
| 207 | 0.801 |
| 209 | 0.061 |
| 213 | 0.195 |
| 218 | 0.037 |
| 220 | 0.165 |
| 221 | 0.317 |
| 222 | 0.235 |
| 225 | 0.028 |
| 227 | 0.099 |
| 232 | 0.065 |
| 234 | 0.123 |
| 235 | 0.025 |
| 238 | 0.147 |
| 239 | 0.372 |
| 246 | 0.014 |
| 249 | 0.013 |
| 250 | 0.159 |
| 250 | 0.018 |

TABLE 2-continued

| Compound | Wnt inhibition (μM) |
|---|---|
| 253 | 0.007 |
| 254 | 0.002 |
| 267 | 4.15 |
| 272 | 0.159 |
| 276 | 0.016 |
| 279 | 0.418 |
| 281 | 0.025 |
| 283 | 0.057 |

The term "comprising" as used herein is synonymous with "including," "containing," or "characterized by," and is inclusive or open-ended and does not exclude additional, unrecited elements or method steps.

What is claimed is:

1. A compound, or pharmaceutically acceptable salt thereof, of Formula I:

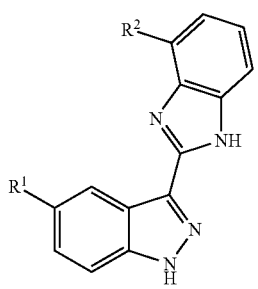

I wherein:
$R^1$ is -pyridinyl$R^3R^4$;
$R^2$ is -pyridinyl$R^5$;
$R^3$ is 1 substituent attached to the heteroaryl ring and is —NHC(=O)$R^8$;
$R^4$ is 1 substituent attached to the pyridinyl ring and is selected from the group consisting of H, $C_{1-3}$ alkyl, —$CF_3$, halide, —CN, —OH, and —$OCF_3$;
$R^5$ is 1-3 substituents attached to the pyridinyl ring and each is independently selected from the group consisting of H, $C_{1-3}$ alkyl, —$CF_3$, halide, —CN, —OH, —($C_{1-3}$ alkyl)$OR^8$, —$NR_9R^{10}$, —($C_{1-3}$ alkyl)$NR^9R^{10}$ and —$OCF_3$;
each $R^8$ is independently selected from the group consisting of $C_{1-9}$ alkyl, -aryl$R^{14}$, carbocyclyl$R^{11}$, —($C_{1-3}$ alkyl)aryl$R^{14}$ and —($C_{1-3}$ alkyl)carbocyclyl$R^{11}$;
each $R^9$ is independently selected from the group consisting of H, $C_{1-6}$ alkyl, -aryl$R^{14}$, carbocyclyl$R^{11}$, —($C_{1-3}$ alkyl)aryl$R^{14}$ and —($C_{1-3}$ alkyl)carbocyclyl$R^{11}$;
each $R^{10}$ is independently selected from the group consisting of H and $C_{1-6}$ alkyl;
$R^{11}$ is 1-3 substituents attached to the carbocyclyl ring and each independently selected from the group consisting of H, $C_{1-3}$ alkyl, —$CF_3$, halide, —CN, —$O(R^{10})$, —($C_{1-3}$ alkyl)$OR^{10}$, —$N(R^{10})_2$, —($C_{1-3}$)alkyl)$N(R^{10})_2$ and —$OCF_3$; and
$R^{14}$ is 1-3 substituents attached to the aryl ring and each is independently selected from the group consisting of H, $C_{1-3}$ alkyl, —$CF_3$, halide, —CN, —$O(R^{10})$, —($C_{1-3}$ alkyl)$OR^{10}$, —$N(R^{10})_2$, —($C_{1-3}$)alkyl)$N(R^{10})_2$ and $OCF_3$.

2. The compound of claim 1, wherein $R^1$ is pyridin-3-yl$R^3R^4$.

3. The compound of claim 2, wherein $R^3$ is NHC(=O)$R^8$.

4. The compound of claim 3, wherein $R^4$ is H and $R^8$ is selected from the group consisting of —$C_{1-5}$ alkyl, —$CH_2$phenyl, phenyl and -carbocyclyl.

5. The compound of claim 2, wherein $R^3$ is selected from the group consisting of:

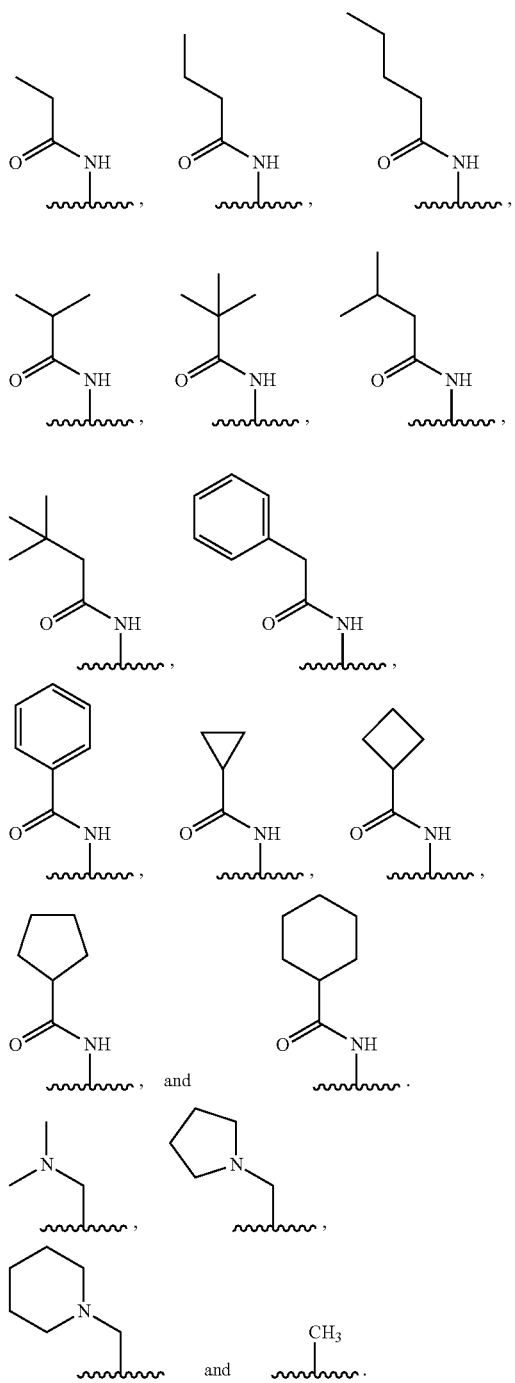

6. The compound of claim 1, wherein the compound of Formula (I) is selected from the group consisting of:

191
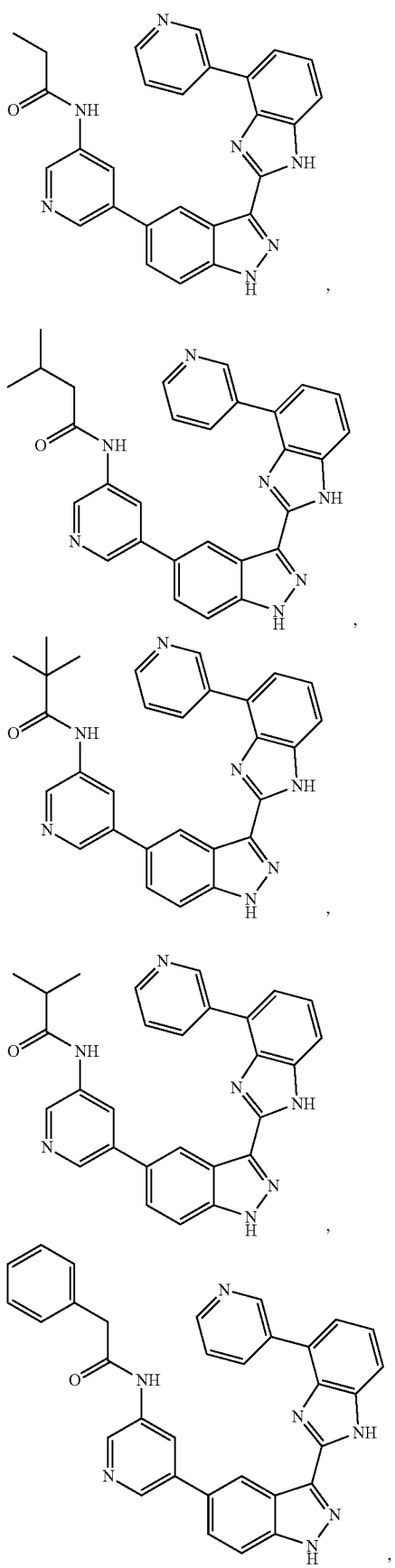
192
-continued
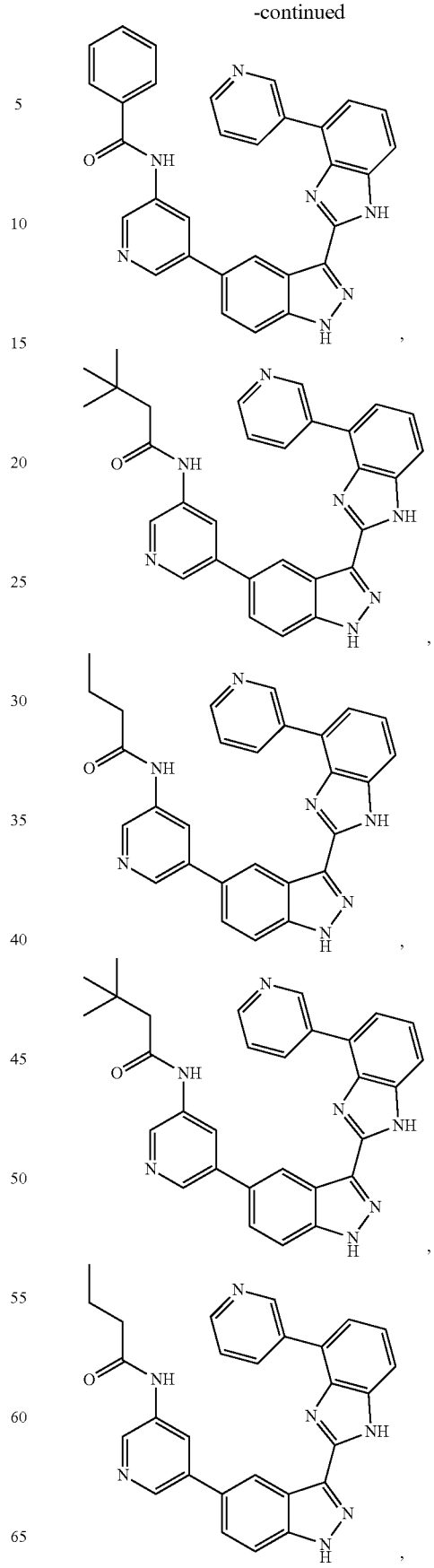

193
-continued
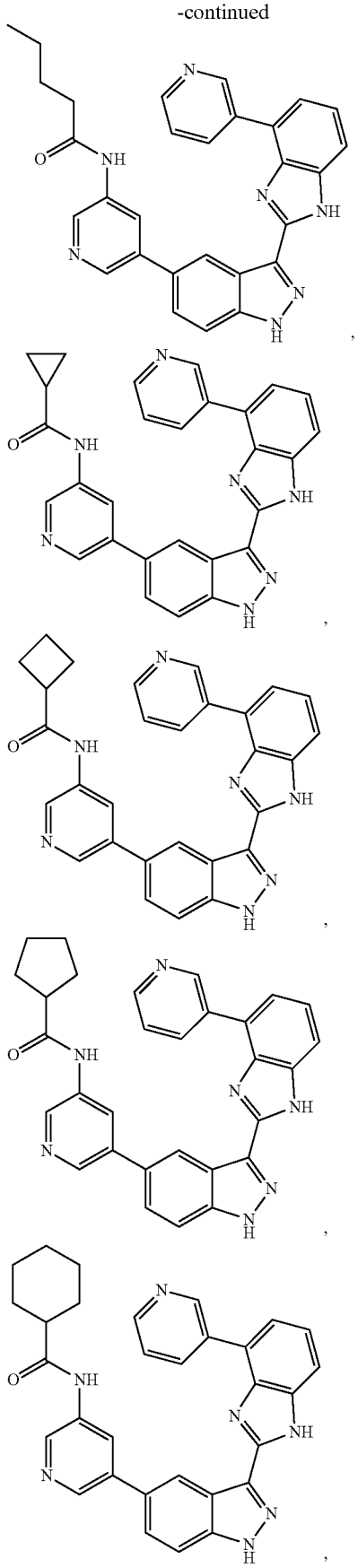
194
-continued
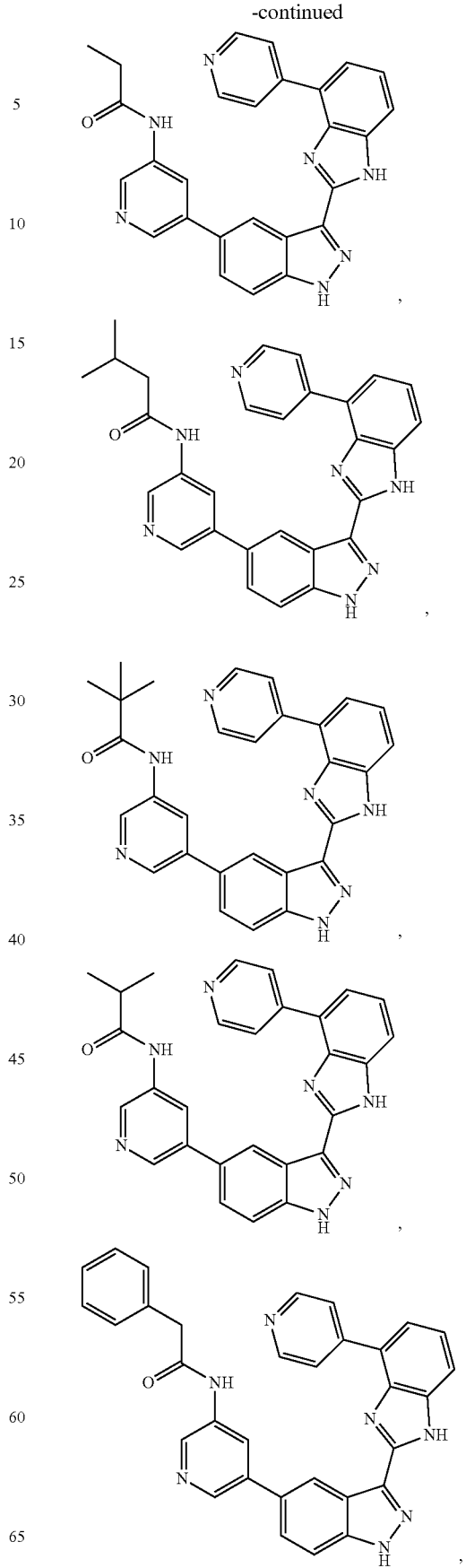

195
-continued
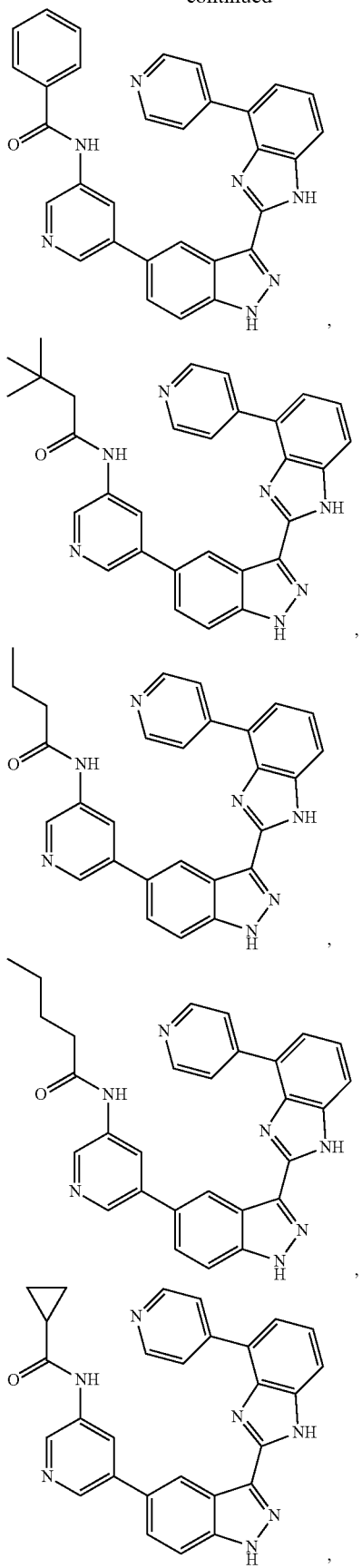
196
-continued
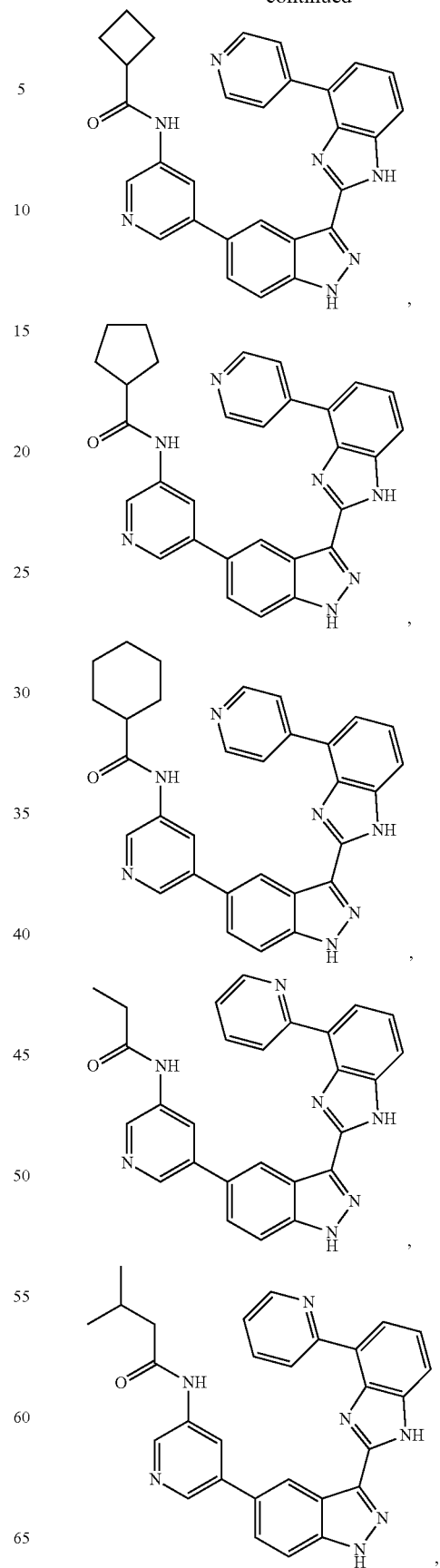

-continued
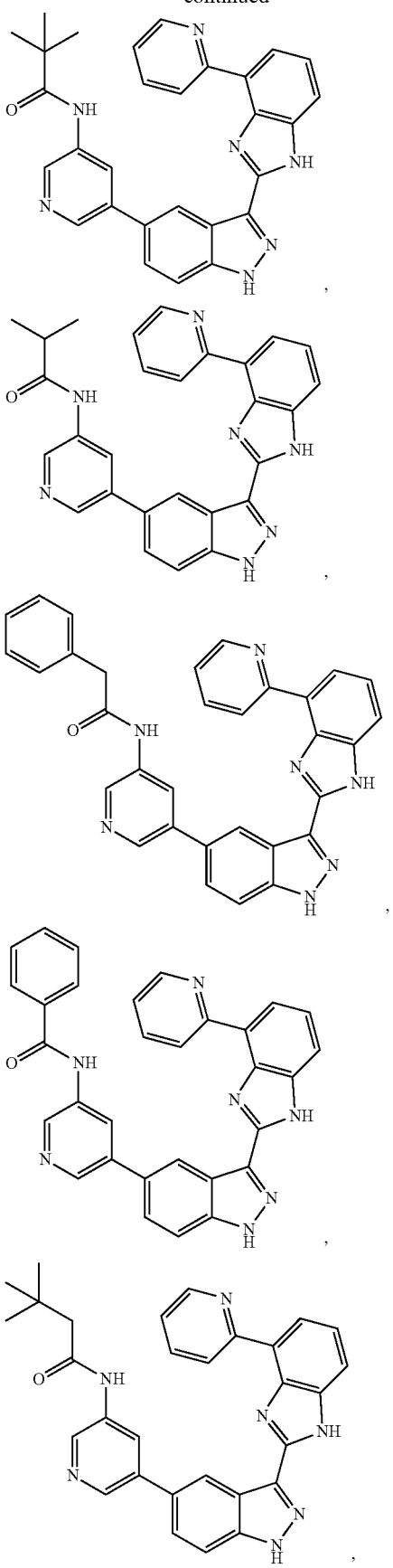
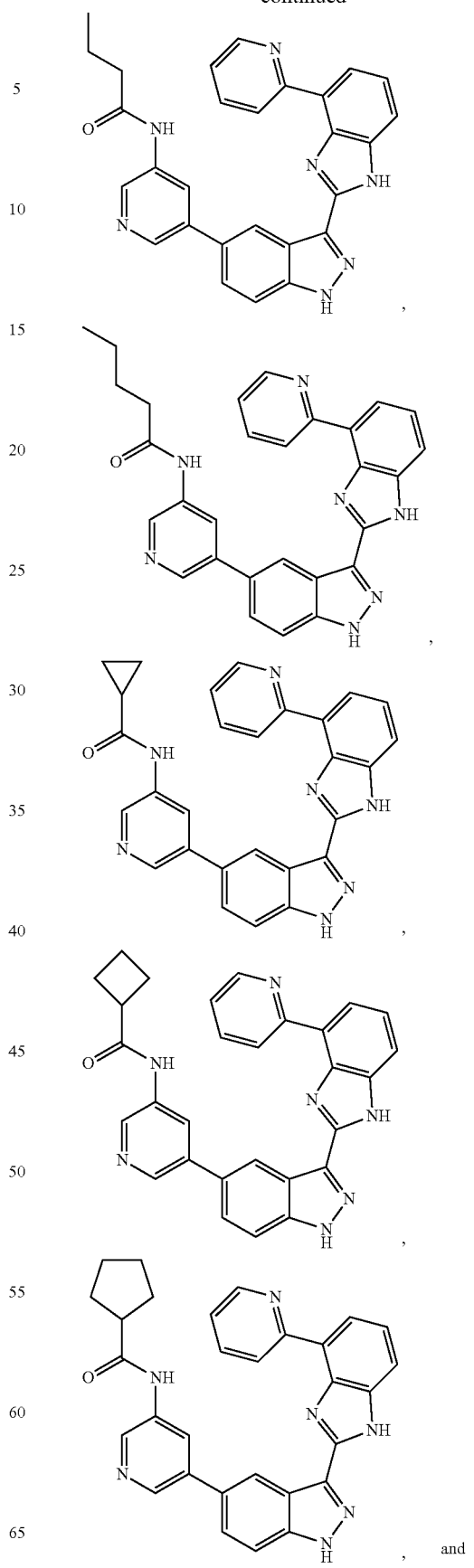
and

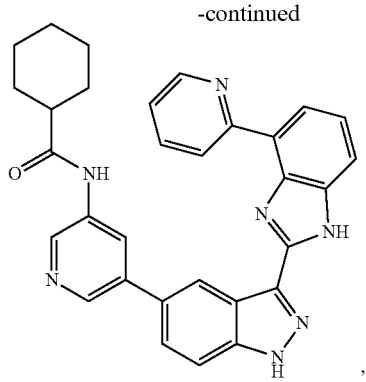,
or a pharmaceutically acceptable salt thereof.
7. A pharmaceutical composition comprising a therapeutically effective amount of a compound according to claim 1, or a pharmaceutically acceptable salt thereof, and a pharmaceutically acceptable excipient.
* * * * *